(12) United States Patent
Biftu et al.

(10) Patent No.: US 11,433,055 B2
(45) Date of Patent: Sep. 6, 2022

(54) CHROMANE MONOBACTAM COMPOUNDS FOR THE TREATMENT OF BACTERIAL INFECTIONS

(71) Applicant: Merck Sharp & Dohme Corp., Rahway, NJ (US)

(72) Inventors: Tesfaye Biftu, Freehold, NJ (US); Xianhai Huang, Warren, NJ (US); Weiguo Liu, Princeton, NJ (US); Weidong Pan, Hillsborough, NJ (US); Min Park, Whippany, NJ (US); Alexander Pasternak, Jamaica Plain, MA (US); Wanying Sun, Edison, NJ (US); Haifeng Tang, Metuchen, NJ (US); Yi Zang, Princeton, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 0 days.

(21) Appl. No.: 16/651,456

(22) PCT Filed: Sep. 27, 2018

(86) PCT No.: PCT/US2018/053039
§ 371 (c)(1),
(2) Date: Mar. 27, 2020

(87) PCT Pub. No.: WO2019/070492
PCT Pub. Date: Apr. 11, 2019

(65) Prior Publication Data
US 2020/0297702 A1    Sep. 24, 2020

Related U.S. Application Data

(60) Provisional application No. 62/566,779, filed on Oct. 2, 2017.

(51) Int. Cl.
*A61K 31/353*        (2006.01)
*A61K 31/397*        (2006.01)
(Continued)

(52) U.S. Cl.
CPC ........ *A61K 31/427* (2013.01); *A61K 31/4425* (2013.01); *A61K 31/506* (2013.01);
(Continued)

(58) Field of Classification Search
CPC .. A61K 31/427; A61K 31/473; A61K 31/498; A61K 31/4985; A61K 31/502;
(Continued)

(56) References Cited

U.S. PATENT DOCUMENTS 10,407,421 B2 *  9/2019  Liu ..................... A61K 45/06
2012/0087861 A1   4/2012  Nitsch et al.
(Continued)

FOREIGN PATENT DOCUMENTS

EP       0531976 A1    3/1993
JP       05213946 A    8/1993
(Continued)

OTHER PUBLICATIONS

Mitton-Fry, Mark, J. et al., Novel monobactams utilizing a siderophore uptake mechanism for the treatment of gram-negative infections, Bioorganic & Medicinal Chemistry Letters, 2012, p. 5989-5994, vol. 22.

*Primary Examiner* — Craig D Ricci
*Assistant Examiner* — Janet L Coppins
(74) *Attorney, Agent, or Firm* — Baerbel R. Brown; Catherine D. Fitch

(57) ABSTRACT

The present invention relates to monobactam compounds of Formula I:

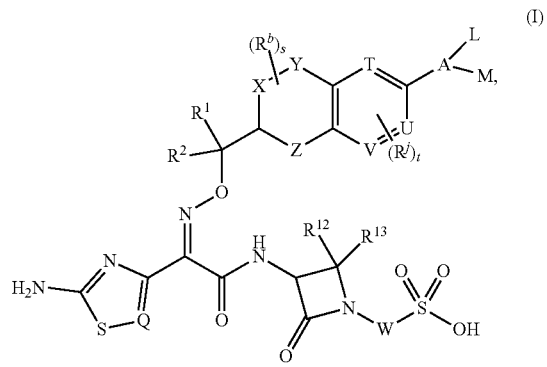

and pharmaceutically acceptable salts thereof. The present invention also relates to compositions which comprise a monobactam compound of the invention or a pharmaceutically acceptable salt thereof, and a pharmaceutically acceptable carrier. The invention further relates to methods for treating a bacterial infection comprising administering to the patient a therapeutically effective amount of a compound of the invention, either alone or in combination with a therapeutically effective amount of a second beta-lactam antibiotic.

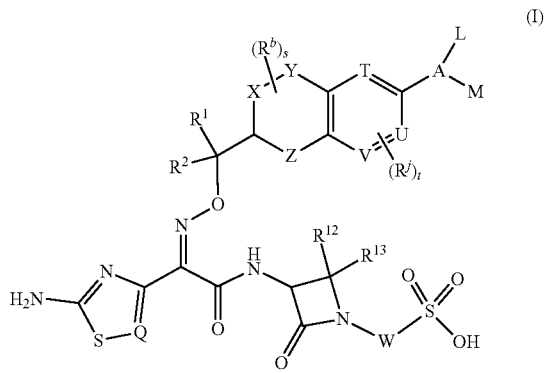

21 Claims, No Drawings

(51) Int. Cl.
| | |
|---|---|
| *A61K 31/427* | (2006.01) |
| *A61P 31/04* | (2006.01) |
| *A61K 31/4425* | (2006.01) |
| *A61K 31/506* | (2006.01) |
| *A61K 31/519* | (2006.01) |
| *C07D 417/14* | (2006.01) |

(52) U.S. Cl.
CPC ............ *A61K 31/519* (2013.01); *A61P 31/04* (2018.01); *C07D 417/14* (2013.01)

(58) Field of Classification Search
CPC .............. A61K 31/5025; A61K 31/517; A61K 31/519; A61K 31/536; A61K 31/5365; A61K 31/538; A61K 31/5386; A61P 31/04
See application file for complete search history.

(56) References Cited

U.S. PATENT DOCUMENTS

| | | |
|---|---|---|
| 2015/0183854 A1 | 7/2015 | Mori et al. |
| 2016/0120841 A1 | 5/2016 | Kym et al. |

FOREIGN PATENT DOCUMENTS

| | | | |
|---|---|---|---|
| JP | 2009518317 A | 5/2009 | |
| JP | 2015504907 A | 2/2015 | |
| WO | 2007065288 A2 | 6/2007 | |
| WO | 2013110643 A1 | 8/2013 | |
| WO | 2015148379 A1 | 10/2015 | |
| WO | 2015200806 A2 | 12/2015 | |
| WO | WO-2016110643 A1 * | 7/2016 | .............. H02M 1/12 |
| WO | 2017106064 A1 | 6/2017 | |
| WO | 2017155765 A1 | 9/2017 | |
| WO | WO-2017155765 A1 * | 9/2017 | ......... A61K 31/4709 |

* cited by examiner

CHROMANE MONOBACTAM COMPOUNDS FOR THE TREATMENT OF BACTERIAL INFECTIONS

CROSS-REFERENCE TO RELATED APPLICATIONS

This application is a U.S. National Phase application under 35 U.S.C. § 371 of PCT Application No. PCT/US2018/053039, filed on Sep. 27, 2018, which claims priority from and the benefit of U.S. Provisional Application No. 62/566,779, filed Oct. 2, 2017.

FIELD OF THE INVENTION

This invention relates to novel monobactam compounds, processes for their preparation and their use as therapeutic agents. In particular, the invention relates to monobactam compounds useful as antibiotic agents for the treatment of bacterial infections.

BACKGROUND OF THE INVENTION

The introduction of antibiotics for treatment of bacterial infections is one of the great medical achievements of the 20$^{th}$ century. Over the past few decades, however, bacteria resistant to multiple antibiotics have begun to emerge throughout the world, threatening the effectiveness of antibiotic therapy. In the United States alone, at least 23,000 people each year die as a direct result of infections caused by antibiotic-resistant bacteria, and numerous others die from pre-existing conditions exacerbated by similar infections. *Antibiotic Resistance Threats in the United States*, 2013, Centers for Disease Control, Atlanta, Ga. New antibiotics are needed to combat the current and future threat of multidrug resistant bacteria.

β-lactams are the most widely used antibiotics for treatment of serious bacterial infections. These include carbapenems, cephalosporins, penicillins, and monobactams. As has been observed for other antibiotic classes, resistance to β-lactams has emerged. For most Gram-negative bacteria, this resistance is primarily driven by the expression of β-lactamases, enzymes that hydrolyze β-lactam compounds. There are 4 different classes of β-lactamases (A, B, C, and D) capable of hydrolyzing overlapping but distinct subsets of β-lactams (Drawz and Bonomo, *Clin. Micro. Rev.*, 2010, 23:160-201). While the class B β-lactamases, also known as metallo β-lactamases (MBLs), are not the most prevalent β-lactamases found in the clinic, the frequency and distribution of their expression is on the rise and represent a significant medical threat because (i) MBLs have the ability to hydrolyze all β-lactams except monobactams, and (ii) unlike the class A and C β-lactamases, there are no inhibitors available for the MBLs.

Aztreonam, a monobactam, was first approved in the U.S. in 1986 for the treatment of aerobic Gram-negative bacterial infections and remains the only monobactam in use in the U.S. today. However, aztreonam has poor activity against *Pseudomonas* and *Acinetobacter* strains. Because monobactams are inherently resistant to hydrolysis by MBLs, several companies have begun developing novel monobactam compounds for the treatment of infections caused by Gram-negative bacteria. Monobactam compounds comprising a siderophore moiety are disclosed in WO 2007/065288, WO2012/073138, *J. Medicinal Chemistry* 56: 5541-5552 (2013), and *Bioorganic and Medicinal Chemistry Letters* 22:5989 (2012).

WO2017/106064 discloses biaryl monobactam compounds and their use to treat bacterial infections. U.S. Patent Application Publication No US 2015/0045340 and No. US 2014/0275007 disclose oxamazin monobactams and their use as antibacterial agents. U.S. Patent Application Publication No. US 2015/0266867 discloses novel monobactam compounds for the use as antibacterial agents. WO 2013/110643 discloses novel amidine substituted monobactam derivatives and their use as antimicrobial reagents. WO 2015/103583 discloses monobactam derivatives useful for treating infectious disease which is bacterial infection.

The need for new antibiotics to overcome multidrug resistance continues. Compounds disclosed in this invention are designed to fill this medical need, through administration either on their own or in combination with a suitable β-lactamase inhibitor.

SUMMARY OF THE INVENTION

The invention relates to the design and synthesis of monobactam analogs, a novel class of highly potent antibiotics effective against a broad range of Gram-negative bacteria. These compounds and their pharmaceutically acceptable salts may be useful as therapeutic agents for clinical treatment of various infections caused by Gram-negative bacteria, including strains that are multidrug resistant. The compounds can be used alone or in combination with a suitable β-lactamase inhibitor. The present invention includes compounds of Formula I:

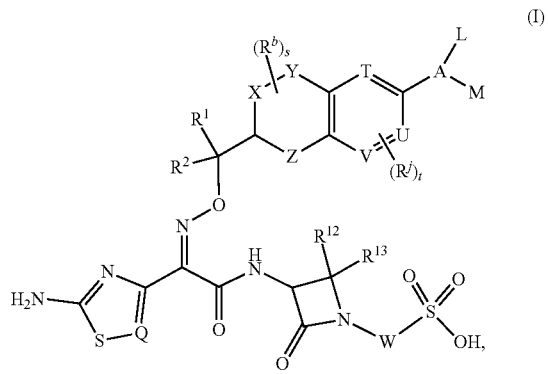

or a pharmaceutically acceptable salt thereof, wherein:
T is CH or N, provided that no more than two of T, U and V is N;
U is CH or N;
V is CH or N;
W is
  1) a bond, or
  2) O;
Q is
  1) N, or
  2) CR$^3$;
X is
  1) O, or
  2) CH$_2$;
Y is
  1) O,
  2) NR$^8$, 3) S, or
4) $CH_2$,
provided that when Y is O, $NR^8$ or S then X is not O;
Z is
1) O,
2) S,
3) $CH_2$, or
4) NH,
provided that when Z is O, S or NH, then X is not O;
A is
1) —C(=NH)—NH,
2) —$(CH_2)_qN(R^7)$-AryC,
3) —$(CH_2)_q$O-AryC,
4) AryC,
5) —$(CH_2)_qN(R^7)$-HetC,
6) —$(CH_2)_q$O-HetC,
7) HetC, or
8) $C_3$-$C_7$ cycloalkyl,
wherein $CH_2$ and $C_3$-$C_7$ cycloalkyl are unsubstituted or substituted with one to four $R^i$;

AryC is a 5- to 6-membered monocyclic aromatic ring with 0, 1, 2, or 3 ring atoms independently selected from N, N as a quaternary salt, O and S, unsubstituted or substituted with one to four $R^i$, wherein AryC is optionally fused to a 4- to 7-membered heterocycloalkyl ring containing one to two heteroatoms selected from O, S and —$NR^g$;

HetC is a 4- to 7-membered saturated or monounsaturated monocyclic ring with 1, 2, or 3 heteroatom ring atoms independently selected from N, N as a quaternary salt, O and S, unsubstituted or substituted with one to four $R^i$;

L is
1) absent,
2) $R^4$,
3) —$NHR^4$,
4) —$N(R^4)_2$,
5) —$OR^4$,
6) —$(CH_2)_nR^4$,
7) —$C(O)R^4$,
8) —$C(NH)R^4$, or
9) —$S(O)_mR^4$,
wherein L is unsubstituted or substituted with 1-4 substituents selected from $R^e$;

M is
1) $R^5$,
2) —$NHR^5$,
3) —$N(R^5)_2$,
4) —$OR^5$,
5) —$(CH_2)_uR^5$,
6) —$C(O)R^5$,
7) —$C(NH)R^5$, or
8) —$S(O)_vR^5$,
wherein M is unsubstituted or substituted with 1-4 substituents selected from $R^6$;

$R^1$ is
1) hydrogen,
2) —$C_1$-$C_8$ alkyl,
3) —$C_3$-$C_7$ cycloalkyl,
4) —$C(O)OR^e$,
5) —$C(O)NR^cR^d$,
6) tetrazolyl,
7) oxadiazolonyl,
8) HetA,
9) AryA,
10) —$S(O)_mR^e$,
11) —$S(O)_mNR^cR^d$, or
12) —$P(O)(R^e)_p$, wherein —$C_1$-$C_8$ alkyl and —$C_3$-$C_7$ cycloalkyl are unsubstituted or substituted with one to three $R^a$;

$R^2$ is
1) hydrogen,
2) —$C_1$-$C_8$ alkyl,
3) —$C_3$-$C_7$ cycloalkyl,
4) —$C(O)OR^e$,
5) —$C(O)NR^cR^d$,
6) tetrazolyl,
7) oxadiazolonyl,
8) HetA,
9) AryA,
10) —$S(O)_mR^e$,
11) —$S(O)_mNR^cR^d$, or
12) —$P(O)(R^e)_p$, wherein —$C_1$-$C_8$ alkyl and —$C_3$-$C_7$ cycloalkyl are unsubstituted or substituted with one to three $R^a$,
provided that when $R^1$ is —$C(O)OR^e$, —$C(O)NR^cR^d$, —$S(O)_mR^e$, —$S(O)_mNR^cR^d$, or —$P(O)(R^e)_p$, then $R^2$ is not —$C(O)OR^e$, —$C(O)NR^cR^d$, —$S(O)_mR^e$, —$S(O)_mNR^cR^d$, or —$P(O)(R^e)_p$;

HetA is a 4- to 7-membered saturated or monounsaturated monocyclic ring with 1, 2, or 3 heteroatom ring atoms independently selected from N, N as a quaternary salt, O and S, unsubstituted or substituted with one to four $R^c$;

AryA is a 5- to 6-membered monocyclic aromatic ring with 0, 1, 2, or 3 ring atoms independently selected from N, N as a quaternary salt, O and S, unsubstituted or substituted with one to four $R^c$;

$R^3$ is
1) hydrogen,
2) $C_1$-$C_4$ alkyl,
3) halogen, or
4) $C_3$-$C_7$cycloalkyl,
wherein $C_1$-$C_4$ alkyl and $C_3$-$C_7$cycloalkyl are unsubstituted or substituted with one to three $R^a$;

each occurrence of $R^4$ is independently:
1) hydrogen,
2) —$C_1$-$C_{10}$ alkyl,
3) —$C_2$-$C_8$ alkenyl,
4) —$(CH_2)_nOR^e$,
5) —$S(O)_mR^e$,
6) —$S(O)_mNR^cR^d$,
7) —$(CH_2)_nNR^cR^d$,
8) —$OC(O)R^e$,
9) —$C(O)OR^e$, —CN,
10) —$C(O)NR^cR^d$,
11) —$NR^cC(O)R^e$,
12) —$NR^cC(O)OR^e$,
13) —$NR^cC(O)NR^cR^d$,
14) —$NR^cS(O)_mR^e$,
15) =$NR^{11}$,
16) —$C_3$-$C_7$ cycloalkyl,
17) —O—$C_3$-$C_6$cycloalkyl,
18) —$C_1$-$C_{10}$alkylene-$C_3$-$C_6$cycloalkyl,
19) —O—$C_1$-$C_{10}$alkylene-$C_3$-$C_6$cycloalkyl,
20) HetB,
21) —O-HetB,
22) —$C_1$-$C_{10}$alkylene-HetB,
23) —O—$C_1$-$C_{10}$alkylene-HetB,
24) AryB,
25) —O-AryB,
26) —$C_1$-$C_{10}$alkylene-AryB, or
27) —O—$C_1$-$C_{10}$alkylene-AryB,
wherein $R^4$ is unsubstituted or substituted with one to four $R^6$;

AryB is a 5- to 6-membered monocyclic aromatic ring with 0, 1, 2, or 3 ring atoms independently selected from N, O and S, unsubstituted or substituted with one to four $R^c$;

HetB is a 4- to 7-membered saturated or monounsaturated monocyclic ring with 1, 2, or 3 heteroatom ring atoms independently selected from N, N as a quaternary salt, O and S, unsubstituted or substituted with one to three $R^a$;

$R^5$ is
1) hydrogen,
2) $C_1$-$C_{10}$ alkyl,
3) —$C_2$-$C_8$ alkenyl,
4) —$(CH_2)_uOR^e$,
5) —$S(O)_vR^e$,
6) —$S(O)_vNR^cR^d$,
7) —$(CH_2)_uNR^cR^d$,
8) —$OC(O)R^e$,
9) —$C(O)OR^e$,
10) —CN,
11) —$C(O)NR^cR^d$,
12) —$NR^cC(O)R^e$,
13) —$NR^cC(O)OR^e$,
14) —$NR^cC(O)NR^cR^d$,
15) —$NR^cS(O)_vR^e$,
16) =$NR^{11}$,
17) —$C_3$-$C_7$ cycloalkyl,
18) —O—$C_3$-$C_6$cycloalkyl,
19) —$C_1$-$C_{10}$alkylene-$C_3$-$C_6$cycloalkyl,
20) —O—$C_1$-$C_{10}$ alkylene-$C_3$-$C_6$cycloalkyl,
21) HetB,
22) —O-HetB,
23) —$C_1$-$C_{10}$alkylene-HetB,
24) —O—$C_1$-$C_{10}$ alkylene-HetB,
25) AryB,
26) —O-AryB,
27) —$C_1$-$C_{10}$alkylene-AryB, or
28) —O—$C_1$-$C_{10}$alkylene-AryB, wherein $R^5$ is unsubstituted or substituted with one to four $R^6$;

each occurrence of $R^6$ is independently
1) halogen,
2) —$C_1$-$C_6$alkyl,
3) —$OR^e$,
4) —$S(O)_vR^e$,
5) —$S(O)_vNR^cR^d$,
6) —$C(O)R^e$,
7) —$OC(O)R^e$,
8) —$C(O)OR^e$,
9) —CN,
10) —$C(O)NR^cR^d$,
11) —$C(NH)NR^cR^d$,
12) —$(CH_2)_uNR^cR^d$,
13) —$(CH_2)_uNR^cR^d$,
14) —$N(R^c)(C(O)R^e)$,
15) —$N(R^c)(C(O)OR^e)$,
16) —$N(R^c)(C(O)NR^cR^d)$,
17) —$N(R^c)(S(O)_vR^e)$, or
18) HetB;

$R^7$ is
1) hydrogen,
2) $C_1$-$C_3$ alkyl, or
3) $C_3$-$C_7$ cycloalkyl, wherein $C_1$-$C_3$ alkyl and $C_3$-$C_7$ cycloalkyl are unsubstituted or substituted with one to three $R^a$;

$R^8$ is
1) hydrogen,
2) $C_1$-$C_4$ alkyl, or
3) $C_3$-$C_7$ cycloalkyl;

$R^9$ is
1) hydrogen,
2) $C_1$-$C_4$ alkyl, or
3) $C_3$-$C_7$ cycloalkyl;

$R^{10}$ is
1) hydrogen,
2) $C_1$-$C_4$ alkyl, or
3) $C_3$-$C_7$ cycloalkyl;

$R^{11}$ is
1) hydrogen,
2) $C_1$-$C_4$ alkyl, or
3) $C_3$-$C_7$ cycloalkyl;

$R^{12}$ and $R^{13}$ are independently
1) hydrogen,
2) —$SC_1$-$C_3$alkyl,
3) $C_1$-$C_3$ alkyl,
4) —$(C_1$-$C_3$alkylene$)_nOC_1$-$C_3$alkyl, or
5) —$(C_1$-$C_3$alkylene$)_nNC_1$-$C_3$alkyl, wherein —$SC_1$-$C_3$alkyl, $C_1$-$C_3$ alkyl, —$(C_1$-$C_3$alkylene$)_nOC_1$-$C_3$alkyl and —$(C_1$-$C_3$alkylene$)_nNC_1$-$C_3$alkyl are unsubstituted or substituted with one to seven fluorines, or, alternatively, $R^{12}$ and $R^{13}$ together with the carbon to which they are attached, form a monocyclic $C_4$-$C_7$ cycloalkyl or a monocyclic $C_4$-$C_7$ heterocycloalkyl with 1, 2, or 3 heteroatom ring atoms independently selected from N, O and S, wherein $C_4$-$C_7$ cycloalkyl and $C_4$-$C_7$ heterocycloalkyl are unsubstituted or substituted with one to three substituents independently selected from —F, —OH and —$OC_1$-$C_3$alkyl;

$R^{14}$ is
1) hydrogen,
2) $C_1$-$C_4$ alkyl, or
3) $C_3$-$C_7$ cycloalkyl;

each occurrence of $R^a$ is independently
1) hydrogen,
2) halogen,
3) $C_1$-$C_3$alkyl,
4) —$NR^cR^d$, or
5) —$OR^e$;

each occurrence of $R^b$ is independently
1) hydrogen,
2) —$C_1$-$C_6$ alkyl,
3) —$OC_1$-$C_6$ alkyl,
4) OH,
5) $N(R^9)_2$, or
6) halogen, wherein —$C_1$-$C_3$ alkyl is unsubstituted or substituted with one to three $R^a$;

each occurrence of $R^c$ and $R^d$ is independently:
1) hydrogen,
2) —$C_1$-$C_{10}$ alkyl,
3) —$C_2$-$C_{10}$ alkenyl,
4) —$C_3$-$C_6$ cycloalkyl,
5) —$C_1$-$C_{10}$ alkylene-$C_3$-$C_6$ cycloalkyl,
6) HetA,
7) —$C_1$-$C_{10}$alkylene-HetB,
8) AryB,
9) —$C_1$-$C_{10}$ alkylene-AryB, or
10) —$C_1$-$C_{10}$ alkylene-HetB, or, alternatively, $R^c$ and $R^d$ together with the nitrogen atom to which they are attached, form a 4- to 7-membered hetercycloalkyl optionally containing one to two additional heteroatoms independently selected from O, S and —$NR^g$, and wherein each $R^c$ and $R^d$ is unsubstituted or substituted with one to three $R^f$;

each occurrence of $R^e$ is independently:
1) hydrogen,
2) —$C_1$-$C_{10}$alkyl,
3) —$C_2$-$C_{10}$ alkenyl,
4) —OH,
5) —$OC_1$-$C_4$ alkyl,
6) —$C_3$-$C_6$ cycloalkyl,
7) —$C_1$-$C_{10}$ alkylene-$C_3$-$C_6$ cycloalkyl,
8) HetB,
9) —$C_1$-$C_{10}$ alkylene-HetB,
10) AryB,
11) —$C_1$-$C_{10}$ alkylene-AryB,
12) —$C_1$-$C_{10}$ alkylene-HetB, or
13) halogen,
wherein each $R^e$ is unsubstituted or substituted with one to three $R^h$;
each occurrence of $R^f$ is independently:
1) halogen,
2) —$C_1$-$C_{10}$ alkyl,
3) —OH,
4) —$OC_1$-$C_4$ alkyl,
5) —$S(O)_m C_1$-$C_4$ alkyl,
6) —CN,
7) —$CF_3$,
8) —$OCHF_2$,
9) —$OCF_3$, or
10) $NH_2$,
wherein —$C_1$-$C_{10}$ alkyl is unsubstituted or substituted with one to three substituents independently selected from —OH, halogen, cyano, and —$S(O)_2CH_3$;
each occurrence of $R^g$ is independently:
1) hydrogen,
2) —$C(O)R^e$, or
3) —$C_1$-$C_{10}$ alkyl,
wherein —$C_1$-$C_{10}$alkyl is unsubstituted or substituted with one to five fluorines;
each occurrence of $R^h$ is independently:
1) halogen,
2) —$C_1$-$C_{10}$alkyl,
3) —OH,
4) —$OC_1$-$C_4$ alkyl,
5) —$S(O)_m C_1$-$C_4$ alkyl,
6) —CN,
7) —$CF_3$,
8) —$OCHF_2$, or
9) —$OCF_3$,
wherein —$C_1$-$C_{10}$ alkyl is unsubstituted or substituted with one to three substituents independently selected from: —OH, halogen, cyano, or —$S(O)_2CH_3$;
each occurrence of $R^i$ is independently:
1) —$C_1$-$C_8$ alkyl,
2) —$C_2$-$C_8$ alkenyl,
3) —$C_2$-$C_8$ alkynyl,
4) halogen,
5) —$OR^e$,
6) —$S(O)_m R^e$,
7) —$S(O)_m NR^c R^d$,
8) —$C(O)R^e$,
9) —$OC(O)R^e$,
10) —$C(O)OR^e$,
11) —CN,
12) —$C(O)NR^c R^d$,
13) —$NR^c R^d$,
14) —$(CH_2)_n NR^c R^d$,
15) —$NR^c C(O)R^e$,
16) —$NR^c C(O)OR^e$,
17) —$NR^c C(O)NR^c R^d$,
18) —$NR^c S(O)_m R^e$,
19) =NH,
20) —$CF_3$,
21) —$OCF_3$, or
22) —$OCHF_2$;
each occurrence of $R^j$ is independently:
1) hydrogen,
2) $C_1$-$C_3$ alkyl,
3) $OR^{10}$,
4) =$NR^{10}$
5) $N(R^{10})_2$, or
6) halogen,
wherein $C_1$-$C_3$ alkyl unsubstituted or substituted with one to three $R^b$;
each n is independently 0, 1, 2, 3, 4, 5 or 6;
each m is independently 0, 1 or 2;
each p is independently 1 or 2;
each q is independently 0, 1, 2, 3, 4, 5 or 6;
each s is independently 0, 1, 2 or 3;
each t is independently 0, 1, 2 or 3;
each u is independently 0, 1, 2, 3, 4, 5 or 6; and
each v is independently 0, 1, or 2.

The present invention also relates to a pharmaceutical composition for treating a bacterial infection in a subject, including infection with multidrug resistant Gram-negative bacterial strains, comprising a monobactam compound of the invention and a pharmaceutically acceptable carrier, diluent or excipient.

The Compounds of Formula (I), also referred to herein as the "monobactam compounds", and pharmaceutically acceptable salts thereof can be useful, for example, for inhibiting the growth of Gram-negative bacterial strains, including but not limited to, *Pseudomonas, Klebsiella* and *Acinetobacter* strains, including *Pseudomonas aeruginosa, Klebsiella pneumoniae* and *Acinetobacter baumannii*, and/or for treating or preventing the clinical manifestations thereof in a patient.

The present invention is also directed to methods of treating Gram-negative bacterial infections in a subject in need of treatment thereof, comprising administering to the subject an effective amount of a monobactam compound of the invention. In specific embodiments of the invention, the method includes administration of a beta lactamase inhibitor compound. Embodiments, sub-embodiments and features of the present invention are either further described in or will be apparent from the ensuing description, examples and appended claims.

DETAILED DESCRIPTION OF THE INVENTION

The invention relates to novel monobactam analogs, a class of highly potent antibiotics effective against a broad range of Gram-negative bacteria. These compounds have utility as therapeutic agents for clinical treatment of various infections caused by Gram-negative bacteria, including strains that are multidrug resistant, and for the treatment or prevention of the clinical pathologies associated therewith.

In each of the various embodiments of the compounds of the invention described herein, each variable including those of Formula (I), and the various embodiments thereof, each variable is selected independently of the others unless otherwise indicated.

The present invention includes the compounds of Formula (I), and the individual diastereoisomers, enantiomers, and epimers of the compounds of Formula (I), and mixtures of diastereoisomers and/or enantiomers thereof including racemic mixtures. The present invention also encompasses any solvates, hydrates, stereoisomers, and tautomers of the compounds of Formula (I), and of any pharmaceutically acceptable salts thereof.

The Compounds of Formula (I)

In one embodiment, the present invention includes compounds of Formula I:

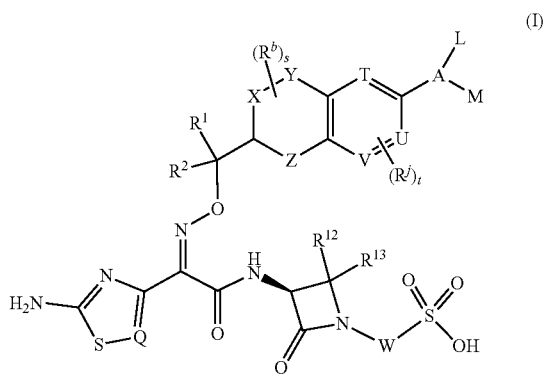

(I)

or pharmaceutically acceptable salts thereof, wherein the compounds may be suitable for use for the treatment of bacterial infections.

In another embodiment of the present invention, T is CH or N, provided that no more than two of T, U and V is N. In a class of this embodiment, T is CH or N. In another class of this embodiment, T is CH. In another class of this embodiment, T is N.

In another embodiment of the present invention, U is CH or N. In a class of this embodiment, U is CH. In another class of this embodiment, U is N.

In another embodiment of the present invention, V=CH or N. In a class of this embodiment, V is CH. In another class of this embodiment, V is N.

In another embodiment of the present invention, T, U and V are CH.

In another embodiment of the present invention, W is a bond or O. In a class of this embodiment, W is a bond. In another class of this embodiment, W is O.

In another embodiment of the present invention, Q is N or $CR^3$. In a class of this embodiment, Q is N. In another class of this embodiment, Q is $CR^3$.

In another embodiment of the present invention, X is O or $CH_2$. In a class of this embodiment, X is O. In another class of this embodiment, X is $CH_2$.

In another embodiment, Y is O, $NR^8$, S or $CH_2$, provided that when Y is O, $NR^8$ or S, then X is not O. In another embodiment, Y is O, $NR^8$, S or $CH_2$, provided that when Y is Y is O, $NR^8$ or S, then X is $CH_2$.

In another embodiment of the present invention, Y is O, $NR^8$, S or $CH_2$. In a class of this embodiment, Y is O or $CH_2$. In another class of this embodiment, Y is $NR^8$ or S.

In another class of this embodiment, Y is O. In another class of this embodiment, Y is $NR^8$. In another class of this embodiment, Y is S. In another class of this embodiment, Y is $CH_2$.

In another embodiment, Z is O, S, $CH_2$ or NH, provided that when Z is O, S or NH, then X is not O. In a class of this embodiment, Z is O, S, $CH_2$, or NH. In another class of this embodiment, Z is O or $CH_2$. In another class of this embodiment, Z is S or NH. In another class of this embodiment, Z is O. In another class of this embodiment, Z is S. In another class of this embodiment, Z is $CH_2$. In another class of this embodiment, Z is NH.

In another embodiment of the present invention, $R^1$ is hydrogen, —$C_1$-$C_8$ alkyl, —$C_3$-$C_7$ cycloalkyl, —C(O)$OR^e$, —C(O)$NR^cR^d$, tetrazolyl, oxadiazolonyl, HetA, AryA, —S(O)$_m R^e$, —S(O)$_m NR^cR^d$, or —P(O)$(R^e)_p$, wherein —$C_1$-$C_8$ alkyl and —$C_3$-$C_7$ cycloalkyl are unsubstituted or substituted with one to three $R^a$, provided that when $R^2$ is —C(O)$OR^e$, —C(O)$NR^cR^d$, —S(O)$_m R^e$, —S(O)$_m NR^cR^d$, or —P(O)$(R^e)_p$, then $R^1$ is not —C(O)$OR^e$, —C(O)$NR^cR^d$, —S(O)$_m R^e$, —S(O)$_m NR^cR^d$, or —P(O)$(R^e)_p$.

In another embodiment of the present invention, $R^1$ is independently selected from: hydrogen, —$C_1$-$C_8$ alkyl, and —C(O)$OR^e$, wherein —$C_1$-$C_8$ alkyl is unsubstituted or substituted with one to three $R^a$, provided that if $R^2$ is —C(O)$OR^e$, then $R^1$ is not —C(O)$OR^e$.

In another embodiment of the present invention, $R^1$ is selected from hydrogen, —$C_1$-$C_8$ alkyl, —$C_3$-$C_7$ cycloalkyl, —C(O)$OR^e$, —C(O)$NR^cR^d$, tetrazolyl, oxadiazolonyl, HetA, AryA, —S(O)$_m R^e$, —S(O)$_m NR^cR^d$, and —P(O)$(R^e)_p$ wherein —$C_1$-$C_8$ alkyl and —$C_3$-$C_7$ cycloalkyl are unsubstituted or substituted with one to three $R^a$. In another embodiment of the present invention, $R^1$ is selected from hydrogen, —$C_1$-$C_8$ alkyl, and —C(O)$OR^e$, wherein —$C_1$-$C_8$ alkyl is unsubstituted or substituted with one to three $R^a$, provided that if $R^2$ is —C(O)$OR^e$, then $R^1$ is selected from hydrogen, and —$C_1$-$C_8$ alkyl. In another embodiment of the present invention, $R^1$ is selected from hydrogen, —$C_1$-$C_8$ alkyl, and —C(O)$OR^e$, wherein —$C_1$-$C_8$ alkyl is unsubstituted or substituted with one to three $R^a$. In another embodiment of the present invention, $R^1$ is selected from hydrogen, —$C_1$-$C_3$ alkyl, and —$CO_2H$. In another embodiment of the present invention, $R^1$ is selected from hydrogen, and —C(O)$OR^e$. In another embodiment of the present invention, $R^1$ is selected from hydrogen, and —$CO_2H$. In another embodiment of the present invention, $R^1$ is hydrogen. In another embodiment of the present invention, $R^1$ is —C(O)$OR^e$. In a class of this embodiment, $R^1$ is $CO_2H$.

In another embodiment of the present invention, $R^1$ is hydrogen, —$C_1$-$C_8$ alkyl, —C(O)$OR^e$, —C(O)$NR^cR^d$, —S(O)$_m R^e$, —S(O)$_m NR^cR^d$, or —P(O)$(R^e)_p$, wherein —$C_1$-$C_8$ alkyl is unsubstituted or substituted with one to three $R^a$.

In another embodiment of the present invention, $R^1$ is —$C_3$-$C_7$ cycloalkyl, tetrazolyl, oxadiazolonyl, HetA, or AryA, wherein —$C_3$-$C_7$ cycloalkyl are unsubstituted or substituted with one to three $R^a$.

In another embodiment of the present invention, $R^1$ is —$C_1$-$C_8$ alkyl, —$C_3$-$C_7$ cycloalkyl, —C(O)$NR^cR^d$, tetrazolyl, oxadiazolonyl, HetA, AryA, —S(O)$_m R^e$, —S(O)$_m NR^cR^d$, or —P(O)$(R^e)_p$, wherein —$C_1$-$C_8$ alkyl and —$C_3$-$C_7$ cycloalkyl are unsubstituted or substituted with one to three $R^a$.

In another embodiment of the present invention, $R^1$ is hydrogen, —$C_1$-$C_8$ alkyl, or —C(O)$OR^e$, wherein —$C_1$-$C_8$ alkyl is unsubstituted or substituted with one to three $R^a$. In a class of this embodiment, $R^1$ is hydrogen, —$C_1$-$C_8$ alkyl, or —C(O)$OR^e$. In another class of this embodiment, $R^1$ is hydrogen, —$C_1$-$C_8$ alkyl, or —$CO_2H$. In another class of this embodiment, $R^1$ is hydrogen, —$CH_3$, or —$CO_2H$. In another class of this embodiment, $R^1$ is —$CH_3$, or —$CO_2H$. In another class of this embodiment, $R^1$ is hydrogen. In another class of this embodiment, $R^1$ is —$CO_2H$. In another class of this embodiment, $R^1$ is $CH_3$.

In another embodiment of the present invention, $R^1$ is hydrogen or —C(O)$OR^e$.

In another embodiment of the present invention, $R^1$ is hydrogen or —$CO_2H$. In a class of this embodiment, $R^1$ is hydrogen. In another class of this embodiment, $R^1$ is —$CO_2H$.

In another embodiment of the present invention, $R^1$ is selected from —$C_1$-$C_6$ alkyl and —$C(O)OR^e$, wherein —$C_1$-$C_6$ alkyl is unsubstituted or substituted with one to three $R^a$, provided that if $R^2$ is —$C(O)OR^e$, then $R^1$ is —$C_1$-$C_6$ alkyl. In a class of this embodiment, $R^1$ is selected from —$CH_3$ and —$C(O)OH$, provided that if $R^2$ is —$C(O)OH$, then $R^1$ is —$CH_3$. In another embodiment of the present invention, $R^1$ is selected from —$C_1$-$C_6$ alkyl and —$C(O)OR^e$. In a class of this embodiment, $R^1$ is selected from —$CH_3$ and —$C(O)OH$.

In another embodiment of the present invention, $R^2$ is hydrogen, —$C_1$-$C_8$ alkyl, —$C_3$-$C_7$ cycloalkyl, —$C(O)OR^e$, —$C(O)NR^cR^d$, tetrazolyl, oxadiazolonyl, HetA, AryA, —$S(O)_mR^e$, —$S(O)_mNR^cR^d$, or —$P(O)(R^e)_p$, wherein —$C_1$-$C_8$ alkyl and —$C_3$-$C_7$ cycloalkyl are unsubstituted or substituted with one to three $R^a$, provided that when $R^1$ is —$C(O)OR^e$, —$C(O)NR^cR^d$, —$S(O)_mR^e$, —$S(O)_mNR^cR^d$, or —$P(O)(R^e)_p$, then $R^2$ is not —$C(O)OR^e$, —$C(O)NR^cR^d$, —$S(O)_mR^e$, —$S(O)_mNR^cR^d$, or —$P(O)(R^e)_p$.

In another embodiment of the present invention, $R^2$ is independently selected from: hydrogen, —$C_1$-$C_8$ alkyl, and —$C(O)OR^e$, wherein —$C_1$-$C_8$ alkyl is unsubstituted or substituted with one to three $R^a$, provided that if $R^1$ is —$C(O)OR^e$, then $R^2$ is not —$C(O)OR^e$.

In another embodiment of the present invention, $R^2$ is hydrogen, —$C_1$-$C_8$ alkyl, —$C_3$-$C_7$ cycloalkyl, —$C(O)OR^e$, —$C(O)NR^cR^d$, tetrazolyl, oxadiazolonyl, HetA, AryA, —$S(O)_mR^e$, —$S(O)_mNR^cR^d$, or —$P(O)(R^e)_p$, wherein —$C_1$-$C_8$ alkyl and —$C_3$-$C_7$ cycloalkyl are unsubstituted or substituted with one to three $R^a$.

In another embodiment of the present invention, $R^2$ is hydrogen, —$C_1$-$C_8$ alkyl, —$C(O)OR^e$, —$C(O)NR^cR^d$, —$S(O)_mR^e$, —$S(O)_mNR^cR^d$, or —$P(O)(R^e)_p$, wherein —$C_1$-$C_8$ alkyl is unsubstituted or substituted with one to three $R^a$.

In another embodiment of the present invention, $R^2$ is —$C_3$-$C_7$ cycloalkyl, tetrazolyl, oxadiazolonyl, HetA, or AryA, wherein —$C_3$-$C_7$ cycloalkyl is unsubstituted or substituted with one to three $R^a$.

In another embodiment of the present invention, $R^2$ is —$C_3$-$C_7$ cycloalkyl, —$C(O)OR^e$, —$C(O)NR^cR^d$, tetrazolyl, oxadiazolonyl, HetA, AryA, —$S(O)_mR^e$, —$S(O)_mNR^cR^d$, or —$P(O)(R^e)_p$, wherein —$C_3$-$C_7$ cycloalkyl is unsubstituted or substituted with one to three $R^a$.

In another embodiment of the present invention, $R^2$ is selected from hydrogen, —$C_1$-$C_8$ alkyl and —$C(O)OR^e$, wherein —$C_1$-$C_8$ alkyl is unsubstituted or substituted with one to three $R^a$, provided that if $R^1$ is —$C(O)OR^e$, then $R^2$ is selected from hydrogen and —$C_1$-$C_8$ alkyl.

In another embodiment of the present invention, $R^2$ is hydrogen, —$C_1$-$C_8$ alkyl, or —$C(O)OR^e$, wherein —$C_1$-$C_8$ alkyl is unsubstituted or substituted with one to three $R^a$. In a class of this embodiment, $R^2$ is hydrogen, —$C_1$-$C_8$ alkyl, or —$C(O)OR^e$. In another class of this embodiment, $R^2$ is hydrogen, —$C_1$-$C_8$ alkyl, or —$CO_2H$. In another class of this embodiment, $R^2$ is hydrogen, —$CH_3$, or —$CO_2H$. In another class of this embodiment, $R^2$ is —$CH_3$, or —$CO_2H$. In another class of this embodiment, $R^2$ is hydrogen. In another class of this embodiment, $R^2$ is —$CO_2H$. In another class of this embodiment, $R^2$ is $CH_3$.

In another embodiment of the present invention, $R^2$ is hydrogen or —$C_1$-$C_8$ alkyl.

In another embodiment of the present invention, $R^2$ is hydrogen or —$CH_3$. In a class of this embodiment, $R^2$ is hydrogen. In another class of this embodiment, $R^2$ is —$CH_3$.

In another embodiment of the present invention, $R^2$ is selected from —$C_1$-$C_6$ alkyl and —$C(O)OR^e$, wherein —$C_1$-$C_6$ alkyl is unsubstituted or substituted with one to three $R^a$, provided that if $R^1$ is —$C(O)OR^e$, then $R^2$ is —$C_1$-$C_6$ alkyl. In another embodiment of the present invention, $R^2$ is selected from —$C_1$-$C_6$ alkyl and —$C(O)OR^e$. In a class of this embodiment, $R^1$ is selected from —$CH_3$ and —$C(O)OH$, provided that if $R^2$ is —$C(O)OH$, then $R^1$ is —$CH_3$. In a class of this embodiment, $R^1$ is selected from —$CH_3$ and —$C(O)OH$.

In another embodiment, $R^1$ and $R^2$ are independently selected from —$CH_3$, and —$CO_2H$, wherein —$CH_3$ is unsubstituted or substituted with one to three $R^a$, provided that if $R^1$ is —$CO_2H$, then $R^2$ is —$CH_3$, and if $R^2$ is —$CO_2H$, then $R^1$ is —$CH_3$.

In another embodiment, $R^3$ is hydrogen, $C_1$-$C_4$ alkyl, halogen, or $C_3$-$C_7$ cycloalkyl, wherein $C_1$-$C_4$ alkyl and $C_3$-$C_7$ cycloalkyl are unsubstituted or substituted with one to three $R^a$. In a class of this embodiment, $R^3$ is hydrogen, $C_1$-$C_4$ alkyl, or halogen, wherein $C_1$-$C_4$ alkyl is unsubstituted or substituted with one to three $R^a$. In a class of this embodiment, $R^3$ is hydrogen or $C_1$-$C_4$ alkyl. In another class of this embodiment, $R^3$ is $C_1$-$C_4$ alkyl. In another class of this embodiment, $R^3$ is hydrogen.

In another embodiment of the present invention, each occurrence of $R^4$ is independently: hydrogen, —$C_1$-$C_{10}$ alkyl, —$C_2$-$C_8$ alkenyl, —$(CH_2)_nOR^e$, —$S(O)_mR^e$, —$S(O)_mNR^cR^d$, —$(CH_2)_nNR^cR^d$, —$OC(O)R^e$, —$C(O)OR^e$, —$CN$, —$C(O)NR^cR^d$, —$NR^cC(O)R^e$, —$NR^cC(O)OR^e$, —$NR^cC(O)NR^cR^d$, —$NR^cS(O)_mR^e$, =$NR^{11}$, —$C_3$-$C_7$ cycloalkyl, —$O$—$C_3$-$C_6$cycloalkyl, —$C_1$-$C_{10}$alkylene-$C_3$-$C_6$cycloalkyl, —$O$—$C_1$-$C_{10}$ alkylene-$C_3$-$C_6$cycloalkyl, HetB, —$O$-HetB, —$C_1$-$C_{10}$alkylene-HetB, —$O$—$C_1$-$C_{10}$alkylene-HetB, AryB, —$O$-AryB, —$C_1$-$C_{10}$alkylene-AryB, or —$O$—$C_1$-$C_{10}$alkylene-AryB, wherein $R^4$ is unsubstituted or substituted with one to four $R^6$, or wherein $R^4$ and M, together with the atoms to which they are attached, form a 4- to 7-membered heterocycloalkyl optionally containing one to two additional heteroatoms independently selected from O, S and —$NR^g$.

In another embodiment of the present invention, each occurrence of $R^4$ is independently: hydrogen, —$C_1$-$C_{10}$ alkyl, —$C_2$-$C_8$ alkenyl, —$(CH_2)_nOR^e$, —$S(O)_mR^e$, —$S(O)_mNR^cR^d$, —$(CH_2)_nNR^cR^d$, —$OC(O)R^e$, —$C(O)OR^e$, —$CN$, —$C(O)NR^cR^d$, —$NR^cC(O)R^e$, —$NR^cC(O)OR^e$, —$NR^cC(O)NR^cR^d$, —$NR^cS(O)_mR^e$, =$NR^{11}$, —$C_3$-$C_7$ cycloalkyl, —$O$—$C_3$-$C_6$cycloalkyl, —$C_1$-$C_{10}$alkylene-$C_3$-$C_6$cycloalkyl, —$O$—$C_1$-$C_{10}$ alkylene-$C_3$-$C_6$cycloalkyl, HetB, —$O$-HetB, —$C_1$-$C_{10}$alkylene-HetB, —$O$—$C_1$-$C_{10}$alkylene-HetB, AryB, —$O$-AryB, —$C_1$-$C_{10}$alkylene-AryB, or —$O$—$C_1$-$C_{10}$alkylene-AryB, wherein $R^4$ is unsubstituted or substituted with one to four $R^6$.

In another embodiment of the present invention, each occurrence of $R^4$ is independently: hydrogen, —$C_1$-$C_{10}$ alkyl, —$(CH_2)_nOR^e$, —$(CH_2)_nNR^cR^d$, =$NR^{11}$, —$C_1$-$C_{10}$alkylene-$C_3$-$C_6$cycloalkyl, or —$C_1$-$C_{10}$alkylene-HetB, wherein $R^4$ is unsubstituted or substituted with one to four $R^6$.

In another embodiment of the present invention, each occurrence of $R^4$ is independently: hydrogen, —$C_1$-$C_{10}$ alkyl, —$(CH_2)_nOR^e$, —$(CH_2)_nNR^cR^d$, or —$C_1$-$C_{10}$alkylene-HetB, wherein $R^4$ is unsubstituted or substituted with one to four $R^6$.

In another embodiment of the present invention, each occurrence of $R^4$ is independently: —$C_1$-$C_{10}$ alkyl, —$(CH_2)_nOR^e$, —$(CH_2)_nNR^cR^d$, or —$C_1$-$C_8$alkylene-HetB, wherein $R^4$ is unsubstituted or substituted with one to four $R^6$.

In another embodiment of the present invention, each occurrence of $R^4$ is: —$C_1$-$C_{10}$ alkyl, wherein $R^4$ is unsubstituted or substituted with one to four $R^6$.

In another embodiment of the present invention, each occurrence of $R^4$ is —$(CH_2)_nOR^e$, wherein $R^4$ is unsubstituted or substituted with one to four $R^6$.

In another embodiment of the present invention, each occurrence of $R^4$ is —$(CH_2)_nNR^cR^d$, wherein $R^4$ is unsubstituted or substituted with one to four $R^6$.

In another embodiment of the present invention, each occurrence of $R^4$ is —$C_1$-$C_6$alkylene-HetB, wherein $R^4$ is unsubstituted or substituted with one to four $R^6$.

In another embodiment of the present invention, each occurrence of $R^4$ is independently: hydrogen, —$C_1$-$C_{10}$ alkyl, —$(CH_2)_nNR^cR^d$, or —$C_1$-$C_{10}$alkylene-HetB, wherein $R^4$ is unsubstituted or substituted with one to four $R^6$.

In another embodiment of the present invention, each occurrence of $R^4$ is independently: —$C_1$-$C_{10}$ alkyl, —$(CH_2)_nNR^cR^d$, or —$C_1$-$C_{10}$alkylene-HetB, wherein $R^4$ is unsubstituted or substituted with one to four $R^6$. In a class of this embodiment, of $R^4$ is independently: —$CH_3$, —$(CH_2)_nNH_2$, or —$CH_2$-HetB, wherein $R^4$ is unsubstituted or substituted with one to four $R^6$. In another class of this embodiment, of $R^4$ is independently: —$CH_3$, —$(CH_2)_2NH_2$, —$(CH_2)_3NH_2$, —$CH_2$-pyrrolidine, or —$CH_2$-azetidine, wherein $R^4$ is unsubstituted or substituted with one to four $R^6$. In another class of this embodiment, of $R^4$ is independently: —$CH_3$, —$(CH_2)_3NH_2$, —$CH_2$-pyrrolidine, or —$CH_2$-azetidine. In another class of this embodiment, of $R^4$ is independently: —$CH_3$, —$(CH_2)_3NH_2$, or —$CH_2$-azetidine, wherein $R^4$ is unsubstituted or substituted with one to four $R^6$. In another class of this embodiment, of $R^4$ is independently: —$CH_3$, —$(CH_2)_3NH_2$, or —$CH_2$-azetidine.

In another class of this embodiment, of $R^4$ is independently: —$CH_2NH_2$, —$(CH_2)_2NH_2$, or —$CH_2$-azetidine. In another class of this embodiment, of $R^4$ is independently: —$CH_2NH_2$, or —$CH_2$-azetidine. In another class of this embodiment, of $R^4$ is independently: —$(CH_2)_2NH_2$, or —$CH_2$-azetidine.

In another embodiment of the present invention, $R^5$ is H, $C_1$-$C_{10}$ alkyl, —$C_1$-$C_6$ alkyl-$(NR^cR^d)_2$, —$C_2$-$C_8$ alkenyl, —$(CH_2)_uOR^e$, —$S(O)_xR^e$, —$S(O)_xNR^cR^d$, —$(CH_2)_uNR^cR^d$, —$OC(O)R^e$, —$C(O)OR^e$, —CN, —$C(O)NR^cR^d$, —$NR^cC(O)R^e$, —$NR^cC(O)OR^e$, —$NR^cC(O)NR^cR^d$, —$NR^cS(O)_xR^e$, =$NR^{14}$, —$C_3$-$C_7$ cycloalkyl, —O—$C_3$-$C_6$cycloalkyl, —$C_1$-$C_{10}$alkylene-$C_3$-$C_6$cycloalkyl, —O—$C_1$-$C_{10}$ alkylene-$C_3$-$C_6$cycloalkyl, HetB, —O-HetB, —$C_1$-$C_{10}$alkylene-HetB, —O—$C_1$-$C_{10}$ alkylene-HetB, AryB, —O-AryB, —$C_1$-$C_{10}$alkylene-AryB, or —O—$C_1$-$C_{10}$alkylene-AryB, wherein $R^5$ is unsubstituted or substituted with one to four $R^6$.

In another embodiment of the present invention, $R^5$ is H, $C_1$-$C_{10}$ alkyl, —$C_1$-$C_6$alkyl-$(NR^cR^d)_2$, —$(CH_2)_uOR^e$, $CH_2)_uNR^cR^d$, —$C_1$-$C_{10}$alkylene-$C_3$-$C_6$cycloalkyl, or —$C_1$-$C_{10}$alkylene-HetB, wherein $R^5$ is unsubstituted or substituted with one to four $R^6$. In another embodiment of the present invention, $R^5$ is H, $C_1$-$C_6$ alkyl, —$C_1$-$C_4$alkyl-$(NR^cR^d)_2$, $(CH_2)_uNR^cR^d$ or —$C_1$-$C_{10}$alkylene-HetB, wherein $R^5$ is unsubstituted or substituted with one to four $R^6$. In another embodiment of the present invention, $R^5$ is —$C_1$-$C_2$alkyl-$(NR^cR^d)_2$, $CH_2)_uNR^cR^d$ or —$C_1$-$C_{10}$alkylene-HetB, wherein $R^5$ is unsubstituted or substituted with one to four $R^6$.

In another embodiment of the present invention, $R^5$ is —$C_1$-$C_2$alkyl-$(NR^cR^d)_2$, $CH_2)_uNR^cR^d$ or —$C_1$-$C_{10}$alkylene-HetB, wherein $R^5$ is unsubstituted or substituted with one to four $R^6$. In a class of this embodiment, $R^5$ is —$CH_2NH_2$, —$(CH_2)_2NH_2$, —$(CH_2)_3NH_2$, —$CH_2$-azetidine, —$CH(CH_2NH_2)_2$, or —$CH_2$—$CH(CH_2NH_2)_2$, wherein $R^5$ is unsubstituted or substituted with 1-4 substituents selected from $R^6$. In another class of this embodiment, $R^5$ is —$CH_2NH_2$, —$(CH_2)_2NH_2$, —$(CH_2)_3NH_2$, —$CH_2$-azetidine, —$CH(CH_2NH_2)_2$, or —$CH_2$—$CH(CH_2NH_2)_2$, wherein $R^5$ is unsubstituted or substituted with 1-4 substituents selected from $R^6$.

In another embodiment of the present invention, $R^5$ is —$C_1$-$C_2$alkyl-$(NR^cR^d)_2$, wherein $R^5$ is unsubstituted or substituted with one to four $R^6$. In a class of this embodiment, $R^5$ is —$CH(CH_2NH_2)_2$ or —$CH_2$—$CH(CH_2NH_2)_2$, wherein $R^5$ is unsubstituted or substituted with 1-4 substituents selected from $R^6$.

In another embodiment of the present invention, $R^5$ is $CH_2)_uNR^cR^d$, wherein $R^5$ is unsubstituted or substituted with one to four $R^6$. In a class of this embodiment, $R^5$ is —$CH_2NH_2$, —$(CH_2)_2NH_2$, or —$(CH_2)_3NH_2$, wherein $R^5$ is unsubstituted or substituted with 1-4 substituents selected from $R^6$. In another class of this embodiment, $R^5$ is —$CH_2NH_2$, —$(CH_2)_2NH_2$, or —$(CH_2)_3NH_2$, wherein $R^5$ is unsubstituted or substituted with 1-4 substituents selected from $R^6$.

In another embodiment of the present invention, $R^5$ is —$C_1$-$C_{10}$alkylene-HetB, wherein $R^5$ is unsubstituted or substituted with one to four $R^6$. In a class of this embodiment, $R^5$ is —$C_1$-$C_4$alkylene-HetB, wherein $R^5$ is unsubstituted or substituted with one to four $R^6$. In another class of this embodiment, $R^5$ is —$CH_2$-azetidine.

In another embodiment of the present invention, $R^5$ is —$C_1$-$C_4$alkyl-$(NR^cR^d)_2$, or —$(CH_2)_uNR^cR^d$, wherein $R^5$ is unsubstituted or substituted with one to four $R^6$. In a class of this embodiment, $R^5$ is —$CH_2NH_2$, —$(CH_2)_2NH_2$, —$(CH_2)_3NH_2$, or —$CH(CH_2NH_2)_2$, wherein $R^5$ is unsubstituted or substituted with one to four $R^6$. In another class of this embodiment, $R^5$ is —$CH_2NH_2$, —$(CH_2)_2NH_2$, —$(CH_2)_3NH_2$, or —$CH(CH_2NH_2)_2$, wherein $R^5$ is unsubstituted or substituted with one to four $OR^e$. In another class of this embodiment, $R^5$ is —$(CH_2)_2NH_2$, —$(CH_2)_3NH_2$, or —$CH(CH_2NH_2)_2$, wherein $R^5$ is unsubstituted or substituted with one to four OH.

In another class of this embodiment, $R^5$ is —$(CH_2)_2NH_2$, —$(CH_2)_3NH_2$, or —$CH(CH_2NH_2)_2$, wherein $R^5$ is unsubstituted or substituted with one to four $R^6$. In another class of this embodiment, $R^5$ is —$(CH_2)_2NH_2$, —$(CH_2)_3NH_2$, or —$CH(CH_2NH_2)_2$, wherein $R^5$ is unsubstituted or substituted with one to four $OR^e$. In another class of this embodiment, $R^5$ is —$(CH_2)_2NH_2$, —$(CH_2)_3NH_2$, or —$CH(CH_2NH_2)_2$, wherein $R^5$ is unsubstituted or substituted with one to four OH.

In another embodiment of the present invention, each occurrence of $R^6$ is independently selected from the group consisting of: halogen, —$C_1$-$C_6$alkyl, —$OR^e$, and —$(CH_2)_uNR^cR^d$.

In another embodiment of the present invention, each occurrence of $R^6$ is independently selected from the group consisting of: halogen, —$C_1$-$C_6$alkyl, and —$OR^e$.

In another embodiment of the present invention, each occurrence of $R^6$ is independently selected from the group consisting of: halogen, —$OR^e$, and —$(CH_2)_uNR^cR^d$In another embodiment of the present invention, each occurrence of $R^6$ is independently selected from the group consisting of: —$C_1$-$C_6$alkyl, and —$OR^e$.

In another embodiment of the present invention, each occurrence of $R^6$ is —$OR^e$. In a class of this embodiment, $R^6$ is OH.

In another embodiment of the present invention, $R^7$ is hydrogen, $C_1$-$C_3$ alkyl or $C_3$-$C_7$ cycloalkyl, wherein $C_1$-$C_3$ alkyl and $C_3$-$C_7$ cycloalkyl are unsubstituted or substituted with one to three $R^a$. In a class of this embodiment, $R^7$ is hydrogen or $C_1$-$C_3$ alkyl, wherein $C_1$-$C_3$ alkyl is unsubstituted or substituted with one to three $R^a$. In a another class of this embodiment, $R^7$ is $C_1$-$C_3$ alkyl, wherein $C_1$-$C_3$ alkyl is unsubstituted or substituted with one to three $R^a$. In another class of this embodiment, $R^7$ is hydrogen.

In another embodiment of the present invention, $R^8$ is hydrogen, $C_1$-$C_4$ alkyl, or $C_3$-$C_7$ cycloalkyl. In a class of this embodiment, $R^8$ is hydrogen or $C_1$-$C_4$ alkyl. In another class of this embodiment, $R^8$ is $C_1$-$C_4$ alkyl. In another class of this embodiment, $R^8$ is hydrogen.

In another embodiment of the present invention, $R^9$ is hydrogen or $C_1$-$C_4$ alkyl. In a class of this embodiment, $R^9$ is $C_1$-$C_4$ alkyl. In another class of this embodiment, $R^9$ is hydrogen.

In another embodiment of the present invention, $R^{10}$ is hydrogen, $C_1$-$C_4$ alkyl, or $C_3$-$C_7$ cycloalkyl. In a class of this embodiment, $R^{10}$ is hydrogen or $C_1$-$C_4$ alkyl. In another class of this embodiment, $R^{10}$ is $C_1$-$C_4$ alkyl. In another class of this embodiment, $R^{10}$ is hydrogen.

In another embodiment of the present invention, $R^{11}$ is hydrogen, $C_1$-$C_4$ alkyl, or $C_3$-$C_7$ cycloalkyl. In a class of this embodiment, $R^{11}$ is hydrogen or $C_1$-$C_4$ alkyl. In another class of this embodiment, $R^{11}$ is $C_1$-$C_4$ alkyl. In another class of this embodiment, $R^{11}$ is hydrogen.

In another embodiment of the present invention, $R^{12}$ and $R^{13}$ are independently hydrogen, —$SC_1$-$C_3$alkyl, $C_1$-$C_3$ alkyl, —$(C_1$-$C_3$alkylene$)_n OC_1$-$C_3$alkyl, or —$(C_1$-$C_3$alkylene$)_n NC_1$-$C_3$alkyl, wherein —$SC_1$-$C_3$alkyl, $C_1$-$C_3$ alkyl, —$(C_1$-$C_3$alkylene$)_n OC_1$-$C_3$alkyl and —$(C_1$-$C_3$alkylene$)_n NC_1$-$C_3$alkyl are unsubstituted or substituted with one to seven fluorines, or, alternatively, $R^{12}$ and $R^{13}$, together with the carbon to which they are attached, form a monocyclic $C_4$-$C_7$ cycloalkyl or a monocyclic $C_4$-$C_7$ heterocycloalkyl with 1, 2, or 3 heteroatom ring atoms independently selected from N, O and S, wherein $C_4$-$C_7$ cycloalkyl and $C_4$-$C_7$ heterocycloalkyl are unsubstituted or substituted with one to three substituents independently selected from —F, —OH and —$OC_1$-$C_3$alkyl.

In another embodiment of the present invention $R^{12}$ and $R^{13}$ are independently hydrogen, —$SC_1$-$C_3$alkyl, or $C_1$-$C_3$ alkyl, wherein —$SC_1$-$C_3$alkyl, and $C_1$-$C_3$ alkyl are unsubstituted or substituted with one to seven fluorines, or alternatively $R^{12}$ and $R^{13}$ together with the carbon to which they are attached form a monocyclic $C_4$-$C_6$ cycloalkyl or a monocyclic $C_4$-$C_6$ heterocycloalkyl with 1, 2, or 3 heteroatom ring atoms independently selected from N, O and S, wherein $C_4$-$C_6$ cycloalkyl and $C_4$-$C_6$ heterocycloalkyl are unsubstituted or substituted with one to three substituents independently selected from —F, —OH and —$OC_1$-$C_3$alkyl. In a class of this embodiment of the present invention $R^{12}$ and $R^{13}$ are independently hydrogen, —$SC_1$-$C_3$alkyl, or $C_1$-$C_3$ alkyl, wherein —$SC_1$-$C_3$alkyl, and $C_1$-$C_3$ alkyl are unsubstituted or substituted with one to seven fluorines.

In another embodiment of the present invention $R^{12}$ and $R^{13}$ are independently $C_1$-$C_3$ alkyl, wherein $C_1$-$C_3$ alkyl is unsubstituted or substituted with one to seven fluorines, or alternatively $R^{12}$ and $R^{13}$ together with the carbon to which they are attached form a monocyclic $C_4$-$C_6$ cycloalkyl unsubstituted or substituted with one to three substituents independently selected from —F, —OH and —$OC_1$-$C_3$alkyl.

In another embodiment of the present invention $R^{12}$ and $R^{13}$ are independently $C_1$-$C_3$ alkyl, wherein $C_1$-$C_3$ alkyl is unsubstituted or substituted with one to seven fluorines.

In a class of this embodiment of the present invention $R^{12}$ and $R^{13}$ are independently $C_1$-$C_3$ alkyl. In another class of this embodiment, $R^{12}$ and $R^{13}$ are independently $CH_3$, wherein $CH_3$ is unsubstituted or substituted with one to three fluorines.

In another embodiment of the present invention $R^{12}$ is $C_1$-$C_3$ alkyl, wherein $C_1$-$C_3$ alkyl is unsubstituted or substituted with one to seven fluorines. In a class of this embodiment, $R^{12}$ is $CH_3$, wherein $CH_3$ is unsubstituted or substituted with one to three fluorines. In another class of this embodiment, $R^{12}$=—$CH_3$.

In another embodiment of the present invention $R^{13}$ is $C_1$-$C_3$ alkyl, wherein the $C_1$-$C_3$ alkyl is unsubstituted or substituted with one to seven fluorines. In a class of this embodiment, $R^{13}$ is $CH_3$, wherein $CH_3$ is unsubstituted or substituted with one to three fluorines. In another class of this embodiment, $R^{13}$=—$CH_3$.

In another embodiment of the present invention, $R^{14}$ is hydrogen or $C_1$-$C_4$ alkyl. In a class of this embodiment, $R^{14}$ is $C_1$-$C_4$ alkyl. In another class of this embodiment, $R^{14}$ is hydrogen.

In another embodiment of the present invention, each occurrence of $R^a$ is independently hydrogen, halogen, $C_1$-$C_3$alkyl, —$NR^cR^d$ or —$OR^e$. In another embodiment of the present invention, each occurrence of $R^a$ is independently hydrogen, halogen, or $C_1$-$C_3$alkyl. In another embodiment of the present invention, each occurrence of $R^a$ is independently hydrogen or $C_1$-$C_3$alkyl. In another embodiment of the present invention, $R^a$ is hydrogen. In another embodiment of the present invention, $R^a$ is $C_1$-$C_3$alkyl.

In another embodiment of the present invention, HetA is a 4- to 7-membered saturated or monounsaturated monocyclic ring with 1, 2, or 3 heteroatom ring atoms independently selected from N, N as a quaternary salt, O and S, unsubstituted or substituted with one to four $R^c$. In a class of this embodiment, Het A is an unsubstituted or substituted saturated monocyclic ring. In another class of this embodiment, HetA is an unsubstituted or substituted monounsaturated monocyclic ring.

In another embodiment of the present invention, HetA is a 4-membered saturated or monounsaturated monocyclic ring with 1, 2, or 3 heteroatom ring atoms independently selected from N, N as a quaternary salt, O and S, unsubstituted or substituted with one to four $R^c$. In a class of this embodiment, Het A is an unsubstituted or substituted saturated monocyclic ring. In another class of this embodiment, HetA is an unsubstituted or substituted monounsaturated monocyclic ring.

In another embodiment of the present invention, HetA is a 5-membered saturated or monounsaturated monocyclic ring with 1, 2, or 3 heteroatom ring atoms independently selected from N, N as a quaternary salt, O and S, unsubstituted or substituted with one to four $R^c$. In a class of this embodiment, Het A is an unsubstituted or substituted saturated monocyclic ring. In another class of this embodiment, HetA is an unsubstituted or substituted monounsaturated monocyclic ring.

In another embodiment of the present invention, HetA is a 6-membered saturated or monounsaturated monocyclic ring with 1, 2, or 3 heteroatom ring atoms independently selected from N, N as a quaternary salt, O and S, unsubstituted or substituted with one to four $R^c$. In a class of this embodiment, Het A is an unsubstituted or substituted saturated monocyclic ring. In another class of this embodiment, HetA is an unsubstituted or substituted monounsaturated monocyclic ring.

In another embodiment of the present invention, HetA is a 7-membered saturated or monounsaturated monocyclic ring with 1, 2, or 3 heteroatom ring atoms independently selected from N, N as a quaternary salt, O and S, unsubstituted or substituted with one to four $R^c$. In a class of this embodiment, Het A is an unsubstituted or substituted saturated monocyclic ring. In another class of this embodiment, HetA is an unsubstituted or substituted monounsaturated monocyclic ring.

In another embodiment of the present invention, AryA is a 5- to 6-membered monocyclic aromatic ring with 0, 1, 2, or 3 ring atoms independently selected from N, N as a quaternary salt, O and S, unsubstituted or substituted with one to four $R^c$.

In another embodiment of the present invention, AryA is a 5-membered monocyclic aromatic ring with 0, 1, 2, or 3 ring atoms independently selected from N, N as a quaternary salt, O and S, unsubstituted or substituted with one to four $R^c$.

In another embodiment of the present invention, AryA is a 6-membered monocyclic aromatic ring with 0, 1, 2, or 3 ring atoms independently selected from N, N as a quaternary salt, O and S, unsubstituted or substituted with one to four $R^c$.

In another embodiment of the present invention, $R^b$ is hydrogen, —$C_1$-$C_6$ alkyl, —O$C_1$-$C_6$ alkyl, OH, N($R^9$)$_2$ or halogen, wherein —$C_1$-$C_3$ alkyl is unsubstituted or substituted with one to three $R^a$. In a class of this embodiment, $R^b$ is hydrogen, —$C_1$-$C_6$ alkyl. In another class of this embodiment, $R^b$ is —$C_1$-$C_6$ alkyl.

In another embodiment of the present invention, A is —C(=NH)—NH, —(CH$_2$)$_q$N($R^7$)-AryC, —(CH$_2$)$_q$O-AryC, AryC, —(CH$_2$)$_q$N($R^7$)-HetC, —(CH$_2$)$_q$O-HetC, HetC, or $C_3$-$C_7$ cycloalkyl, wherein A is unsubstituted or substituted with one to four $R^i$.

In another embodiment of the present invention, A is —C(=NH)—NH, AryC, or HetC, wherein A is unsubstituted or substituted with one to four $R^i$.

In another embodiment of the present invention, A is —C(=NH)—NH, wherein A is unsubstituted or substituted with one to four $R^i$.

In another embodiment of the present invention, A is AryC or HetC, wherein A is unsubstituted or substituted with one to four $R^i$.

In another class of this embodiment, A is pyrazole, imidazole, pyridine, pyrimidine, dihydroimidazole, dihydropyrimidine, tetrahydropyrimidine, or tetrahydropyridopyrimidine, wherein A is unsubstituted or substituted with one to four $R^i$.

In another class of this embodiment, A is pyrazole, imidazole, pyridine, pyrimidine, 2,3-dihydroimidazole, 4,5-dihydroimidazole, 1,4,5,6-tetrahydropyrimidine, 3,4,5,6-tetrahydropyrimidine, 3,4-dihydropyrimidine or 1,2,3,4-tetrahydropyrido[1,2-a]pyrimidine, wherein A is unsubstituted or substituted with one to four $R^i$.

In another embodiment of the present invention, A is pyridine, pyrazole, pyrimidine, tetrahydropyrimidine, dihydroimidazole or 1,2,3,4-tetrahydropyrido[1,2-a]pyrimidine. In a class of this embodiment, A is pyridine, pyrazole, pyrimidine, 1,4,5,6-tetrahydropyrimidine, 3,4,5,6-tetrahydropyrimidine, 4,5-dihydroimidazole or 1,2,3,4-tetrahydropyrido[1,2-a]pyrimidine. In another class of this embodiment, A is pyridine, pyrazole, pyrimidine, 3,4,5,6-tetrahydropyrimidine, 4,5-dihydroimidazole or 1,2,3,4-tetrahydropyrido[1,2-a]pyrimidine. In another class of this embodiment, A is pyridine, pyrazole, pyrimidine, 1,4,5,6-tetrahydropyrimidine, 1,2,3,4-tetrahydropyridopyridine; 4,5-dihydroimidazole, or 1,2,3,4-tetrahydropyrido[1,2-a]pyrimidine.

In another embodiment of the present invention, A is pyridine, pyrazole, pyrimidine, tetrahydropyrimidine, or dihydroimidazole. In a class of this embodiment, A is pyridine, pyrazole, pyrimidine, 1,4,5,6-tetrahydropyrimidine, 3,4,5,6-tetrahydropyrimidine, or 4,5-dihydroimidazole. In another class of this embodiment, A is pyridine, pyrazole, pyrimidine, 3,4,5,6-tetrahydropyrimidine, or 4,5-dihydroimidazole. In another class of this embodiment, A is pyridine, pyrazole, pyrimidine, 1,4,5,6-tetrahydropyrimidine, 1,2,3,4-tetrahydropyridopyridine; or 4,5-dihydroimidazole.

In another embodiment of the present invention, A is pyrazole, imidazole, pyridine, pyrimidine, dihydroimidazole, tetrahydropyrimidine or tetrahydropyridopyrimidine. In a class of this embodiment, A is pyrazole, imidazole, pyridine, pyrimidine, 4,5-dihydroimidazole, 1,4,5,6-tetrahydropyrimidine, or 1,2,3,4-tetrahydropyrido[1,2-a]pyrimidine. In another class of this embodiment, A is pyrazole, imidazole, pyridine, pyrimidine, 4,5-dihydroimidazole, 1,2,3,4-tetrahydropyridopyridine, or 1,2,3,4-tetrahydropyrido[1,2-a]pyrimidine. In another class of this embodiment, A is pyrazole, imidazole, pyridine, pyrimidine, 4,5-dihydroimidazole, or 1,4,5,6-tetrahydropyrimidine. In another class of this embodiment, A is pyrazole, imidazole, pyridine, pyrimidine, 4,5-dihydroimidazole, or 1,2,3,4-tetrahydropyridopyridine. In another class of this embodiment, A is 1,2,3,4-tetrahydropyrido[1,2-a]pyrimidine.

In another embodiment of the present invention, A is pyrazole, pyridine, pyrimidine, dihydroimidazole or tetrahydropyridopyrimidine. In a class of this embodiment, A is pyridine, pyrazole, pyrimidine, 4,5-dihydroimidazole, or 1,2,3,4-tetrahydropyrido[1,2-a]pyrimidine. In another class of this embodiment, A is pyridine, pyrazole, pyrimidine, or 4,5-dihydroimidazole. In another class of this embodiment, A is pyridine. In another class of this embodiment, A is pyrazole. In another class of this embodiment, A is pyrimidine. In another class of this embodiment, A is 4,5-dihydroimidazole. In another class of this embodiment, A is 1,2,3,4-tetrahydropyrido[1,2-a]pyrimidine.

In another embodiment, AryC is a 5- to 6-membered monocyclic aromatic ring with 0, 1, 2, or 3 ring atoms independently selected from N, N as a quaternary salt, O and S, unsubstituted or substituted with one to four $R^i$, wherein AryC is optionally fused to a 4- to 7-membered heterocycloalkyl ring containing one to two heteroatoms selected from O, S and —$NR^g$.

In another embodiment, AryC is a 5- to 6-membered monocyclic aromatic ring with 0, 1, or 2 ring atoms independently selected from N, N as a quaternary salt, O and S, unsubstituted or substituted with one to four $R^i$, wherein AryC is optionally fused to a 4- to 6-membered heterocycloalkyl ring containing one to two heteroatoms selected from O, S and —$NR^g$.

In another embodiment, AryC is a 5- to 6-membered monocyclic aromatic ring with 0, 1, 2, or 3 ring atoms independently selected from N, N as a quaternary salt, O and S, unsubstituted or substituted with one to four $R^i$, wherein AryC is optionally fused to a 6-membered heterocycloalkyl ring containing one to two heteroatoms selected from O, S and —NR$^g$.

In another embodiment, AryC is a 6-membered monocyclic aromatic ring with 0, 1, 2, or 3 ring atoms independently selected from N, N as a quaternary salt, O and S, unsubstituted or substituted with one to four R$^i$, wherein AryC is optionally fused to a 6-membered heterocycloalkyl ring containing one to two heteroatoms selected from O, S and —NR$^g$.

In another embodiment of the present invention, AryC is a 5- to 6-membered monocyclic aromatic ring with 0, 1, 2, or 3 ring atoms independently selected from N, N as a quaternary salt, O and S, unsubstituted or substituted with one to four R$^i$, wherein AryC is optionally fused to a 4- to 7-membered heterocycloalkyl ring containing one to two heteroatoms selected from O, S and —NR$^g$. In a class of this embodiment, AryC is optionally fused to a 4- to 6-membered heterocycloalkyl ring containing one to two heteroatoms selected from O, S and —NR$^g$. In another class of this embodiment, AryC is optionally fused to a 6-membered heterocycloalkyl ring containing one to two heteroatoms selected from O, S and —NR$^g$. In another class of this embodiment, AryC is optionally fused to a piperidine ring.

In another embodiment, AryC is a 6-membered monocyclic aromatic ring with 0, 1, 2, or 3 ring atoms independently selected from N, N as a quaternary salt, O and S, unsubstituted or substituted with one to four R$^i$, wherein AryC is optionally fused to a 6-membered heterocycloalkyl ring containing one to two heteroatoms selected from O, S and —NR$^g$. In a class of this embodiment, AryC is optionally fused to a piperidine ring.

In another embodiment of the present invention, AryC is a 5- to 6-membered monocyclic aromatic ring with 0, 1, 2, or 3 ring atoms independently selected from N, N as a quaternary salt, O and S, unsubstituted or substituted with one to four R$^i$, wherein AryC is optionally fused to a 4- to 7-membered heterocycloalkyl ring containing one to two heteroatoms selected from O, S and —NR$^g$. In a class of this embodiment, AryC is optionally fused to a 4- to 6-membered heterocycloalkyl ring containing one to two heteroatoms selected from O, S and —NR$^g$. In another class of this embodiment, AryC is optionally fused to a 6-membered heterocycloalkyl ring containing one to two heteroatoms selected from O, S and —NR$^g$. In another class of this embodiment, AryC is optionally fused to a piperidine ring.

In another embodiment of the present invention, AryC is a 5-membered monocyclic aromatic ring with 0, 1, 2, or 3 ring atoms independently selected from N, N as a quaternary salt, O and S, unsubstituted or substituted with one to four R$^i$, wherein AryC is optionally fused to a 4 to 7-membered heterocycloalkyl ring containing one to two heteroatoms selected from O, S and —NR$^g$. In a class of this embodiment, AryC is optionally fused to a 4- to 6-membered heterocycloalkyl ring containing one to two heteroatoms selected from O, S and —NR$^g$. In another class of this embodiment, AryC is optionally fused to a 6-membered heterocycloalkyl ring containing one to two heteroatoms selected from O, S and —NR$^g$. In another class of this embodiment, AryC is optionally fused to a piperidine ring.

In another embodiment of the present invention, AryC is a 5-membered monocyclic aromatic ring with 0, 1, 2, or 3 ring atoms independently selected from N, N as a quaternary salt, O and S, unsubstituted or substituted with one to four R$^i$.

In another embodiment of the present invention, AryC is a 6-membered monocyclic aromatic ring with 0, 1, 2, or 3 ring atoms independently selected from N, N as a quaternary salt, O and S, unsubstituted or substituted with one to four R$^i$, wherein AryC is optionally fused to a 4- to 7-membered heterocycloalkyl ring containing one to two heteroatoms selected from O, S and —NR$^g$. In a class of this embodiment, AryC is optionally fused to a 4- to 6-membered heterocycloalkyl ring containing one to two heteroatoms selected from O, S and —NR$^g$. In another class of this embodiment, AryC is optionally fused to a 6-membered heterocycloalkyl ring containing one to two heteroatoms selected from O, S and —NR$^g$. In another class of this embodiment, AryC is optionally fused to a piperidine ring.

In another embodiment of the present invention, AryC is a 6-membered monocyclic aromatic ring with 0, 1, 2, or 3 ring atoms independently selected from N, N as a quaternary salt, O and S, unsubstituted or substituted with one to four R$^i$.

In another embodiment, AryC is pyrazole, imidazole, pyridine, or pyrimidine, wherein A is unsubstituted or substituted with one to four R$^i$, and wherein AryC is optionally fused to a 4- to 7-membered heterocycloalkyl ring containing one to two heteroatoms selected from O, S and —NR$^g$. In a class of this embodiment, AryC is optionally fused to a 4- to 6-membered heterocycloalkyl ring containing one to two heteroatoms selected from O, S and —NR$^g$. In another class of this embodiment, AryC is optionally fused to a 6-membered heterocycloalkyl ring containing one to two heteroatoms selected from O, S and —NR$^g$. In another class of this embodiment, AryC is optionally fused to a piperidine ring.

In another embodiment, AryC is pyrazole, pyridine, or pyrimidine, wherein A is unsubstituted or substituted with one to four R$^i$.

In another embodiment of the present invention, AryC is pyridine, pyrazole, or pyrimidine, wherein AryC is optionally fused to a piperidine ring.

In another embodiment of the present invention, AryC is pyridine, pyrazole, or pyrimidine.

In another embodiment of the present invention, AryC is pyridine, wherein AryC is optionally fused to a piperidine ring.

In another embodiment of the present invention, AryC is pyridine.

In another embodiment of the present invention, AryC is pyrazole.

In another embodiment of the present invention, AryC is pyrimidine.

In another embodiment of the present invention, HetC is a 4- to 7-membered saturated or monounsaturated monocyclic ring with 1, 2, or 3 heteroatom ring atoms independently selected from N, N as a quaternary salt, O and S, unsubstituted or substituted with one to four R$^i$, wherein HetC is optionally fused to a 4- to 7-membered heterocycloalkyl ring containing one to two heteroatoms selected from O, S and —NR$^g$. In a class of this embodiment, HetC is a 4- to 7-membered saturated or monounsaturated monocyclic ring with 1, 2, or 3 heteroatom ring atoms independently selected from N, O and S, unsubstituted or substituted with one to four R$^i$, wherein HetC is optionally fused to a 4- to 7-membered heterocycloalkyl ring containing one to two heteroatoms selected from O, S and —NR$^g$. In another class of this embodiment, HetC is a 4- to 7-membered saturated or monounsaturated monocyclic ring with 1, 2, or 3 heteroatom ring atoms independently selected from N, N as a quaternary salt, O and S, unsubstituted or substituted with one to four R$^i$. In this embodiment, HetC is a 4- to 7-membered saturated or monounsaturated monocyclic ring with 1, 2, or 3 heteroatom ring atoms independently selected from N, O and S, unsubstituted or substituted with one to four $R^i$.

In another class of this embodiment, HetC is a 4- to 7-membered saturated or monounsaturated monocyclic ring with 1, 2, or 3 heteroatom ring atoms independently selected from N, N as a quaternary salt, O and S, unsubstituted or substituted with one to four $R^i$, wherein HetC is optionally fused to a 4- to 7-membered heterocycloalkyl ring containing one to two heteroatoms selected from O, S and —$NR^g$. In another class of this embodiment, HetC is a 4- to 7-membered saturated or monounsaturated monocyclic ring with 1, 2, or 3 heteroatom ring atoms independently selected from N, O and S, unsubstituted or substituted with one to four $R^i$, wherein HetC is optionally fused to a 4- to 7-membered heterocycloalkyl ring containing one to two heteroatoms selected from O, S and —$NR^g$.

In another class of this embodiment, HetC is a 4- to 7-membered saturated or monounsaturated monocyclic ring with 1, 2, or 3 heteroatom ring atoms independently selected from N, N as a quaternary salt, O and S, unsubstituted or substituted with one to four $R^i$. In another class of this embodiment, HetC is a 4- to 7-membered saturated or monounsaturated monocyclic ring with 1, 2, or 3 heteroatom ring atoms independently selected from N, O and S, unsubstituted or substituted with one to four $R^i$.

In another class of this embodiment, HetC is a 4- to 7-membered saturated or monounsaturated monocyclic ring with 1, 2, or 3 heteroatom ring atoms independently selected from N, N as a quaternary salt, O and S, unsubstituted or substituted with one to four $R^i$, wherein HetC is optionally fused to a 4- to 7-membered heterocycloalkyl ring containing one to two heteroatoms selected from O, S and —$NR^g$.

In another class of this embodiment, HetC is a 4- to 7-membered saturated or monounsaturated monocyclic ring with 1, 2, or 3 heteroatom ring atoms independently selected from N, O and S, unsubstituted or substituted with one to four $R^i$, wherein HetC is optionally fused to a 4- to 7-membered heterocycloalkyl ring containing one to two heteroatoms selected from O, S and —$NR^g$. In another class of this embodiment, HetC is a 4- to 7-membered saturated or monounsaturated monocyclic ring with 1, 2, or 3 heteroatom ring atoms independently selected from N, N as a quaternary salt, O and S, unsubstituted or substituted with one to four $R^i$. In another class of this embodiment, HetC is a 4- to 7-membered saturated or monounsaturated monocyclic ring with 1, 2, or 3 heteroatom ring atoms independently selected from N, O and S, unsubstituted or substituted with one to four $R^i$.

In another class of this embodiment, HetC is an unsubstituted or substituted saturated monocyclic ring. In another class of this embodiment, HetC is an unsubstituted or substituted monounsaturated monocyclic ring.

In another embodiment of the present invention, HetC is a 4-membered saturated or monounsaturated monocyclic ring with 1, 2, or 3 heteroatom ring atoms independently selected from N, N as a quaternary salt, O and S, unsubstituted or substituted with one to four $R^i$. In a class of this embodiment, HetC is a 4-membered saturated or monounsaturated monocyclic ring with 1, 2, or 3 heteroatom ring atoms independently selected from N and S, unsubstituted or substituted with one to four $R^i$.

In another class of this embodiment of the present invention, HetC is a 4-membered saturated or monounsaturated monocyclic ring with 1, 2, or 3 heteroatom ring atoms independently selected from N, N as a quaternary salt, O and S, unsubstituted or substituted with one to four $R^i$. In another class of this embodiment of the present invention, HetC is a 4-membered saturated or monounsaturated monocyclic ring with 1, 2, or 3 heteroatom ring atoms independently selected from N, O and S, unsubstituted or substituted with one to four $R^i$.

In another class of this embodiment of the present invention, HetC is a 4-membered saturated or monounsaturated monocyclic ring with 1, 2, or 3 heteroatom ring atoms independently selected from N, N as a quaternary salt, O and S, unsubstituted or substituted with one to four $R^i$. In another class of this embodiment of the present invention, HetC is a 4-membered saturated or monounsaturated monocyclic ring with 1, 2, or 3 heteroatom ring atoms independently selected from N, O and S, unsubstituted or substituted with one to four $R^i$. In another class of this embodiment, HetC is an unsubstituted or substituted saturated monocyclic ring. In another class of this embodiment, HetC is an unsubstituted or substituted monounsaturated monocyclic ring.

In another embodiment of the present invention, HetC is a 5-membered saturated or monounsaturated monocyclic ring with 1, 2, or 3 heteroatom ring atoms independently selected from N, N as a quaternary salt, O and S, unsubstituted or substituted with one to four $R^i$. In a class of this embodiment, HetC is a 5-membered saturated or monounsaturated monocyclic ring with 1, 2, or 3 heteroatom ring atoms independently selected from N, O and S, unsubstituted or substituted with one to four $R^i$. In another class of this embodiment, HetC is a 5-membered saturated or monounsaturated monocyclic ring with 1, 2, or 3 heteroatom ring atoms independently selected from N, N as a quaternary salt, O and S, unsubstituted or substituted with one to four $R^i$. In another class of this embodiment, HetC is a 5-membered saturated or monounsaturated monocyclic ring with 1, 2, or 3 heteroatom ring atoms independently selected from N, O and S, unsubstituted or substituted with one to four $R^i$. In another class of this embodiment, HetC is a 5-membered saturated or monounsaturated monocyclic ring with 1, 2, or 3 heteroatom ring atoms independently selected from N, N as a quaternary salt, O and S, unsubstituted or substituted with one to four $R^i$. In another class of this embodiment, HetC is a 5-membered saturated or monounsaturated monocyclic ring with 1, 2, or 3 heteroatom ring atoms independently selected from N, O and S, unsubstituted or substituted with one to four $R^i$. In another class of this embodiment, HetC is an unsubstituted or substituted saturated monocyclic ring. In another class of this embodiment, HetC is an unsubstituted or substituted monounsaturated monocyclic ring.

In another embodiment of the present invention, HetC is a 6-membered saturated or monounsaturated monocyclic ring with 1, 2, or 3 heteroatom ring atoms independently selected from N, N as a quaternary salt, O and S, unsubstituted or substituted with one to four $R^i$, wherein HetC is optionally fused to a 5- to 6-membered monocyclic aromatic ring. In a class of this embodiment, HetC is a 6-membered saturated or monounsaturated monocyclic ring with 1, 2, or 3 heteroatom ring atoms independently selected from N, O and S, unsubstituted or substituted with one to four $R^i$, wherein HetC is optionally fused to a 5- to 6-membered monocyclic aromatic ring.

In another embodiment of the present invention, HetC is a 6-membered saturated or monounsaturated monocyclic ring with 1, 2, or 3 heteroatom ring atoms independently selected from N, N as a quaternary salt, O and S, unsubstituted or substituted with one to four $R^i$, wherein HetC is optionally fused to a phenyl ring. In a class of this embodiment, HetC is a 6-membered saturated or monounsaturated monocyclic ring with 1, 2, or 3 heteroatom ring atoms independently selected from N, O and S, unsubstituted or substituted with one to four $R^i$, wherein HetC is optionally fused to a phenyl ring.

In another embodiment of the present invention, HetC is a 6-membered saturated or monounsaturated monocyclic ring with 1, 2, or 3 heteroatom ring atoms independently selected from N, N as a quaternary salt, O and S, unsubstituted or substituted with one to four $R^i$. In a class of this embodiment, HetC is a 6-membered saturated or monounsaturated monocyclic ring with 1, 2, or 3 heteroatom ring atoms independently selected from N, O and S, unsubstituted or substituted with one to four $R^i$.

In another class of this embodiment, HetC is an unsubstituted or substituted saturated monocyclic ring. In another class of this embodiment, HetC is an unsubstituted or substituted monounsaturated monocyclic ring.

In another embodiment of the present invention, HetC is a 7-membered saturated or monounsaturated monocyclic ring with 1, 2, or 3 heteroatom ring atoms independently selected from N, N as a quaternary salt, O and S, unsubstituted or substituted with one to four $R^i$. In a class of this embodiment, HetC is a 7-membered saturated or monounsaturated monocyclic ring with 1, 2, or 3 heteroatom ring atoms independently selected from N, O and S, unsubstituted or substituted with one to four $R^i$. In another class of this embodiment, HetC is an unsubstituted or substituted saturated monocyclic ring. In another class of this embodiment, HetC is an unsubstituted or substituted monounsaturated monocyclic ring.

In another embodiment of the present invention, HetC is dihydroimidazole, dihydropyrimidine, tetrahydropyrimidine, or tetrahydropyridopyrimidine, wherein A is unsubstituted or substituted with one to four $R^i$.

In another embodiment of the present invention, HetC is dihydroimidazole, dihydropyrimidine, tetrahydropyrimidine, or tetrahydropyrido[1,2-a]pyrimidine, wherein A is unsubstituted or substituted with one to four $R^i$.

In another embodiment, HetC is 2,3-dihydroimidazole, 4,5-dihydroimidazole, 1,4,5,6-tetrahydropyrimidine, 3,4,5,6-tetrahydropyrimidine, 3,4-dihydropyrimidine, or 1,2,3,4-tetrahydropyrido[1,2-a]pyrimidine, wherein HetC is unsubstituted or substituted with one to four $R^i$.

In another embodiment, HetC is dihydroimidazole, or tetrahydropyridopyrimidine, wherein HetC is unsubstituted or substituted with one to four $R^i$.

In another embodiment, HetC is 2,3-dihydroimidazole, 4,5-dihydroimidazole, or 1,2,3,4-tetrahydropyrido[1,2-a]pyrimidine, wherein HetC is unsubstituted or substituted with one to four $R^i$.

In another embodiment of the present invention, HetC is dihydroimidazole. In a class of this embodiment, HetC is 2,3-dihydroimidazole. In another class of this embodiment, HetC is 4,5-dihydroimidazole.

In another embodiment of the present invention, HetC is tetrahydropyridopyrimidine. In a class of this embodiment, HetC is 1,2,3,4-tetrahydropyrido[1,2-a]pyrimidine.

In another embodiment of the present invention, L is absent, $R^4$, —$NHR^4$, —$N(R^4)_2$, —$OR^4$, —$(CH_2)_nR^4$, —$C(O)R^4$, —$C(NH)R^4$, or —$S(O)_mR^4$, wherein L is unsubstituted or substituted with 1-4 substituents selected from $R^e$. In a class of this embodiment, L is $R^4$, —$NHR^4$, —$N(R^4)_2$, —$OR^4$, —$(CH_2)_nR^4$, —$C(O)R^4$, —$C(NH)R^4$, or —$S(O)_mR^4$, wherein L is unsubstituted or substituted with 1-4 substituents selected from $R^e$. In another embodiment of the present invention, L is —$OR^4$, —$(CH_2)_nR^4$, —$C(O)R^4$, —$C(NH)R^4$, or —$S(O)_mR^4$, wherein L is unsubstituted or substituted with 1-4 substituents selected from $R^e$. In a class of this embodiment, L is —$OR^4$, —$(CH_2)_nR^4$, —$C(O)R^4$, —$C(NH)R^4$, or —$S(O)_mR^4$, wherein L is unsubstituted or substituted with 1-4 substituents selected from $R^e$.

In another embodiment of the present invention, L is absent.

In another embodiment of the present invention, L is absent, $R^4$, —$NHR^4$, or —$N(R^4)_2$, wherein L is unsubstituted or substituted with 1-4 substituents selected from $R^e$. In another embodiment of the present invention, L is absent, $R^4$, or —$NHR^4$, wherein L is unsubstituted or substituted with 1-4 substituents selected from $R^e$. In another embodiment of the present invention, L is absent, $R^4$ or —$N(R^4)_2$, wherein L is unsubstituted or substituted with 1-4 substituents selected from $R^e$.

In another embodiment of the present invention, L is absent or $R^4$, wherein L is unsubstituted or substituted with 1-4 substituents selected from $R^e$.

In another embodiment, L is absent, hydrogen, —$C_1$-$C_{10}$ alkyl, —$(CH_2)_nNR^cR^d$, —$NH(CH_2)_nNR^cR^d$, —$(CH_2)_nOR^e$, or —$C_1$-$C_{10}$alkylene-HetB, wherein L is unsubstituted or substituted with 1-4 substituents selected from $R^e$.

In another embodiment, L is absent, —$C_1$-$C_8$ alkyl, —$(CH_2)_nNR^cR^d$, —$NH(CH_2)_nNR^cR^d$, —$(CH_2)_nOR^e$, or —$C_1$-$C_{10}$alkylene-HetB, wherein L is unsubstituted or substituted with 1-4 substituents selected from $R^e$.

In another embodiment, L is absent, —$C_1$-$C_8$ alkyl, —$(CH_2)_nNR^cR^d$, —$(CH_2)_nOR^e$, or —$C_1$-$C_{10}$alkylene-HetB, wherein L is unsubstituted or substituted with 1-4 substituents selected from $R^e$. In a class of this embodiment, L is —$C_1$-$C_8$ alkyl, —$(CH_2)_nNR^cR^d$, —$(CH_2)_nOR^e$, or —$C_1$-$C_{10}$alkylene-HetB, wherein L is unsubstituted or substituted with 1-4 substituents selected from $R^e$.

In another embodiment of the present invention, L is absent, —$CH_3$, —$(CH_2)$—$NH_2$, —$(CH_2)_2$—$NH_2$, —$(CH_2)_3$—$NH_2$, —$(CH_2)_3$—$OH$, —$CH_2$-pyrrolidine or —$CH_2$-azetidine, wherein L is unsubstituted or substituted with 1-4 substituents selected from OH. In a class of this embodiment, L is absent, —$CH_3$, —$CH_2$-pyrrolidine, —$CH_2$-azetidine, —$(CH_2)$—$NH_2$, or —$(CH_2)_3$—$NH_2$, wherein L is unsubstituted or substituted with 1-4 substituents selected from OH.

In another embodiment, L is —$C_1$-$C_8$ alkyl, wherein L is unsubstituted or substituted with 1-4 substituents selected from $R^e$. In a class of this embodiment, L is —$CH_3$, wherein L is unsubstituted or substituted with 1-4 substituents selected from OH.

In another embodiment, L is —$(CH_2)_nNR^cR^d$, wherein L is unsubstituted or substituted with 1-4 substituents selected from $R^e$. In a class of this embodiment, L is —$(CH_2)$—$NH_2$, —$(CH_2)_2$—$NH_2$, or —$(CH_2)_3$—$NH_2$, wherein L is unsubstituted or substituted with 1-4 substituents selected from OH. In another class of this embodiment, L is —$(CH_2)$—$NH_2$ or —$(CH_2)_3$—$NH_2$, wherein L is unsubstituted or substituted with 1-4 substituents selected from OH.

In another embodiment, L is —$(CH_2)_nOR^e$, wherein L is unsubstituted or substituted with 1-4 substituents selected from $R^e$. In a class of this embodiment, L is —$(CH_2)_3$—$OH$, wherein L is unsubstituted or substituted with 1-4 substituents selected from OH.

In another embodiment, L is -$C_1$-$C_{10}$alkylene-HetB, wherein L is unsubstituted or substituted with 1-4 substituents selected from $R^e$. In a class of this embodiment, L is $CH_2$-azetidine or —$CH_2$-pyrrolidine, wherein L is unsubstituted or substituted with 1-4 substituents selected from $R^e$. In another class of this embodiment, L is $CH_2$-azetidine, wherein L is unsubstituted or substituted with 1-4 substituents selected from $R^e$. In another class of this embodiment, L is —$CH_2$-pyrrolidine, wherein L is unsubstituted or substituted with 1-4 substituents selected from $R^e$.

In another embodiment of the present invention, L is absent, or $R^4$, wherein L is unsubstituted or substituted with 1-4 substituents selected from $R^e$. In a class of this embodiment, L is absent, or $R^4$.

In another embodiment of the present invention, HetB is a 4- to 7-membered saturated or monounsaturated monocyclic ring with 1, 2, or 3 heteroatom ring atoms independently selected from N, N as a quaternary salt, O and S, unsubstituted or substituted with one to three $R^a$. In a class of this embodiment, HetB is azetidine or pyrrolidine. In another class of this embodiment, HetB is azetidine. In another class of this embodiment, HetB is pyrrolidine.

In another embodiment of the present invention, HetB is a 4- to 6-membered saturated or monounsaturated monocyclic ring with 1, 2, or 3 heteroatom ring atoms independently selected from N, N as a quaternary salt, O and S, unsubstituted or substituted with one to three $R^a$. In a class of this embodiment, HetB is azetidine or pyrrolidine. In another class of this embodiment, HetB is azetidine. In another class of this embodiment, HetB is pyrrolidine.

In another embodiment of the present invention, HetB is a 5- to 6-membered saturated or monounsaturated monocyclic ring with 1, 2, or 3 heteroatom ring atoms independently selected from N, N as a quaternary salt, O and S, unsubstituted or substituted with one to three $R^a$. In a class of this embodiment, HetB is pyrrolidine.

In another embodiment of the present invention, HetB is a 4-membered saturated or monounsaturated monocyclic ring with 1, 2, or 3 heteroatom ring atoms independently selected from N, N as a quaternary salt, O and S, unsubstituted or substituted with one to three $R^a$.

In another embodiment of the present invention, HetB is a 4-membered saturated or monounsaturated monocyclic ring with 1, 2, or 3 heteroatom ring atoms independently selected from N, N as a quaternary salt, O and S, unsubstituted or substituted with one to three $R^a$. In a class of this embodiment, HetB is azetidine.

In another embodiment of the present invention, HetB is a 5-membered saturated or monounsaturated monocyclic ring with 1, 2, or 3 heteroatom ring atoms independently selected from N, N as a quaternary salt, O and S, unsubstituted or substituted with one to three $R^a$. In a class of this embodiment, HetB is pyrrolidine.

In another embodiment of the present invention, HetB is a 6-membered saturated or monounsaturated monocyclic ring with 1, 2, or 3 heteroatom ring atoms independently selected from N, N as a quaternary salt, O and S, unsubstituted or substituted with one to three $R^a$.

In another embodiment of the present invention, HetB is a 7-membered saturated or monounsaturated monocyclic ring with 1, 2, or 3 heteroatom ring atoms independently selected from N, N as a quaternary salt, O and S, unsubstituted or substituted with one to three $R^a$.

In another embodiment of the present invention, M is $R^5$, —$NHR^5$, —$N(R^5)_2$, —$OR^5$, —$(CH_2)_uR^5$, —$C(O)R^5$, —$C(NH)R^5$, or —$S(O)_vR^5$, wherein M is unsubstituted or substituted with 1-4 substituents selected from $R^6$.

In another embodiment of the present invention, M is $R^5$ or —$NHR^5$, wherein M is unsubstituted or substituted with 1-4 substituents selected from $R^6$.

In another embodiment of the present invention, M is —$(CH_2)_2NH_2$, —$(CH_2)_3NH_2$, —$NH(CH_2)_2NH_2$, —$NH(CH_2)_3NH_2$, —$N(CH_2\text{-azetidine})(CH_2CH_2NH_2)$, —$NH$—$CH(CH_2NH_2)_2$, —$CH_2$—$CH(CH_2NH_2)_2$, wherein M is unsubstituted or substituted with 1-4 substituents selected from $R^6$. In a class of this embodiment of the present invention, M is —$(CH_2)_2NH_2$, —$(CH_2)_3NH_2$, —$NH(CH_2)_2NH_2$, —$NH(CH_2)_3NH_2$, —$N(CH_2\text{-azetidine})(CH_2CH_2NH_2)$, —$NH$—$CH(CH_2NH_2)_2$, —$CH_2$—$CH(CH_2NH_2)_2$, wherein M is unsubstituted or substituted with 1-4 substituents selected from $OR^e$. In another class of this embodiment of the present invention, M is —$(CH_2)_2NH_2$, —$(CH_2)_3NH_2$, —$NH(CH_2)_2NH_2$, —$NH(CH_2)_3NH_2$, —$N(CH_2\text{-azetidine})(CH_2CH_2NH_2)$, —$NH$—$CH(CH_2NH_2)_2$, —$CH_2$—$CH(CH_2NH_2)_2$, wherein M is unsubstituted or substituted with 1-4 substituents selected from OH.

In another embodiment of the present invention, M is —$(CH_2)_3NH_2$, —$NH(CH_2)_2NH_2$, —$NH(CH_2)_3NH_2$, or —$NH$—$CH(CH_2NH_2)_2$, wherein M is unsubstituted or substituted with 1-4 substituents selected from $R^6$. In a class of this embodiment, M is —$(CH_2)_3NH_2$, —$NH(CH_2)_2NH_2$, —$NH(CH_2)_3NH_2$, or —$NH$—$CH(CH_2NH_2)_2$, wherein M is unsubstituted or substituted with 1-4 substituents selected from $OR^e$. In another class of this embodiment, M is —$(CH_2)_3NH_2$, —$NH(CH_2)_2NH_2$, —$NH(CH_2)_3NH_2$, or —$NH$—$CH(CH_2NH_2)_2$, wherein M is unsubstituted or substituted with 1-4 substituents selected from OH.

In another embodiment of the present invention, AryB is a 5- to 6-membered monocyclic aromatic ring with 0, 1, 2, or 3 ring atoms independently selected from N, O and S, unsubstituted or substituted with one to four $R^c$.

In another embodiment of the present invention, AryB is a 5-membered monocyclic aromatic ring with 0, 1, 2, or 3 ring atoms independently selected from N, O and S, unsubstituted or substituted with one to four $R^c$.

In another embodiment of the present invention, AryB is a 6-membered monocyclic aromatic ring with 0, 1, 2, or 3 ring atoms independently selected from N, O and S, unsubstituted or substituted with one to four $R^c$.

In another embodiment of the present invention, each occurrence of $R^6$ is independently selected from the group consisting of: halogen, —$C_1$-$C_6$alkyl, —$OR^e$, —$S(O)_vR^e$, —$S(O)_vNR^cR^d$, —$C(O)R^e$, —$OC(O)R^e$, —$C(O)OR^e$, —CN, —$C(O)NR^cR^d$, —$C(NH)NR^cR^d$, —$(CH_2)_uNR^cR^d$, —$(CH_2)_uNR^cR^d$, —$N(R^c)(C(O)R^e)$, —$N(R^c)(C(O)OR^e)$, —$N(R^c)(C(O)NR^cR^d)$, —$N(R^c)(S(O)_vR^e)$, and HetB.

In another embodiment of the present invention, each occurrence of $R^c$ and $R^d$ is independently selected from: hydrogen, —$C_1$-$C_{10}$ alkyl, —$C_2$-$C_{10}$ alkenyl, —$C_3$-$C_6$ cycloalkyl, —$C_1$-$C_{10}$ alkylene-$C_3$-$C_6$ cycloalkyl, HetA, —$C_1$-$C_{10}$alkylene-HetB, AryB, —$C_1$-$C_{10}$ alkylene-AryB, and —$C_1$-$C_{10}$ alkylene-HetB, or, alternatively, $R^c$ and $R^d$ together with the nitrogen atom to which they are attached, form a 4- to 7-membered heterocycloalkyl optionally containing one to two additional heteroatoms independently selected from O, S and —$NR^g$, and wherein each $R^c$ and $R^d$ is unsubstituted or substituted with one to three $R^f$. In a class of this embodiment, each occurrence of $R^c$ and $R^d$ is independently selected from: hydrogen, —$C_1$-$C_{10}$ alkyl, —$C_2$-$C_{10}$ alkenyl, —$C_3$-$C_6$ cycloalkyl, —$C_1$-$C_{10}$ alkylene-$C_3$-$C_6$ cycloalkyl, HetA, —$C_1$-$C_{10}$alkylene-HetB, AryB, —$C_1$-$C_{10}$ alkylene-AryB, and —$C_1$-$C_{10}$ alkylene-HetB, wherein each $R^c$ and $R^d$ is unsubstituted or substituted with one to three $R^f$. In another class of this embodiment, each occurrence of $R^c$ and $R^d$ is independently selected from: hydrogen, —$C_1$-$C_{10}$ alkyl, and —$C_2$-$C_{10}$ alkenyl, wherein each $R^c$ and $R^d$ is unsubstituted or substituted with one to three $R^f$. In another class of this embodiment, each occurrence of $R^c$ and $R^d$ is independently selected from: hydrogen, and —$C_1$-$C_{10}$ alkyl, wherein each $R^c$ and $R^d$ is unsubstituted or substituted with one to three $R^f$. In another class of this embodiment, each occurrence of $R^c$ and $R^d$ is independently selected from: —$C_1$-$C_{10}$ alkyl, wherein each $R^c$ and $R^d$ is unsubstituted or substituted with one to three $R^f$. In another class of this embodiment, $R^c$ and $R^d$ are hydrogen.

In another embodiment of the present invention, each occurrence of $R^c$ is independently selected from: hydrogen, —$C_1$-$C_{10}$ alkyl, —$C_2$-$C_{10}$ alkenyl, —$C_3$-$C_6$ cycloalkyl, —$C_1$-$C_{10}$ alkylene-$C_3$-$C_6$ cycloalkyl, HetA, —$C_1$-$C_{10}$alkylene-HetB, AryB, —$C_1$-$C_{10}$ alkylene-AryB, and —$C_1$-$C_{10}$ alkylene-HetB, or, alternatively, $R^c$ and $R^d$ together with the nitrogen atom to which they are attached, form a 4- to 7-membered heterocycloalkyl optionally containing one to two additional heteroatoms independently selected from O, S and —$NR^g$, and wherein each $R^c$ is unsubstituted or substituted with one to three $R^f$. In a class of this embodiment, each occurrence of $R^c$ is independently selected from: hydrogen, —$C_1$-$C_{10}$ alkyl, —$C_2$-$C_{10}$ alkenyl, —$C_3$-$C_6$ cycloalkyl, —$C_1$-$C_{10}$ alkylene-$C_3$-$C_6$ cycloalkyl, HetA, —$C_1$-$C_{10}$alkylene-HetB, AryB, —$C_1$-$C_{10}$ alkylene-AryB, and —$C_1$-$C_{10}$ alkylene-HetB, wherein each $R^c$ is unsubstituted or substituted with one to three $R^f$. In another class of this embodiment, each occurrence of $R^c$ is independently selected from: hydrogen, —$C_1$-$C_{10}$ alkyl, and —$C_2$-$C_{10}$ alkenyl, wherein each $R^c$ is unsubstituted or substituted with one to three $R^f$. In another class of this embodiment, each occurrence of $R^c$ is independently selected from: hydrogen, and —$C_1$-$C_{10}$ alkyl, wherein each $R^c$ is unsubstituted or substituted with one to three $R^f$. In another class of this embodiment, each occurrence of $R^c$ is independently selected from: —$C_1$-$C_{10}$ alkyl, wherein each $R^c$ is unsubstituted or substituted with one to three $R^f$. In another class of this embodiment, $R^c$ is hydrogen.

In another embodiment of the present invention, each occurrence of $R^d$ is independently selected from: hydrogen, —$C_1$-$C_{10}$ alkyl, —$C_2$-$C_{10}$ alkenyl, —$C_3$-$C_6$ cycloalkyl, —$C_1$-$C_{10}$ alkylene-$C_3$-$C_6$ cycloalkyl, HetA, —$C_1$-$C_{10}$alkylene-HetB, AryB, —$C_1$-$C_{10}$ alkylene-AryB, and —$C_1$-$C_{10}$ alkylene-HetB, or, alternatively, $R^c$ and $R^d$ together with the nitrogen atom to which they are attached, form a 4- to 7-membered heterocycloalkyl optionally containing one to two additional heteroatoms independently selected from O, S and —$NR^g$, and wherein each $R^d$ is unsubstituted or substituted with one to three $R^f$.

In another embodiment of the present invention, each occurrence of $R^d$ is independently selected from: hydrogen, —$C_1$-$C_{10}$ alkyl, —$C_2$-$C_{10}$ alkenyl, —$C_3$-$C_6$ cycloalkyl, —$C_1$-$C_{10}$ alkylene-$C_3$-$C_6$ cycloalkyl, HetA, —$C_1$-$C_{10}$alkylene-HetB, AryB, —$C_1$-$C_{10}$ alkylene-AryB, and —$C_1$-$C_{10}$ alkylene-HetB, wherein each $R^d$ is unsubstituted or substituted with one to three $R^f$. In a class of this embodiment, each occurrence of $R^d$ is independently selected from: hydrogen, —$C_1$-$C_{10}$ alkyl, and —$C_2$-$C_{10}$ alkenyl, wherein each $R^d$ is unsubstituted or substituted with one to three $R^f$. In another class of this embodiment, each occurrence of $R^d$ is independently selected from: hydrogen, and —$C_1$-$C_{10}$ alkyl, wherein each $R^d$ is unsubstituted or substituted with one to three $R^f$. In another class of this embodiment, each occurrence of $R^d$ is independently selected from: —$C_1$-$C_{10}$ alkyl, wherein each $R^d$ is unsubstituted or substituted with one to three $R^f$. In another class of this embodiment, $R^d$ is hydrogen.

In another embodiment of the present invention, each occurrence of $R^e$ is independently: hydrogen, —$C_1$-$C_{10}$alkyl, —$C_2$-$C_{10}$ alkenyl, —OH, —$OC_1$-$C_4$ alkyl, —$C_3$-$C_6$ cycloalkyl, —$C_1$-$C_{10}$ alkylene-$C_3$-$C_6$ cycloalkyl, HetB, —$C_1$-$C_{10}$ alkylene-HetB, AryB, —$C_1$-$C_{10}$ alkylene-AryB, —$C_1$-$C_{10}$ alkylene-HetB, or halogen, wherein each $R^e$ is unsubstituted or substituted with one to three $R^h$. In a class of this embodiment, each occurrence of $R^e$ is independently: hydrogen, —$C_1$-$C_{10}$alkyl, —$C_2$-$C_{10}$ alkenyl, —OH, —$OC_1$-$C_4$ alkyl, or halogen, wherein each $R^e$ is unsubstituted or substituted with one to three $R^h$. In another class of this embodiment, each occurrence of $R^e$ is independently: hydrogen, —$C_1$-$C_{10}$alkyl, —$C_2$-$C_{10}$ alkenyl, —OH, or —$OC_1$-$C_4$ alkyl, wherein each $R^e$ is unsubstituted or substituted with one to three $R^h$. In another class of this embodiment, each occurrence of $R^e$ is independently: hydrogen, —$C_1$-$C_{10}$alkyl, —OH, or —$OC_1$-$C_4$ alkyl, wherein each $R^e$ is unsubstituted or substituted with one to three $R^h$. In another class of this embodiment, each occurrence of $R^e$ is independently: hydrogen, or —$C_1$-$C_{10}$alkyl, wherein each $R^e$ is unsubstituted or substituted with one to three $R^h$. In another class of this embodiment, each occurrence of $R^e$ is independently: —$C_1$-$C_{10}$alkyl, wherein each $R^e$ is unsubstituted or substituted with one to three $R^h$. In another class of this embodiment, each occurrence of $R^e$ is independently: hydrogen.

In another embodiment of the present invention, each occurrence of $R^f$ is independently: halogen, —$C_1$-$C_{10}$ alkyl, —OH, —$OC_1$-$C_4$ alkyl, —$S(O)_m C_1$-$C_4$ alkyl, —CN, —$CF_3$, —$OCHF_2$, —$OCF_3$, or $NH_2$, wherein —$C_1$-$C_{10}$ alkyl is unsubstituted or substituted with one to three substituents independently selected from: —OH, halogen, cyano, and —$S(O)_2CH_3$. In a class of this embodiment, each occurrence of $R^f$ is independently: halogen, —$C_1$-$C_{10}$ alkyl, —OH, or —$OC_1$-$C_4$ alkyl, wherein —$C_1$-$C_{10}$ alkyl is unsubstituted or substituted with one to three substituents independently selected from: —OH, halogen, cyano, and —$S(O)_2CH_3$. In another class of this embodiment, each occurrence of $R^f$ is independently: halogen, or —$C_1$-$C_{10}$ alkyl, wherein —$C_1$-$C_{10}$ alkyl is unsubstituted or substituted with one to three substituents independently selected from: —OH, halogen, cyano, and —$S(O)_2CH_3$. In another class of this embodiment, each occurrence of $R^f$ is independently: halogen. In another class of this embodiment, each occurrence of $R^f$ is independently: —$C_1$-$C_{10}$ alkyl, wherein —$C_1$-$C_{10}$ alkyl is unsubstituted or substituted with one to three substituents independently selected from: —OH, halogen, cyano, and —$S(O)_2CH_3$.

In another embodiment, each occurrence of $R^g$ is independently: hydrogen, —$C(O)R^e$, or —$C_1$-$C_{10}$ alkyl, wherein —$C_1$-$C_{10}$alkyl is unsubstituted or substituted with one to five fluorines. In a class of this embodiment, each occurrence of $R^g$ is independently: hydrogen, or —$C_1$-$C_{10}$ alkyl, wherein —$C_1$-$C_{10}$alkyl is unsubstituted or substituted with one to five fluorines. In another class of this embodiment, each occurrence of $R^g$ is independently: hydrogen, or —$C_1$-$C_{10}$ alkyl, wherein —$C_1$-$C_{10}$alkyl is unsubstituted or substituted with one to five fluorines. In another class of this embodiment, each occurrence of $R^g$ is independently: —$C_1$-$C_{10}$ alkyl, wherein —$C_1$-$C_{10}$alkyl is unsubstituted or substituted with one to five fluorines. In another class of this embodiment, each occurrence of $R^g$ is independently: hydrogen.

In another embodiment of the present invention, each occurrence of $R^h$ is independently: halogen, —$C_1$-$C_{10}$alkyl, —OH, —O$C_1$-$C_4$ alkyl, —S(O)$_m$$C_1$-$C_4$ alkyl, —CN, —$CF_3$, —$OCHF_2$, or —$OCF_3$; wherein —$C_1$-$C_{10}$ alkyl is unsubstituted or substituted with one to three substituents independently selected from: —OH, halogen, cyano, or —S(O)$_2$$CH_3$. In a class of this embodiment, each occurrence of $R^h$ is independently: halogen, —$C_1$-$C_{10}$alkyl, —OH, or —O$C_1$-$C_4$ alkyl, wherein —$C_1$-$C_{10}$ alkyl is unsubstituted or substituted with one to three substituents independently selected from: —OH, halogen, cyano, or —S(O)$_2$$CH_3$. In another class of this embodiment, each occurrence of $R^h$ is independently: halogen, or —$C_1$-$C_{10}$alkyl, wherein —$C_1$-$C_{10}$ alkyl is unsubstituted or substituted with one to three substituents independently selected from: —OH, halogen, cyano, or —S(O)$_2$$CH_3$. In another class of this embodiment, each occurrence of $R^h$ is independently: —$C_1$-$C_{10}$alkyl, wherein —$C_1$-$C_{10}$ alkyl is unsubstituted or substituted with one to three substituents independently selected from: —OH, halogen, cyano, or —S(O)$_2$$CH_3$. In another class of this embodiment, each occurrence of $R^h$ is independently: halogen.

In another embodiment of the present invention, each occurrence of $R^i$ is independently: —$C_1$-$C_8$ alkyl, —$C_2$-$C_8$ alkenyl, —$C_2$-$C_8$ alkynyl, halogen, —$OR^e$, —S(O)$_m$$R^e$, —S(O)$_m$$NR^c$$R^d$, —C(O)$R^e$, —OC(O)$R^e$, —C(O)$OR^e$, —CN, —C(O)$NR^c$$R^d$, —$NR^c$$R^d$, —($CH_2$)$_n$$NR^c$$R^d$; —$NR^c$C(O)$R^e$, —$NR^c$C(O)$OR^e$, —$NR^c$C(O)$NR^c$$R^d$, —$NR^c$S(O)$_m$$R^e$, =NH, —$CF_3$, —$OCF_3$, or —$OCHF_2$. In a class of this embodiment, each occurrence of $R^i$ is independently: —$C_1$-$C_8$ alkyl, -halogen, —$OR^e$, —OC(O)$R^e$, —C(O)$OR^e$, —CN, —$NR^c$$R^d$, —($CH_2$)$_n$$NR^c$$R^d$; =NH, —$CF_3$, —$OCF_3$, or —$OCHF_2$. In another class of this embodiment, each occurrence of $R^i$ is independently: —$C_1$-$C_6$alkyl, halogen, —$OR^e$, =NH, —$CF_3$, —$OCF_3$, or —$OCHF_2$. In another class of this embodiment, each occurrence of $R^i$ is independently: —$C_1$-$C_6$alkyl, halogen, —$OR^e$, or =NH. In another class of this embodiment, each occurrence of $R^i$ is independently: —$C_1$-$C_6$alkyl, or =NH. In another class of this embodiment, each occurrence of $R^i$ is —$C_1$-$C_3$alkyl. In another class of this embodiment, each occurrence of $R^i$ is =NH.

In another embodiment of the present invention, each occurrence of $R^j$ is independently hydrogen, $C_1$-$C_3$ alkyl, $OR^{10}$, =$NR^{10}$, $N(R^{10})_2$, or halogen, wherein $C_1$-$C_3$ alkyl unsubstituted or substituted with one to three $R^b$. In a class of this embodiment, each occurrence of $R^j$ is independently hydrogen, $C_1$-$C_3$ alkyl, or halogen, wherein $C_1$-$C_3$ alkyl unsubstituted or substituted with one to three $R^b$. In another class of this embodiment, each occurrence of $R^j$ is independently hydrogen, or $C_1$-$C_3$ alkyl, wherein $C_1$-$C_3$ alkyl unsubstituted or substituted with one to three $R^b$. In another class of this embodiment, each occurrence of $R^j$ is $C_1$-$C_3$ alkyl, wherein $C_1$-$C_3$ alkyl unsubstituted or substituted with one to three $R^b$. In another class of this embodiment, each occurrence of $R^j$ is hydrogen.

In another embodiment of the present invention, each n is independently 0, 1, 2, 3, 4, 5 or 6. In a class of this embodiment, each n is independently 0, 1, 2, 3 or 4. In another class of this embodiment, each n is independently 0, 1, 2, or 3. In another class of this embodiment, each n is independently 1, 2, or 3. In another class of this embodiment, each n is independently 1 or 3. In another class of this embodiment, n is 0 or 1. In another class of this embodiment, n is 1 or 2. In another class of this embodiment, n is 0 or 2. In another class of this embodiment, n is 0. In another class of this embodiment, n is 1. In another class of this embodiment, n is 2. In another class of this embodiment, n is 3. In another class of this embodiment, n is 4.

In another embodiment of the present invention, each m is independently 0, 1, or 2. In a class of this embodiment, m is 0 or 1. In another class of this embodiment, m is 1 or 2. In another class of this embodiment, m is 0 or 2. In another class of this embodiment, m is 0. In another class of this embodiment, m is 1. In another class of this embodiment, m is 2.

In another embodiment of the present invention, each p is independently 1 or 2. In another class of this embodiment, p is 0 or 2. In another class of this embodiment, p is 0. In another class of this embodiment, p is 1. In another class of this embodiment, p is 2.

In another embodiment of the present invention, each q is independently 0, 1, 2, 3, 4, 5 or 6. In a class of this embodiment, each q is independently 0, 1, or 2. In another class of this embodiment, q is 0 or 1. In another class of this embodiment, q is 1 or 2. In another class of this embodiment, q is 0 or 2. In another class of this embodiment, q is 0. In another class of this embodiment, q is 1. In another class of this embodiment, q is 2.

In another embodiment of the present invention, each s is independently 0, 1, 2, or 3. In a class of this embodiment, s is 0, 1, or 2. In another class of this embodiment, s is 0 or 1. In another class of this embodiment, s is 1 or 2. In another class of this embodiment, s is 0 or 2. In another class of this embodiment, s is 0. In another class of this embodiment, s is 1. In another class of this embodiment, s is 2. In another class of this embodiment, s is 3.

In another embodiment of the present invention, each t is independently 0, 1, 2, or 3. In a class of this embodiment, t is 0, 1, or 2. In another class of this embodiment, t is 0 or 1. In another class of this embodiment, t is 1 or 2. In another class of this embodiment, t is 0 or 2. In another class of this embodiment, t is 0. In another class of this embodiment, t is 1. In another class of this embodiment, t is 2. In another class of this embodiment, t is 3.

In another embodiment of the present invention, each u is independently 0, 1, 2, 3, 4, 5 or 6. In a class of this embodiment, each u is independently 0, 1, 2, or 3. In another class of this embodiment, u is 0, 1, or 2. In another class of this embodiment, u is 0 or 1. In another class of this embodiment, u is 1 or 2. In another class of this embodiment, u is 0 or 2. In another class of this embodiment, u is 0. In another class of this embodiment, u is 1. In another class of this embodiment, u is 2. In another class of this embodiment, u is 3.

In another embodiment of the present invention, each v is independently 0, 1, or 2. In a class of this embodiment, v is 0 or 1. In another class of this embodiment, v is 1 or 2. In another class of this embodiment, v is 0 or 2. In another class of this embodiment, v is 0. In another class of this embodiment, v is 1. In another class of this embodiment, v is 2.

In another embodiment of the present invention, the invention relates to compounds of structural formula Ia:

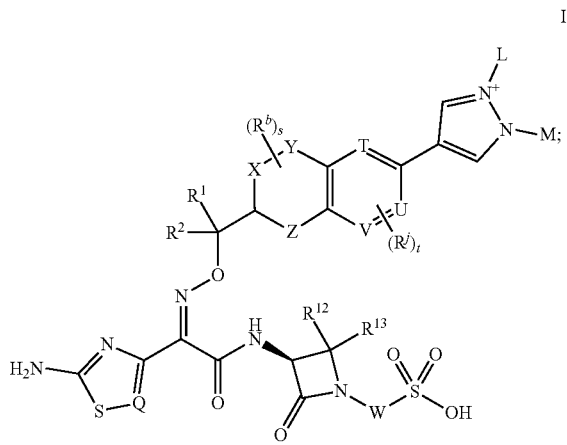

Ia or a pharmaceutically acceptable salt thereof.

In another embodiment of the present invention, the invention relates to compounds of structural formula Ib:

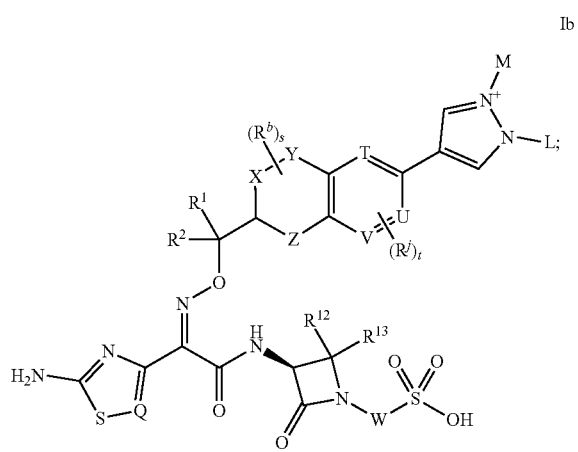

Ib or a pharmaceutically acceptable salt thereof.

In another embodiment of the present invention, the invention relates to compounds of structural formula Ic:

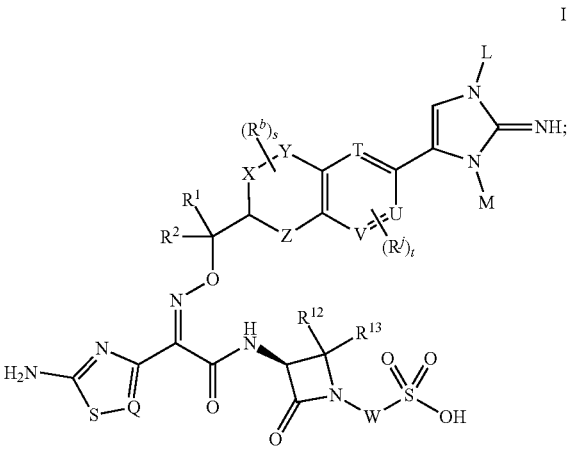

Ic or a pharmaceutically acceptable salt thereof.

In another embodiment of the present invention, the invention relates to compounds of structural formula Id:

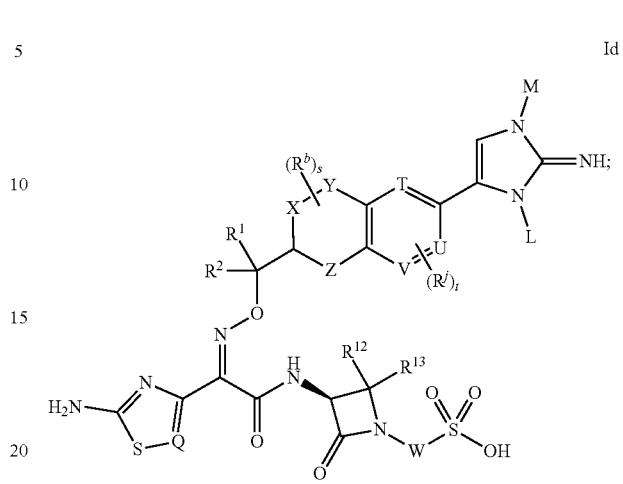

Id or a pharmaceutically acceptable salt thereof.

In another embodiment of the present invention, the invention relates to compounds of structural formula Ie:

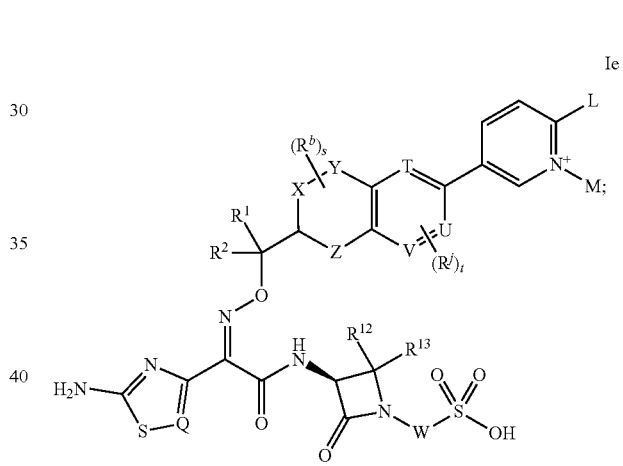

Ie or a pharmaceutically acceptable salt thereof.

In another embodiment of the present invention, the invention relates to compounds of structural formula Ie:

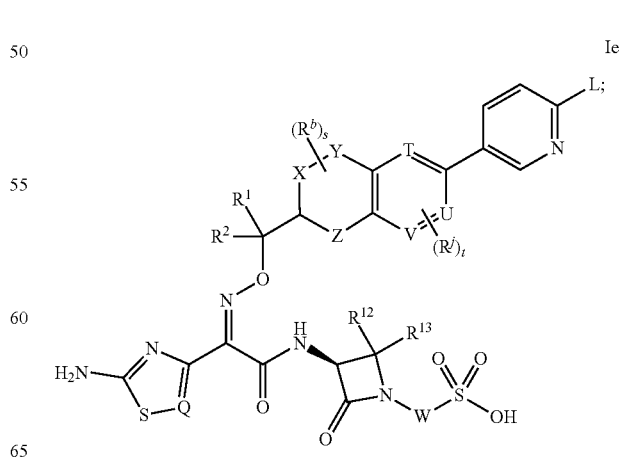

Ie or a pharmaceutically acceptable salt thereof.

In another embodiment of the present invention, the invention relates to compounds of structural formula Ig:

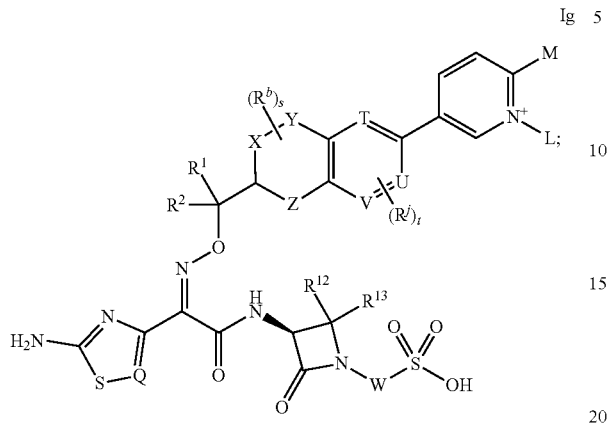

or a pharmaceutically acceptable salt thereof.

In another embodiment of the present invention, the invention relates to compounds of structural formula Ih:

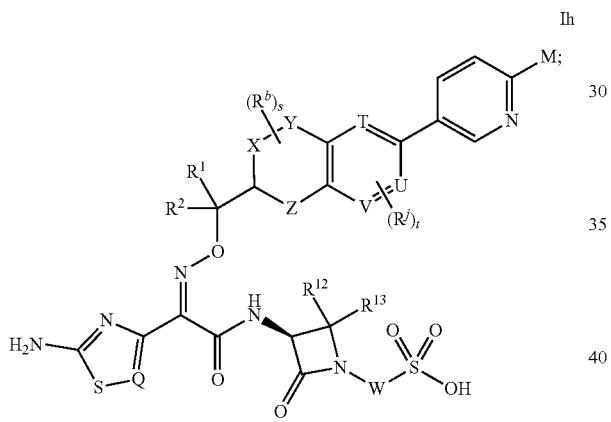

or a pharmaceutically acceptable salt thereof.

In another embodiment of the present invention, the invention relates to compounds of structural formula Ii:

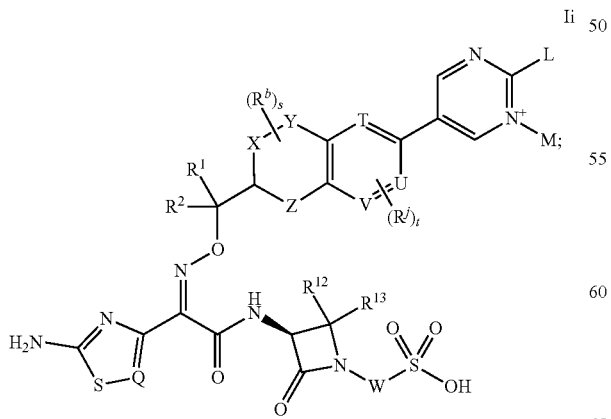

or a pharmaceutically acceptable salt thereof.

In another embodiment of the present invention, the invention relates to compounds of structural formula Ij:

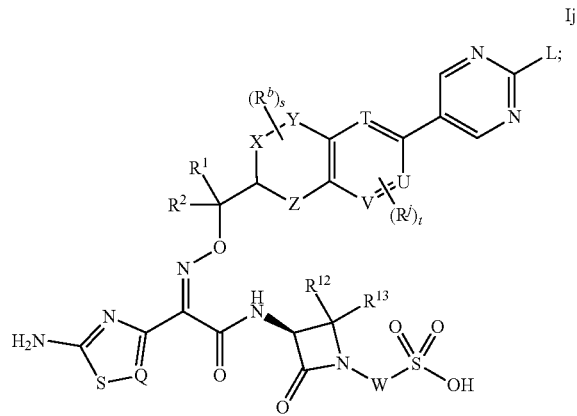

or a pharmaceutically acceptable salt thereof.

In another embodiment of the present invention, the invention relates to compounds of structural formula Ik:

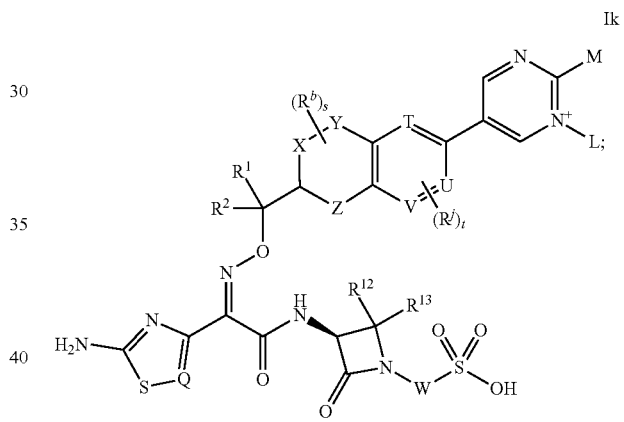

or a pharmaceutically acceptable salt thereof.

In another embodiment of the present invention, the invention relates to compounds of structural formula Il:

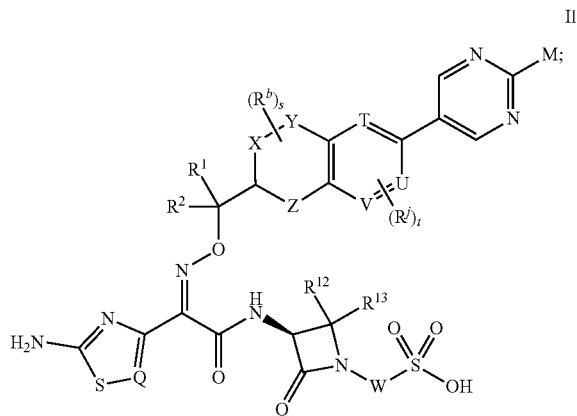

or a pharmaceutically acceptable salt thereof.

In another embodiment of the present invention, the invention relates to compounds of structural formula Im:

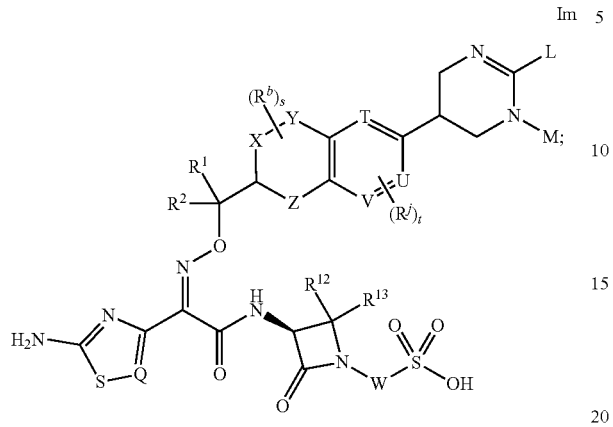

Im or a pharmaceutically acceptable salt thereof.

In another embodiment of the present invention, the invention relates to compounds of structural formula In:

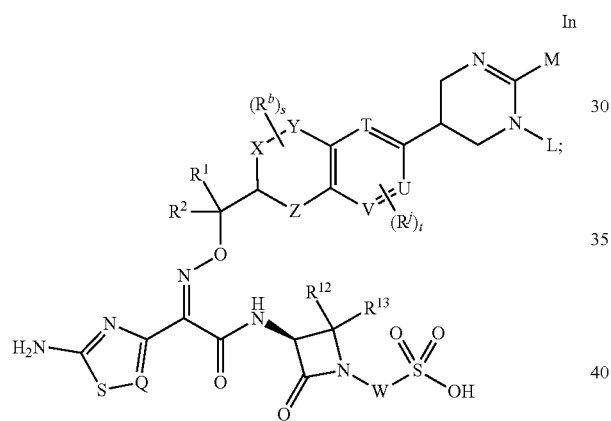

In or a pharmaceutically acceptable salt thereof.

In another embodiment of the present invention, the invention relates to compounds of structural formula Io:

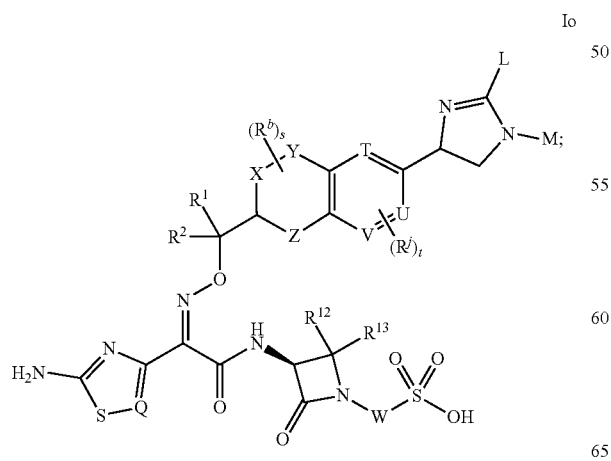

Io or a pharmaceutically acceptable salt thereof.

In another embodiment of the present invention, the invention relates to compounds of structural formula Ip:

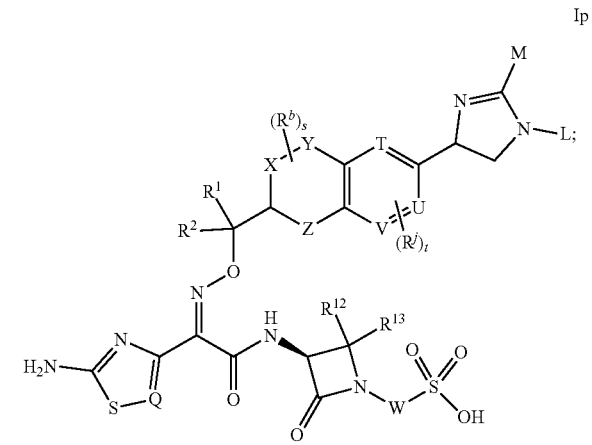

Ip or a pharmaceutically acceptable salt thereof.

In another embodiment of the present invention, the invention relates to compounds of structural formula Iq:

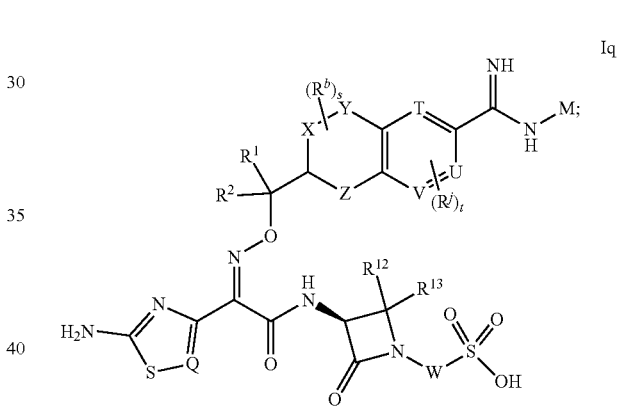

Iq or a pharmaceutically acceptable salt thereof.

In another embodiment of the present invention, the invention relates to compounds of structural formula Ir:

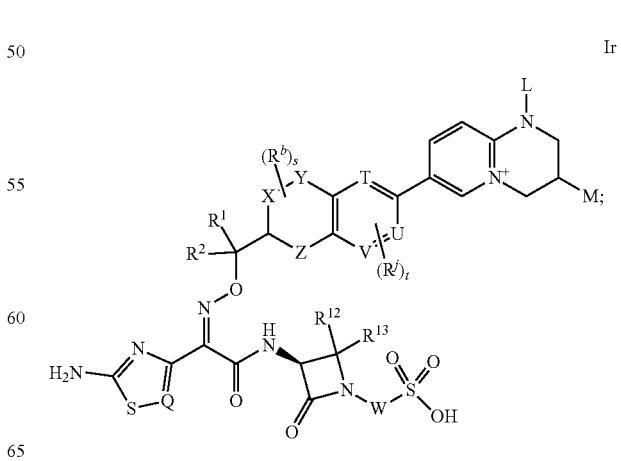

Ir or a pharmaceutically acceptable salt thereof.

In another embodiment of the present invention, the invention relates to compounds of structural formula Is:

Is

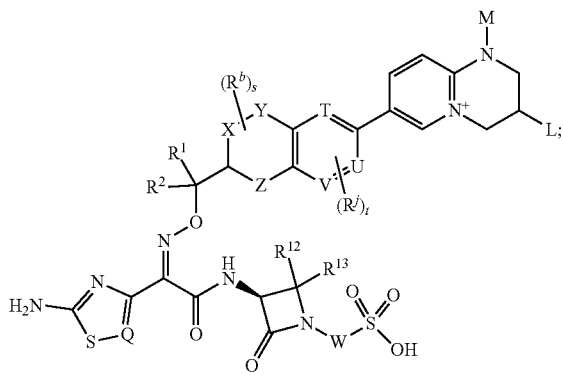

or a pharmaceutically acceptable salt thereof.

The compound of structural formula I includes the compounds of structural formulas Ia, Ib, Ic, Id, Ie, If, Ig, Ih, Ii, Ij, Ik, Il, Im, In, Io, Ip, Iq, Ir and Is, and pharmaceutically acceptable salts, hydrates and solvates thereof.

Another embodiment of the present invention relates to compounds of structural formula I wherein:
T, U and V are CH;
W is O;
Q is $CR^3$;
X is $CH_2$;
Y is O or $CH_2$;
Z is O or $CH_2$;
$R^1$ and $R^2$ are independently selected from:
  1) hydrogen,
  2) —$C_1$-$C_8$ alkyl, and
  3) —C(O)$OR^e$,
wherein —$C_1$-$C_8$ alkyl is unsubstituted or substituted with one to three $R^a$, provided that if $R^1$ is —C(O)$OR^e$, then $R^2$ is independently selected from hydrogen and —$C_1$-$C_8$ alkyl;
$R^3$ is hydrogen;
$R^{12}$ and $R^{13}$ are independently $C_1$-$C_3$ alkyl, wherein $C_1$-$C_3$ alkyl is unsubstituted or substituted with one to seven fluorines, or alternatively $R^{12}$ and $R^{13}$ together with the carbon to which they are attached form a monocyclic $C_4$-$C_6$ cycloalkyl unsubstituted or substituted with one to three substituents independently selected from —F, —OH and —$OC_1$-$C_3$alkyl;
A is
  1) —C(=NH)—NH,
  2) AryC, or
  3) HetC,
wherein A is unsubstituted or substituted with one to four $R^i$;
L is
  1) absent, or
  2) $R^4$,
wherein L is unsubstituted or substituted with 1-4 substituents selected from $R^e$;
each occurrence of $R^4$ is independently:
  1) hydrogen,
  2) —$C_1$-$C_{10}$ alkyl,
  3) —$(CH_2)_n OR^e$,
  4) —$(CH_2)_n NR^c R^d$, or
  5) —$C_1$-$C_{10}$alkylene-HetB,
wherein $R^4$ is unsubstituted or substituted with one to four $R^6$;

M is
  1) $R^5$, or
  2) —$NHR^5$,
wherein M is unsubstituted or substituted with 1-4 substituents selected from $R^6$; and
$R^5$ is
  1) hydrogen,
  2) —$C_1$-$C_6$ alkyl,
  3) —$C_1$-$C_4$alkyl-$(NR^c R^d)_2$,
  4) —$(CH_2)_u NR^c R^d$ or
  5) —$C_1$-$C_{10}$alkylene-HetB,
wherein $R^5$ is unsubstituted or substituted with one to four $R^6$;
or a pharmaceutically acceptable salt thereof.

In a class of this embodiment, $R^1$ and $R^2$ are independently selected from
  1) —$CH_3$, and
  2) —$CO_2H$,
wherein —$CH_3$ is unsubstituted or substituted with one to three $R^a$, provided that if $R^1$ is —$CO_2H$, then $R^2$ is —$CH_3$, and if $R^2$ is —$CO_2H$, then $R^1$ is —$CH_3$.

Another embodiment of the present invention relates to compounds of structural formula I wherein:
T, U and V are CH;
W is O;
Q is $CR^3$;
$R^3$ is hydrogen;
X is $CH_2$;
Y is $CH_2$;
Z is O;
$R^1$ and $R^2$ are independently selected from
  1) —$C_1$-$C_6$ alkyl, and
  2) —C(O)$OR^e$,
wherein —$C_1$-$C_6$ alkyl is unsubstituted or substituted with one to three $R^a$, provided that if $R^1$ is —C(O)$OR^e$, then $R^2$ is —$C_1$-$C_6$ alkyl;
$R^{12}$ and $R^{13}$ are independently $C_1$-$C_3$ alkyl, wherein $C_1$-$C_3$ alkyl is unsubstituted or substituted with one to seven fluorines;
A is AryC or HetC, wherein A is unsubstituted or substituted with one to four $R^i$;
L is
  1) absent, or
  2) $R^4$,
wherein L is unsubstituted or substituted with 1-4 substituents selected from $R^e$;
each occurrence of $R^4$ is independently:
  1) —$C_1$-$C_{10}$ alkyl,
  2) —$(CH_2)_n NR^c R^d$, or
  3) —$C_1$-$C_{10}$alkylene-HetB,
wherein $R^4$ is unsubstituted or substituted with one to four $R^6$;
M is
  1) $R^5$, or
  2) —$NHR^5$,
wherein M is unsubstituted or substituted with 1-4 substituents selected from $R^6$;
$R^5$ is
  1) —$C_1$-$C_4$alkyl-$(NR^c R^d)_2$, or
  2) —$(CH_2)_u NR^c R^d$,
wherein $R^5$ is unsubstituted or substituted with one to four $R^6$;
or a pharmaceutically acceptable salt thereof.

In a class of this embodiment, $R^1$ and $R^2$ are independently selected from
  1) —$CH_3$, and
  2) —$CO_2H$, wherein —CH$_3$ is unsubstituted or substituted with one to three R$^a$, provided that if R$^1$ is —CO$_2$H, then R$^2$ is —CH$_3$, and if R$^2$ is —CO$_2$H, then R$^1$ is —CH$_3$.

Another embodiment of the present invention relates to compounds of structural formula I wherein:
T, U and V are CH;
W is O;
Q is CR$^3$;
X is CH$_2$;
Y is CH$_2$ or O;
Z is CH$_2$ or O;
R$^1$ and R$^2$ are independently selected from:
1) hydrogen,
2) —C$_1$-C$_8$ alkyl, and
3) —C(O)OR$^e$,
wherein —C$_1$-C$_8$ alkyl is unsubstituted or substituted with one to three R$^a$, provided that if R$^1$ is —C(O)OR$^e$, then R$^2$ is independently selected from hydrogen and —C$_1$-C$_8$ alkyl;
R$^3$ is hydrogen;
R$^{12}$ and R$^{13}$ are independently C$_1$-C$_3$ alkyl, wherein C$_1$-C$_3$ alkyl is unsubstituted or substituted with one to seven fluorines,
or alternatively R$^{12}$ and R$^{13}$ together with the carbon to which they are attached form a monocyclic C$_4$-C$_6$ cycloalkyl unsubstituted or substituted with one to three substituents independently selected from —F, —OH and —OC$_1$-C$_3$alkyl;
A is HetC, wherein HetC is unsubstituted or substituted with one to four R$^i$;
L is
1) absent, or
2) R$^4$,
wherein L is unsubstituted or substituted with 1-4 substituents selected from R$^e$;
each occurrence of R$^4$ is independently:
1) hydrogen,
2) —C$_1$-C$_{10}$ alkyl,
3) —(CH$_2$)$_n$OR$^e$,
4) —(CH$_2$)$_n$NR$^c$R$^d$, or
5) —C$_1$-C$_{10}$alkylene-HetB,
wherein R$^4$ is unsubstituted or substituted with one to four R$^6$;
M is
1) R$^5$, or
2) —NHR$^5$,
wherein M is unsubstituted or substituted with 1-4 substituents selected from R$^6$; and
R$^5$ is
1) hydrogen,
2) —C$_1$-C$_6$ alkyl,
3) —C$_1$-C$_4$alkyl-(NR$^c$R$^d$)$_2$,
4) —(CH$_2$)$_u$NR$^c$R$^d$ or
5) —C$_1$-C$_{10}$alkylene-HetB,
wherein R$^5$ is unsubstituted or substituted with one to four R$^6$;
or a pharmaceutically acceptable salt thereof.

In a class of this embodiment, R$^1$ and R$^2$ are independently selected from
1) —CH$_3$, and
2) —CO$_2$H,
wherein —CH$_3$ is unsubstituted or substituted with one to three R$^a$, provided that if R$^1$ is —CO$_2$H, then R$^2$ is —CH$_3$, and if R$^2$ is —CO$_2$H, then R$^1$ is —CH$_3$.

Another embodiment of the present invention relates to compounds of structural formula I wherein:
T, U and V are CH;
W is O;
Q is CR$^3$;
R$^3$ is hydrogen;
X is CH$_2$;
Y is CH$_2$;
Z is O;
R$^1$ and R$^2$ are independently selected from
1) —C$_1$-C$_6$ alkyl, and
2) —C(O)OR$^e$,
wherein —C$_1$-C$_6$ alkyl is unsubstituted or substituted with one to three R$^a$, provided that if R$^1$ is —C(O)OR$^e$, then R$^2$ is —C$_1$-C$_6$ alkyl;
R$^{12}$ and R$^{13}$ are independently C$_1$-C$_3$ alkyl, wherein C$_1$-C$_3$ alkyl is unsubstituted or substituted with one to seven fluorines;
A is HetC, wherein HetC is unsubstituted or substituted with one to four R$^i$;
L is R$^4$;
R$^4$ is —(CH$_2$)$_n$NR$^c$R$^d$, wherein R$^4$ is unsubstituted or substituted with one to four R$^6$;
M is R$^5$;
R$^5$ is —(CH$_2$)$_u$NR$^c$R$^d$, wherein R$^5$ is unsubstituted or substituted with one to four R$^6$;
or a pharmaceutically acceptable salt thereof.

In a class of this embodiment, R$^1$ and R$^2$ are independently selected from
1) —CH$_3$, and
2) —C$_{O2}$H,
wherein —CH$_3$ is unsubstituted or substituted with one to three R$^a$, provided that if R$^1$ is —CO$_2$H, then R$^2$ is —CH$_3$, and if R$^2$ is —CO$_2$H, then R$^1$ is —CH$_3$.

Illustrative, but non-limiting, examples of the compounds of the present invention are the following compounds:

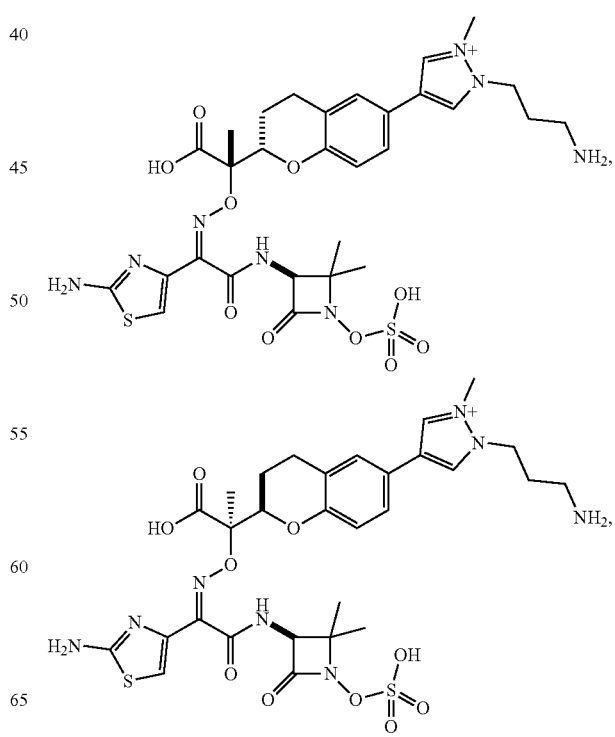

41
-continued
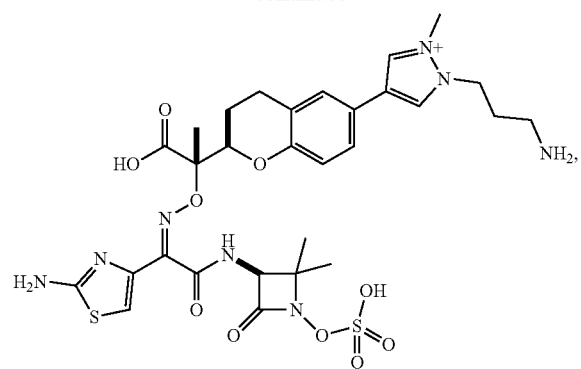
42
-continued
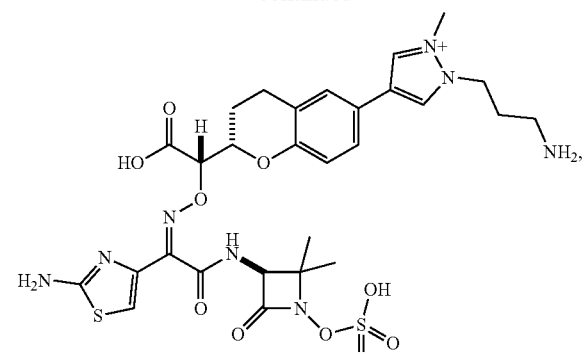

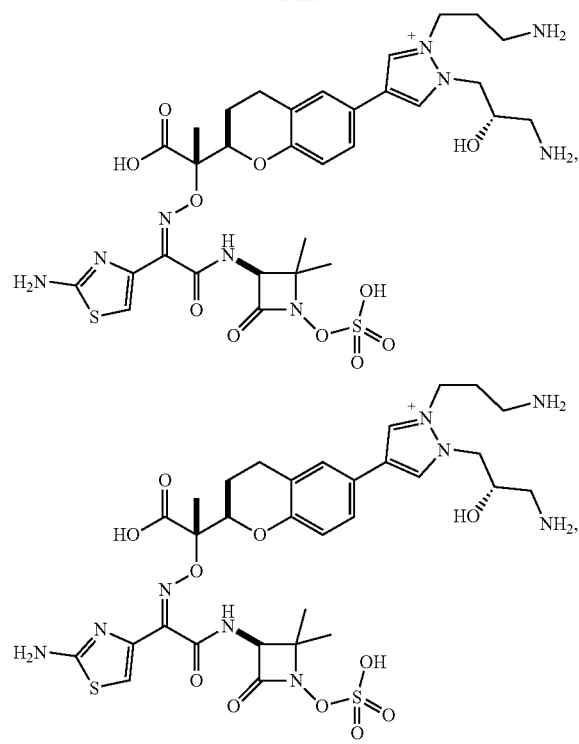
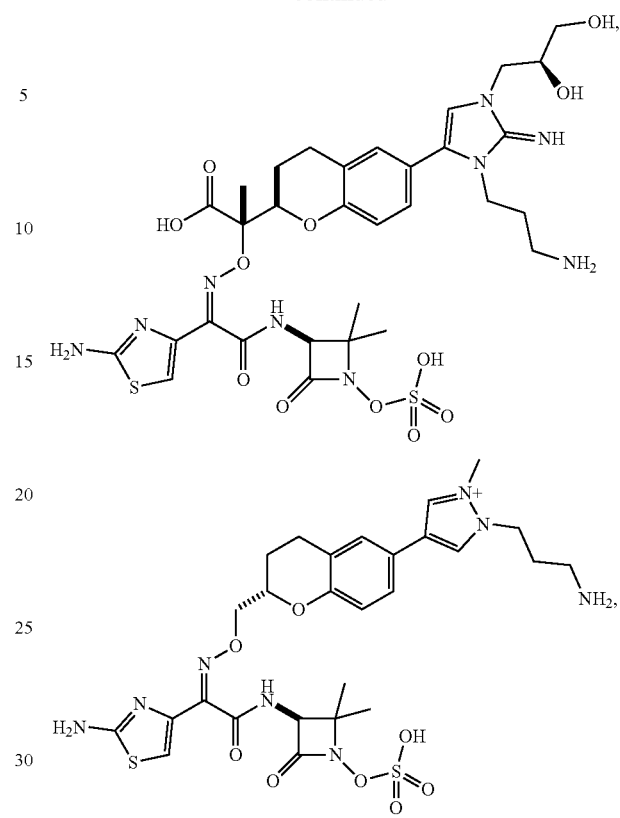
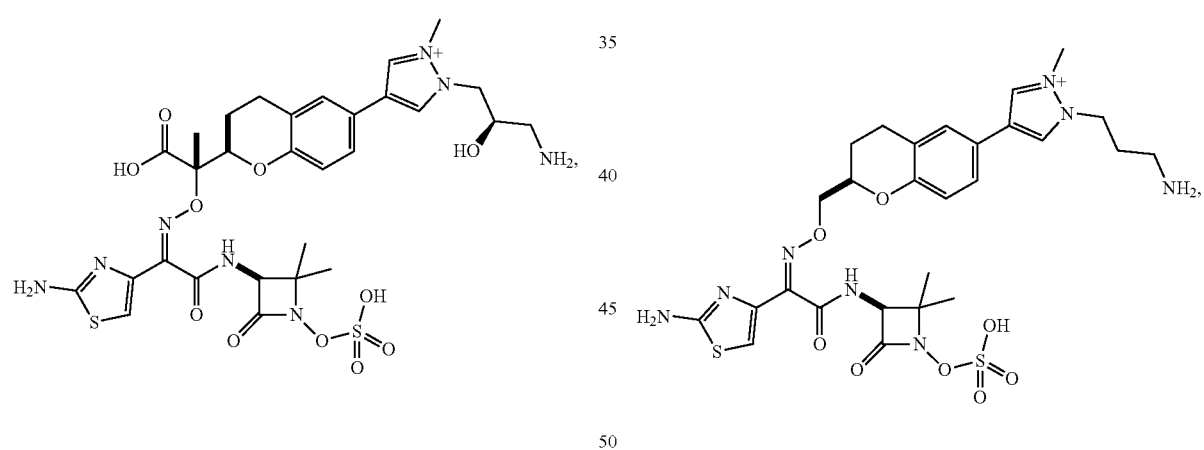
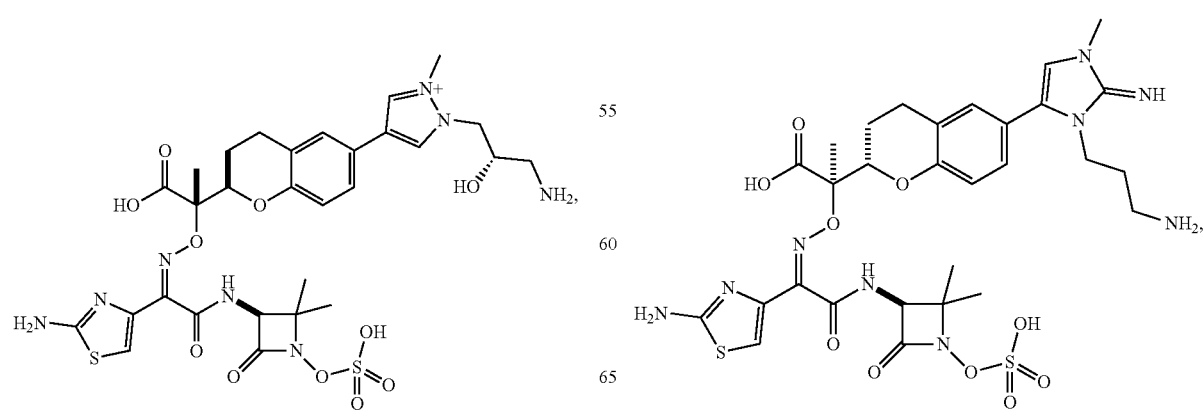

45
-continued
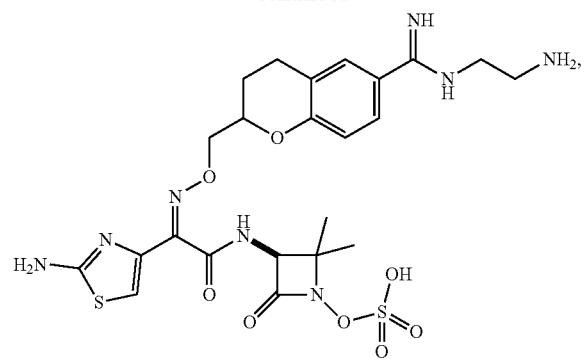
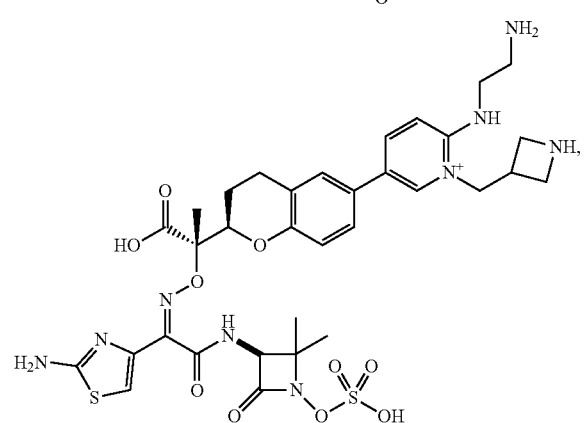
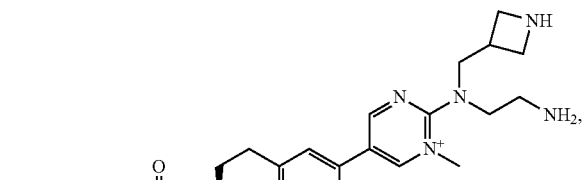
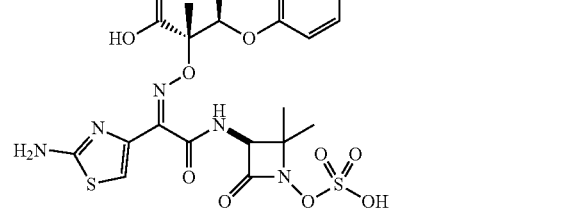
46
-continued
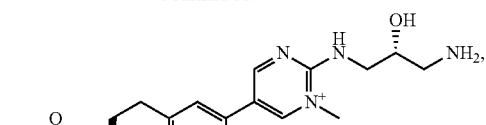
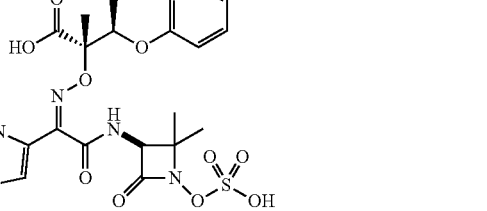
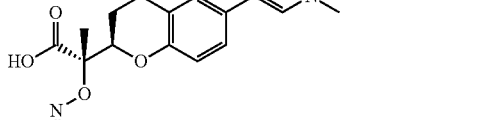
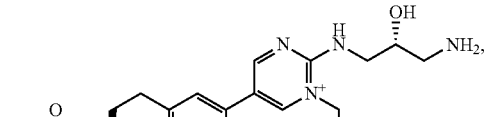
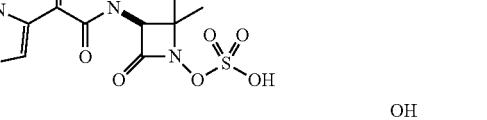
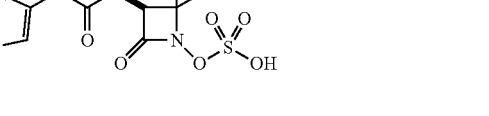
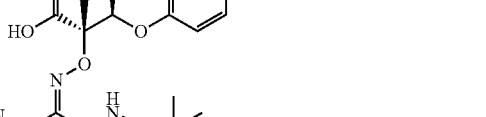

47
-continued
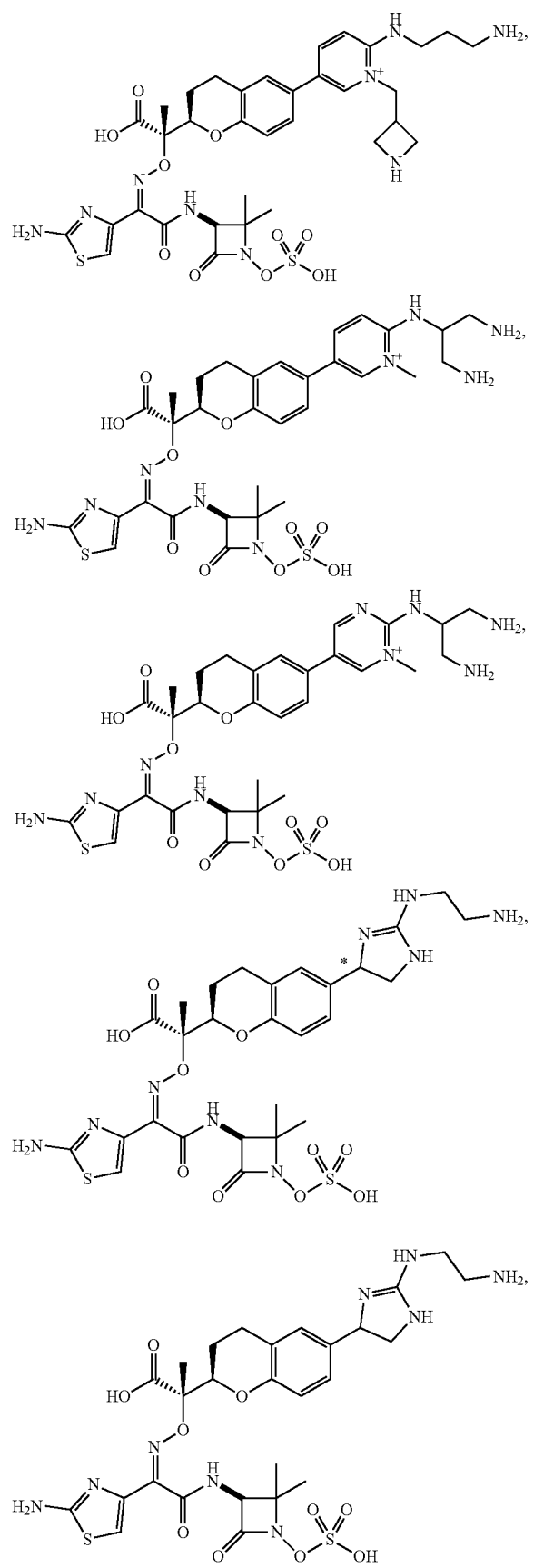
48
-continued
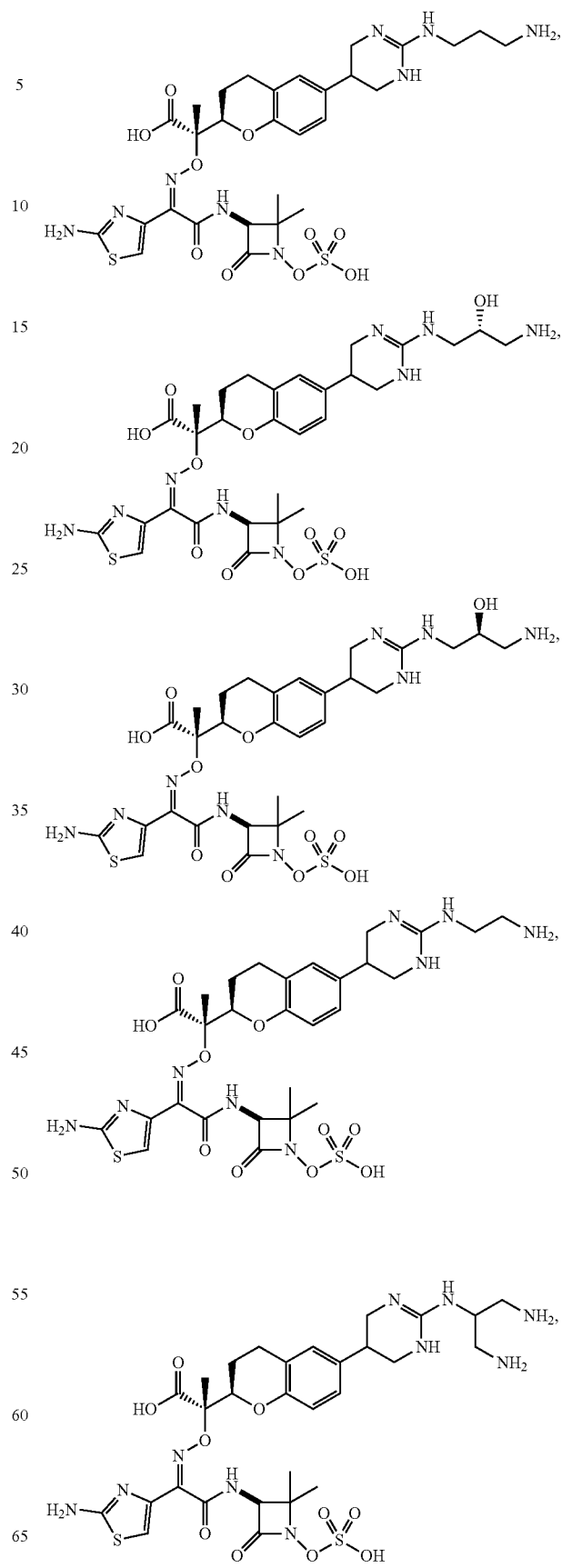

49
-continued
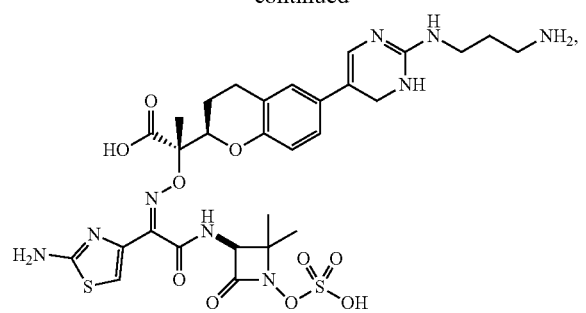
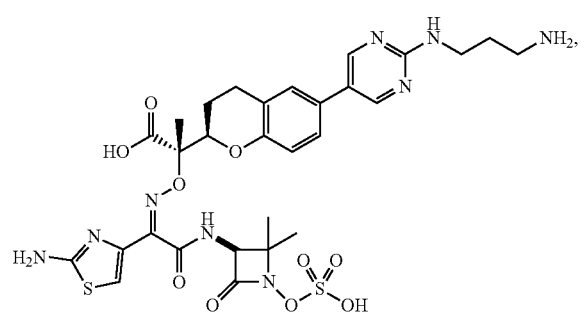
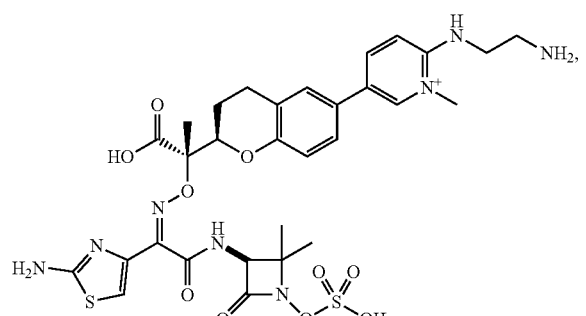
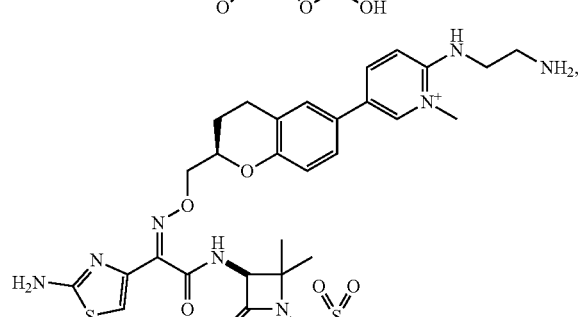
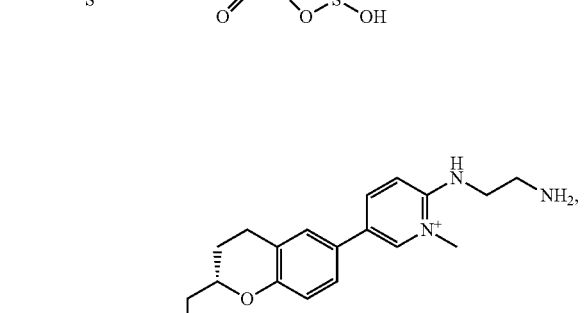
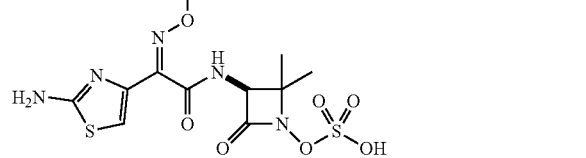
50
-continued
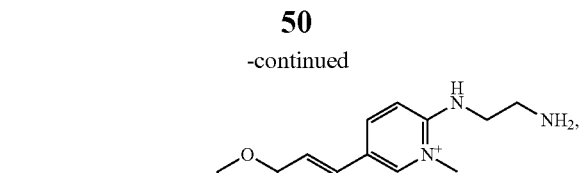
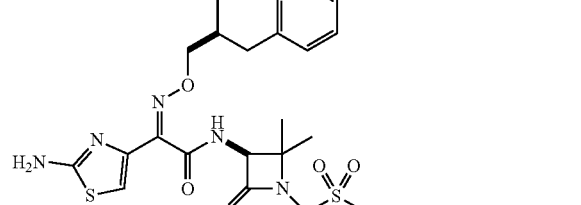
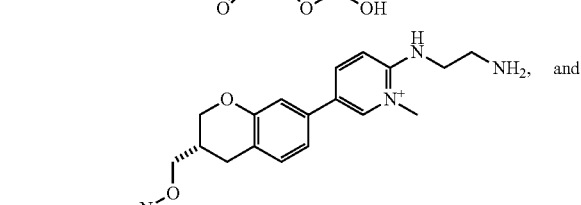
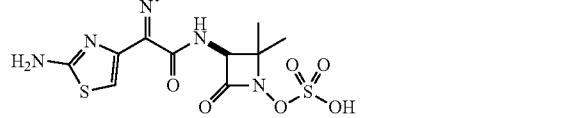
and
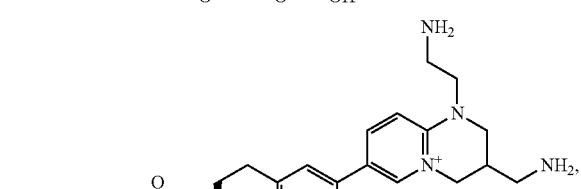
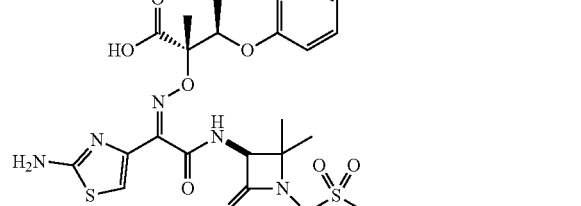
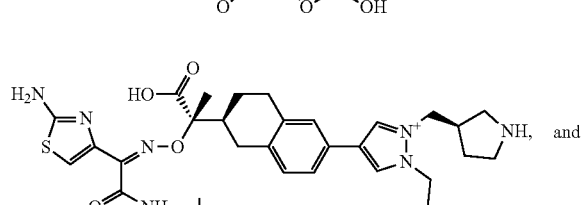
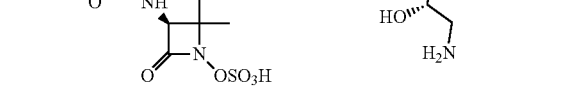
and
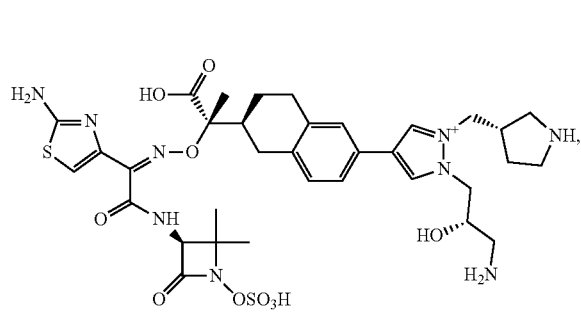
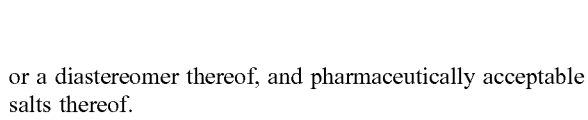
or a diastereomer thereof, and pharmaceutically acceptable salts thereof.

Illustrative, but non-limiting, examples of the compounds of the present invention are the following compounds:
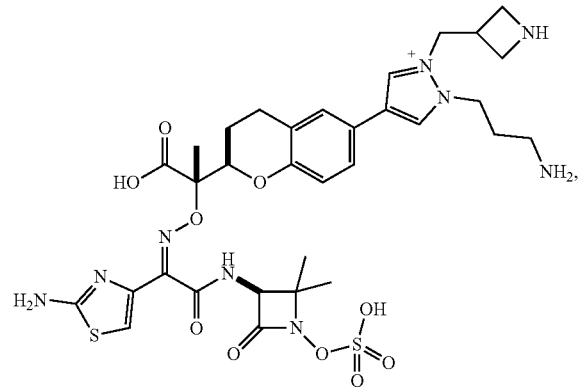
5
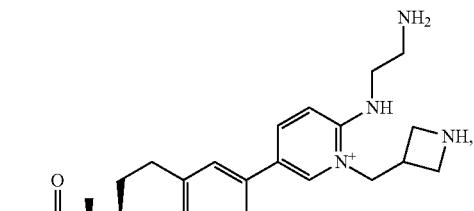
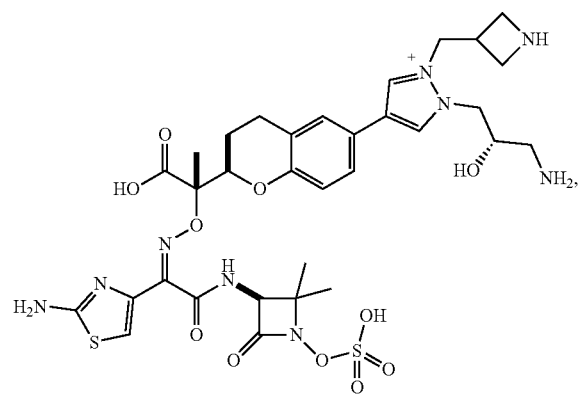
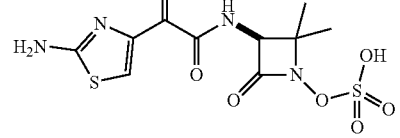
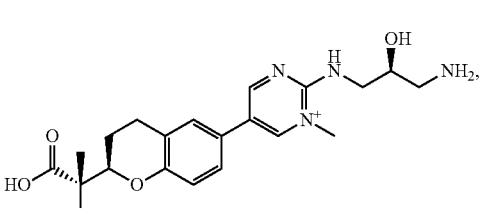
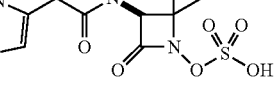
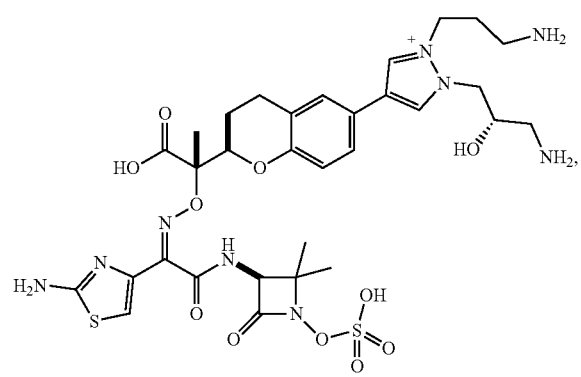
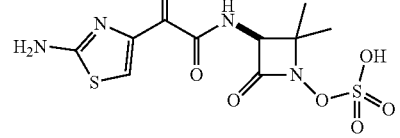
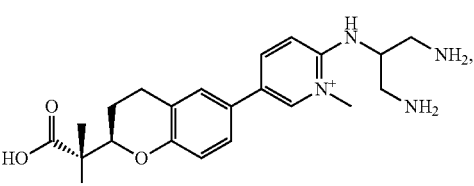
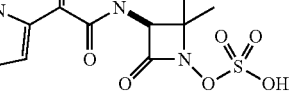
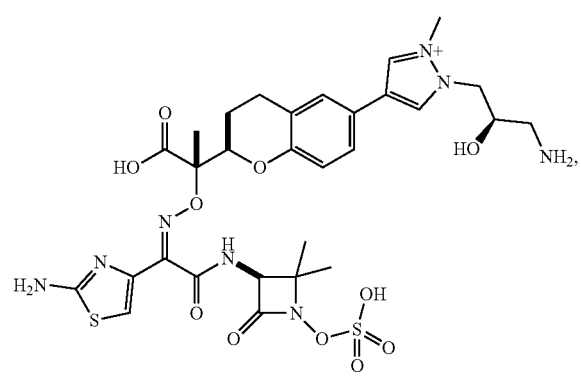
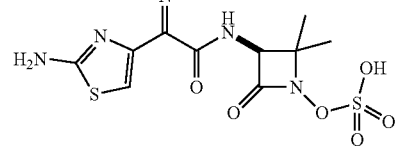
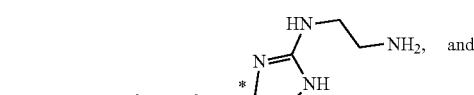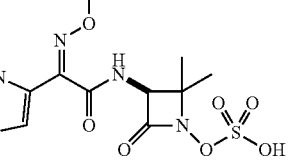

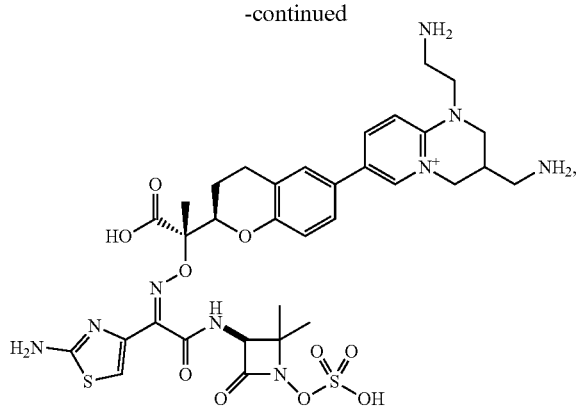

or a diastereomer thereof, and pharmaceutically acceptable salts thereof.

Other embodiments of the present invention include the following:
(a) A pharmaceutical composition comprising an effective amount of a compound of Formula (I) as defined herein, or a pharmaceutically acceptable salt thereof, and a pharmaceutically acceptable carrier.
(b) The pharmaceutical composition of (a), further comprising a second compound, wherein the second compound is a beta-lactamase inhibitor.
(c) The pharmaceutical composition of (b), wherein the second compound is selected from the group consisting of: relebactam, tazobactam, clavulanic acid, sulbactam, and avibactam, or a pharmaceutically acceptable salt thereof.
(d) A pharmaceutical composition comprising (i) a compound of Formula (I), or a pharmaceutically acceptable salt thereof, and (ii) a second compound, wherein the second compound is an beta-lactamase inhibitor compound, wherein the compound of Formula (I), and the second compound are each employed in an amount that renders the combination effective for treating or preventing bacterial infection.
(e) The combination of (d), wherein the second compound is selected from the group consisting of: relebactam, tazobactam, clavulanic acid, sulbactam, and avibactam, or a pharmaceutically acceptable salt thereof.
(f) A method for treating a bacterial infection in a subject which comprises administering to a subject in need of such treatment an effective amount of a compound of Formula (I), or a pharmaceutically acceptable salt thereof.
(g) A method for preventing and/or treating a bacterial infection which comprises administering to a subject in need of such treatment a pharmaceutical composition comprising an effective amount of a compound of Formula (I), or a pharmaceutically acceptable salt thereof, and a pharmaceutically acceptable carrier.
(h) A method for treating a bacterial infection which comprises administering to a subject in need of such treatment a therapeutically effective amount of the composition of (a), (b), (c), (d), or (e).
(i) The method of treating a bacterial infection as set forth in (f), (g), or (h), wherein the bacterial infection is due to Gram negative bacteria
(j) The method of treating a bacterial infection as set forth in (f), (g), (h), or (i), wherein the bacterial infection is due to *Pseudomonas aeruginosa* or *Acinetobacter baumannii*.
The present invention also includes a compound of Formula (I), or a pharmaceutically acceptable salt thereof, (i) for use in, (ii) for use as a medicament for, or (iii) for use in the preparation (or manufacture) of a medicament for, medicine or treating bacterial infection, including infection with a multidrug resistant bacterial strain. In these uses, the compounds of the present invention can optionally be employed in combination with one or more second therapeutic agents including relebactam, tazobactam, clavulanic acid, sulbactam, and avibactam, or a pharmaceutically acceptable salt thereof.

Additional embodiments of the invention include the pharmaceutical compositions, combinations and methods set forth in (a)-(j) above and the uses set forth in the preceding paragraph, wherein the compound of the present invention employed therein is a compound of one of the embodiments, sub-embodiments, classes or sub-classes described above. The compound may optionally be used in the form of a pharmaceutically acceptable salt in these embodiments.

In the embodiments of the compounds and salts provided above, it is to be understood that each embodiment may be combined with one or more other embodiments, to the extent that such a combination provides a stable compound or salt and is consistent with the description of the embodiments. It is further to be understood that the embodiments of compositions and methods provided as (a) through (j) above are understood to include all embodiments of the compounds and/or salts, including such embodiments as result from combinations of embodiments.

Additional embodiments of the present invention include each of the pharmaceutical compositions, combinations, methods and uses set forth in the preceding paragraphs, wherein the compound of the present invention or its salt employed therein is substantially pure. With respect to a pharmaceutical composition comprising a compound of Formula (I) or its salt and a pharmaceutically acceptable carrier and optionally one or more excipients, it is understood that the term "substantially pure" is in reference to a compound of Formula (I) or its salt per se; i.e., the purity of this active ingredient in the composition.

Definitions and Abbreviations

The terms used herein have their ordinary meaning and the meaning of such terms is independent at each occurrence thereof. That notwithstanding and except where stated otherwise, the following definitions apply throughout the specification and claims.

Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc.

As used herein, and throughout this disclosure, the following terms, unless otherwise indicated, shall be understood to have the following meanings:

The term "β-lactamase inhibitor" refers to a compound which is capable of inhibiting enzyme activity from β-lactamases. As used herein, inhibiting β-lactamase activity means inhibiting the activity of a class A, C, and/or D β-lactamase. For antimicrobial applications inhibition at a 50% inhibitory concentration is preferably achieved at or below about 100 micrograms/mL, or at or below about 50 micrograms/mL, or at or below about 25 micrograms/mL. The terms "class A", "class B", "class C", and "class D" β-lactamases are understood by those skilled in the art and are described in S. G. Waley, β-lactamase: mechanisms of action, in The Chemistry of 13-Lactams, M. I. Page, Ed.; Chapman and Hall, London, (1992) 198-228.

The term "metallo-β-lactamase" denotes a metalloprotein capable of inactivating a β-lactam antibiotic. The β-lactamase can be an enzyme which catalyzes the hydrolysis of the β-lactam ring of a β-lactam antibiotic. Of particular interest herein are microbial metallo-β-lactamases. The metallo-β-lactamase can be, for example, a zinc metallo-β-lactamase. β-Lactamases of interest include those disclosed in, e.g., S. G. Waley, β-lactamase: mechanisms of action, in The Chemistry of β-Lactams, M. I. Page, Ed.; Chapman and Hall, London, (1992) 198-228. β-Lactamases of particular interest herein include metallo-β-lactamases of *Escherichia coli* (such as New Delhi Metallo-J-lactamase, NDM), *Serratia marcescens* (such as IMP), and *Klebsiella* spp. (such as Verona integron-encoded metallo-3-lactamase, VIM).). Additional metallo-β-lactamases of interest herein include SPM-, GIM-, SIM-, KHM-, AIM-, DIM-, SMB-, TMB-, and FIM-type enzymes.

The term "antibiotic" refers to a compound or composition which decreases the viability of a microorganism, or which inhibits the growth or proliferation of a microorganism. The phrase "inhibits the growth or proliferation" means increasing the generation time (i.e., the time required for the bacterial cell to divide or for the population to double) by at least about 2-fold. Preferred antibiotics are those which can increase the generation time by at least about 10-fold or more (e.g., at least about 100-fold or even indefinitely, as in total cell death). As used in this disclosure, an antibiotic is further intended to include an antimicrobial, bacteriostatic, or bactericidal agent. Examples of antibiotics include penicillins, cephalosporins and carbapenems.

The term "β-lactam antibiotic" refers to a compound with antibiotic properties that contains a β-lactam functionality. Non-limiting examples of β-lactam antibiotics include penicillins, cephalosporins, penems, carbapenems, and monobactams.

The term "about", when modifying the quantity (e.g., kg, L, or equivalents) of a substance or composition, or the value of a physical property, or the value of a parameter characterizing a process step (e.g., the temperature at which a process step is conducted), or the like refers to variation in the numerical quantity that can occur, for example, through typical measuring, handling and sampling procedures involved in the preparation, characterization and/or use of the substance or composition; through inadvertent error in these procedures; through differences in the manufacture, source, or purity of the ingredients employed to make or use the compositions or carry out the procedures; and the like. In certain embodiments, "about" can mean a variation of +0.1, 0.2, 0.3, 0.4, 0.5, 1.0, 2.0, 3.0, 4.0, or 5.0 of the appropriate unit. In certain embodiments, "about" can mean a variation of +1%, 2%, 3%, 4%, 5%, 10%, or 20%.

Another embodiment of the present invention is a compound of Formula (I), or a pharmaceutically acceptable salt thereof, as originally defined or as defined in any of the foregoing embodiments, sub-embodiments, aspects, classes or sub-classes, wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula (I) or its salt (e.g., the product isolated from a reaction mixture affording the compound or salt) consists of the compound or salt. The level of purity of the compounds and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined, then the method providing the highest level of purity governs. A compound or salt of 100% purity is one which is free of detectable impurities as determined by a standard method of analysis.

With respect to a compound of the invention which has one or more asymmetric centers and can occur as mixtures of stereoisomers, a substantially pure compound can be either a substantially pure mixture of the stereoisomers or a substantially pure individual diastereomer or enantiomer unless expressly depicted otherwise. The present invention encompasses all stereoisomeric forms of the compounds of Formula (I). Unless a specific stereochemistry is indicated, the present invention is meant to comprehend all such isomeric forms of these compounds. Centers of asymmetry that are present in the compounds of Formula (I) can all independently of one another have (R) configuration or (S) configuration.

When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula (I) or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. Unless a particular isomer, salt, solvate (including hydrates) or solvated salt of such racemate, enantiomer, diastereomer or tautomer is indicated, the present invention includes all such isomers, as well as salts, solvates (including hydrates) and solvated salts of such racemates, enantiomers, diastereomers and tautomers and mixtures thereof.

"Ac" is acetyl, which is $CH_3C(=O)-$.

"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkylene" or "alkyl" as used herein, refers to an alkyl group, as defined above, wherein one of the alkyl group's hydrogen atoms has been replaced with a bond. Non-limiting examples of alkylene groups include $-CH_2-$, $-CH_2CH_2-$, $-CH_2CH_2CH_2-$, $-CH_2CH_2CH_2CH_2-$, $-CH(CH_3)CH_2CH_2-$, $-CH(CH_3)-$ and $-CH_2CH(CH_3)CH_2-$. In one embodiment, an alkylene group has from 1 to about 6 carbon atoms. In one embodiment, an alkylene group has from 1 to about 3 carbon atoms. In another embodiment, an alkylene group is branched. In another embodiment, an alkylene group is linear. In one embodiment, an alkylene group is $-CH_2-$. The term "$C_1$-$C_6$ alkylene" refers to an alkylene group having from 1 to 6 carbon atoms.

"Alkenyl" means carbon chains which contain at least one carbon-carbon double bond, and which may be linear or branched, or combinations thereof, unless otherwise defined. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched, or combinations thereof, unless otherwise defined. Examples of alkynyl include ethynyl, propargyl, 3-methyl-1-pentynyl, 2-heptynyl and the like.

"Aromatic ring system" or "aromatic" in reference to a ring means monocyclic, bicyclic or tricyclic aromatic ring or ring system containing 5-14 ring atoms, wherein at least one of the rings is aromatic. The term may be used to describe a saturated or monounsaturated carbocyclic ring fused to an aryl group. For example, a 5-7-membered cycloalkyl can be fused through two adjacent ring atoms to a 5-6-membered heteroaryl containing 1, 2, or 3 heteroatom ring atoms selected from N, O, and S. In other example, a heteromonocyclic ring is fused through two ring atoms to a phenyl or 5-6-membered heteroaryl containing 1, 2, or 3 heteroatoms selected from N, O, and S. In the case of a heteromonocyclic ring containing one or more N atoms, the N can be in the form of quaternary amine. In certain embodiments, an N ring atom can be in the form of an N-oxide.

"Aryl" means a monocyclic, bicyclic or tricyclic carbocyclic aromatic ring or ring system containing 6-14 carbon atoms, wherein at least one of the rings is aromatic. Examples of aryl include phenyl and naphthyl. In one embodiment of the present invention, aryl is phenyl.

"Cycloalkyl" means a saturated monocyclic, bicyclic or bridged carbocyclic ring, having a specified number of carbon atoms. Examples of cycloalkyl include cyclopropyl, cyclobutyl, cyclopentyl, cyclohexyl, cycloheptyl, indanyl, and the like. In one embodiment of the present invention, cycloalkyl is selected from: cyclopropane, cyclobutane, cyclopentane, and cyclohexane.

"Cycloalkenyl" means a nonaromatic monocyclic or bicyclic carbocylic ring containing at least one double bond. Examples of cycloalkenyl include cyclopropenyl, cyclobutenyl, cyclopentenyl, cyclohexenyl, cycloheptenyl, cyclooxtenyl and the like.

The term "heterocycloalkyl," as used herein, refers to a non-aromatic saturated and partially unsaturated monocyclic or multicyclic ring system comprising 3 to 11 ring atoms, wherein from 1 to 4 of the ring atoms are independently N, NH, S (including SO and $SO_2$) and O, and the remainder of the ring atoms are carbon atoms. A heterocycloalkyl group can be joined via a ring carbon or ring nitrogen atom (if present). Where the ring or ring system contains one or more N atoms, the N can be in the form of quaternary amine. In one embodiment, a heterocycloalkyl group is monocyclic and has from about 3 to about 7 ring atoms. In another embodiment, a heterocycloalkyl group is monocyclic has from about 4 to about 7 ring atoms. In another embodiment, a heterocycloalkyl group is bicyclic and has from about 7 to about 11 ring atoms. When a heterocycloalkyl contains two rings, the rings may be fused or spirocyclic. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. A heterocycloalkyl group can be optionally substituted by one or more "ring system substituents" which may be the same or different, and are as defined herein below. The nitrogen or sulfur atom of the heterocycloalkyl (if present) can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, delta-lactam, delta-lactone, silacyclopentane, silapyrrolidine and the like, and all isomers thereof.

"Drug resistant" means, in connection with a Gram-negative bacterial strain, a strain which is no longer susceptible to at least one previously effective drug; which has developed the ability to withstand antibiotic attack by at least one previously effective drug. "Multidrug resistant" means a strain that is no longer susceptible to two or more previously effective drugs; which has developed the ability to withstand antibiotic attack by two or more previously effective drugs. A drug resistant strain may relay that ability to withstand to its progeny. This resistance may be due to random genetic mutations in the bacterial cell that alters its sensitivity to a single drug or to different drugs.

"Heterocycloalkenyl" means a nonaromatic monocyclic, bicyclic or bridged carbocyclic ring or ring system containing at least one double bond and containing at least one heteroatom selected from N, NH, S and O.

"Heteroaryl" means monocyclic, bicyclic or tricyclic ring or ring system containing 5-14 ring atoms and containing at least one ring heteroatom selected from N, NH, S (including SO and $SO_2$) and O, wherein at least one of the heteroatom containing rings is aromatic. In the case of a heteroaryl ring system where one or more of the rings are saturated and contain one or more N atoms, the N can be in the form of quaternary amine. In one embodiment, a heteroaryl group has 5 to 10 ring atoms. In another embodiment, a heteroaryl group is monocyclic and has 5 or 6 ring atoms. In another embodiment, a heteroaryl group is bicyclic. A heteroaryl group can be optionally substituted by one or more ring system substituents which may be the same or different. Any nitrogen atom of a heteroaryl can be optionally oxidized to the corresponding N-oxide. The term "heteroaryl" also encompasses a heteroaryl group, as defined above, which is fused to a benzene ring. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzopyrazolyl, benzofuranyl, benzothiophenyl (including S-oxide and dioxide), benzotriazolyl, furo(2,3-b)pyridyl, quinolyl, indolyl, isoquinolyl, quinazolinyl, dibenzofuranyl, and the like. In one embodiment of the present invention, heteroaryl is selected from: pyrazole, imidazole, pyridine and pyrimidine. In another embodiment of the present invention, heteroaryl is pyrazole, pyridine and pyrimidine.

"Heterocycle" means a monocyclic or bicyclic saturated, partially unsaturated, or unsaturated ring system containing 5-10 atoms and containing at least one ring heteroatom selected from N, S and O. In select embodiments, the ring system contains 1-4 heteroatoms selected from N, S and O. When a heterocycle contains two rings, the rings may be fused, bridged or spirocyclic. Examples of monocyclic heterocycle rings include dihydroimidazole, dihydropyrimidine, tetrahydropyrimidine and tetrahydropyridopyrimidine, piperazine, piperidine, and morpholine. In one embodiment of the present invention, monocyclic heterocycle rings include dihydroimidazole, dihydropyrimidine, and tetrahydropyrimidine. In another embodiment of the present invention, monocyclic heterocycle rings include dihydroimidazole. In another embodiment of the present invention, heterocycle rings include piperidine.

"Halogen" includes fluorine, chlorine, bromine and iodine. In one embodiment, halogen is fluorine, chlorine and bromine. In another embodiment, halogen is fluorine. In another embodiment, halogen is chlorine. In another embodiment, halogen is bromine.

"Oxo" means an oxygen atom connected to another atom by a double bond and is can be represented "=O".

"Quaternary salt" means a cation formed by four covalent bonds to nitrogen.

When any variable (e.g., $R^1$, $R^a$, etc.) occurs more than one time in any constituent or in Formula (I), its definition on each occurrence is independent of its definition at every other occurrence. Also, combinations of substituents and/or variables are permissible only if such combinations result in stable compounds. A squiggly line across a bond in a substituent variable represents the point of attachment.

A "stable" compound is a compound which can be prepared and isolated and whose structure and properties remain or can be caused to remain essentially unchanged for a period of time sufficient to allow use of the compound for the purposes described herein (e.g., therapeutic administration to a subject). The compounds of the present invention are limited to stable compounds embraced by Formula (I).

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different. When a group, e.g., $C_1$-$C_8$ alkyl, is indicated as being substituted, such substitutions can also occur where such group is part of a larger substituent, e.g., —$C_1$-$C_6$alkyl-$C_3$-$C_7$cycloalkyl and —$C_1$-$C_8$alkyl-aryl.

In the compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula (I). For example, different isotopic forms of hydrogen (H) include protium ($^1$H) and deuterium ($^2$H or D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula (I) can be prepared without undue experimentation by conventional techniques well known to those skilled in the art or by processes analogous to those described in the Schemes and Examples herein using appropriate isotopically-enriched reagents and/or intermediates.

Unless expressly stated to the contrary in a particular context, any of the various cyclic rings and ring systems described herein may be attached to the rest of the compound at any ring atom (i.e., any carbon atom or any heteroatom) provided that a stable compound results.

Unless expressly stated to the contrary, all ranges cited herein are inclusive. For example, a heteroaromatic ring described as containing from "1 to 4 heteroatoms" means the ring can contain 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, and 4 heteroatoms. Similarly, $C_1$-$C_6$ when used with a chain, for example an alkyl chain, means that the chain can contain 1, 2, 3, 4, 5 or 6 carbon atoms. It also includes all ranges contained therein including $C_1$-$C_5$, $C_1$-$C_4$, $C_1$-$C_3$, $C_1$-$C_2$, $C_2$-$C_6$, $C_3$-$C_6$, $C_4$-$C_6$, $C_5$-$C_6$, and all other possible combinations.

It should also be noted that any carbon as well as heteroatom with unsatisfied valences in the text, schemes, examples and tables herein is assumed to have the sufficient number of hydrogen atom(s) to satisfy the valences.

The compounds of the present invention have at least one asymmetric center and can have one or more additional centers as a result of the presence of certain substituents and/or substituent patterns. Accordingly, compounds of the invention can occur as mixtures of stereoisomers, or as individual diastereomers, or enantiomers. All isomeric forms of these compounds, whether individually or in mixtures, are within the scope of the present invention.

The term "compound" refers to the free compound and, to the extent they are stable, any hydrate or solvate thereof. A hydrate is the compound complexed with water, and a solvate is the compound complexed with an organic solvent.

As indicated above, the compounds of the present invention can be employed in the form of pharmaceutically acceptable salts. It will be understood that, as used herein, the compounds of the instant invention can also include the pharmaceutically acceptable salts, and also salts that are not pharmaceutically acceptable when they are used as precursors to the free compounds or their pharmaceutically acceptable salts or in other synthetic manipulations.

The term "pharmaceutically acceptable salt" refers to a salt which possesses the effectiveness of the parent compound and which is not biologically or otherwise undesirable (e.g., is neither toxic nor otherwise deleterious to the recipient thereof). The term "pharmaceutically acceptable salt" refers to salts prepared from pharmaceutically acceptable non-toxic bases or acids including inorganic or organic bases and inorganic or organic acids.

Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

The compound of the invention can also be employed in the form of a prodrug. Any prodrug precursor known in the art can be used to form a prodrug of the invention. In certain aspects of this embodiment, the hydrogen in —COOH in formula I can be replaced with any the following groups: $C_{1-6}$alkyl, $C_{3-6}$cycloalkyl, —$C_{1-6}$alkylene-$C_{3-6}$cycloalkyl, $C_{3-7}$heterocycloalkyl, —$C_{1-6}$alkylene-$C_{3-7}$heterocycloalkyl, aryl, —$C_{1-10}$alkylene-aryl, heteroaryl, and —$C_{1-10}$alkylene-heteroaryl. In certain aspects of this embodiment, the $C_{1-6}$alkyl, $C_{3-6}$cycloalkyl, or $C_{3-7}$heterocycloalkyl can be substituted. In other aspects of this embodiment, each aryl and heteroaryl can be substituted.

As set forth above, the present invention includes pharmaceutical compositions comprising a compound of Formula I of the present invention, optionally one other active components (e.g., a β-lactamase inhibitor), and a pharmaceutically acceptable carrier. The characteristics of the carrier will depend on the route of administration. By "pharmaceutically acceptable" is meant that the ingredients of the pharmaceutical composition must be compatible with each other, do not interfere with the effectiveness of the active ingredient(s), and are not deleterious (e.g., toxic) to the recipient thereof. Thus, compositions according to the invention may, in addition to the inhibitor, contain diluents, fillers, salts, buffers, stabilizers, solubilizers, and other materials well known in the art.

Also as set forth above, the present invention includes a method for treating a bacterial infection which comprises administering to a subject in need of such treatment a therapeutically effective amount of a compound of Formula (I), or a pharmaceutically acceptable salt thereof, optionally in combination with a β-lactamase inhibitor. The term "subject" (or, alternatively, "patient") as used herein refers to an animal, preferably a mammal, most preferably a human, who has been the object of treatment, observation or experiment. The term "administration" and variants thereof (e.g., "administering" a compound) in reference to a compound of Formula (I) mean providing the compound, or a pharmaceutically acceptable salt thereof, to the individual in need of treatment. When a compound or a salt thereof is provided in combination with one or more other active agents (e.g., a β-lactamase inhibitor), "administration" and its variants are each understood to include provision of the compound or its salt and the other agents at the same time or at different times. When the agents of a combination are administered at the same time, they can be administered together in a single composition or they can be administered separately.

It is understood that a "combination" of active agents can be a single composition containing all of the active agents or multiple compositions each containing one or more of the active agents. In the case of two active agents a combination can be either a single composition comprising both agents or two separate compositions each comprising one of the agents; in the case of three active agents a combination can be either a single composition comprising all three agents, three separate compositions each comprising one of the agents, or two compositions one of which comprises two of the agents and the other comprises the third agent; and so forth.

The compositions and combinations of the present invention are suitably administered in effective amounts. The term "effective amount" as used herein means the amount of active compound sufficient to inhibit bacterial growth and thereby elicit the response being sought (i.e., an "inhibition effective amount") in a cell, tissue, system, animal or human. In one embodiment, the effective amount is a "therapeutically effective amount" for the alleviation of the symptoms of the disease or condition being treated (e.g., the healing of conditions associated with bacterial infection, and/or bacterial drug resistance). In another embodiment, the effective amount is a "prophylactically effective amount" for prophylaxis of the symptoms of the disease or condition being prevented. When the active compound (i.e., active ingredient) is administered as the salt, references to the amount of active ingredient are to the free acid or free base form of the compound.

The administration of a composition of the present invention is suitably parenteral, oral, sublingual, transdermal, topical, intranasal, intratracheal, intraocular, or intrarectal, wherein the composition is suitably formulated for administration by the selected route using formulation methods well known in the art, including, for example, the methods for preparing and administering formulations described in chapters 39, 41, 42, 44 and 45 in Remington—The Science and Practice of Pharmacy, 21$^{st}$ edition, 2006. In one embodiment, compounds of the invention are administered intravenously in a hospital setting. In another embodiment, administration is oral in the form of a tablet or capsule or the like. When administered systemically, a therapeutic composition is for example, suitably administered at a sufficient dosage to attain a blood level of inhibitor of at least about 1 microgram/mL, and in additional embodiment at least about 10 micrograms/mL, and at least about 25 micrograms/mL. For localized administration, much lower concentrations than this may be effective, and much higher concentrations may be tolerated.

Intravenous administration of a compound of the invention can be conducted by reconstituting a powdered form of the compound with an acceptable solvent. Suitable solvents include, for example, saline solutions (e.g., 0.9% Sodium Chloride Injection) and sterile water (e.g., Sterile Water for Injection, Bacteriostatic Water for Injection with methylparaben and propylparaben, or Bacteriostatic Water for Injection with 0.9% benzyl alcohol). The powdered form of the compound can be obtained by gamma-irradiation of the compound or by lyophilization of a solution of the compound, after which the powder can be stored (e.g., in a sealed vial) at or below room temperature until it is reconstituted. The concentration of the compound in the reconstituted IV solution can be, for example, in a range of from about 0.1 mg/mL to about 20 mg/mL.

The present invention also includes a method for inhibiting bacterial growth which comprises administering to a bacterial cell culture, or to a bacterially infected cell culture, tissue, or organism, an inhibition effective amount of a compound of Formula (I). Additional embodiments of the invention include the bacterial growth inhibiting method just described, wherein the compound of the present invention employed therein is a compound of one of the embodiments, sub-embodiments or classes described above. The compound may optionally be used in the form of a pharmaceutically acceptable salt in these embodiments. The method can involve administration of a compound of Formula (I) to an experimental cell culture in vitro to prevent the growth of β-lactam resistant bacteria. The method can alternatively involve administration of a compound of Formula I to an animal, including a human, to prevent the growth of β-lactam resistant bacteria in vivo. In these cases the compound of Formula (I) is typically co-administered with a β-lactamase inhibitor.

The methods of the presently disclosed subject matter are useful for treating these conditions in that they inhibit the onset, growth, or spread of the condition, cause regression of the condition, cure the condition, or otherwise improve the general well-being of a subject afflicted with, or at risk of, contracting the condition. Thus, in accordance with the presently disclosed subject matter, the terms "treat", "treating", and grammatical variations thereof, as well as the phrase "method of treating", are meant to encompass any desired therapeutic intervention, including but not limited to a method for treating an existing infection in a subject, and a method for the prophylaxis (i.e., preventing) of infection, such as in a subject that has been exposed to a microbe as disclosed herein or that has an expectation of being exposed to a microbe as disclosed herein.

Compounds of the invention can be employed for the treatment, prophylaxis or inhibition of bacterial growth or infections due to bacteria that are resistant to β-lactam antibiotics. More particularly, the bacteria can be metallo-β-lactamase positive strains that are highly resistant to β-lactam antibiotics. The terms "slightly resistant" and "highly resistant" are well-understood by those of ordinary skill in the art (see, e.g., Payne et al., *Antimicrobial Agents and Chemotherapy* 38:767-772 (1994); Hanaki et al., *Antimicrobial Agents and Chemotherapy* 30:11.20-11.26 (1995)). For the purposes of this invention, bacterial strains which are highly resistant to imipenem are those against which the MIC of imipenem is >16 μg/mL, and bacterial strains which are slightly resistant to imipenem are those against which the MIC of imipenem is >4 μg/mL.

Compounds of the invention can be used in combination with a β-lactamase inhibitor for the treatment of infections caused by β-lactamase producing strains, in addition to those infections which are subsumed within the antibacterial spectrum of the antibiotic agent. Examples of β-lactamase producing bacteria are *Pseudomonas aeruginosa, Pseudomonas putida, Enterobacter cloacae, Klebsiella pneumoniae, Klebsiella oxytoca, Escherichia coli, Serratia marcescens, Enterobacter aerogenes, Enterobacter asburiae, Citrobacter freundii, Proteus mirabilis, Morganella morganii, Providencia rettgeri, Stenotrophomonas maltophilia* and *Acinetobacter baumannii*.

It is generally advantageous to use a compound of Formula (I) in admixture or conjunction with a β-lactamase inhibitor, or a prodrug thereof. It is advantageous to use a compound of Formula I in combination with a class A and C β-lactamase inhibitor because of the class B β-lactamase resistant properties of the compounds. It is also advantageous to use a compound of Formula I in combination with one or more Class A, C, or D β-lactamase inhibitors to further limit β-lactam susceptibility. As already noted, the compound of Formula I and the β-lactamase inhibitor can be administered separately (at the same time or as different times) or in the form of a single composition containing both active ingredients. Relebactam, tazobactam, clavulanic acid, sulbactam, avibactam and other β-lactamase and metallo-β- lactamase inhibitors suitable for use in the present invention include those known to show inhibitory activity to β-lactamases.

Abbreviations employed herein include the following: aq.=aqueous; ACN=acetonitrile; AcOH is acetic acid; BLI=β-lactamase inhibitor; Bn=benzyl; BOC (or Boc)=t-butyloxycarbonyl; BOC₂O=di-tert-butyl dicarbonate; CAN=ceric ammonium nitrate; CBZ (or Cbz)=carbobenzoxy (alternatively, benzyloxycarbonyl); CDCl₃=deuterated chloroform; CH₃CN=acetonitrile; Co-Catalyst=(R,R')—N,N'-bis(3,5-di-tert-butylsalicylidene)-1,2-cyclohexanediamino-cobalt(III) 1,1,1,3,3,3-hexafluoro-2-(trifluoromethyl)propan-2-olate; cv=column volume(s); DBU=1,8-diazabicyclo[5.4.0]undec-7-ene; DCC=dicyclohexyl carbodiimide; DCE=dichloroethane; DCM=dichloromethane; DEAD=diethyl azodicarboxylate; DIAD=diisopropyl azodicarboxylate; DIEA or DIPEA=diisopropylethylamine; DMA=dimethylacetamide; DMAP=4-dimethylaminopyridine or N,N-dimethylaminopyridine; DMF=N,N-dimethylformamide; DMSO=dimethyl sulfoxide; EDC=1-ethyl-3-(3-dimethylaminopropyl) carbodiimide; eq. or equiv.=equivalent(s); Et=ethyl; Et₃N=triethyl amine; Et₂O=ethylene oxide; EA or EtOAc=ethyl acetate; EtOH=ethanol; eq is equivalents; g=gram(s); FA is formic acid; h or hr or hrs=hour(s); HATU is 1-[Bis(dimethylamino)methylene]-1H-1,2,3-triazolo[4,5-b]pyridinium 3-oxid hexafluorophosphate; hex=hexane; HiVac=high vacuum; HMDS=hexamethyl-disilazide; HOBT=1-hydroxy benzotriazole; HPLC=high-performance liquid chromatography; IPA=isopropyl alcohol; iPrMgCl=isopropyl magnesium chloride; IPAc=isopropyl acetate; L or l=liter(s); LC/MS or LC-MS=liquid chromatography/mass spectrometry; LDA=lithium diisopropylamide; M is molar; min=minute(s); mg=milligram(s); ml, mL or ML=milliliter(s); m-CPBA=m-chloroperoxybenzoic acid; MBL=metallo β-lactamase; Me=methyl; MeCN=acetonitrile; MeOH=methanol; MeI=methyl iodide; MITC=minimum inhibitory threshold concentration; MOPS=3-(N-morpholino)propanesulfonic acid; MPLC=medium pressure liquid chromatography; MTBE=methyl tert-butyl ether; NBS=N-bromo-succinimide; NCS=N-chlorosuccinimide; NMR=nuclear magnetic resonance; MS=mass spectrometry; MW=molecular weight; Pd/c=palladium on carbon; OTf is triflate; PdCl₂(dppf)₂=[1,1' bis(diphenyl-phosphino)-ferrocene] dichloropalladium (II); di-t-BuDPPF-PdCl₂=1,1'-bis(di-tert-butylphosphino) ferrocene palladium dichloride; PE=petroleum ether; PG=protective group; Ph=phenyl; PPTS=pyridinium p-toluenesulfonate; RP is reverse phase; RP-HPLC=reverse-phase high-performance liquid chromatography; rt, r.t., R.T. or RT=room temperature; sat'd=saturated; SFC is super critical fluid chromatography; tBu=tert-butyl; TBAI=tetrabutylammonium iodide; TBAF=tetrabutylammonium fluoride; TBS=tert-butyldimethylsilyl; TBS-Cl=tert-butyldimethylsilyl chloride; TBDMS-Cl=tert-butyldimethylsilyl chloride; t-BuOH=tert-butanol; TBSO=tert-butyldimethylsilyl; TEA=triethylamine; TEMPO is (2,2,6,6-tetramethylpiperidin-1-yl)oyl; TFA=trifluoroacetic acid; THF=tetrahydrofuran; TLC=thin layer chromatography; TMS=trimethylsilyl; TMS-Cl=trimethylsilyl chloride; TMS-I=trimethylsilyl iodide; and TMS-N₃=trimethylsilyl azide.

Methods for Making the Compounds of Formula (I):

The compounds disclosed herein can be prepared and tested according to the following reaction schemes and Examples, or modifications thereof, using readily available starting materials, reagents and conventional synthesis procedures. In these reactions, it is also possible to make use of variations which are themselves known to those of ordinary skill in this art, but are not mentioned here in greater detail. Furthermore, other methods for preparing compounds disclosed herein will be readily apparent to the person of ordinary skill in the art in light of the following reaction scheme and Examples. Unless otherwise indicated, all variables are as defined above.

GENERAL SCHEME

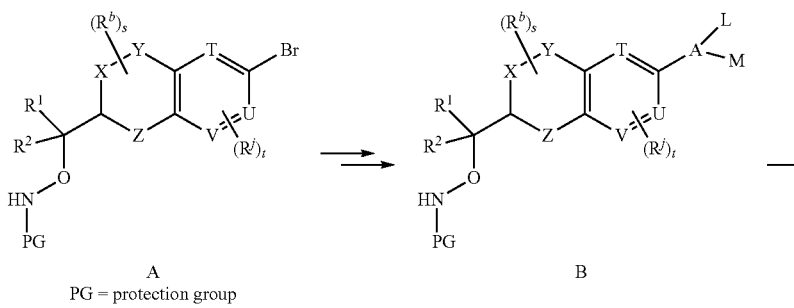

PG = protection group

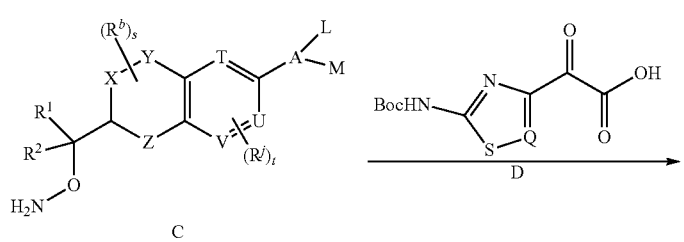

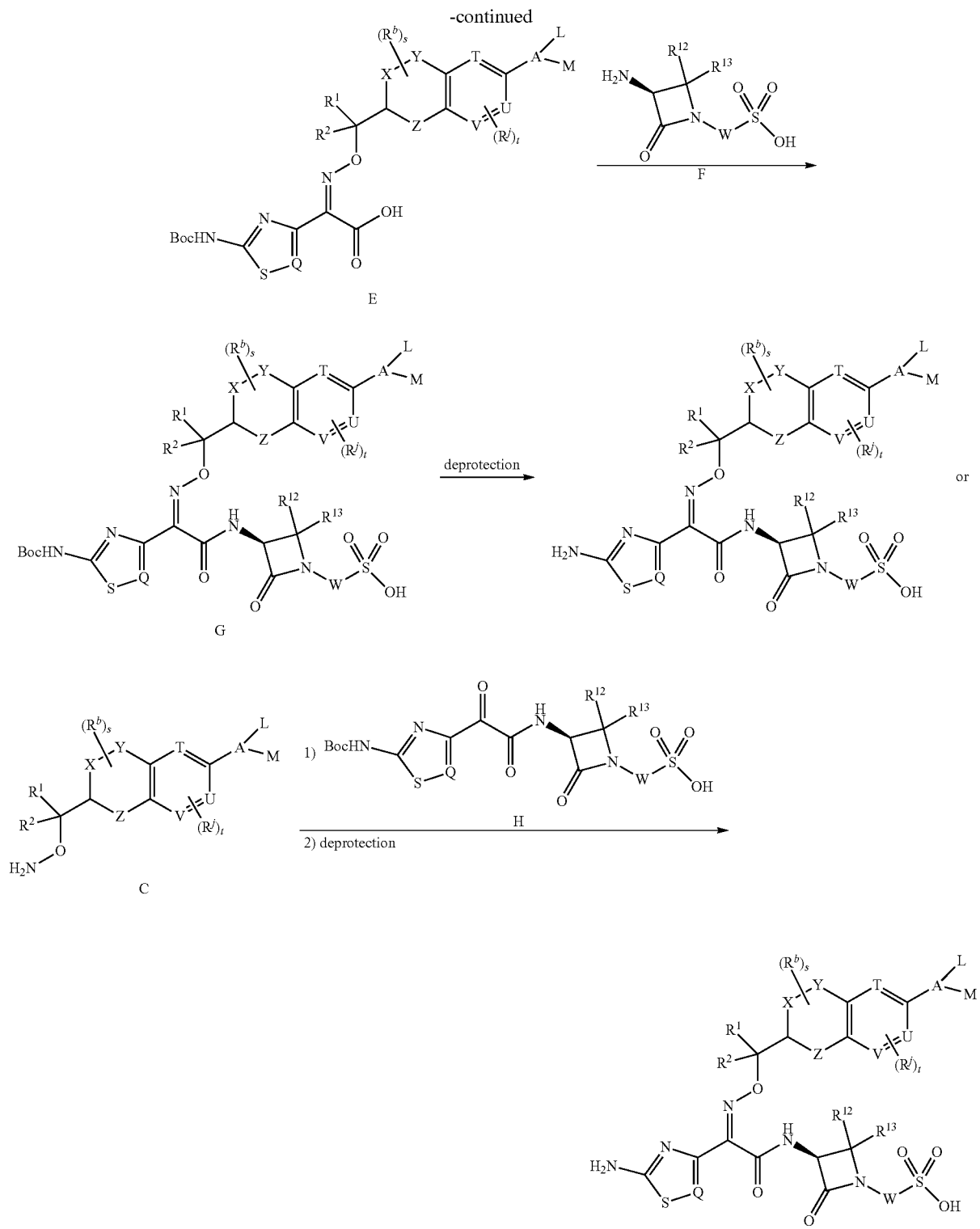

The chroman bromide A was converted to intermediate B via a Suzuki coupling reaction, followed by functional group manipulations. Then the protecting group (PG) in B was removed to give alkoxyamine C, which was condensed with ketoacid D to give Compound E. Compound E was then coupled with amine F to give compound G, which was deprotected to give the final product. Alternatively, compound C was condensed with ketoamide H, followed by deprotection to give the final product. The (β-lactam intermediate F can be either purchased from commercial sources or synthesized following a procedure reported in detail in the literature (See EP 0229012). This amine can be converted to the final monobactam compounds as illustrated above with a similar procedure demonstrated in the following Examples.

Intermediate 1 tert-Butyl (S)-2-(aminooxy)-2-((R)-6-bromochroman-2-yl)propanoate

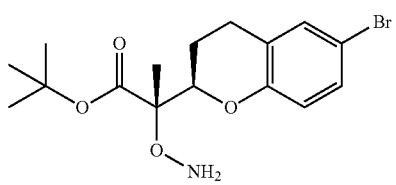

I-1

Step A: 6-bromochroman-2-carboxylic Acid

To a solution of ethyl 6-bromochroman-2-carboxylate (40 g, 140 mmol) dissolved in ethanol (200 ml) was added LiOH (16.8 g, 421 mmol) in water (200 mL). The reaction was stirred at 20° C. for 1 h. Then the reaction solution was concentrated to about its half volume and acidified with 6N hydrochloric acid to pH=2, and extracted with ethyl acetate (200 mL×3). The combined organic layers were washed with brine (200 mL×2), dried over anhydrous $Na_2SO_4$, and filtered. The filtrate was evaporated under reduced pressure to give the title compound, which was used directly in next step. $^1$H NMR (400 MHz, chloroform-d) δ 7.14-7.26 (m, 2H), 6.82 (d, J=9.00 Hz, 1H), 4.77 (dd, J=3.52, 7.43 Hz, 1H), 2.72-2.90 (m, 2H), 2.28-2.40 (m, 1H), 2.15-2.26 (m, 1H).

Step B: 6-bromo-N-methoxy-N-methylchroman-2-carboxamide

To a mixture of 6-bromochroman-2-carboxylic acid (35 g, 136 mmol) and TEA (57 ml, 410 mmol) in DMF (500 mL) was added HATU (78 g, 205 mmol) and N,O-dimethylhydroxyl-amine (12.5 g, 205 mmol). The reaction mixture was stirred at 20° C. for 18 hours, then diluted with water (500 mL). The aqueous layer was separated and extracted with EtOAc (500 mL×3). The combined organic layers were washed with brine (500 mL×2), dried over anhydrous $Na_2SO_4$, filtered and concentrated under reduced pressure. The resulting residue was purified by silica gel column chromatography (PE/EA=20:1 to 1:1) to give the title compound. $^1$H NMR (400 MHz, chloroform-d) δ 8.13 (d, J=8.16 Hz, 2H), 7.91 (d, J=8.16 Hz, 2H), 7.40 (d, J=8.38 Hz, 2H), 6.91 (d, J=8.60 Hz, 2H), 5.75 (s, 2H), 3.81 (s, 3H), 1.23-1.44 (m, 12H).

Step C: 1-(6-bromochroman-2-yl)ethanone

A solution of 1.6 M methyllithium (77 mL, 123 mmol) in THF was added dropwise to a solution of 6-bromo-N-methoxy-N-methylchroman-2-carboxamide (18.4 g, 61.3 mmol) in 240 mL of THF at −30° C. The reaction mixture was stirred for 20 min at −10° C., then quenched with saturated $NH_4Cl$ solution (240 mL). The mixture was extracted EtOAc (240 mL×3). The organic layer was separated, washed with brine (240 mL×2), dried over magnesium sulfate, filtered and concentrated under vacuum. The resulting residue was purified by silica gel column chromatography (PE/EA=20:1 to 3:1) to give the title compound. $^1$H NMR (400 MHz, chloroform-d) δ 7.15-7.26 (m, 2H), 6.81 (d, J=8.61 Hz, 1H), 4.46 (dd, J=3.33, 8.80 Hz, 1H), 2.78-2.86 (m, 1H), 2.68-2.76 (m, 1H), 2.30 (s, 3H), 2.16-2.23 (m, 1H), 1.99-2.06 (m, 1H).

Step D: 1-(6-bromochroman-2-yl)ethanone

To a solution of 1-(6-bromochroman-2-yl)ethanone (20 g, 78 mmol) in MTBE (100 ml) and AcOH (100 ml) was added KCN (15.31 g, 235 mmol). The reaction was stirred at 25° C. for 2 hours under a nitrogen atmosphere. Then the reaction mixture was added dropwise into 200 mL of saturated aqueous sodium carbonate solution, followed by the addition of sodium carbonate (solid) to neutralize the reaction solution. The mixture was extracted with MTBE (200 mL×3). The organic layer was separated, washed with brine (100 mL×3), dried over anhydrous $Na_2SO_4$, and filtered. The filtrate was concentrated under vacuum. The resulting residue was purified on flash chromatography (80 g silica, 0-40% EtOAc in hexane) to give the title compound. $^1$H NMR (400 MHz, chloroform-d) δ 7.17-7.26 (m, 2H), 6.79 (dd, J=4.50, 8.41 Hz, 1H), 3.88-4.05 (m, 1H), 3.66 (s, 1H), 3.04 (br. s., 1H), 2.84-2.92 (m, 2H), 2.13-2.21 (m, 1H), 1.88-2.01 (m, 1H), 1.66-1.73 (m, 3H)

Step E: 2-(6-bromochroman-2-yl)-2-hydroxypropanoic Acid

To a solution of 2-(6-bromochroman-2-yl)-2-hydroxypropanenitrile (11 g, 39 mmol) in AcOH (100 ml) was slowly added HCl (concentrated, 112 ml, 1360 mmol). The reaction mixture was heated to 110° C. and stirred for 3 hours under a nitrogen atmosphere, then the reaction mixture was concentrated under reduced pressure to give the title compound. $^1$H NMR (400 MHz, chloroform-d) δ 7.14-7.21 (m, 2H), 6.64-6.74 (m, 1H), 4.23-4.30 (m, 1H), 4.08-4.15 (m, 1H), 3.75-3.82 (m, 2H), 2.77-2.89 (m, 2H), 2.08-2.17 (m, 1H), 1.86-2.01 (m, 3H), 1.49-1.65 (m, 3H)

Step F: tert-butyl 2-(6-bromochroman-2-yl)-2-hydroxypropanoate

To a suspension of 2-(6-bromochroman-2-yl)-2-hydroxypropanoic acid (13.4 g, 44.5 mmol) in THF (200 ml) was added (Z)-tert-butyl N,N'-diisopropylcarbamimidate (44.6 g, 222 mmol). The reaction mixture was stirred at 75° C. for 16 h, and then concentrated in vacuo. Cyclohexane (300 mL) was added to the resulting residue, and the resulting mixture was filtered over Celite™. The filtrate was concentrated in vacuo and the resulting crude oil was purified by flash chromatography ($SiO_2$, PE-EtOAc, 3:1) to give the title compound. $^1$H NMR (400 MHz, chloroform-d) δ 7.11-7.20 (m, 2H), 6.59-6.74 (m, 1H), 4.01-4.15 (m, 1H), 3.37-3.50 (m, 1H), 2.77-2.88 (m, 2H), 1.89-2.08 (m, 2H), 1.50 (d, J=9.04 Hz, 12H)

Step G: tert-butyl 2-(aminooxy)-2-(6-bromochroman-2-yl)propanoate

Tert-butyl 2-(6-bromochroman-2-yl)-2-hydroxypropanoate (4 g, 11.2 mmol) was dissolved in dry THF (50 ml) under a $N_2$ atmosphere, and the mixture was cooled to 0° C. Then NaH (0.54 g, 13.4 mmol, 60%) was added in one portion, followed by the addition of O-(mesitylsulfonyl)-hydroxylamine (2.89 g, 13.44 mmol). The reaction mixture was stirred at 0° C. for 2 hours, then quenched with saturated aqueous $NH_4Cl$ (30 ml), and extracted with EtOAc (50 mL×3). The combined organic layers were washed with brine (30 mL×3), dried over Na₂SO₄, filtered and concentrated in vacuo. The resulting residue was purified by column chromatography on silica gel (EtOAc/pentane=0~30%) to afford the title compound. ¹H NMR (400 MHz, chloroform-d) δ 7.13-7.15 (m, 2H), 6.68 (t, J=8.8 Hz, 1H), 5.47 (s, 1H), 5.37 (s, 1H), 4.10-4.18 (m, 1H), 2.74-2.84 (m, 2H), 1.97-2.02 (m, 1H), 1.81-1.86 (m, 1H), 1.51 (s, 9H), 1.50 (s, 9H).

Step H: tert-butyl 2-(aminooxy)-2-(6-bromochroman-2-yl)propanoate

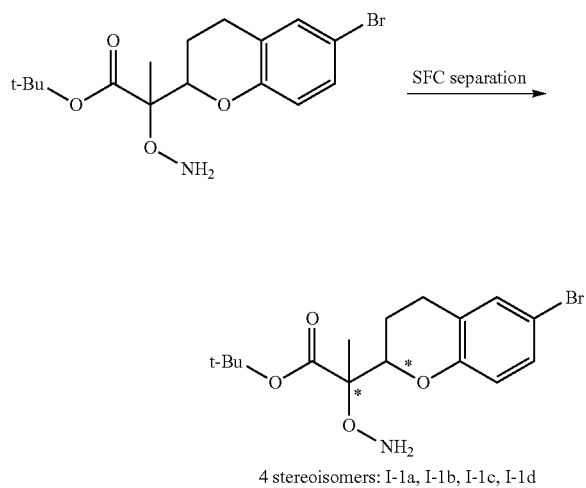

4 stereoisomers: I-1a, I-1b, I-1c, I-1d

Tert-butyl 2-(aminooxy)-2-(6-bromochroman-2-yl)propanoate (10 g, 26.9 mmol) was separated by SFC (Column: Chiralpak AD-3 250*50 mm I.D, 10 μm Mobile phase: A: CO₂ B: IPA (0.05% NH₃.H₂O). Gradient: from 5% to 40% of B in 5 min and hold 40% for 2.5 min, then 5% of B for 2.5 min Flow rate: 200 mL/min Column temp.: 35° C. Wavelength: 220 nm) to afford I-1a (first eluent), I-1b (second eluent), I-1c (third eluent) and I-1d (fourth eluent).

I-1a: LCMS:MS (ESI) m/z: 316.0 [M+H-56]⁺; ¹H NMR (400 MHz, chloroform-d) δ 7.12-7.14 (m, 2H), 6.65 (d, J=9.6 Hz, 1H), 5.35 (s, 2H), 4.12 (dd, J=1.6, 11.2 Hz, 1H), 2.73-2.81 (m, 2H), 1.94-1.99 (m, 1H), 1.81-1.85 (m, 1H), 1.50 (s, 3H), 1.49 (s, 9H).

I-1b: LCMS:MS (ESI) m/z: 316.0 [M+H-56]⁺; ¹H NMR (400 MHz, chloroform-d) δ 7.14-7.16 (m, 2H), 6.68 (d, J=9.6 Hz, 1H), 5.38 (s, 2H), 4.15 (dd, J=1.6, 11.2 Hz, 1H), 2.76-2.83 (m, 2H), 1.97-2.02 (m, 1H), 1.84-1.87 (m, 1H), 1.52 (s, 3H), 1.51 (s, 9H).

I-1c: LCMS:MS (ESI) m/z: 316.0 [M+H-56]⁺; ¹H NMR (400 MHz, chloroform-d) δ 7.14-7.16 (m, 2H), 6.70 (d, J=8.4 Hz, 1H), 5.49 (s, 2H), 4.15 (dd, J=1.6, 11.2 Hz, 1H), 2.75-2.85 (m, 2H), 2.02-2.06 (m, 1H), 1.84-1.86 (m, 1H), 1.53 (s, 3H), 1.52 (s, 9H).

I-1d: LCMS:MS (ESI) m/z: 316.0 [M+H-56]⁺; ¹H NMR (400 MHz, chloroform-d) δ 7.14-7.16 (m, 2H), 6.70 (d, J=9.6 Hz, 1H), 5.48 (s, 2H), 4.16 (dd, J=1.6, 11.2 Hz, 1H), 2.78-2.85 (m, 2H), 2.01-2.06 (m, 1H), 1.84-1.89 (m, 1H), 1.52 (s, 3H), 1.51 (s, 9H).

Intermediate 2 tert-Butyl (3-(4-(4,4,5,5-tetramethyl-1,3,2-dioxaborolan-2-yl)-1H-pyrazol-1-yl)propyl)carbamate

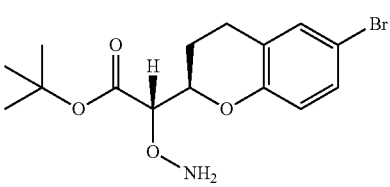

Step A: ethyl 4-oxo-4H-chromene-2-carboxylate

Sodium (41 g, 1.8 mol) was dissolved in absolute ethanol (2 L) and then 1-(2-hydroxyphenyl) ethanone (50 g, 367 mmol) and diethyl oxalate (140 g, 960 mmol) was added. The mixture was stirred at 78° C. for 1 h, then cooled and concentrated HCl was added until the pH of mixture was pH 1. Then the mixture was stirred at 78° C. for 1 h, cooled and filtered. The filtrate was concentrated to give crude product, which was dissolved in water (450 mL) and extracted with ethyl acetate (3×500 mL). The organic layer was separated, dried over anhydrous sodium sulfate and concentrated. The resulting residue was purified on silica gel (PE:EA=10:1 to 5:1) to the title compound. ¹H NMR (400 MHz, chloroform-d) δ 8.24-8.20 (m, 1H), 7.80-7.73 (m, 1H), 7.63 (d, J=8.6 Hz, 1H), 7.47 (t, J=7.5 Hz, 1H), 7.16 (s, 1H), 4.48 (q, J=7.1 Hz, 2H), 1.45 (t, J=7.1 Hz, 3H)

Step B: Ethyl chroman-2-carboxylate

Acetic acid (40 mL) was added to a solution of ethyl 4-oxo-4H-chromene-2-carboxylate (103 g, 470 mmol) and palladium/carbon (5 g) in absolute ethanol (1.2 L). The mixture was stirred under H₂ (50 psi) for 20 hours, then filtered through silica gel and concentrated to give the title compound. ¹H NMR (400 MHz, chloroform-d) δ 7.14-7.07 (m, 1H), 7.02 (d, J=7.3 Hz, 1H), 6.92 (d, J=8.2 Hz, 1H), 6.89-6.83 (m, 1H), 4.71 (dd, J=3.4, 7.6 Hz, 1H), 4.25 (q, J=7.1 Hz, 2H), 2.87-2.73 (m, 2H), 2.30-2.16 (m, 2H), 1.29 (t, J=7.1 Hz, 3H)

Step C: Ethyl 6-bromochroman-2-carboxylate

To a mixture of ethyl chroman-2-carboxylate (96 g, 465 mmol) in CH₂Cl₂ (900 mL) and AcOH (100 mL) was added dropwise Br₂ (372 mmol, 19 mL). The reaction mixture was stirred at 30° C. for 1.5 hours, then partitioned between DCM (600 mL×3) and H₂O (400 mL×3). The organic layer was separated, concentrated in vacuo, and then a K₂CO₃ solution was added until the pH was pH 7. Then the mixture was extracted with DCM (400 mL×2), and the organic layer was concentrated to give the title compound. ¹H NMR (400 MHz, chloroform-d) δ 7.21-7.09 (m, 2H), 6.81-6.74 (m, 1H), 4.68 (d, J=2.9 Hz, 1H), 4.27-4.17 (m, 2H), 2.81-2.64 (m, 2H), 2.25-2.10 (m, 2H), 1.26 (d, J=3.5 Hz, 3H)

Step D: (6-bromochroman-2-yl)methanol

To the mixture of ethyl 6-bromochroman-2-carboxylate (20 g, 70 mmol) in dry THF (200 ml) was added lithium borohydride (4.6 g, 210 mmol). The reaction mixture was stirred at 0° C. for 3 hours, then quenched by the addition of H$_2$O (300 mL). The mixture was partitioned between EA (200 mL×3) and H$_2$O (150 mL×3). The organic layer was separated and concentrated to give the title compound, which was used directly without further purification. $^1$H NMR (400 MHz, chloroform-d) δ 7.19 (br. s., 2H), 6.76-6.66 (m, 1H), 4.14-4.07 (m, 1H), 3.88-3.73 (m, 2H), 2.87 (d, J=5.9 Hz, 1H), 2.81-2.72 (m, 1H), 2.00-1.92 (m, 1H), 1.85 (d, J=5.5 Hz, 1H)

Step E: 6-bromochroman-2-carbaldehyde

To a mixture of (COCl)$_2$ (3.5 ml, 40 mmol) in DCM (100 mL) was added DMSO (5.7 ml, 80 mmol) at −78° C. under N$_2$. The reaction mixture was stirred at −78° C. for 0.5 hour. Then (6-Bromochroman-2-yl) methanol (6.5 g, 27 mmol)) dissolved in DCM (100 mL) was added to the reaction mixture at −78° C. The reaction was stirred at −78° C. for 1 hour. Then TEA (22 mL, 160 mmol) was added to the reaction at −78° C. The reaction was stirred at −78° C. for 1 hour, then diluted with water (200 mL). The aqueous layer was separated and extracted with DCM (100 mL). The combined organic layers were dried over Na$_2$SO$_4$, filtered and concentrated in vacuo to give the title compound, which was used directly for next step without purification. $^1$H NMR (400 MHz, chloroform-d) δ 9.81 (s, 1H), 7.20 (br s, 2H), 6.84 (br d, J=8.61 Hz, 1H), 4.49 (br dd, J=3.13, 8.61 Hz, 1H), 2.78 (br d, J=5.09 Hz, 2H), 2.25-2.30 (m, 1H), 2.08 (br d, J=7.43 Hz, 1H)

Step F: 2-(6-bromochroman-2-yl)-2-hydroxyacetonitrile

A solution of 6-bromochroman-2-carbaldehyde (7 g, 29 mmol) in MTBE (70 ml) and cyanopotassium (5.7 g, 87 mmol) was mixed with AcOH (70 ml) and stirred for 48 hour at 25° C. under a nitrogen atmosphere. Then the reaction mixture was added dropwise into 200 ml of saturated aqueous sodium carbonate solution under slow stirring, followed the addition of solid sodium carbonate until the reaction solution pH was neutral. Then the reaction mixture was extracted with MTBE (200 ml×3). The organic layer was separated, washed with brine (100 ml×3), dried with anhydrous Na$_2$SO$_4$, and filtered. The filtrate was concentrated in vacuo. The resulting residue was purified on flash chromatography (80 g silica, 0-40% EtOAc in hexane) to give the title compound. $^1$H NMR (400 MHz, chloroform-d) δ 7.20-7.25 (m, 2H), 6.77 (br d, J=9.39 Hz, 1H), 4.65 (br t, J=3.91 Hz, 1H), 4.20-4.27 (m, 1H), 2.78-2.97 (m, 3H), 2.10-2.19 (m, 1H), 1.95-2.04 (m, 1H)

Step G: methyl 2-(6-bromochroman-2-yl)-2-hydroxyacetate

To a solution of 2-(6-bromochroman-2-yl)-2-hydroxyacetonitrile (3.6 g, 13.4 mmol) in methanol (50 ml) was added HCl-MeOH (200 ml, 800 mmol, 4M). The reaction was stirred for 16 hours at 20° C. under a nitrogen atmosphere. Then the solvent was removed under vacuum to give the title compound, which was used directly for next step without purification. $^1$H NMR (400 MHz, DMSO-d$_6$) δ 7.27-7.15 (m, 2H), 6.74-6.60 (m, 1H), 6.75-6.58 (m, 1H), 4.39-4.26 (m, 1H), 4.18-4.13 (m, 1H), 3.7 (br s, 3H), 3.16 (s, 1H), 3.06 (s, 1H), 2.87-2.69 (m, 2H), 2.04-1.70 (m, 2H)

Step H: 2-(6-bromochroman-2-yl)-2-hydroxyacetic Acid

To a solution of methyl 2-(6-bromochroman-2-yl)-2-hydroxyacetate (4.3 g, 14.3 mmol) in THF (20 ml) and water (20 ml) was added LiOH (1.03 g, 42.8 mmol) at 0° C. The reaction mixture was stirred for 3 hours at 0° C., then the pH of the reaction mixture was adjusted to pH=2 with 1M HCl. The mixture was extracted with EtOAc (150 ml×3). The combined organic layers were washed with brine (40 ml*3), dried with anhydrous Na$_2$SO$_4$, and filtered. The filtrate solvent was removed under vacuum to give the title compound, which was used directly without further purification. $^1$H NMR (400 MHz, DMSO-d$_6$) δ 7.27-7.17 (m, 2H), 6.65 (dd, J=8.6, 20.0 Hz, 1H), 4.30 (br d, J=11.0 Hz, 1H), 4.23-4.13 (m, 2H), 2.83-2.71 (m, 2H), 1.96-1.80 (m, 2H)

Step I: tert-butyl 2-(6-bromochroman-2-yl)-2-hydroxyacetate

To a solution of 2-(6-bromochroman-2-yl)-2-hydroxyacetic acid (4.1 g, 14.3 mmol) in THF (100 mL) was added (Z)-tert-butyl N,N'-diisopropylcarbamimidate (14.3 g, 71 mmol). The reaction was stirred for 10 hours at 60° C. under a nitrogen atmosphere, then the reaction solvent was removed in vacuo. The resulting residue was purified via flash chromatography (SiO$_2$, 0-40% EtOAc in hexane) to give the title compound. $^1$H NMR (400 MHz, chloroform-d) δ 7.22-7.14 (m, 2H), 6.75-6.60 (m, 1H), 4.35-4.29 (m, 1H), 4.28-4.20 (m, 1H), 3.13-3.02 (m, 1H), 3.13-3.01 (m, 1H), 3.13-3.01 (m, 1H), 2.92-2.78 (m, 2H), 2.04-1.96 (m, 1H), 1.92-1.84 (m, 1H), 1.51 (d, J=8.8 Hz, 9H)

Step J: O-(mesitylsulfonyl)hydroxylamine

A solution of (E)-ethyl N-(mesitylsulfonyl)oxy-acetamidate (2.5 g, 8.8 mmol) in 1,4-dioxane (3 mL) was cooled to 0° C. and perchloric acid (0.90 ml, 0.90 mmol) was slowly added dropwise. After stirring for 15 minutes the reaction mixture solidified. To the solidified reaction mixture was added water (25 mL) and tert-butyl methyl ether (25 mL). The resulting reaction mixture was extracted with tert-butyl methyl ether (3×25 mL). The combined organic layers were neutralized, partially dried with anhydrous potassium carbonate and then filtered. The filtrate was concentrated to less than 10 mL total volume, then poured into 30 mL of ice cold hexane and left to crystallize for 30 minutes. The resulting crystals of the title compound were isolated by filtration, and used in the next step without further purification.

Step K: tert-butyl 2-(aminooxy)-2-(6-bromochroman-2-yl)acetate

Tert-butyl 2-(6-bromochroman-2-yl)-2-hydroxyacetate (1.0 g, 2.9 mmol) was dissolved in dry THF (16 mL) under a N$_2$ atmosphere. The mixture was cooled to 0° C., then NaH (0.14 g, 3.5 mmol, 60%) was added in one portion, followed by the addition of O-(mesitylsulfonyl)hydroxylamine (0.75 g, 3.5 mmol). The reaction mixture was stirred at 0° C. for 2 hours, then quenched with ice water (20 ml), and extracted with EtOAc (3×15 mL). The combined organic layers were washed by saturated brine (30 ml×3), dried over Na$_2$SO$_4$, filtered and concentrated in vacuo. The resulting residue was purified by column chromatography on silica gel (SiO$_2$, EtOAc/Pentane=0~20%) to give the title compound. LC-MS (ESI) calc'd for C$_{15}$H$_{20}$BrNO$_4$ [M+H-56]+:302.0, found: 302.0; 304.0.

Step L: tert-butyl 2-(aminooxy)-2-(6-bromochroman-2-yl)acetate

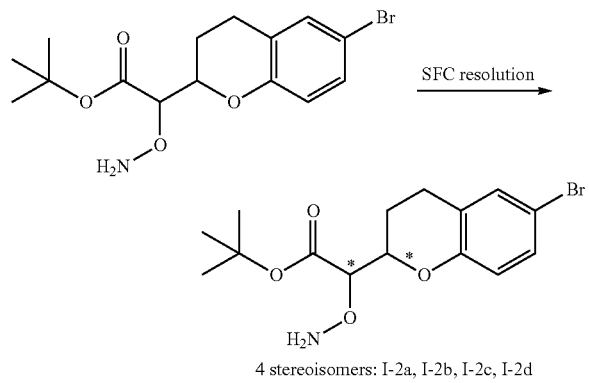

4 stereoisomers: I-2a, I-2b, I-2c, I-2d

Tert-butyl 2-(aminooxy)-2-(6-bromochroman-2-yl)acetate (4.2 g, 11.7 mmol) was separated by SFC (Column: Chiralpak AD-3 250*30 mm I.D, 5 um Mobile phase: A: $CO_2$ B: IPA (0.05% $NH_3*H_2O$) Gradient: from 5% to 40% of B in 5 min and hold 40% for 2.5 min, then 5% of B for 2.5 min Flow rate: 75 mL/min Column temp.: 35° C. Wavelength: 220 nm) to afford four isomers in the order of elution.

I-2a: LC/MS:MS (ESI) m/z: 302.1 [M+H$^+$-56]. $^1$H NMR (400 MHz, chloroform-d) δ 7.18-7.16 (m, 2H), 6.72-6.69 (m, 1H), 5.82 (br s, 1H), 4.32 (d, J=4.0 Hz, 1H), 4.27-4.22 (m, 1H), 2.82-2.76 (m, 2H), 2.02-1.97 (m, 1H), 1.51 (s, 9H).

I-2b: LC/MS:MS (ESI) m/z: 302.1 [M+H$^+$-56]. $^1$H NMR (400 MHz, chloroform-d) δ 7.18-7.16 (m, 2H), 6.72-6.69 (m, 1H), 5.82 (br s, 1H), 4.32 (d, J=4.0 Hz, 1H), 4.27-4.22 (m, 1H), 2.82-2.73 (m, 2H), 2.03-1.97 (m, 1H), 1.51 (s, 9H).

I-2c: LC/MS:MS (ESI) m/z: 302.1 [M+H$^+$-56]. $^1$H NMR (400 MHz, CHLOROFORM-d) δ 7.17-7.15 (m, 2H), 6.69 (d, J=8.0 Hz, 9H), 5.88 (br s, 1H), 4.33-4.30 (m, 1H), 4.24-4.23 (m, 1H), 2.88-2.81 (m, 2H), 2.07-1.97 (m, 1H), 1.53 (d, J=2.8 Hz, 9H).

I-2d: LC/MS:MS (ESI) m/z: 302.1 [M+H$^+$-56]. $^1$H NMR (400 MHz, CHLOROFORM-d) δ 7.16-7.14 (m, 2H), 6.68 (dd, J=2.8, 8.4 Hz, 1H), 5.89 (br s, 1H), 4.33-4.29 (m, 1H), 4.24-4.22 (m, 1H), 2.86-2.76 (m, 2H), 2.06-1.95 (m, 1H), 1.53 (d, J=3.2 Hz, 9H).

Intermediate 3 tert-butyl (3-(4-(4,4,5,5-tetramethyl-1,3,2-dioxaborolan-2-yl)-1H-pyrazol-1-yl)propyl)carbamate

I-3

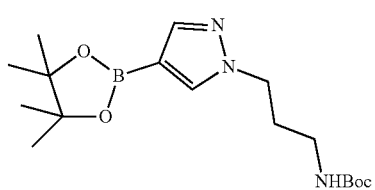

A solution of 4-(4,4,5,5-tetramethyl-1,3,2-dioxaborolan-2-yl)-1H-pyrazole (0.82 g, 4.2 mmol), tert-butyl (3-bromopropyl)carbamate (1 g, 4.2 mmol), and $Cs_2CO_3$ (2.1 g, 6.3 mmol) in DMF (10 ml) was stirred at RT overnight. Then the reaction mixture was diluted with water (30 ml) and extracted with EtOAc (3×10 ml). The combined organic layers were dried over MgSO$_4$ and concentrated to give the crude product, which was purified by Biotage SiO$_2$ column (24 g), and eluted with Hexane/EtOAc (0-100%) to give the title compound. LC-MS [M+1]: m/z 352.44

Intermediate 4

(S)-3-(2-(2-((tert-Butoxycarbonyl)amino)thiazol-4-yl)-2-oxoacetamido)-2,2-dimethyl-4-oxoazetidin-1-yl Hydrogen Sulfate

I-4

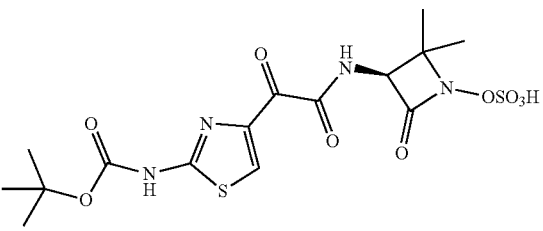

To a solution of 2-(2-((tert-butoxycarbonyl)amino)thiazol-4-yl)-2-oxoacetic acid (2 g, 7.4 mmol), (S)-3-amino-2,2-dimethyl-4-oxoazetidin-1-yl hydrogen sulfate (3.1 g, 14.7 mmol, CAS: 102507-49-3) and pyridine (1.782 ml, 22.04 mmol) in MeCN (36.7 mL) was added EDC (3.5 g, 18.4 mmol) at 0° C. The reaction was allowed to warm to ambient temperature overnight. After 16 h, the reaction was poured into brine (100 mL) and extracted with MeCN (50 mL). The combined organic layers were dried over MgSO$_4$, filtered, and concentrated in vacuo. The resulting residue was purified by SiO$_2$ flash chromatography and eluted with hexanes/(3:1 EtOAc/EtOH) 0-100% to afford the title compound. LC-MS [M+H]: m/z 465.2

Intermediate 5 tert-Butyl (S)-(2-((tert-butyldimethylsilyl)oxy)-3-(4-(4,4,5,5-tetramethyl-1,3,2-dioxaborolan-2-yl)-1H-pyrazol-1-yl)propyl)carbamate

I-5

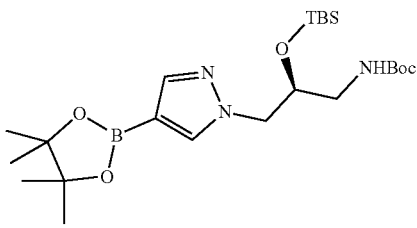

Cesium carbonate (4.9 g, 15 mmol) was added to a room temperature mixture of 4-(4,4,5,5-tetramethyl-1,3,2-dioxaborolan-2-yl)-1H-pyrazole (2.4 g, 12.5 mmol)), tert-butyl (3-bromo-(S)-2-((tert-butyldimethylsilyl)oxy)propyl)carbamate (4.6 g, 12.5 mmol)) in 10 mL of DMF. The reaction mixture was stirred at 60° C. overnight, and then stirred at 70° C. for 24 hrs. LC-MS showed the major peak was

Intermediate 6 tert-Butyl 3-((tert-butoxycarbonyl)amino)-3-((4-(4,4,5,5-tetramethyl-1,3,2-dioxaborolan-2-yl)-1H-pyrazol-1-yl)methyl)azetidine-1-carboxylate

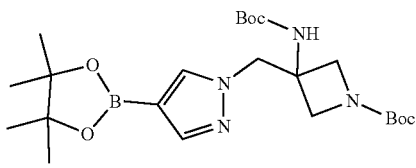

I-6

Step A: tert-Butyl 3-((tert-butoxycarbonyl)amino)-3-(((methylsulfonyl)oxy)methyl)-azetidine-1-carboxylate To a solution of tert-butyl 3-((tert-butoxycarbonyl)amino)-3-(hydroxymethyl)azetidine-1-carboxylate (500 mg, 1.65 mmol) in CH$_2$Cl$_2$ (5 ml) was added DIPEA (0.32 ml, 1.8 mmol) and methanesulfonyl chloride (0.14 ml, 1.8 mmol). The reaction mixture was stirred at RT for 3 hr, then diluted with DCM, washed with saturated NH$_4$Cl, brine, dried over Na$_2$SO$_4$, and filtered. The filtrate solvent was removed in vacuo to give the title compound. LC-MS [M+1]: m/z 381.49.

Step B: tert-Butyl 3-((tert-butoxycarbonyl)amino)-3-((4-(4,4,5,5-tetramethyl-1,3,2-dioxaborolan-2-yl)-1H-pyrazol-1-yl)methyl)azetidine-1-carboxylate To a solution of tert-butyl 3-((tert-butoxycarbonyl)amino)-3-(((methylsulfonyl)oxy)methyl) azetidine-1-carboxylate (0.63 g, 1.65 mmol) in DMF (5 ml) was added 4-(4,4,5,5-tetramethyl-1,3,2-dioxaborolan-2-yl)-1H-pyrazole (0.32 g, 1.65 mmol) and Cs$_2$CO$_3$ (1.08 g, 3.3 mmol). The reaction mixture was stirred at RT overnight, then diluted with EtOAc, washed with water and brine, dried over Na$_2$SO$_4$, and filtered. The filtrate solvent was removed in vacuo. The resulting residue was purified by column chromatography on silica gel Redi 24 g gold, eluting with EtOAc/hexane (0-30%, 6 cv; 30%, 10 cv) to give the title compound. LC-MS [M+1]: m/z 480.53.

product. The reaction mixture was cooled to RT, and diluted with EtOAc and water. The water layer was separated and extracted with EtOAc. The combined organic layers were washed with brine, dried over MgSO$_4$, filtered and concentrated in vacuo. The resulting residue was purified by column chromatography on silica gel, eluting with EtOAc/isohexane (5-60%) to give the title compound. LC-MS [M+H]: m/z 482.5

Intermediate 7

(6-bromochroman-2-yl)methanol

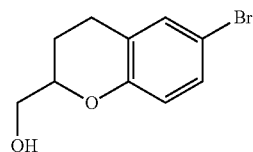

6-bromochroman-2-carboxylic acid (7.0 g, 7.8 mmol) was dissolved in anhydrous THF (136 mL), and the mixture was purged with N$_2$ for 5 min. To this solution at 0° C. was added borane tetrahydrofuran complex (45 ml, 45 mmol), and the resulting mixture was stirred at RT for 3 hours. The reaction was quenched by the addition of water, and the resulting mixture was extracted with EOAc (2×50 mL). The combined organic layers were washed with brine, dried over sodium sulfate, filtered and concentrated. The resulting residue was purified on ISCO column (3:1 EtOAc:EtOH/hexane 0-80%) to give title compound as a racemic mixture. LC-MS [M+1]: m/z 243.02.

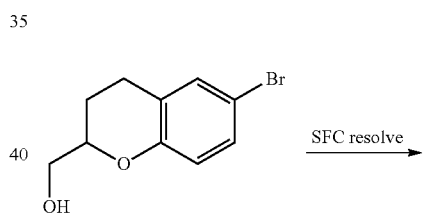

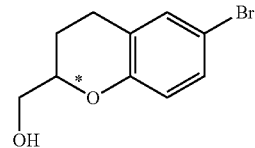 [SMILES: OCC1CCc2cc(Br)ccc2O1]

2 stereoisomers: I-7a, I-7b

The racemic mixture was separated via SFC(Column: Chiralpak AD-3 150×4.6 mm I.D., 3 m Mobile phase: A: CO$_2$ B: ethanol (0.05% DEA) gradient to give two enantiomers I-7a and I-7b.

Intermediate 8

(7-bromochroman-3-yl)methanol&(7-bromochroman-3-yl)methanol

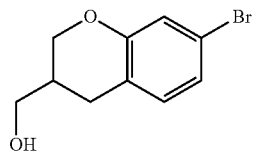 [SMILES: OCC1COc2cc(Br)ccc2C1]

Step A: 4-bromo-1-(bromomethyl)-2-iodobenzene

A solution of 4-bromo-2-iodo-1-methylbenzene (16 g, 53 mmol) in $C_1CH_2CH_2C_1$ (80 mL) was stirred at 20° C. under nitrogen. Benzoyl peroxide (0.64 g, 2.6 mmol) and NBS (10.4 g, 58 mmol) were added to the solution at once, and the resulting mixture was heated to 90° C. for 5 h. The reaction mixture was allowed to cool to 20° C. The resulting precipitate was filtered off and washed with EtOAc (10 mL). The filtrate was dried over $Na_2SO_4$ and filtered. The filtrate solvent was removed under reduced pressure. The resulting residue was purified by silica-gel chromatography ($SiO_2$, PE:EA=100%) to give the title compound. $^1H$ NMR (400 MHz, chloroform-d, ppm) δ=7.99 (d, J=1.6 Hz, 1H), 7.50-7.39 (m, 1H), 7.31 (d, J=8.2 Hz, 1H), 4.52 (s, 2H).

Step B: diethyl 2-(4-bromo-2-iodobenzyl)malonate

To a suspension of 60% sodium hydride (0.80 g, 20 mmol) in dry THF (70 mL) was added dropwise diethyl malonate (1.8 g, 20 mmol). When the gas evolution finished, 4-bromo-1-(bromomethyl)-2-iodobenzene (7 g, 19 mmol) was added and the reaction mixture was stirred for 18 h at 25° C. Then the reaction mixture was quenched with a saturated aqueous solution of ammonium chloride (70 mL) and extracted with ethyl acetate (2×60 mL). The combined organic layers were dried over anhydrous sodium sulfate, and filtered. The filtrate was evaporated at reduced pressure to give a residue, which was purified by flash chromatography (silica gel, ethyl acetate/pet ether=0% to 10%) to give the title compound. $^1H$ NMR (400 MHz, chloroform-d, ppm) δ=7.95 (d, J=1.6 Hz, 1H), 7.36 (dd, J=1.8, 8.0 Hz, 1H), 7.10 (d, J=8.2 Hz, 1H), 4.21-4.10 (m, 4H), 3.75 (t, J=7.8 Hz, 1H), 3.26 (d, J=7.8 Hz, 2H), 1.25-1.12 (m, 6H)

Step C: 2-(4-bromo-2-iodobenzyl)propane-1,3-diol

To a solution of lithium chloride (1.4 g, 33 mmol) and $NaBH_4$ (1.25 g, 33 mmol) in ethanol (80 mL) was added diethyl 2-(4-bromo-2-iodobenzyl)malonate (5 g, 11 mmol) in THF (80 mL) at 0° C. The reaction was stirred at 20° C. for 14 h, then quenched with water (80 mL) and concentrated in vacuo to remove ethanol and THF. The resulting residue was extracted with EtOAc (3×70 mL), dried over $Na_2SO_4$, filtered and concentrated. The resulting residue was purified by silica-gel chromatography ($SiO_2$, PE:EA=0% to 70%) to give the title compound. $^1H$ NMR (400 MHz, chloroform-d, ppm) δ=7.95 (d, J=2.0 Hz, 1H), 7.38 (dd, J=1.6, 8.2 Hz, 1H), 7.10 (d, J=8.2 Hz, 1H), 3.83 (dd, J=3.5, 10.6 Hz, 2H), 3.68 (dd, J=6.3, 11.0 Hz, 2H), 2.73 (d, J=7.4 Hz, 2H), 2.10-2.04 (m, 1H)

Step D: (7-bromochroman-3-yl)methanol

A solution of 2-(4-bromo-2-iodobenzyl)propane-1,3-diol (3 g, 8.1 mmol) in DMF (30 mL) was stirred at 20° C. Then copper (I) iodide (0.31 g, 1.62 mmol), 2,2'-bipyridine (0.25 g, 1.6 mmol) and potassium 2-methylpropan-2-olate (2.7 g, 24 mmol) were added. The reaction mixture was stirred at 120° C. for 24 h, then filtered and diluted with EtOAc (300 mL), washed with saturated brine (3×200 mL). The organic layer was dried over $Na_2SO_4$, filtered and concentrated. The resulting residue was purified by silica-gel chromatography ($SiO_2$, EA:PE=0% to 30%) to give the title compound. $^1H$ NMR (400 MHz, chloroform-d, ppm) δ=7.01-6.91 (m, 2H), 6.91-6.86 (m, 1H), 4.27 (ddd, J=1.3, 3.0, 10.8 Hz, 1H), 3.98 (dd, J=7.6, 10.8 Hz, 1H), 3.70-3.63 (m, 2H), 2.80 (br dd, J=5.6, 16.3 Hz, 1H), 2.52 (dd, J=7.8, 16.4 Hz, 1H), 2.28-2.22 (m, 1H)

Step E: (7-bromochroman-3-yl)methanol&(7-bromochroman-3-yl)methanol

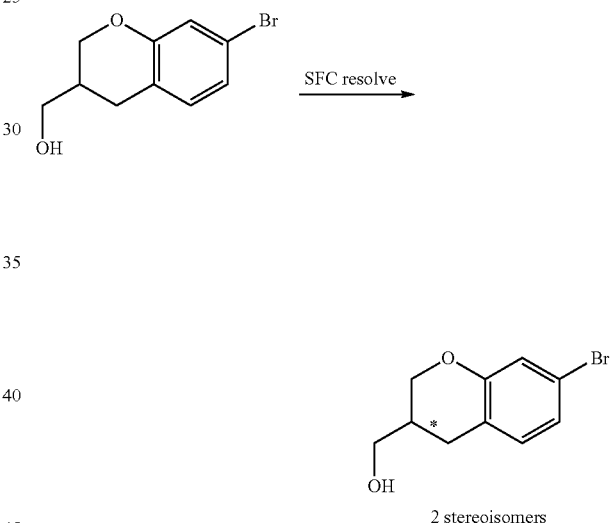

A solution of (7-bromochroman-3-yl)methanol (1.2 g, 4.9 mmol) was separated by SFC (Column: Chiralpak AD-3 150×4.6 mm I.D., 3 m Mobile phase: A: $CO_2$ B: ethanol (0.05% DEA) Gradient: from 5% to 40% of B in 5 min and hold 40% for 2.5 min, then 5% of B for 2.5 min Flow rate: 2.5 mL/min Column temp.: 35° C.) to give I-8a (peak 1: Rt=4.480 min) and I-8b (peak 2: Rt=5.525 min).

I-8a (isomer 1): $^1H$ NMR (400 MHz, chloroform-d, ppm) δ=7.04-6.91 (m, 2H), 6.90-6.87 (m, 1H), 4.30-4.25 (m, 1H), 3.98 (dd, J=7.7, 10.7 Hz, 1H), 3.71-3.62 (m, 2H), 2.78 (br d, J=5.7 Hz, 1H), 2.54 (br d, J=8.0 Hz, 1H), 2.28-2.21 (m, 1H); LCMS (ESI) calc'd for $C_{26}H_{37}BrN_4O_6[M+3H]^+$:583.1, found: 583.2.

I-8b (isomer 2): $^1H$ NMR (400 MHz, chloroform-d, ppm) δ=7.01-6.96 (m, 2H), 6.94-6.91 (m, 1H), 4.31 (ddd, J=1.4, 3.1, 10.9 Hz, 1H), 4.02 (dd, J=7.3, 10.8 Hz, 1H), 3.76-3.65

(m, 2H), 2.84 (dd, J=5.6, 16.4 Hz, 1H), 2.57 (dd, J=7.9, 16.4 Hz, 1H), 2.33-2.25 (m, 1H); LCMS (ESI) calc'd for $C_{26}H_{37}BrN_4O_6[M+3H]^+$:583.1, found: 583.2.

Examples 1a, 1b, 1c, 1d (S)-3-((Z)-2-(((S)-1-((S)-6-(1-(3-aminopropyl)-2-methyl-H-pyrazol-2-ium-4-yl)chroman-2-yl)-1-carboxyethoxy)imino)-2-(2-aminothiazol-4-yl)acetamido)-2,2-dimethyl-4-oxoazetidin-1-yl Sulfate (1a)

(S)-3-((Z)-2-(((R)-1-((R)-6-(1-(3-aminopropyl)-2-methyl-H-pyrazol-2-ium-4-yl)chroman-2-yl)-1-carboxyethoxy)imino)-2-(2-aminothiazol-4-yl)acetamido)-2,2-dimethyl-4-oxoazetidin-1-yl Sulfate (1b)

(S)-3-((Z)-2-(((S)-1-((R)-6-(1-(3-Aminopropyl)-2-methyl-1H-pyrazol-2-ium-4-yl)chroman-2-yl)-1-carboxyethoxy)imino)-2-(2-aminothiazol-4-yl)acetamido)-2,2-dimethyl-4-oxoazetidin-1-yl Sulfate (1c)

(S)-3-((Z)-2-(((R)-1-((S)-6-(1-(3-aminopropyl)-2-methyl-H-pyrazol-2-ium-4-yl)chroman-2-yl)-1-carboxyethoxy)imino)-2-(2-aminothiazol-4-yl)acetamido)-2,2-dimethyl-4-oxoazetidin-1-yl Sulfate (1d)

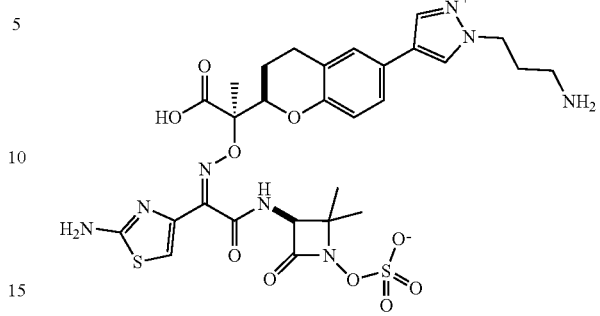

1a

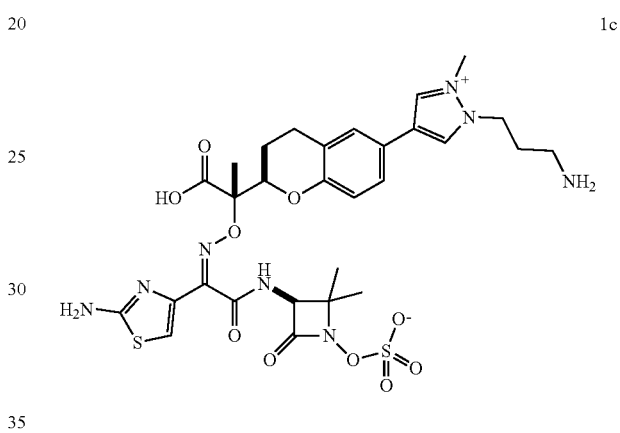

1b

1c

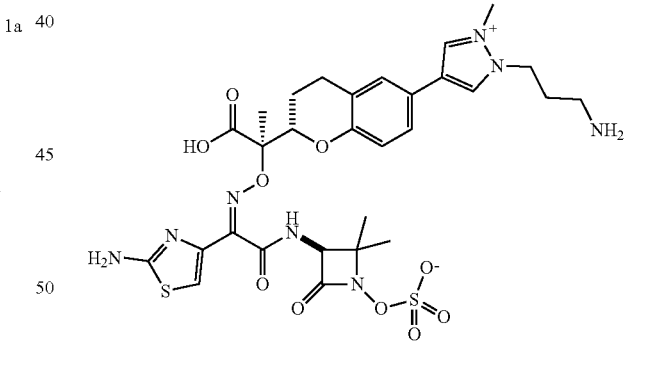

1d

Synthesis of Example 1c

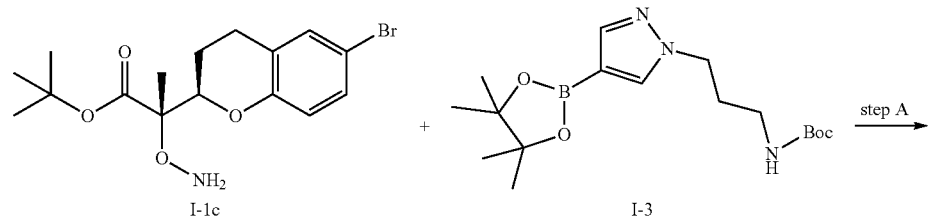

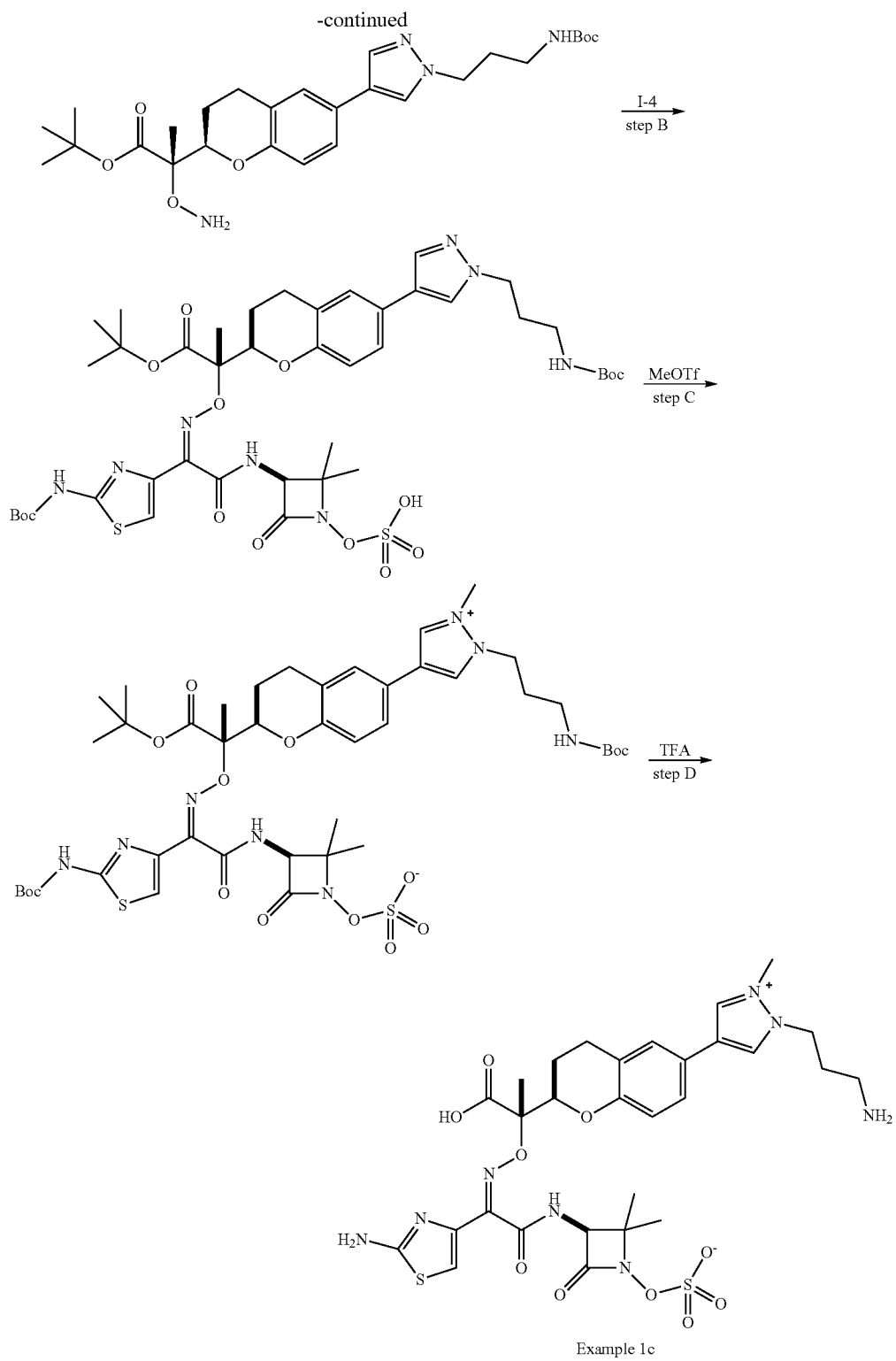

Example 1c

Step A: tert-Butyl (S)-2-(aminooxy)-2-((R)-6-(1-(3-((tert-butoxycarbonyl)amino)propyl)-1H-pyrazol-4-yl)chroman-2-yl)propanoate A mixture of (E)-tert-butyl (4-bromo-1-(3-((tert-butoxycarbonyl)amino)propyl)-3-methyl-1H-imidazol-2(3H)-ylidene)carbamate (530 mg, 1.5 mmol), tert-butyl (S)-2-(aminooxy)-2-((R)-6-bromochroman-2-yl)propanoate (Intermediate 1: I-1c, 500 mg, 1.34 mmol), 1,1'-bis(di-tert-butylphosphino)ferrocene palladium dichloride (175 mg, 0.27 mmol) and potassium phosphate tribasic (2.0 ml, 4.0 mmol, 2M) in THF (8 ml) was degassed and refilled with $N_2$ three times. The reaction mixture was heated at 60° C. for 3 h, then diluted with water, and extracted with EtOAc (3×).

The combined organic layers were dried over MgSO$_4$, filtered and the filtrate was concentrated. The resulting residue was purified by column chromatography on silica gel (pre-packed 40 g Redi Gold™ column) eluting with EtOAc/hexane (0-80%, 6 cv; 80%, 10 column volumes (cv)) to give the title compound. LC-MS [M+1]: m/z 518.52.

Step B: tert-Butyl (S)-2-((R)-6-(1-(3-((tert-butoxy-carbonyl)amino)propyl)-1H-pyrazol-4-yl)chroman-2-yl)-2-((((Z)-1-(2-((tert-butoxycarbonyl)amino) thiazol-4-yl)-2-(((S)-2,2-dimethyl-4-oxo-1-(sulfooxy)azetidin-3-yl)amino)-2-oxoethylidene) amino)oxy)propanoate To a solution of tert-butyl (S)-2-(aminooxy)-2-((R)-6-(1-(3-((tert-butoxycarbonyl)amino)-propyl)-1H-pyrazol-4-yl) chroman-2-yl)propanoate (0.42 g, 0.81 mmol) in MeOH (5 ml) and CH$_2$C$_1$CH$_2$C$_1$ (2.5 ml) were added (S)-3-(2-(2-((tert-butoxycarbonyl) amino)thiazol-4-yl)-2-oxoacet-amido)-2,2-dimethyl-4-oxoazetidin-1-yl hydrogen sulfate (0.48 g, 0.81 mmol, 78%) and p-toluenesulfonic acid polymer-bond (2-3 mmol/g, 30 mg, 0.17 mmol). The mixture was stirred at RT for 7 h, then filtered, and the filtrate was concentrated to give the title compound. LC-MS [M+1]: m/z 964.01.

Step C: (S)-3-((Z)-2-((((S)-1-(tert-Butoxy)-2-((R)-6-(1-(3-((tert-butoxy carbonyl)amino)-propyl)-2-methyl-1H-pyrazol-2-ium-4-yl)chroman-2-yl)-1-oxopropan-2-yl)oxy)imino)-2-(2-((tert-butoxycarbonyl)amino)thiazol-4-yl)acetamido)-2,2-dimethyl-4-oxoazetidin-1-yl Sulfate TFA To a solution of tert-butyl (S)-2-((R)-6-(1-(3-((tert-butoxycarbonyl)-amino)propyl)-1H-pyrazol-4-yl)chroman-2-yl)-2-((((Z)-1-(2-((tert-butoxycarbonyl)amino)-thiazol-4-yl)-2-(((S)-2,2-dimethyl-4-oxo-1-(sulfooxy)azetidin-3-yl) amino)-2-oxoethylidene)-amino)oxy)propanoate (780 mg, 0.81 mmol) in acetonitrile (6 ml) were added sodium carbonate (1.7 g, 16 mmol) and methyl trifluoromethane-sulfonate (0.089 ml, 0.81 mmol). The mixture was stirred at RT for 1 hr, then the resulting solid was filtered off, and the solvent was removed. The resulting residue was dissolved in 1 mL DMSO and purified on RPHPLC (Gilson C-18 column), eluting with 20-100% ACN/Water containing 0.05% TFA (12 min) to give the title compound. LC-MS [M+1]: m/z 978.06.

Step D: (S)-3-((Z)-2-(((S)-1-((R)-6-(1-(3-Aminopropyl)-2-methyl-1H-pyrazol-2-ium-4-yl)chroman-2-yl)-1-carboxyethoxy)imino)-2-(2-aminothiazol-4-yl) acetamido)-2,2-dimethyl-4-oxoazetidin-1-yl Sulfate To a solution of (S)-3-((Z)-2-((((S)-1-(tert-butoxy)-2-((R)-6-(1-(3-((tert-butoxycarbonyl)amino)propyl)-2-methyl-1H-pyrazol-2-ium-4-yl)chroman-2-yl)-1-oxopropan-2-yl)oxy)imino)-2-(2-((tert-butoxycarbonyl)amino) thiazol-4-yl)acetamido)-2,2-dimethyl-4-oxoazetidin-1-yl sulfate TFA salt (340 mg, 0.28 mmol) in CH$_2$Cl$_2$ (1 mL) was added TFA (2 mL). The solution was stirred at RT for 0.5 hr, then the solvent was removed. The resulting residue was washed with Et$_2$O three times and dried. The crude solid product was purified on RPHPLC (Gilson C-18 column), eluting with 0-40% ACN/water containing 0.1% formic acid (12 min) to give title compound 1-1c. LC-MS [M+1]: m/z 721.67. $^1$HNMR (500 MHz, D$_2$O) $\delta_H$ 8.44 (1H, s), 8.38 (1H, s), 7.25 (1H, s), 7.22 (1H, d), 6.88 (1H, s), 6.77 (1H, d), 4.55 (2H, t), 4.48 (1H, d), 4.10 (3H, s), 3.12 (2H, m), 2.74 (1H, m), 2.33 (2H, m), 2.08 (1H, m), 1.82 (1H, m), 1.54 (3H, s), 1.36 (3H, s), 1.20 (3H, s).

Using the same procedure with corresponding isomers of intermediate I-1a, I-1b, and I-1d, examples 1a, 1b, and 1d were prepared:

1a: (S)-3-((Z)-2-(((S)-1-((S)-6-(1-(3-aminopropyl)-2-methyl-1H-pyrazol-2-ium-4-yl)chroman-2-yl)-1-carboxy-ethoxy)imino)-2-(2-aminothiazol-4-yl)acetamido)-2,2-dimethyl-4-oxoazetidin-1-yl sulfate. LC-MS [M+1]: m/z 721.47

1b: (S)-3-((Z)-2-(((R)-1-((R)-6-(1-(3-aminopropyl)-2-methyl-1H-pyrazol-2-ium-4-yl)chroman-2-yl)-1-carboxy-ethoxy)imino)-2-(2-aminothiazol-4-yl)acetamido)-2,2-dimethyl-4-oxoazetidin-1-yl sulfate. LC-MS [M+1]: m/z 721.41

1d: (S)-3-((Z)-2-(((R)-1-((S)-6-(1-(3-aminopropyl)-2-methyl-1H-pyrazol-2-ium-4-yl)chroman-2-yl)-1-carboxy-ethoxy)imino)-2-(2-aminothiazol-4-yl)acetamido)-2,2-dimethyl-4-oxoazetidin-1-yl sulfate. LC-MS [M+1]: m/z 721.34

Example 2a, 2b, 2c, 2d (S)-3-((Z)-2-(((S)—(R)-6-(1-(3-Aminopropyl)-2-methyl-1H-pyrazol-2-ium-4-yl)chroman-2-yl)(carboxy)methoxy)imino)-2-(2-aminothiazol-4-yl)acet-amido)-2,2-dimethyl-4-oxoazetidin-1-yl Sulfate (2a)

(S)-3-((Z)-2-(((R)—(R)-6-(1-(3-Aminopropyl)-2-methyl-1H-pyrazol-2-ium-4-yl)chroman-2-yl)(carboxy)methoxy)imino)-2-(2-aminothiazol-4-yl)acet-amido)-2,2-dimethyl-4-oxoazetidin-1-yl Sulfate (2b)

(S)-3-((Z)-2-(((S)—(S)-6-(1-(3-Aminopropyl)-2-methyl-1H-pyrazol-2-ium-4-yl)chroman-2-yl)(carboxy)methoxy)imino)-2-(2-aminothiazol-4-yl)acet-amido)-2,2-dimethyl-4-oxoazetidin-1-yl Sulfate (2c)

(S)-3-((Z)-2-(((R)—(S)-6-(1-(3-Aminopropyl)-2-methyl-1H-pyrazol-2-ium-4-yl)chroman-2-yl)(carboxy)methoxy)imino)-2-(2-aminothiazol-4-yl)acet-amido)-2,2-dimethyl-4-oxoazetidin-1-yl Sulfate (2d)

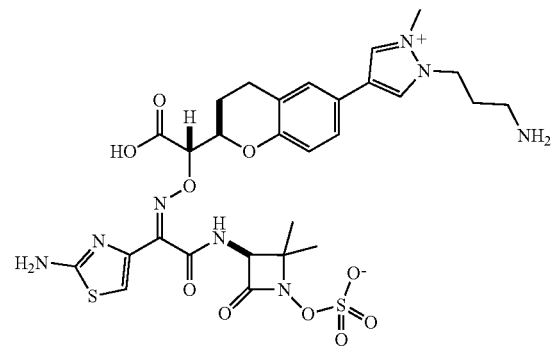

2a

-continued

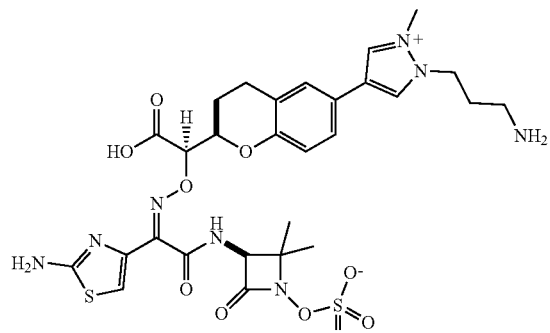

2b

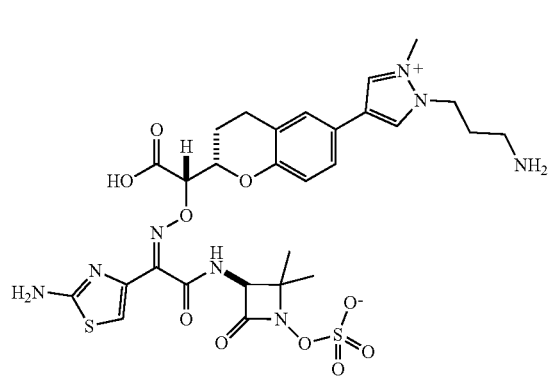

2c

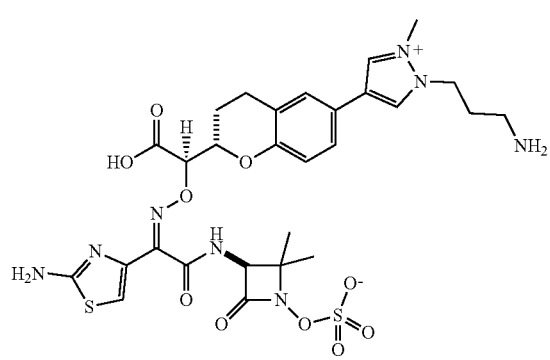

2d

Synthesis of Example 2a

Step A: tert-Butyl (S)-2-(aminooxy)-2-((R)-6-(1-(3-((tert-butoxycarbonyl)amino)propyl)-1H-pyrazol-4-yl)chroman-2-yl)acetate A mixture of tert-butyl (3-(4-(4,4,5,5-tetramethyl-1,3,2-dioxaborolan-2-yl)-1H-pyrazol-1-yl)propyl)carbamate (119 mg, 0.34 mmol), tert-butyl (S)-2-(aminooxy)-2-((R)-6-bromochroman-2-yl)acetate (110 mg, 0.31 mmol), 1,1'-bis(di-tert-butylphosphino)ferrocene palladium dichloride (40 mg, 0.061 mmol) and potassium phosphate tribasic (0.46 ml, 0.92 mmol, 2M) in THF (2 ml) was degassed and refilled with $N_2$ three times. The reaction mixture was heated at 60° C. for 3 h, then diluted with water, and extracted with EtOAc 3 times. The combined organic layers were dried over $MgSO_4$, filtered, and the filtrate solution was concentrated. The resulting residue was purified by column chromatography on silica gel Redi-sep 24 g gold, eluting with EtOAc/hexane (0-80%, 6 cv; 80%, 10 cv) to give the title compound. LC-MS [M+1]: m/z 503.60.

Step B: tert-Butyl (S)-2-((R)-6-(1-(3-((tert-butoxycarbonyl)amino)propyl)-1H-pyrazol-4-yl)chroman-2-yl)-2-((((Z)-1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)acetate To a solution of (S)-3-(2-(2-((tert-butoxycarbonyl)amino)thiazol-4-yl)-2-oxoacetamido)-2,2-dimethyl-4-oxoazetidin-1-yl hydrogen sulfate (59 mg, 0.099 mmol, 78%) in MeOH (2 mL) were added tert-butyl (S)-2-(aminooxy)-2-((R)-6-(1-(3-((tert-butoxycarbonyl)amino)-propyl)-1H-pyrazol-4-yl)chroman-2-yl)acetate (50 mg, 0.099 mmol) and polymer-bond p-toluenesulfonic acid (2-3 mmol/g, 2 mg, 0.012 mmol). The mixture was stirred at RT overnight. The resulting solid was filtered off and the filtrate was concentrated to give the title compound. LC-MS [M+1]: m/z 949.94.

Step C: (S)-3-((Z)-2-(((S)-2-(tert-Butoxy)-1-((R)-6-(1-(3-((tert-butoxycarbonyl)amino)-propyl)-2-methyl-1H-pyrazol-2-ium-4-yl)chroman-2-yl)-2-oxoethoxy)imino)-2-(2-((tert-butoxycarbonyl)amino)thiazol-4-yl)acetamido)-2,2-dimethyl-4-oxoazetidin-1-yl Sulfate To a solution of tert-butyl (S)-2-((R)-6-(1-(3-((tert-butoxycarbonyl)amino)propyl)-1H-pyrazol-4-yl)chroman-2-yl)-2-((((Z)-1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)acetate (94 mg, 0.099 mmol) in acetonitrile (1 ml) was added methyl trifluoromethanesulfonate (11 µl, 0.099 mmol). The mixture was stirred at RT for 0.5 hr. Then the solvent was removed. The resulting residue was dissolved in 1 mL DMSO and purified on RPHPLC (Gilson C-18 column), eluting with 20-100% ACN/water containing 0.05% TFA (12 min) to give the title compound. LC-MS [M+1]: m/z 963.90

Step D: (S)-3-((Z)-2-(((S)—(R)-6-(1-(3-Aminopropyl)-2-methyl-1H-pyrazol-2-ium-4-yl)chroman-2-yl)(carboxy)methoxy)imino)-2-(2-aminothiazol-4-yl)acetamido)-2,2-dimethyl-4-oxoazetidin-1-yl Sulfate (2a)

To a solution of (S)-3-((Z)-2-(((S)-2-(tert-butoxy)-1-((R)-6-(1-(3-((tert-butoxycarbonyl) amino)propyl)-2-methyl-1H-pyrazol-2-ium-4-yl)chroman-2-yl)-2-oxoethoxy)imino)-2-(2-((tert-butoxycarbonyl)amino)thiazol-4-yl)acetamido)-2,2-dimethyl-4-oxoazetidin-1-yl sulfate (52 mg, 0.054 mmol) in $CH_2Cl_2$ (0.5 ml) was added TFA (1 mL, 13 mmol). The solution was stirred at RT for 0.5 hr. Then the solvent was removed; and the residue was washed with $Et_2O$ three times and dried. The resulting solid was purified on RPHPLC (Gilson C-18 column), eluting with 0-40% ACN/water containing 0.1% formic acid (12 min) to give the title compound. LC-MS [M+1]: m/z 707.52 $^1$HNMR (500 MHz, $D_2O$) $\delta_H$ 8.49 (1H, s), 8.43 (1H, s), 7.44 (2H, d), 7.27 (1H, d), 7.19 (1H, s), 6.80 (1H, d), 5.16 (1H, s), 4.13 (3H, s), 3.12 (2H, d), 2.77 (1H, m), 2.33 (2H, m), 2.10-1.90 (2H, m), 1.53 (3H, s), 1.34 (3H, s).

Using the same procedure with corresponding isomers of intermediate I-2, 2b, 2c, 2d isomers were prepared:

2b: (S)-3-((Z)-2-(((R)—((R)-6-(1-(3-Aminopropyl)-2-methyl-1H-pyrazol-2-ium-4-yl)chroman-2-yl)(carboxy)methoxy)imino)-2-(2-aminothiazol-4-yl)acetamido)-2,2-dimethyl-4-oxoazetidin-1-yl sulfate LC-MS [M+1]: m/z 707.56

2c: (S)-3-((Z)-2-(((S)—((S)-6-(i-(3-Aminopropyl)-2-methyl-1H-pyrazol-2-ium-4-yl)chroman-2-yl)(carboxy)methoxy)imino)-2-(2-aminothiazol-4-yl)acetamido)-2,2-dimethyl-4-oxoazetidin-1-yl sulfate LC-MS [M+1]: m/z 707.61

2d: (S)-3-((Z)-2-(((R)—((S)-6-(1-(3-Aminopropyl)-2-methyl-1H-pyrazol-2-ium-4-yl)chroman-2-yl)(carboxy)methoxy)imino)-2-(2-aminothiazol-4-yl)acetamido)-2,2-dimethyl-4-oxoazetidin-1-yl sulfate LC-MS [M+1]: m/z 707.52

Example 3

(S)-3-((Z)-2-(((S)-1-((R)-6-(1-(3-Aminopropyl)-2-(azetidin-3-ylmethyl)-1H-pyrazol-2-ium-4-yl)chroman-2-yl)-1-carboxyethoxy)imino)-2-(2-aminothiazol-4-yl)acetamido)-2,2-dimethyl-4-oxoazetidin-1-yl Sulfate

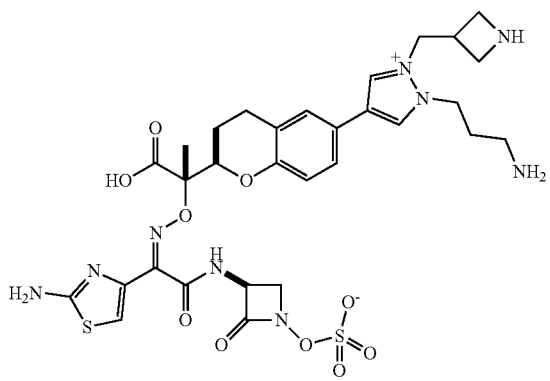

Step A: tert-Butyl (S)-2-((((allyloxy)carbonyl)amino)oxy)-2-((R)-6-(1-(3-((tert-butoxycarbonyl)amino)propyl)-1H-pyrazol-4-yl)chroman-2-yl)propanoate To a solution of tert-butyl (S)-2-(aminooxy)-2-((R)-6-(1-(3-((tert-butoxycarbonyl)amino)propyl)-1H-pyrazol-4-yl)chroman-2-yl)propanoate (1.1 g, 2.05 mmol, compound of Example 1, Step A) and DIPEA (0.54 ml, 3.1 mmol) in CH$_2$Cl$_2$ (20 ml) was added allyl carbonochloridate (0.26 ml, 2.5 mmol). The mixture was stirred at room temperature for 1 hr, then the solvent was removed. The resulting residue was purified by column chromatography on silica gel Redi 40 g gold, eluting with EtOAc/Hexane (0-70%, 5 cv, 70%, 6 cv) to give the title compound. LC-MS [M+1]: m/z 601.3.

Step B: 1-(3-((tert-Butoxycarbonyl)amino)propyl)-2-((1-(tert-butoxycarbonyl)azetidin-3-yl)methyl)-4-((R)-2-((S)-2,2,5-trimethyl-4,8-dioxo-3,6,9-trioxa-7-azadodec-11-en-5-yl)chroman-6-yl)-1H-pyrazol-2-ium Triflate A solution of tert-butyl 3-(hydroxymethyl)-azetidine-1-carboxylate (1.14 g, 6.1 mmol) in CH$_2$Cl$_2$ (6 ml) was cooled to −78° C. To the solution was added dropwise trifluoromethanesulfonic anhydride (1.5 ml, 9.1 mmol) and Hunig's base (2.6 ml, 15 mmol). The reaction mixture was stirred at −78° C. for 20 min, then quenched with saturated NaHCO$_3$ aqueous solution. The mixture was warmed up to RT and partitioned between DCM and saturated NaHCO$_3$. The organic layer was separated, washed with brine, and dried over Na$_2$SO$_4$, and concentrated in vacuo to give tert-butyl 3-((((trifluoromethyl)sulfonyl)oxy)methyl)azetidine-1-carboxylate. To a solution of tert-butyl 3-((((trifluoromethyl)-sulfonyl)oxy)methyl) azetidine-1-carboxylate in ACN (2 ml) was added a solution of tert-butyl (S)-2-((((allyloxy)carbonyl)amino)oxy)-2-((R)-6-(1-(3-((tert-butoxycarbonyl)-amino)propyl)-1H-pyrazol-4-yl)chroman-2-yl)propanoate (0.91 g, 1.5 mmol) in anhydrous CH$_3$CN (6.0 mL) and sodium bicarbonate (1.3 g, 15 mmol). The resulting mixture was heated at 60° C. for 1 hr. Then the solid was filtered off, and the solvent was removed. The resulting residue was triturated with Et$_2$O (10 mL×2). The resulting residue was dried in vacuo, then dissolved in DCM, and purified by column chromatography on silica gel Redi 40 g gold, eluting with MeOH/DCM (0-10%, 10 cv; 10%, 8 cv) to give the title compound. LC-MS [M+1]: m/z 770.97.

Step C: 4-((R)-2-((S)-2-(Aminooxy)-1-(tert-butoxy)-1-oxopropan-2-yl)chroman-6-yl)-1-(3-((tert-butoxycarbonyl)amino)propyl)-2-((1-(tert-butoxycarbonyl)azetidin-3-yl)methyl)-1H-pyrazol-2-ium Triflate To the solution of 1-(3-((tert-butoxycarbonyl)amino)propyl)-2-((1-(tert-butoxycarbonyl)azetidin-3-yl)methyl)-4-((R)-2-((S)-2,2,5-trimethyl-4,8-dioxo-3,6,9-trioxa-7-azadodec-11-en-5-yl)chroman-6-yl)-1H-pyrazol-2-ium triflate salt (1 g, 1.3 mmol) in THF (5 mL) was added tetrakis(triphenylphosphine)palladium(0) (0.15 g, 0.13 mmol) and phenylsilane (0.64 ml, 5.2 mmol). The resulting solution was stirred at RT for 20 min. The resulting solid was filtered off and the filtrate was concentrated to give the title compound. LC-MS [M+1]: m/z 686.74.

Step D: 4-((R)-2-((S)-1-(tert-Butoxy)-2-((((Z)-(2-((tert-butoxycarbonyl)amino)thiazol-4-yl)(carboxy)methylene)amino)oxy)-1-oxopropan-2-yl)chroman-6-yl)-1-(3-((tert-butoxycarbonyl)amino)propyl)-2-((1-(tert-butoxycarbonyl)azetidin-3-yl)methyl)-1H-pyrazol-2-ium Triflate To a solution of 4-((R)-2-((S)-2-(aminooxy)-1-(tert-butoxy)-1-oxopropan-2-yl)chroman-6-yl)-1-(3-((tert-butoxycarbonyl)amino)propyl)-2-((1-(tert-butoxycarbonyl)azetidin-3-yl)methyl)-1H-pyrazol-2-ium triflate (0.89 g, 1.3 mmol) in EtOH (4 ml) and CH$_2$Cl$_2$ (2 mL) was added 2-(2-((tert-butoxycarbonyl)amino)thiazol-4-yl)-2-oxoacetic acid (0.35 g, 1.3 mmol). The reaction mixture was stirred at RT overnight and then concentrated to give the title compound. LC-MS [M+1]: m/z 941.18.

Step E: (S)-3-((Z)-2-((((S)-1-(tert-Butoxy)-2-((R)-6-(1-(3-((tert-butoxycarbonyl)-amino)propyl)-2-((1-(tert-butoxycarbonyl)azetidin-3-yl)methyl)-1H-pyrazol-2-ium-4-yl)chroman-2-yl)-1-oxopropan-2-yl)oxy)imino)-2-(2-((tert-butoxycarbonyl)amino)thiazol-4-yl)acetamido)-2,2-dimethyl-4-oxoazetidin-1-yl Sulfate TFA To a solution of 4-((R)-2-((S)-1-(tert-butoxy)-2-((((Z)-(2-((tert-butoxycarbonyl)amino)thiazol-4-yl)(carboxy)methylene)-amino)oxy)-1-oxopropan-2-yl)chroman-6-yl)-1-(3-((tert-butoxycarbonyl)amino)propyl)-2-((1-(tert-butoxycarbonyl)azetidin-3-yl)methyl)-1H-pyrazol-2-ium OTf (1.223 g, 1.3 mmol) in DMF (7 ml) were added DCC (0.80 g, 3.9 mmol), and HOBT (0.60 g, 3.9 mmol). The resulting solution was stirred at RT for 30 min, then (S)-3-amino-2,2-dimethyl-4-oxoazetidin-1-yl hydrogen sulfate (0.68 g, 3.2 mmol) and sodium bicarbonate (0.55 g, 6.5 mmol) were added. The reaction mixture was stirred at RT overnight. The resulting solid was filtered off. The filtrate was purified on RP-HPLC (C-18 column, 130 g), eluting with 20-100% ACN/water containing 0.05% TFA (10 cv) to give the title compound. LC-MS [M+1]: m/z 1133.56.

Step F: (S)-3-((Z)-2-(((S)-1-((R)-6-(1-(3-Aminopropyl)-2-(azetidin-3-ylmethyl)-1H-pyrazol-2-ium-4-yl)chroman-2-yl)-1-carboxyethoxy)imino)-2-(2-aminothiazol-4-yl)acetamido)-2,2-dimethyl-4-oxoazetidin-1-yl Sulfate, Formic Acid To a solution of (S)-3-((Z)-2-((((S)-1-(tert-butoxy)-2-((R)-6-(1-(3-((tert-butoxycarbonyl)amino) propyl)-2-((1-(tert-butoxycarbonyl)-azetidin-3-yl)methyl)-1H-pyrazol-2-ium-4-yl)chroman-2-yl)-1-oxopropan-2-yl)oxy)imino)-2-(2-((tert-butoxycarbonyl)amino)thiazol-4-yl)acetamido)-2,2-dimethyl-4-oxoazetidin-1-yl sulfate (2.0 g, 1.6 mmol) in CH$_2$Cl$_2$ (3 ml) was added TFA (6 mL). The reaction was stirred at RT for 1 hr. Then the solvent was removed, and the resulting residue was washed with Et$_2$O 5 times and dried to give the crude solid product. The crude product was dissolved in DMSO (3 mL), then solid NaHCO$_3$ (6-10 eq) were added. The mixture was stirred at RT for 4 hr. The resulting solid was filtered off. The filtrate was diluted with 60 mL water containing 0.1% formic acid. The resulting aqueous solution was purified on a C-18 RP-HPLC column (415 g), eluting with ACN/water+0.1% FA (0% 7 cv, 0-20% 6 cv) to give the title compound. LC-MS [M+1]: m/z 776.92. $^1$HNMR (500 MHz, D$_2$O) $\delta_H$ 8.59 (1H, s), 8.48 (1H, s), 8.41 (1H, s), 7.28 (1H, s), 7.22 (1H, d), 6.82 (1H, s), 6.75 (1H, d), 4.84 (2H, t), 4.57 (1H, d), 4.51 (1H, m), 4.31 (2H, m), 4.13 (2H, m), 3.66 (1H, m), 3.14 (2H, m), 2.75 (2H, m), 2.37 (2H, m), 2.10 (1H, m), 1.85 (1H, m), 1.53 (3H, s), 1.34 (3H, s), 1.18 (3H, s).

Example 4

(S)-3-((Z)-2-(((S)-1-((R)-6-(1-((S)-3-Amino-2-hydroxypropyl)-2-(azetidin-3-ylmethyl)-1H-pyrazol-2-ium-4-yl)chroman-2-yl)-1-carboxyethoxy)imino)-2-(2-aminothiazol-4-yl)acetamido)-2,2-dimethyl-4-oxoazetidin-1-yl Sulfate

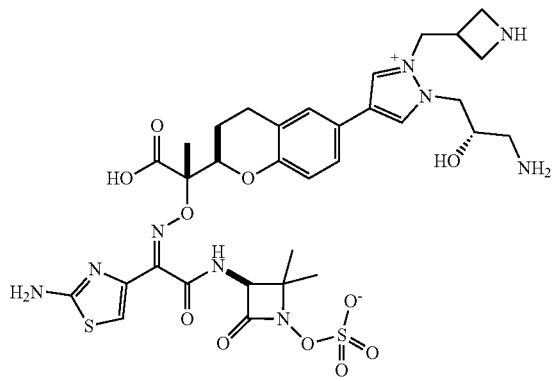

Step A: tert-Butyl (S)-2-(aminooxy)-2-((R)-6-(1-((S)-3-((tert-butoxycarbonyl)amino)-2-((tert-butyldimethylsilyl)oxy)propyl)-1H-pyrazol-4-yl)chroman-2-yl)propanoate A mixture of tert-butyl (S)-2-(aminooxy)-2-((R)-6-bromochroman-2-yl)propanoate (1.46 g, 3.9 mmol, Intermediate 1), tert-butyl (S)-(2-((tert-butyldimethylsilyl)oxy)-3-(4-(4,4,5,5-tetramethyl-1,3,2-dioxaborolan-2-yl)-1H-pyrazol-1-yl)propyl)carbamate (3.0 g, 6.3 mmol, Intermediate 5), 1,1'-bis(di-tert-butylphosphino)ferrocene palladium dichloride (0.26 g, 0.39 mmol) and potassium phosphate (5.9 ml, 12 mmol, 2M) in THF (8 ml) was degassed and refilled with N$_2$ three times. The reaction mixture was heated at 60° C. for 3 hrs, then diluted with water, and extracted with EtOAc (3×). The combined organic layers were dried over MgSO$_4$, filtered, and the filtrate was concentrated in vacuo. The resulting residue was purified by column chromatography on silica gel Redi 80 g gold, eluting with EtOAc/hexane (0-80%, 6 cv; 80%, 10 cv) to give the title compound. LC-MS [M+1]: m/z 647.68.

Step B tert-Butyl (S)-2-((((allyloxy)carbonyl)amino) oxy)-2-((R)-6-(1-((S)-3-((tert-butoxycarbonyl) amino)-2-((tert-butyldimethylsilyl)ox)propyl)-1H-pyrazol-4-yl)chroman-2-yl)propanoate A solution of tert-butyl (S)-2-(aminooxy)-2-((R)-6-(1-((S)-3-((tert-butoxycarbonyl)amino)-2-((tert-butyldimethylsilyl)oxy)propyl)-1H-pyrazol-4-yl)chroman-2-yl)propanoate (1.6 g, 2.5 mmol) and DIPEA (0.65 ml, 3.7 mmol) in CH$_2$Cl$_2$ (30 ml) was added allyl carbonochloridate (0.32 ml, 3.0 mmol). The reaction mixture was stirred at room temperature for 1 hr, and then the solvent was removed. The resulting residue was purified by column chromatography on silica gel Redi 80 g gold, eluting with EtOAc/Hexane (0-70%, 5 cv, 70%, 6 cv) to give the title compound. LC-MS [M+1]: m/z 731.81.

Step C: 1-((S)-3-((tert-Butoxycarbonyl)amino)-2-((tert-butyldimethylsilyl)oxy)propyl)-2-((1-(tert-butoxycarbonyl)azetidin-3-yl)methyl)-4-((R)-2-((S)-2,2,5-trimethyl-4,8-dioxo-3,6,9-trioxa-7-azadodec-11-en-5-yl)chroman-6-yl)-1H-pyrazol-2-ium Triflate A solution of tert-butyl 3-(hydroxymethyl)azetidine-1-carboxylate (1.23 g, 6.6 mmol) in CH$_2$Cl$_2$ (20 ml) was cooled to −78° C. To the solution was added dropwise trifluoromethanesulfonic anhydride (1.6 ml, 9.8 mmol) and Hunig's base (2.9 ml, 16 mmol). The reaction mixture was kept at −78° C. for 20 min and then quenched with NaHCO$_3$ (saturated) solution. The mixture was warmed to RT and partitioned between DCM and saturated NaHCO$_3$. The organic layer was separated, washed with brine, dried over Na$_2$SO$_4$, and concentrated in vacuo to give tert-butyl 3-(((((trifluoromethyl) sulfonyl)oxy)methyl)azetidine-1-carboxylate. To a solution of tert-butyl 3-(((((trifluoromethyl) sulfonyl)oxy)methyl) azetidine-1-carboxylate in ACN (10 mL) was added a solution of tert-butyl (S)-2-((((allyloxy) carbonyl)amino)oxy)-2-((R)-6-(1-((S)-3-((tert-butoxycarbonyl)amino)-2-((tert-butyldimethylsilyl)oxy)propyl)-1H-pyrazol-4-yl)chroman-2-yl)propanoate (1.2 g, 1.6 mmol) in CH$_3$CN (anhydrous, 6 ml) and sodium bicarbonate (1.4 g, 16 mmol). The resulting mixture was heated at 60° C. for 1.5 hrs. Then the solid was filtered off and the solvent was removed. The resulting residue was triturated with Et$_2$O (10 mL×2). The resulting solid was dried in vacuo, then dissolved in DCM, and purified by column chromatography on silica gel Redi 120 g gold, eluting with MeOH/DCM (0-10%, 10 cv; 10%, 8 cv) to give the title compound. LC-MS [M+1]: m/z 901.07.

Step D: 4-((R)-2-((S)-2-(Aminooxy)-1-(tert-butoxy)-1-oxopropan-2-yl)chroman-6-yl)-1-((S)-3-((tert-butoxycarbonyl)amino)-2-((tert-butyldimethylsilyl)oxy)propyl)-2-((1-(tert-butoxycarbonyl)azetidin-3-yl)methyl)-1H-pyrazol-2-ium Triflate To a solution of 1-((S)-3-((tert-Butoxycarbonyl)amino)-2-((tert-butyldimethylsilyl) oxy) propyl)-2-((1-(tert-butoxycarbonyl)azetidin-3-yl)methyl)-4-((R)-2-((S)-2,2,5-trimethyl-4,8-dioxo-3,6,9-trioxa-7-azadodec-11-en-5-yl)chroman-6-yl)-1H-pyrazol-2-ium triflate (1.4 g, 1.6 mmol) in THF (15 ml) was added palladium tetrakis (0.18 g, 0.16 mmol) and phenylsilane (0.76 ml, 6.2 mmol). The resulting solution was stirred at RT for 20 min. Then the solid was filtered off and solvent was removed to give the title compound. LC-MS [M+1]: m/z 817.03.

Step E: 4-((R)-2-((S)-2-(Aminooxy)-1-(tert-butoxy)-1-oxopropan-2-yl)chroman-6-yl)-1-((S)-3-((tert-butoxycarbonyl)amino)-2-hydroxypropyl)-2-((1-(tert-butoxycarbonyl)azetidin-3-yl)methyl)-1H-pyrazol-2-ium Trifluoroacetate To a solution of 4-((R)-2-((S)-2-(aminooxy)-1-(tert-butoxy)-1-oxopropan-2-yl)chroman-6-yl)-1-((S)-3-((tert-butoxy-carbonyl)amino)-2-((tert-butyldimethylsilyl)oxy)propyl)-2-((1-(tert-butoxycarbonyl)-azetidin-3-yl)methyl)-1H-pyrazol-2-ium triflate (1.3 g, 1.6 mmol) in THF (20 ml) was added TBAF (4.7 ml, 4.7 mmol, 1M) at RT. The reaction was stirred at RT for 2 hrs, then the solvent was removed under reduced pressure. The resulting residue was purified on RP-HPLC C-18 column (275 g), eluting with 10-100% ACN/water with 0.05% TFA (12 cv) to give the title compound. LC-MS [M+1]: m/z 702.88.

Step F: 4-((R)-2-((S)-1-(tert-Butoxy)-2-((((Z)-(2-((tert-butoxycarbonyl)amino)thiazol-4-yl)(carboxy)methylene)amino)oxy)-1-oxopropan-2-yl)chroman-6-yl)-1-((S)-3-((tert-butoxycarbonyl)amino)-2-hydroxypropyl)-2-((1-(tert-butoxycarbonyl)azetidin-3-yl)methyl)-1H-pyrazol-2-ium Trifluoroacetate To a solution of 4-((R)-2-((S)-2-(aminooxy)-1-(tert-butoxy)-1-oxopropan-2-yl)chroman-6-yl)-1-((S)-3-((tert-butoxycarbonyl)amino)-2-hydroxypropyl)-2-((1-(tert-butoxycarbonyl)azetidin-3-yl)methyl)-1H-pyrazol-2-ium trifluoroacetate (0.64 g, 0.91 mmol) in EtOH (5 mL) and CH$_2$Cl$_2$ (2.5 mL) was added 2-(2-((tert-butoxycarbonyl)amino)thiazol-4-yl)-2-oxoacetic acid (0.25 g, 0.91 mmol). The reaction mixture was stirred at RT overnight and then concentrated to give the title compound. LC-MS [M+1]: m/z 957.21.

Step G: (S)-3-((Z)-2-((((S)-1-(tert-Butoxy)-2-((R)-6-(1-((S)-3-((tert-butoxycarbonyl)amino)-2-hydroxypropyl)-2-((1-(tert-butoxycarbonyl)azetidin-3-yl)methyl)-1H-pyrazol-2-ium-4-yl)chroman-2-yl)-1-oxopropan-2-yl)oxy)imino)-2-(2-((tert-butoxycarbonyl)amino)thiazol-4-yl)acetamido)-2,2-dimethyl-4-oxoazetidin-1-yl sulfate Trifluoroacetate To a solution of 4-((R)-2-((S)-1-(tert-butoxy)-2-((((Z)-(2-((tert-butoxycarbonyl)amino)thiazol-4-yl)(carboxy)-methylene)amino)oxy)-1-oxopropan-2-yl)chroman-6-yl)-1-((S)-3-((tert-butoxycarbonyl)amino)-2-hydroxypropyl)-2-((1-(tert-butoxycarbonyl)azetidin-3-yl)methyl)-1H-pyrazol-2-ium TFA (0.58 g, 0.61 mmol) in DMF (5 ml) was added DCC (0.38 g, 1.8 mmol), and HOBT (0.28 g, 1.8 mmol). The resulting solution was stirred at RT for 30 min before the addition of (S)-3-amino-2,2-dimethyl-4-oxoazetidin-1-yl hydrogen sulfate (0.32 g, 1.5 mmol) and sodium bicarbonate (0.26 g, 3.0 mmol). The reaction mixture was stirred at RT overnight. Then the solid was filtered off. The solution was purified on RP (C-18 column, 130 g), eluting with 20-100% ACN/water containing 0.05% TFA (10 cv) to give the title compound. LC-MS [M+1]: m/z 1149.44.

Step H: (S)-3-((Z)-2-(((S)-1-((R)-6-(1-((S)-3-Amino-2-hydroxypropyl)-2-(azetidin-3-ylmethyl)-1H-pyrazol-2-ium-4-yl)chroman-2-yl)-1-carboxyethoxy)imino)-2-(2-aminothiazol-4-yl)acetamido)-2,2-dimethyl-4-oxoazetidin-1-yl Sulfate To a solution of (S)-3-((Z)-2-((((S)-1-(tert-butoxy)-2-((R)-6-(1-((S)-3-((tert-butoxycarbonyl)amino)-2-hydroxypropyl)-2-((1-(tert-butoxycarbonyl)azetidin-3-yl)methyl)-1H-pyrazol-2-ium-4-yl)chroman-2-yl)-1-oxopropan-2-yl)oxy)imino)-2-(2-((tert-butoxycarbonyl)amino)thiazol-4-yl)acetamido)-2,2-dimethyl-4-oxoazetidin-1-yl sulfate (420 mg, 0.33 mmol) in CH$_2$Cl$_2$ (1 ml) was added TFA (2 ml). The solution was stirred at RT for 1 hr, then the solvent was removed. The resulting residue was washed with Et$_2$O (5×) and dried to give the crude product. The crude product was dissolved in DMSO (3 mL) and solid NaHCO$_3$ (6-10 eq) was added. The mixture was stirred at RT for 4 hrs, then the solid was filtered off. The solution was diluted with 60 ml water containing 0.1% formic acid, and purified on C-18 RP column (415 g), eluting with ACN/water+0.1% FA (0% 7 cv, 0-20% 6 cv) to give the title compound. LC-MS [M+1]: m/z 792.78. $^1$HNMR (500 MHz, D$_2$O) $\delta_H$ 8.52 (1H, s), 8.45 (1H, s), 8.33 (1H, s), 7.17 (1H, s), 7.13 (1H, d), 6.73 (1H, s), 6.64 (1H, d), 4.49 (2H, t), 4.33 (1H, m), 4.27 (1H, m), 4.21 (2H, m), 4.04 (2H, m), 3.59 (1H, m), 3.26 (1H, m), 2.99 (1H, m), 2.61 (2H, m), 1.95 (1H, m), 1.67 (1H, m), 1.42 (3H, s), 1.27 (3H, s), 1.13 (3H, s).

Example 5

(3 S)-3-((Z)-2-(((1 S)-1-(6-(1-((S)-3-amino-2-hydroxypropyl)-2-(3-aminopropyl)-1H-pyrazol-2-ium-4-yl)chroman-2-yl)-1-carboxyethoxy)imino)-2-(2-aminothiazol-4-yl)acetamido)-2,2-dimethyl-4-oxoazetidin-1-yl Sulfate

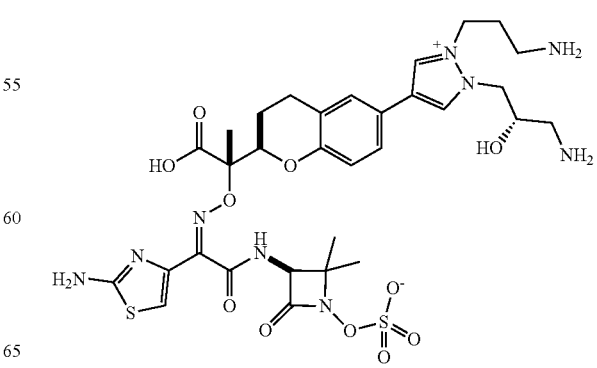

Step A: 2-(3-azidopropyl)-1-((S)-3-((tert-butoxycarbonyl)amino)-2-((tert-butyldimethylsilyl)oxy)propyl)-4-((R)-2-((S)-2,2,5-trimethyl-4,8-dioxo-3,6,9-trioxa-7-azadodec-11-en-5-yl)chroman-6-yl)-1H-pyrazol-2-ium Trifluoromethanesulfonic anhydride (5.0 ml, 5.0 mmol) was added to a stirred, cooled −78° C. mixture of 3-azidopropan-1-ol (0.38 ml, 4.2 mmol), and DIPEA (1.4 ml, 7.9 mmol) in DCM. The reaction mixture was stirred at −78° C. for 90 min, then quenched with saturated NaHCO$_3$. The mixture was warmed up to 0° C., and then partitioned between DCM and aqueous NaHCO$_3$ solution. The organic layer was separated and washed with brine, dried over Na$_2$SO$_4$, filtered and concentrated to dryness to give 3-azidopropyl trifluoromethanesulfonate. 3-azidopropyl trifluoromethanesulfonate 0.96 g, 4.1 mmol) was added to a stirred, room temperature mixture of (S)-tert-butyl 2-((((allyloxy)-carbonyl)amino)oxy)-2-((R)-6-(1-((S)-3-((tert-butoxycarbonyl)amino)-2-((tert-butyldimethylsilyl)oxy)propyl)-1H-pyrazol-4-yl)chroman-2-yl)propanoate (from Step B, Example 4, 0.75 g, 1.0 mmol), and sodium bicarbonate (0.69 g, 8.2 mmol) in acetonitrile. The mixture was stirred at 60° C. for 1 hr, then filtered and the filtrate was concentrated. The resulting residue was purified by column chromatography on silica gel 40 g column, eluting with CH$_2$Cl$_2$/MeOH (100-90%) to give the title compound. LC-MS [M]$^+$: m/z 814.80

Step B: 4-((R)-2-((S)-2-(aminooxy)-1-(tert-butoxy)-1-oxopropan-2-yl)chroman-6-yl)-2-(3-azidopropyl)-1-((S)-3-((tert-butoxycarbonyl)amino)-2-((tert-butyldimethylsilyl)oxy)propyl)-1H-pyrazol-2-ium Palladium tetrakis (0.17 g, 0.15 mmol) was added to a stirred mixture of 2-(3-azidopropyl)-1-((S)-3-((tert-butoxycarbonyl)amino)-2-((tert-butyldimethylsilyl)-oxy)propyl)-4-((R)-2-((S)-2,2,5-trimethyl-4,8-dioxo-3,6,9-trioxa-7-azadodec-11-en-5-yl)chroman-6-yl)-1H-pyrazol-2-ium (1.0 g, 0.98 mmol), and phenylsilane (0.30 ml, 2.5 mmol) in THF. The reaction mixture was stirred at room temperature for 15 min, then diluted with EtOAc, and washed with saturated NaHCO$_3$ and brine. The organic layer was separated, dried over MgSO$_4$, filtered and the filtrate was concentrated. The resulting residue was purified by column chromatography on silica gel (50 g prepacked) eluting with CH$_2$Cl$_2$/MeOH (100-88%) to give the title compound. LC-MS [M]$^+$: m/z 730.75

Step C: 2-(3-azidopropyl)-4-((R)-2-((S)-1-(tert-butoxy)-2-(((Z)-((2-((tert-butoxy-carbonyl)amino)thiazol-4-yl)(carboxy)methylene)amino)oxy)-1-oxopropan-2-yl)chroman-6-yl)-1-((S)-3-((tert-butoxycarbonyl)amino)-2-((tert-butyldimethylsilyl)oxy)propyl)-1H-pyrazol-2-ium 2-(2-((tert-butoxycarbonyl)amino)thiazol-4-yl)-2-oxoacetic acid (250 mg, 0.93 mmol) was added to a stirred mixture of 4-((R)-2-((S)-2-(aminooxy)-1-(tert-butoxy)-1-oxopropan-2-yl)chroman-6-yl)-2-(3-azidopropyl)-1-((S)-3-((tert-butoxycarbonyl)amino)-2-((tert-butyldimethylsilyl)oxy)propyl)-1H-pyrazol-2-ium (850 mg, 0.93 mmol) in EtOH/CH$_3$C$_1$. The reaction mixture was stirred at room temperature for 2 hrs, then concentrated to dryness to give the title compound. LC-MS [M]$^+$: m/z 985.47

Step D: 2-(3-aminopropyl)-4-((R)-2-((S)-1-(tert-butoxy)-2-(((Z)-((2-((tert-butoxy-carbonyl)amino)thiazol-4-yl)(carboxy)methylene)amino)oxy)-1-oxopropan-2-yl)chroman-6-yl)-1-((S)-3-((tert-butoxycarbonyl)amino)-2-((tert-butyldimethylsilyl)oxy)propyl)-1H-pyrazol-2-ium To a mixture of 2-(3-azidopropyl)-4-((R)-2-((S)-1-(tert-butoxy)-2-(((Z)-((2-((tert-butoxycarbonyl)amino)thiazol-4-yl)(carboxy)methylene)amino)oxy)-1-oxopropan-2-yl)chroman-6-yl)-1-((S)-3-((tert-butoxycarbonyl)amino)-2-((tert-butyldimethylsilyl)-oxy)propyl)-1H-pyrazol-2-ium (560 mg, 0.57 mmol) in MeOH (6 mL) was added Pd—C (10%, 91 mg, 0.085 mmol). The resulting mixture was stirred at room temperature under an H$_2$ balloon for 2.5 hrs. Then the mixture was filtered and the filtrate was concentrated to dryness to give the title compound. LC-MS [M]$^+$: m/z 958.90

Step E: 4-((R)-2-((S)-1-(tert-butoxy)-2-(((Z)-((2-((tert-butoxycarbonyl)amino)thiazol-4-yl)(carboxy)methylene)amino)oxy)-1-oxopropan-2-yl)chroman-6-yl)-1-((S)-3-((tert-butoxycarbonyl)amino)-2-((tert-butyldimethylsilyl)oxy)propyl)-2-(3-((tert-butoxycarbonyl)amino)propyl)-1H-pyrazol-2-ium To a solution of 2-(3-aminopropyl)-4-((R)-2-((S)-1-(tert-butoxy)-2-(((Z)-((2-((tert-butoxycarbonyl)amino)thiazol-4-yl)(carboxy)methylene)amino)oxy)-1-oxopropan-2-yl)chroman-6-yl)-1-((S)-3-((tert-butoxycarbonyl)amino)-2-((tert-butyldimethylsilyl)oxy)propyl)-1H-pyrazol-2-ium (500 mg, 0.52 mmol), and triethylamine (0.073 ml, 0.52 mmol) in DCM was added BOC-anhydride (0.15 ml, 0.63 mmol). The mixture was stirred at room temperature for 2 hrs, then concentrated to dryness. The resulting residue was purified by preparative reverse phase (C-18) chromatography, eluting with acetonitrile/water+0.1% TFA (2-100%) to give the title compound. LC-MS [M]$^+$: m/z 1058.99

Step F: 4-((R)-2-((S)-1-(tert-butoxy)-2-(((Z)-((2-((tert-butoxycarbonyl)amino)thiazol-4-yl)(carboxy)methylene)amino)oxy)-1-oxopropan-2-yl)chroman-6-yl)-1-((S)-3-((tert-butoxycarbonyl)amino)-2-hydroxypropyl)-2-(3-((tert-butoxycarbonyl)amino)propyl)-1H-pyrazol-2-ium To a solution of 4-((R)-2-((S)-1-(tert-butoxy)-2-(((Z)-((2-((tert-butoxycarbonyl)amino)thiazol-4-yl)(carboxy)methylene)amino)oxy)-1-oxopropan-2-yl)chroman-6-yl)-1-((S)-3-((tert-butoxycarbonyl)amino)-2-((tert-butyldimethylsilyl)-oxy)propyl)-2-(3-((tert-butoxycarbonyl)amino)propyl)-1H-pyrazol-2-ium (620 mg, 0.52 mmol) in THF was added TBAF (270 mg, 1.04 mmol). The mixture was stirred at room temperature for 90 min, then diluted with EtOAc, washed with saturated NaHCO$_3$, and brine. The organic layer was separated, dried over MgSO$_4$, filtered and concentrated. The resulting residue was purified by preparative reverse phase (C-18) column chromatography, eluting with acetonitrile/water+0.1% TFA, to give the title compound. LC-MS [M]$^+$: m/z 944.81

Step G: (S)-3-(((Z)-2-(((((S)-1-(tert-butoxy)-2-((R)-6-(1-((S)-3-((tert-butoxycarbonyl)amino)-2-hydroxypropyl)-2-(3-((tert-butoxy carbonyl)amino)propyl)-1H-pyrazol-2-ium-4-yl)-chroman-2-yl)-1-oxopropan-2-yl)oxy)imino)-2-(2-((tert-butoxycarbonyl)amino)thiazol-4-yl)acetamido)-2,2-dimethyl-4-oxoazetidin-1-yl Sulfate To a solution of 4-((R)-2-((S)-1-(tert-butoxy)-2-(((Z)-((2-((tert-butoxycarbonyl)amino)thiazol-4-yl)(carboxy)methylene)amino)-oxy)-1-oxopropan-2-yl)chroman-6-yl)-1-((S)-3-((tert-butoxycarbonyl)amino)-2-hydroxypropyl)-2-(3-((tert-butoxycarbonyl)amino)propyl)-1H-pyrazol-2-ium (300 mg, 0.32 mmol) and (S)-3-amino-2,2-dimethyl-4-oxoazetidin-1-yl hydrogen sulfate (134 mg, 0.64 mmol)) in acetonitrile (anhydrous, 12 ml) at −10° C. was added pyridine (0.077 ml, 0.96 mmol) under $N_2$, followed by $N_1$-((ethylimino)methylene)-$N_3$,$N_3$-dimethylpropane-1,3-diamine hydrochloride (134 mg, 0.70 mmol)). The reaction mixture as stirred at −10 to 0° C. for 1 h, then concentrated to dryness. The resulting residue was purified by preparative reverse phase (C-18) column chromatography, eluting with acetonitrile/water+0.1% TFA, to give the title compound. LC-MS [M]$^+$: m/z 1136.71

Step H: (S)-3-((Z)-2-(((S)-1-((R)-6-(1-((S)-3-amino-2-hydroxypropyl)-2-(3-aminopropyl)-1H-pyrazol-2-ium-4-yl)chroman-2-yl)-1-carboxyethoxy)imino)-2-(2-aminothiazol-4-yl)acetamido)-2,2-dimethyl-4-oxoazetidin-1-yl Sulfate To a solution of (S)-3-((Z)-2-((((S)-1-(tert-butoxy)-2-((R)-6-(1-((S)-3-((tert-butoxycarbonyl)amino)-2-hydroxypropyl)-2-(3-((tert-butoxycarbonyl)amino)propyl)-1H-pyrazol-2-ium-4-yl)chroman-2-yl)-1-oxopropan-2-yl)oxy)imino)-2-(2-((tert-butoxycarbonyl)amino)thiazol-4-yl)acetamido)-2,2-dimethyl-4-oxoazetidin-1-yl sulfate (130 mg, 0.11 mmol) in DCM (5 mL) was added TFA (3 ml, 39 mmol). The reaction mixture was stirred at room temperature for 90 min, then quickly concentrated to dryness under vacuum at room temperature. The resulting residue was dissolved in DMSO (1 ml) and purified by preparative HPLC, eluting with acetonitrile/water (2~35%) to give the title compound as the TFA salt. LC-MS [M]$^+$: m/z 780.37. $^1$HNMR (500 MHz, $D_2O$) $\delta_H$ 8.56 (1H, s), 8.54 (1H, s), 8.36 (1H, s), 7.29 (1H, s), 7.26 (2H, d), 6.79 (H, s), 6.78 (2H, s), 4.52 (2H, t), 4.38 (1H, m), 4.20 (1H, m), 4.21 (2H, m), 3.27 (1H, m), 3.03 (2H, m), 2.99 (2H, m), 2.76 (2H, m), 2.31 (3H, m), 2.01 (2H, m), 1.76 (2H, m), 1.49 (3H, s), 1.32 (3H, s), 1.16 (3H, s).

Example 6

(S)-3-((Z)-2-(((S)-1-((R)-6-(1-((3-Aminoazetidin-3-yl)methyl)-2-methyl-1H-pyrazol-2-ium-4-yl)chroman-2-yl)-1-carboxyethoxy)imino)-2-(2-aminothiazol-4-yl)acetamido)-2,2-dimethyl-4-oxoazetidin-1-yl Sulfate

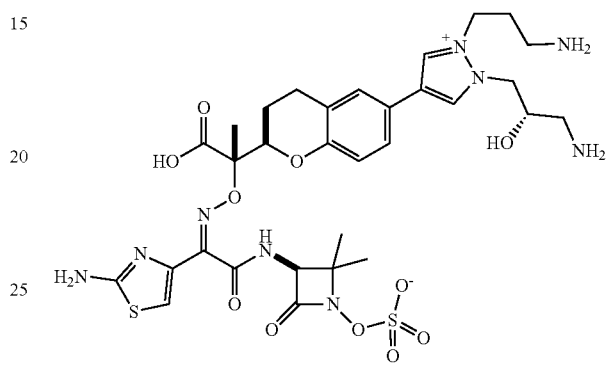

The title compound was prepared by using the same procedure as Example 1, starting with the Intermediate 1 and Intermediate 6. LC-MS [M+1]: m/z 748.76. $^1$HNMR (500 MHz, $D_2O$) $\delta_H$ 8.57 (1H, s), 8.53 (1H, s), 7.36 (1H, s), 7.32 (1H, d), 7.02 (1H, s), 6.84 (1H, d), 4.90 (2H, s), 4.59 (2H, m), 4.36 (2H, m), 4.17 (3H, s), 4.12 (2H, m), 2.81 (2H, m), 2.15 (1H, m), 1.89 (1H, m), 1.64 (3H, s), 1.36 (3H, s), 1.13 (3H, s).

TABLE 1

The compounds of Exampes 7-13 were prepared using a similar procedure to the above examples using the appropriate intermediates.

| Example | Structure | Name | LCMS [M + H]$^+$ |
|---|---|---|---|
| 7 | 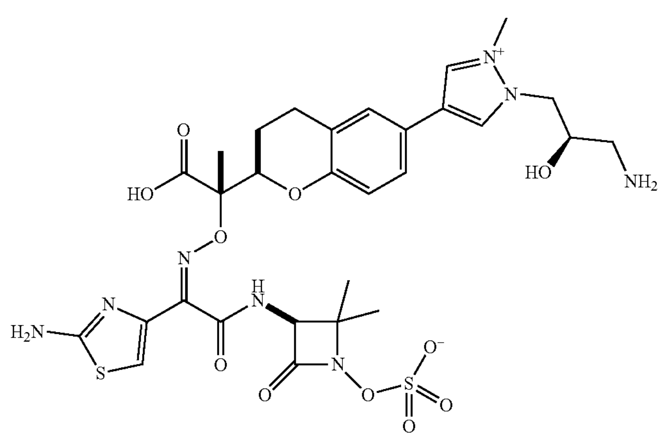 | (S)-3-((Z)-2-(((S)-1-((R)-6-(1-((R)-3-amino-2-hydroxypropyl)-2-methyl-1H-pyrazol-2-ium-4-yl)chroman-2-yl)-1-carboxyethoxy)imino)-2-(2-aminothiazol-4-yl)acetamido)-2,2-dimethyl-4-oxoazetidin-1-yl sulfate | 737.54 |

TABLE 1-continued

The compounds of Exampes 7-13 were prepared using a similar procedure to the above examples using the appropriate intermediates.

| Example | Structure | Name | LCMS [M + H]+ |
|---|---|---|---|
| 8 | 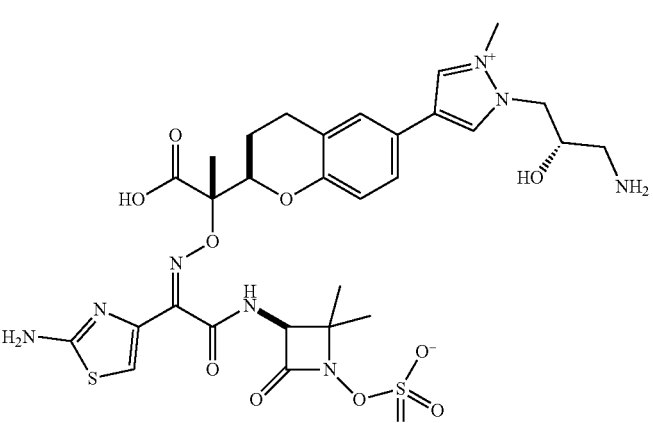 | (S)-3-((Z)-2-(((S)-1-((R)-6-(1-((S)-3-amino-2-hydroxypropyl)-2-methyl-1H-pyrazol-2-ium-4-yl)chroman-2-yl)-1-carboxyethoxy)imino)-2-(2-aminothiazol-4-yl)acetamido)-2,2-dimethyl-4-oxoazetidin-1-yl sulfate | 737.29 |
| 9 | 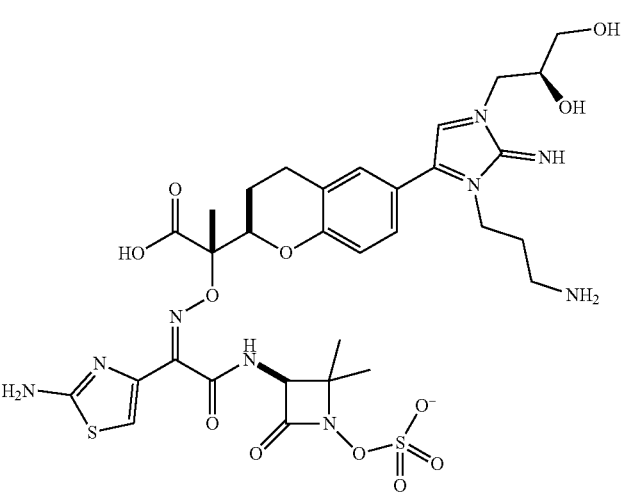 | (S)-3-((Z)-2-(((S)-1-((R)-6-(1-(3-aminopropyl)-3-((S)-2,3-dihydroxypropyl)-2-imino-2,3-dihydro-1H-imidazol-4-yl)chroman-2-yl)-1-carboxyethoxy)imino)-2-(2-aminothiazol-4-yl)acetamido)-2,2-dimethyl-4-oxoazetidin-1-yl sulfate | 795.95 |
| 10 | 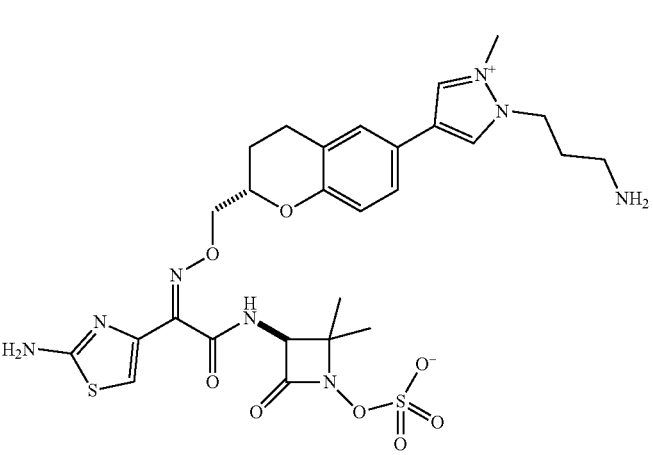 | (S)-3-((Z)-2-((((S)-6-(1-(3-aminopropyl)-2-methyl-1H-pyrazol-2-ium-4-yl)chroman-2-yl)methoxy)imino)-2-(2-aminothiazol-4-yl)acetamido)-2,2-dimethyl-4-oxoazetidin-1-yl sulfate | 663.55 |

TABLE 1-continued

The compounds of Exampes 7-13 were prepared using a similar procedure to the above examples using the appropriate intermediates.

| Example | Structure | Name | LCMS [M + H]+ |
|---|---|---|---|
| 11 | 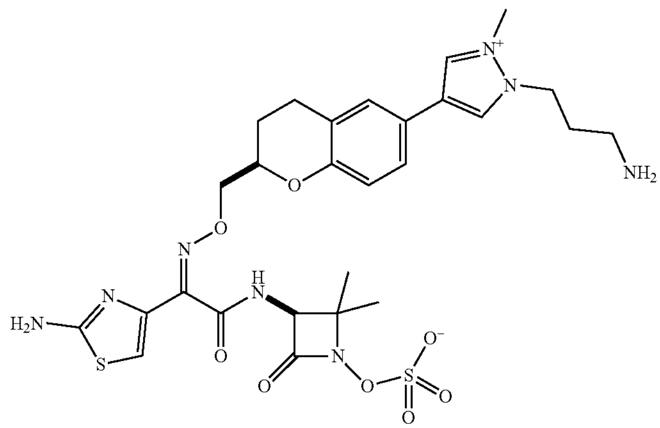 | (S)-3-((Z)-2-((((R)-6-(1-(3-aminopropyl)-2-methyl-1H-pyrazol-2-ium-4-yl)chroman-2-yl)methoxy)imino)-2-(2-aminothiazol-4-yl)acetamido)-2,2-dimethyl-4-oxoazetidin-1-yl sulfate | 663.47 |
| 12 | 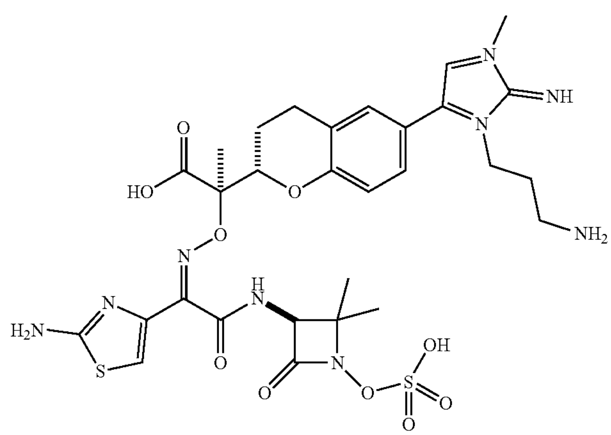 | (R)-2-((S)-6-(1-(3-aminopropyl)-2-imino-3-methyl-2,3-dihydro-1H-imidazol-4-yl)chroman-2-yl)-2-(((Z)-(1-(2-aminothiazol-4-yl)-2-(((S)-2,2-dimethyl-4-oxo-1-(sulfooxy)azetidin-3-yl)amino)-2-oxoethylidene)amino)oxy)propanoic acid | 736.34 |
| 13 | 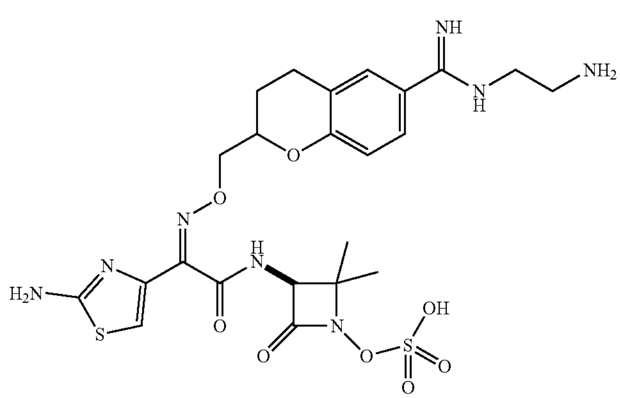 | (3S)-3-((Z)-2-(((6-(N-(2-aminoethyl)carbamimidoyl)chroman-2-yl)methoxy)imino)-2-(2-aminothiazol-4-yl)acetamido)-2,2-dimethyl-4-oxoazetidin-1-yl hydrogen sulfate | 611.49 |

Example 14

Preparation of (S)-3-((Z)-2-(((S)-1-((R)-6-(6-((2-aminoethyl)amino)-1-(azetidin-1-ium-3-ylmethyl)pyridin-1-ium-3-yl)chroman-2-yl)-1-carboxyethoxy)imino)-2-(2-aminothiazol-4-yl)acetamido)-2,2-dimethyl-4-oxoazetidin-1-yl Sulfate Formate

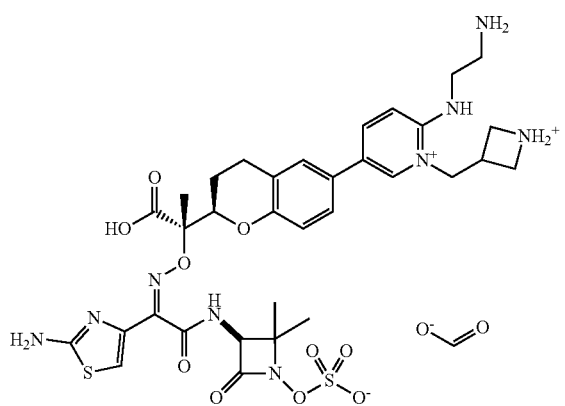

Step A: (S)-tert-butyl 2-((R)-6-bromochroman-2-yl)-2-(((tert-butoxycarbonyl)-amino)oxy)propanoate Boc-anhydride (6.8 ml, 29 mmol) was added to a stirred mixture of (S)-tert-butyl 2-(aminooxy)-2-((R)-6-bromochroman-2-yl)propanoate (3300 mg, 8.9 mmol, Intermediate 1) in DCM (10 ml). The reaction mixture was stirred at 50° C. for 1 h, then the mixture was cooled and the solvent was removed. The resulting residue was purified by ISCO (80 g gold), eluting with 0-30% EtOAc/isohexane gradient to give the title compound. LC-MS [M+H]$^+$: m/z 472.3.

Step B: tert-butyl 2-(6-(6-((2-((tert-butoxycarbonyl)amino)ethyl)amino)pyridin-3-yl)chroman-2-yl)-2-(((tert-butoxycarbonyl)amino)oxy)propanoate A mixture of (2S)-tert-butyl 2-(6-bromochroman-2-yl)-2-(((tert-butoxycarbonyl)amino)oxy)propanoate (0.5 g, 1.1 mmol), bis(pinacolato)diboron (0.28 g, 1.1 mmol), potassium acetate (0.31 g, 3.2 mmol), and 1,1'-bis(di-tert-butylphosphino)ferrocene palladium dichloride (0.10 g, 0.16 mmol) in dioxane (5.29 ml) was degassed by vacuum/N$_2$ exchange three times. The reaction mixture was heated at 70° C. overnight. The reaction mixture was cooled, and 1,1'-bis(di-tert-butylphosphino)ferrocene palladium dichloride (0.069 g, 0.1 eq), tert-butyl (2-((5-bromopyridin-2-yl)amino)ethyl)carbamate (0.37 g, 1.2 mmol), and 1 M aqueous solution of potassium phosphate tribasic (3.2 ml, 3.2 mmol) were added. The reaction mixture was degassed by vacuum/N$_2$ exchange three times, then heated at 70° C. for 5 hours and filtered through Celite™. The filtrate was concentrated, and the resulting residue was purified by ISCO (40 g) using 0-50% EtOAc/hexane to give the title compound. LC-MS [M+H]$^+$: m/z 629.8.

Step C: 2-((2-((tert-butoxycarbonyl)amino)ethyl)amino)-1-((1-(tert-butoxycarbonyl)azetidin-3-yl)methyl)-5-((R)-2-((S)-2,2,7,10,10-pentamethyl-4,8-dioxo-3,6,9-trioxa-5-azaundecan-7-yl)chroman-6-yl)pyridin-1-ium To a solution of tert-butyl 3-(hydroxymethyl)azetidine-1-carboxylate (0.3 g, 1.6 mmol) and DIEA (0.70 ml, 4.0 mmol) in CH$_2$Cl$_2$ (8.0 ml) at −78° C. was added trifluoromethanesulfonic anhydride (0.40 ml, 2.4 mmol). The reaction mixture was stirred at −78° C. for 0.5 hr, then quenched with water, and allowed to warm to RT. The mixture was partitioned between CH$_2$Cl$_2$ and water. The organic layer was separated and washed with saturated aqueous NaHCO$_3$ and brine. The organic layers were combined, dried over MgSO$_4$, and concentrated in vacuo to give the crude triflate. A mixture of (S)-tert-butyl 2-((R)-6-(6-((2-((tert-butoxycarbonyl)amino)ethyl)amino)pyridin-3-yl)chroman-2-yl)-2-(((tert-butoxycarbonyl)-amino)oxy)propanoate (0.25 g, 0.40 mmol), the crude triflate, and sodium bicarbonate (0.11 g, 1.3 mmol) in CH$_3$CN (8.0 ml) in a microwave vial was heated at 60° C. for 2 hrs. Then the mixture was cooled to RT and filtered. The filtrate was concentrated. The resulting residue was purified by ISCO 40 g (0-100% using 3:1 EtOAc:EtOH in Hexane) to give the title compound. LC-MS [M]$^+$: m/z 798.9.

Step D: 2-((2-aminoethyl)amino)-5-((R)-2-((S)-2-(aminooxy)-1-(tert-butoxy)-1-oxopropan-2-yl)chroman-6-yl)-1-(azetidin-3-ylmethyl)pyridin-1-ium TFA (1.5 ml) was added to a solution of 2-((2-((tert-butoxycarbonyl)amino)ethyl)amino)-1-((1-(tert-butoxycarbonyl)-azetidin-3-yl)methyl)-5-((R)-2-((S)-2,2,7,10,10-pentamethyl-4,8-dioxo-3,6,9-trioxa-5-azaundecan-7-yl)chroman-6-yl)pyridin-1-ium (0.19 g, 0.24 mmol) in CH$_2$Cl$_2$ (1.5 ml). The reaction mixture was stirred at room temperature for 1 hr, then the solvent was removed in vacuo. Ether was added to the resulting residue and the mixture was concentrated in vacuo. Ether was added to the resulting residue, and the resulting solid residue was dried in vacuo to give the title compound as the TFA salt. LC-MS [M]$^+$: m/z 498.5.

Step E: (S)-3-((Z)-2-((((S)-2-((R)-6-(6-((2-aminoethyl)amino)-1-(azetidin-3-ylmethyl)-pyridin-1-ium-3-yl)chroman-2-yl)-1-(tert-butoxy)-1-oxopropan-2-yl)oxy)imino)-2-(2-((tert-butoxycarbonyl)amino)thiazol-4-yl)acetamido)-2,2-dimethyl-4-oxoazetidin-1-yl Sulfate A solution of 2-((2-aminoethyl)amino)-5-((R)-2-((S)-2-(aminooxy)-1-(tert-butoxy)-1-oxopropan-2-yl)chroman-6-yl)-1-(azetidin-3-ylmethyl)pyridin-1-ium (0.20 g, 0.24 mmol) and (S)-3-(2-(2-((tert-butoxycarbonyl)amino)thiazol-4-yl)-2-oxoacetamido)-2,2-dimethyl-4-oxoazetidin-1-yl hydrogen sulfate (0.17 g, 0.29 mmol) in MeOH (2.4 ml) was stirred at RT for 2 hrs. Then the reaction solids were filtered off, and the filtrate was concentrated to give the title compound. LC-MS [M]$^+$: m/z 945.1.

Step F: (S)-3-((Z)-2-(((S)-1-((R)-6-(6-((2-aminoethyl)amino)-1-(azetidin-3-ylmethyl)pyridin-1-ium-3-yl)chroman-2-yl)-1-carboxyethoxy)imino)-2-(2-aminothiazol-4-yl)acetamido)-2,2-dimethyl-4-oxoazetidin-1-yl Sulfate To a solution of (S)-3-((Z)-2-((((S)-2-((R)-6-(6-((2-aminoethyl)amino)-1-(azetidin-3-ylmethyl)pyridin-1-ium-3-yl)chroman-2-yl)-1-(tert-butoxy)-1-oxopropan-2-yl)oxy)imino)-2-(2-((tert-butoxycarbonyl)amino)thiazol-4-yl)acetamido)-2,2-dimethyl-4-oxoazetidin-1-yl sulfate (0.22 g, 0.24 mmol) in CH$_2$Cl$_2$ (0.79 ml) was added TFA (1.6 ml). The reaction mixture was stirred at RT for 1 hr, then concentrated in vacuo. The resulting solid residue was dried under vacuum, then dissolved in 3 mL of DMSO and purified using reverse phase HPLC purification (0-25% MeCN/water (both with 0.1% formic acid) gradient) to give the title compound as the formic acid salt. LC-MS [M+H]⁺: m/z 788.5. H¹ NMR (500 MHz, D₂O, ppm): δ 8.13 (d, J=10 Hz, 1H), 8.07 (s, 1H), 7.17 (m, 3H), 6.79 (s, 1H), 6.71 (d, J=5 Hz, 1H), 4.51 (br. s, 2H), 4.36 (d, J=10 Hz, 1H), 4.31 (s, 1H), 4.10 (m, 2H), 4.04 (m, 2H), 3.73 (t, 2H), 3.50 (m, 1H), 3.21 (t, 2H), 2.69 (m, 2H), 1.99 (m, 1H), 1.71 (m, 1H), 1.45 (s, 3H), 1.27 (s, 3H), 1.08 (s, 3H).

TABLE 2

The compounds of Examples 15-24 were prepared using a similar procedure to Example 14 using the appropriate intermediates

| Example | Structure | Name | LCMS [M + H]⁺ |
|---|---|---|---|
| 15 | 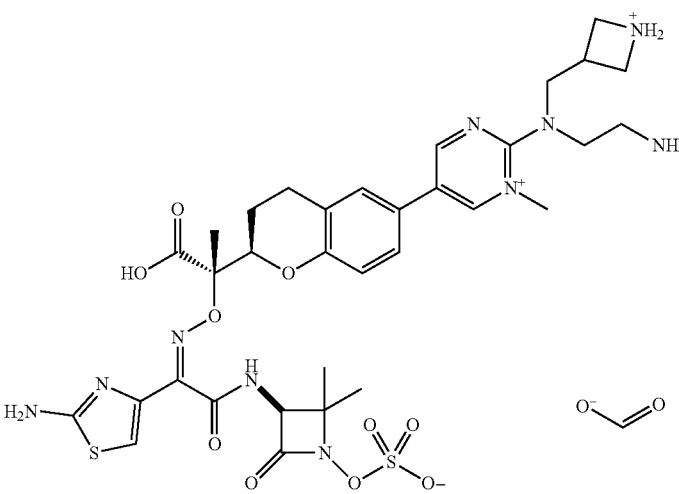 | (S)-3-((Z)-2-(((S)-1-((R)-6-(2-((2-aminoethyl)(azetidin-1-ium-3-ylmethyl)amino)-1-methylpyrimidin-1-ium-5-yl)chroman-2-yl)-1-carboxyethoxy)imino)-2-(2-aminothiazol-4-yl)acetamido)-2,2-dimethyl-4-oxoazetidin-1-yl sulfate formate | 803.6 |
| 16 | 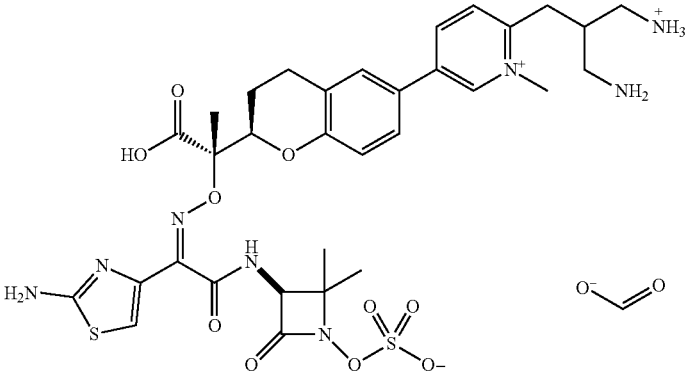 | (3S)-3-((Z)-2-(((1S)-1-((2R)-6-(6-(3-amino-2-(ammoniomethyl)propyl)-1-methylpyridin-1-ium-3-yl)chroman-2-yl)-1-carboxyethoxy)imino)-2-(2-aminothiazol-4-yl)acetamido)-2,2-dimethyl-4-oxoazetidin-1-yl sulfate formate | 761.7 |
| 17 | 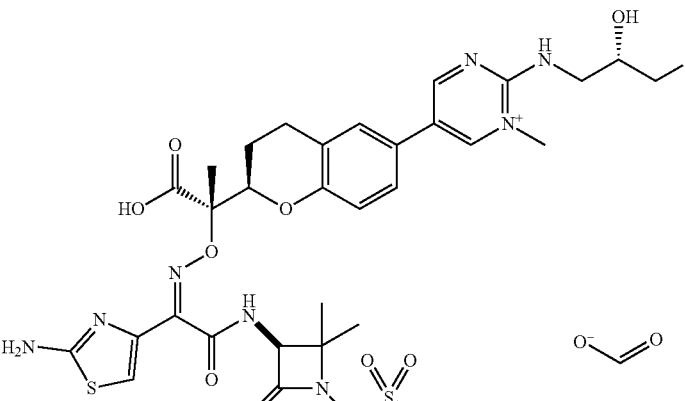 | (S)-3-((Z)-2-(2-aminothiazol-4-yl)-2-(((S)-1-((R)-6-(2-(((R)-3-ammonio-2-hydroxy-propyl)amino)-1-methyl-pyrimidin-1-ium-5-yl)chroman-2-yl)-1-carboxy-ethoxy)imino)acetamido)-2,2-dimethyl-4-oxoazetidin-1-yl sulfate formate | 765 |

TABLE 2-continued

The compounds of Examples 15-24 were prepared using a similar procedure to Example 14 using the appropriate intermediates

| Example | Structure | Name | LCMS [M + H]+ |
|---|---|---|---|
| 18 | 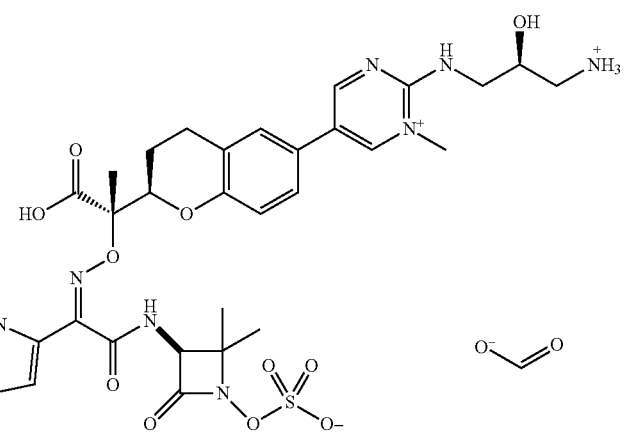 | (S)-3-((Z)-2-(2-aminothiazol-4-yl)-2-(((S)-1-((R)-6-(2-(((S)-3-ammonio-2-hydroxy-propyl)amino)-1-methylpyrimidin-1-ium-5-yl)chroman-2-yl)-1-carboxy-ethoxy)imino)acetamido)-2,2-dimethyl-4-oxoazetidin-1-yl sulfate formate | 764.7 |
| 19 | 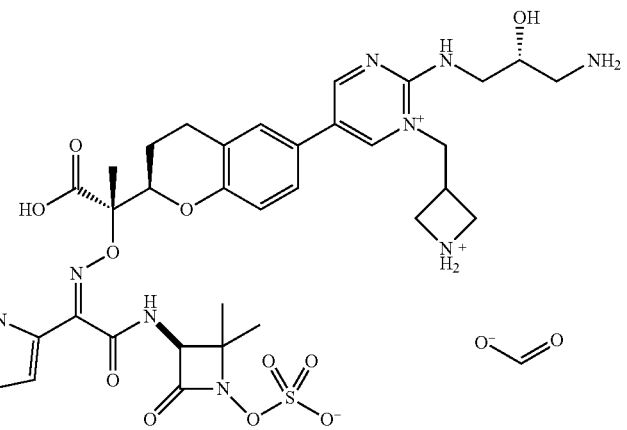 | (S)-3-((Z)-2-(((S)-1-((R)-6-(2-(((R)-3-amino-2-hydroxy-propyl)amino)-1-(azetidin-1-ium-3-ylmethyl)pyrimidin-1-ium-5-yl)chroman-2-yl)-1-carboxyethoxy)imino)-2-(2-aminothiazol-4-yl)acetamido)-2,2-dimethyl-4-oxoazetidin-1-yl sulfate formate | 819.8 |
| 20 | 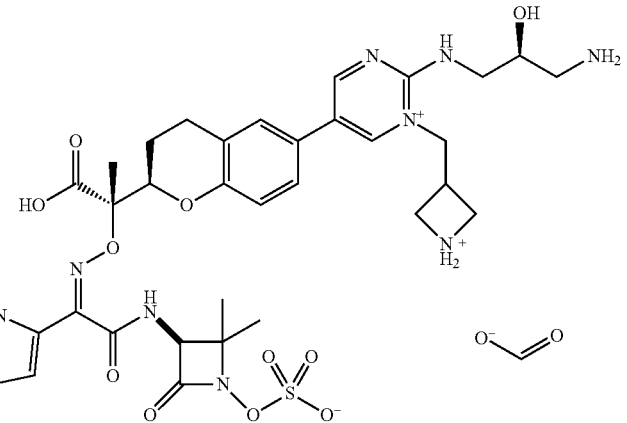 | (S)-3-((Z)-2-(((S)-1-((R)-6-(2-(((S)-3-amino-2-hydroxy-propyl)amino)-1-(azetidin-1-ium-3-ylmethyl)pyrimidin-1-ium-5-yl)chroman-2-yl)-1-carboxyethoxy)imino)-2-(2-aminothiazol-4-yl)acetamido)-2,2-dimethyl-4-oxoazetidin-1-yl sulfate formate | 820.4 |

TABLE 2-continued

The compounds of Examples 15-24 were prepared using a similar procedure to Example 14 using the appropriate intermediates

| Example | Structure | Name | LCMS [M + H]+ |
|---|---|---|---|
| 21 | 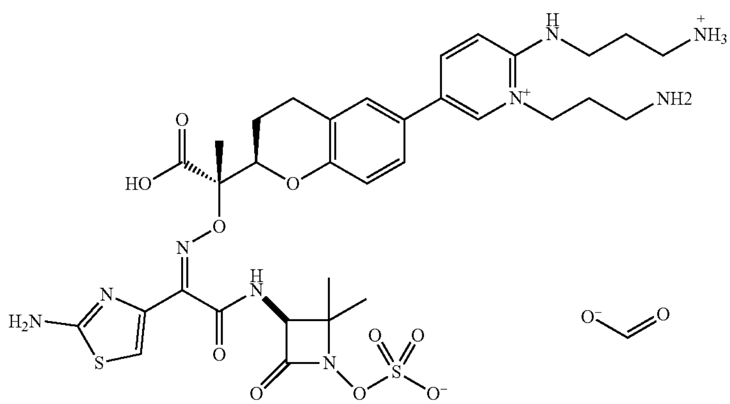 | (S)-3-((Z)-2-(((S)-1-((R)-6-(1-(3-aminopropyl)-6-((3-ammoniopropyl)amino)pyridin-1-ium-3-yl)chroman-2-yl)-1-carboxyethoxy)imino)-2-(2-aminothiazol-4-yl)acetamido)-2,2-dimethyl-4-oxoazetidin-1-yl sulfate formate | 790.6 |
| 22 | 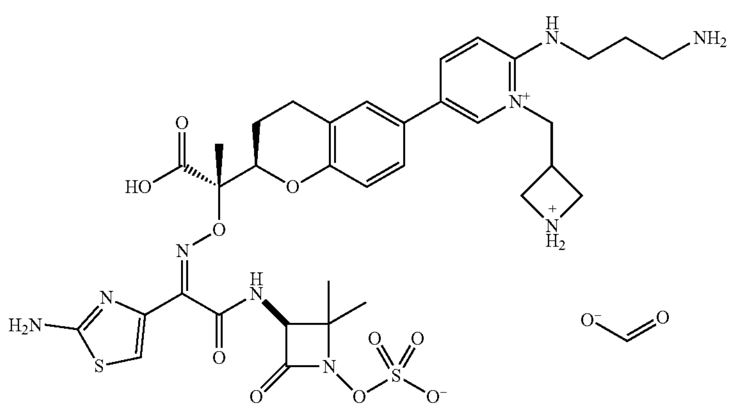 | (S)-3-((Z)-2-(((S)-1-((R)-6-(6-((3-aminopropyl)amino)-1-(azetidin-1-ium-3-ylmethyl)pyridin-1-ium-3-yl)chroman-2-yl)-1-carboxyethoxy)imino)-2-(2-aminothiazol-4-yl)acetamido)-2,2-dimethyl-4-oxoazetidin-1-yl sulfate formate | 802.7 |
| 23 | 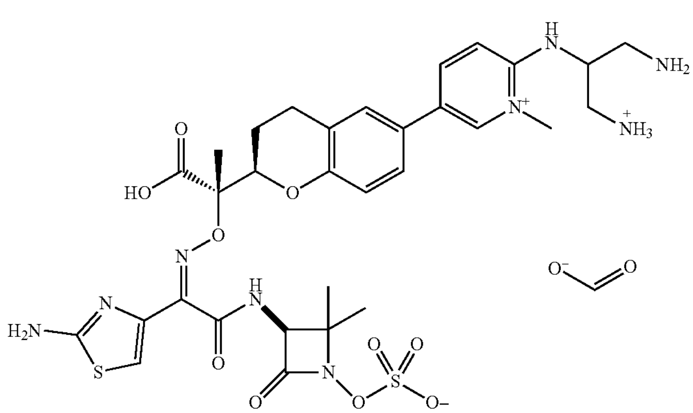 | (3S)-3-((Z)-2-(((1S)-1-((2R)-6-(6-((1-amino-3-ammoniopropan-2-yl)amino)-1-methylpyridin-1-ium-3-yl)chroman-2-yl)-1-carboxyethoxy)imino)-2-(2-aminothiazol-4-yl)acetamido)-2,2-dimethyl-4-oxoazetidin-1-yl sulfate formate | 762.2 |

TABLE 2-continued

The compounds of Examples 15-24 were prepared using a similar procedure to Example 14 using the appropriate intermediates

| Example | Structure | Name | LCMS [M + H]+ |
|---|---|---|---|
| 24 | 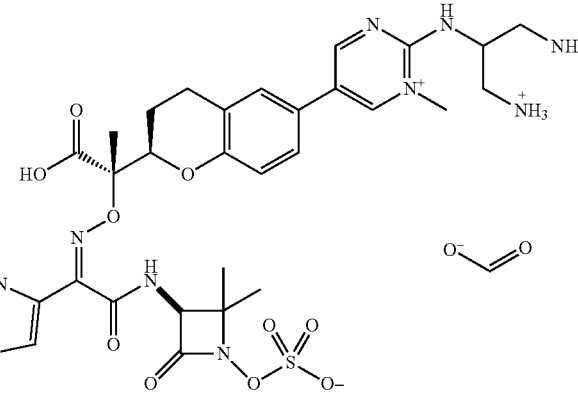 | (3S)-3-((Z)-2-(((1S)-1-((2R)-6-(2-((1-amino-3-ammonio-propan-2-yl)amino)-1-methyl-pyrimidin-1-ium-5-yl)chroman-2-yl)-1-carboxyethoxy)imino)-2-(2-aminothiazol-4-yl)acetamido)-2,2-dimethyl-4-oxoazetidin-1-yl sulfate formate | 763.2 |

Example 25

Preparation of (2S)-2-((2R)-6-(2-((2-aminoethyl)amino)-4,5-dihydro-1H-imidazol-4-yl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy)propanoic Acid

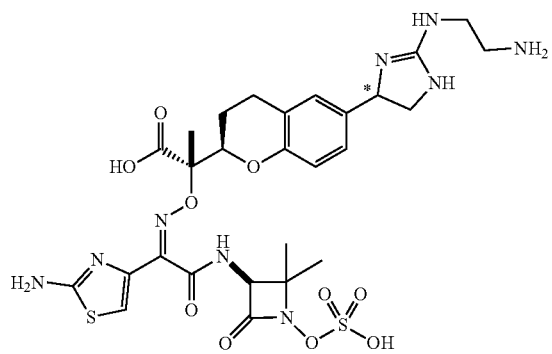 [SMILES: CC1(C)[C@H](NC(=O)/C(=N\O[C@](C)(C(=O)O)[C@H]2CCc3cc(C4CNC(NCCN)=N4)ccc3O2)c2csc(N)n2)C(=O)N1OS(=O)(=O)O]

Step A: (2S)-tert-butyl 2-(((tert-butoxycarbonyl)amino)oxy)-2-(6-vinylchroman-2-yl)propanoate To a solution of (2S)-tert-butyl 2-(6-bromochroman-2-yl)-2-(((tert-butoxycarbonyl)amino)oxy)propanoate (2.0 g, 4.2 mmol, Intermediate 1) in EtOH (20 mL) were added potassium vinyltrifluoroborate (850 mg, 6.4 mmol), Et$_3$N (0.88 mL, 6.4 mmol), and PdCl$_2$(dppf)-CH$_2$Cl$_2$ adduct (173 mg, 0.21 mmol). The mixture was N$_2$/vacuum exchanged 3 times and then heated to reflux for 4 hours. Then the mixture was cooled to RT, diluted with EtOAc and washed with water and brine. The organic layer was separated, dried over MgSO$_4$, and filtered. The filtrate was evaporated under reduced pressure to give a residue, which was purified by ISCO (80 g gold), eluting with 0-40% EtOAc/isohexane gradient, to give the title compound.

Step B: (2S)-tert-butyl 2-(((tert-butoxycarbonyl)amino)oxy)-2-((2R)-6-(1,2-diazidoethyl)chroman-2-yl)propanoate Acetic acid (4 ml) was added to a stirred mixture of (S)-tert-butyl 2-(((tert-butoxycarbonyl)amino)oxy)-2-((R)-6-vinylchroman-2-yl)propanoate (2.0 g, 4.8 mmol), sodium periodate (1020 mg, 4.8 mmol) and sodium azide (930 mg, 14.3 mmol) in DMSO (12 ml). The reaction mixture was stirred at 70° C. for 3.5 hrs under nitrogen. Then the reaction mixture was cooled, diluted with ethyl acetate, washed with saturated aqueous NaHCO$_3$ solution (1×), Na$_2$S$_2$O$_3$ solution (1×), water (2×) and brine, dried (MgSO$_4$), and filtered. The filtrate was evaporated under reduced pressure to give a residue, which was purified by column chromatography on silica gel (ISCO, 80 g gold), eluting with EtOAc/hexane gradient 0-20% to give the title compound.

Step C: (2S)-tert-butyl 2-(((tert-butoxycarbonyl)amino)oxy)-2-(6-(1,2-diaminoethyl)-chroman-2-yl)propanoate To a solution of (2S)-tert-butyl 2-(((tert-butoxycarbonyl)amino)-oxy)-2-(6-(1,2-diazidoethyl)chroman-2-yl)propanoate (1600 mg, 3.2 mmol) in THF (16 ml) and water (3.2 ml) was added triphenylphosphine resin (3300 mg, 13 mmol, ~4 g, 3.2 mmol/g). The reaction mixture was heated at 80° C. for 1 hr. Then the mixture was cooled, diluted with DCM, dried over MgSO$_4$, and filtered. The filtrate was concentrated to give the title compound, which was used directly in the next step. LC-MS [M+H]: m/z 452.4.

Step D: (2S)-tert-butyl 2-(((tert-butoxycarbonyl) amino)oxy)-2-((2R)-6-(2-thioxoimidazolidin-4-yl) chroman-2-yl)propanoate 1,1'-thiocarbonyldiimidazole (610 mg, 3.4 mmol) was added to a stirred mixture of (2S)-tert-butyl 2-(((tert-butoxycarbonyl)-amino)oxy)-2-((2R)-6-(1,2-diaminoethyl)chroman-2-yl)propanoate (1400 mg, 3.1 mmol) in DCM (50 ml). The reaction mixture was stirred at room temperature for 15 min, then the solvent was removed under reduced pressure. The resulting residue was purified on a silica gel column (80 g) using 0-60% EtOAc/hexane to give (2S)-tert-butyl 2-(((tert-butoxy-carbonyl)amino)oxy)-2-((2R)-6-(2-thioxoimidazolidin-4-yl)chroman-2-yl)propanoate as a mixture of two isomers. The racemic mixture of (2S)-tert-butyl 2-(((tert-butoxycarbonyl)-amino)oxy)-2-((2R)-6-(2-thioxoimidazolidin-4-yl)chroman-2-yl)propanoate (900 mg, 1.8 mmol) was resolved with SFC separation (IC 2×25 cm; 45% ethanol/$CO_2$, 100 bar; 60 mL/min, 220 nm; inj. Vol.: 1.5 mL, 10 mg/mL methanol) to give two isomers (Isomer 1 and 2 in the order of elution). LC-MS [M+H]: m/z 494.3.

Step E: tert-butyl (2S)-2-(((tert-butoxycarbonyl) amino)oxy)-2-((2R)-6-(2-(methylthio)-4,5-dihydro-1H-imidazol-4-yl)chroman-2-yl)propanoate Iodomethane (0.23 ml, 3.6 mmol) was added to a stirred mixture of (S)-tert-butyl 2-(((tert-butoxycarbonyl)amino) oxy)-2-((R)-6-((R)-2-thioxoimidazolidin-4-yl)chroman-2-yl)propanoate (Isomer 1, 360 mg, 0.729 mmol) in MeCN (5 ml). The reaction mixture was stirred at 70° C. for 2 hrs, then cooled and concentrated in vacuo to give the title compound, which was used directly for the next step. LC-MS [M+H]$^+$: m/z 508.3.

Step F: tert-butyl (2S)-2-((2R)-6-(2-((2-((tert-butoxycarbonyl)amino)ethyl)amino)-4,5-dihydro-1H-imidazol-4-yl)chroman-2-yl)-2-(((tert-butoxycarbonyl)amino)oxy)propanoate Acetic acid (0.17 ml, 2.9 mmol) was added to a stirred mixture of N-Boc-ethylenediamine (160 mg, 1.0 mmol) and tert-butyl (2S)-2-(((tert-butoxycarbonyl)amino)oxy)-2-((2R)-6-(2-(methylthio)-4,5-dihydro-1H-imidazol-4-yl) chroman-2-yl)propanoate (370 mg, 0.73 mmol) in dioxane (5 ml). The reaction mixture was stirred at 55° C. overnight, then cooled and concentrated in vacuo to give the title compound, which was used directly for the next step. LC-MS [M+H]$^+$: m/z 620.5.

Step G: tert-butyl (2S)-2-((2R)-6-(2-((2-aminoethyl) amino)-4,5-dihydro-1H-imidazol-4-yl)chroman-2-yl)-2-(aminooxy)propanoate TFA (3.5 ml) was added to a solution of (tert-butyl (2S)-2-((2R)-6-(2-((2-(((tert-butoxycarbonyl)amino)ethyl) amino)-4,5-dihydro-1H-imidazol-4-yl)chroman-2-yl)-2-(((tert-butoxycarbonyl)amino)oxy)propanoate (450 mg, 0.73 mmol) in $CH_2Cl_2$ (7 ml). The reaction mixture was stirred at room temperature for 1 hr, then concentrated in vacuo. Ether was added to the resulting residue, followed by the removal of solvent under reduced pressure. Ether was added to the resulting residue to obtain a solid residue, which was dried under vacuum to give the title compound as the TFA salt. LC-MS [M+H]$^+$: m/z 420.4.

Step H: tert-butyl (2S)-2-((2R)-6-(2-((2-aminoethyl) amino)-4,5-dihydro-1H-imidazol-4-yl)chroman-2-yl)-2-((((Z)-1-(2-((tert-butoxycarbonyl)amino)thiazol-4-yl)-2-(((S)-2,2-dimethyl-4-oxo-1-(sulfooxy) azetidin-3-yl)amino)-2-oxoethylidene)amino)oxy) propanoate To the solution of tert-butyl (2S)-2-((2R)-6-(2-((2-aminoethyl)amino)-4,5-dihydro-1H-imidazol-4-yl)chroman-2-yl)-2-(aminooxy)propanoate (305 mg, 0.73 mmol) in methanol (6 ml) at RT was added (S)-3-(2-(2-((tert-butoxycarbonyl) amino)thiazol-4-yl)-2-oxoacetamido)-2,2-dimethyl-4-oxoazetidin-1-yl hydrogen sulfate (400 mg, 0.87 mmol). The reaction mixture was stirred at RT for 3 h, then concentrated to give the title compound, which was used in the next step. LC-MS [M+H]$^+$: m/z 867.0.

Step I: (2S)-2-((2R)-6-(2-((2-aminoethyl)amino)-4, 5-dihydro-1H-imidazol-4-yl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene) amino)oxy)propanoic Acid TFA (10 ml) was added to a solution of tert-butyl (2S)-2-((2R)-6-(2-((2-aminoethyl)amino)-4,5-dihydro-1H-imidazol-4-yl)-chroman-2-yl)-2-((((Z)-1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino) oxy)propanoate (630 mg, 0.73 mmol) in $CH_2Cl_2$ (5 ml). The reaction mixture was stirred at room temperature for 45 min, and then concentrated under reduced pressure. Ether was added to the resulting residue, followed by removal of the solvent under reduced pressure. Ether was added to the resulting residue to give a solid residue. The solid residue was dried under vacuum, then dissolved in DMSO (5 mL) and purified using reverse phase HPLC purification with standard formic acid conditions (0-25% gradient MeCN (with 0.1% formic acid (FA))/water (with 0.1% formic acid)) to give the title compound as the formic acid salt. LC-MS [M+H]$^+$: m/z 710.7. $H^1$ NMR (500 MHz, $D_2O$, ppm): δ 6.99 (br. s, 2H), 6.86 (s, 1H), 6.72 (d, J=10 Hz, 1H), 4.96 (t, J=10 Hz, 1H), 4.60 (s, 1H), 4.28 (d, J=10 Hz, 1H), 3.96 (t, J=10 Hz, 1H), 3.48 (t, J=5 Hz, 2H), 3.43 (t, J=10 Hz, 1H), 3.12 (t, J=5 Hz, 2H), 2.70 (m, 2H), 1.96 (m, 1H), 1.66 (m, 1H), 1.47 (s, 3H), 1.37 (s, 3H), 1.16 (s, 3H).

TABLE 3

The compound of Example 26 was prepared using a similar procedure as Example 25 starting from Isomer 2 of Example 25, Step D.

| Example | Structure | Name | LCMS [M + H]+ |
|---|---|---|---|
| 26 | 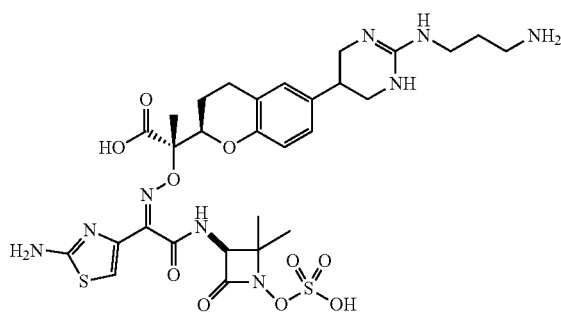 | (2S)-2-((2R)-6-(2-((2-aminoethyl)amino)-4,5-dihydro-1H-imidazol-4-yl)chroman-2-yl)-2-((((Z)-1-(2-aminothiazol-4-yl)-2-(((S)-2,2-dimethyl-4-oxo-1-(sulfooxy)azetidin-3-yl)amino)-2-oxoethylidene)amino)oxy) propanoic acid | 710.5 |

Example 27

Preparation of (2S)-2-((2R)-6-(2-((3-aminopropyl)amino)-1,4,5,6-tetrahydropyrimidin-5-yl)chroman-2-yl)-2-(((Z)-1-(2-aminothiazol-4-yl)-2-(((S)-22-dimethyl-4-oxo-1-(sulfooxy)azetidin-3-yl)amino)-2-oxoethylidene)amino)oxy)propanoic Acid

Step A: tert-butyl (3-((5-bromopyrimidin-2-yl)amino)propyl)carbamate

A mixture of 5-bromo-2-chloropyrimidine (0.67 g, 3.5 mmol), tert-butyl (3-aminopropyl)carbamate (0.73 g, 4.2 mmol), and TEA (1.5 ml, 10.4 mmol) in ethanol (14 ml) in a sealed tube was heated at 80° C. for 4 hrs. Then the reaction mixture was cooled, concentrated in vacuo, and CH$_2$Cl$_2$ was added. The resulting solid was filtered, and the filtrate was concentrated and dried under vacuum to give the title compound. LC-MS [M+H]+: m/z 332.2.

Step B: tert-butyl (3-((5-(4,4,5,5-tetramethyl-1,3,2-dioxaborolan-2-yl)pyrimidin-2-yl)amino)propyl)carbamate To a solution of tert-butyl (3-((5-bromopyrimidin-2-yl)amino)propyl)carbamate (550 mg, 1.7 mmol), 4,4,4',4',5,5,5',5'-octamethyl-2,2'-bi(1,3,2-dioxaborolane, 630 mg, 2.5 mmol), and 1,1'-bis(diphenylphosphino)ferrocene-palladium(II) dichloride dichloromethane complex PdCl$_2$(dppf)$_2$ CH$_2$Cl$_2$ (136 mg, 0.17 mmol) in 1,4-dioxane (10 mL) was added potassium acetate (490 mg, 5.0 mmol). The reaction mixture was degassed and refilled with nitrogen and heated at 85° C. overnight. Then the mixture was filtered and concentrated to dryness under vacuum and purified by ISCO column (40 g gold, 0-100% EtOAc/hexane gradient) to give the title compound.

Step C: (S)-tert-butyl 2-(((tert-butoxycarbonyl)amino)oxy)-2-((R)-6-(2-((3-((tert-butoxy carbonyl)amino)propyl)amino)pyrimidin-5-yl)chroman-2-yl) propanoate To a solution of PdCl$_2$(dppf)-CH$_2$Cl$_2$ adduct (60 mg, 0.074 mmol), tert-butyl (3-((5-(4,4,5,5-tetramethyl-1,3,2-dioxaborolan-2-yl)pyrimidin-2-yl)amino)propyl)carbamate (290 mg, 0.78 mmol) and (S)-tert-butyl 2-((R)-6-bromochroman-2-yl)-2-(((tert-butoxycarbonyl)amino)-oxy) propanoate (350 mg, 0.74 mmol) in dioxane (4.5 ml) was added Na$_2$CO$_3$ (240 mg, 2.2 mmol) in water (1.5 ml). The resulting mixture was N$_2$/vacuum exchanged 3 times, then heated at 100° C. under microwave reaction conditions for 1 hour. Then the mixture was cooled and diluted with EtOAc, dried with MgSO$_4$, filtered, and concentrated. The resulting residue was purified on silica gel column (ISCO gold, 80 g) using 0-100% EtOAc/hexane to give the title compound. LC-MS [M+H]+: m/z 644.5.

Step D: (2S)-tert-butyl 2-(((tert-butoxycarbonyl)amino)oxy)-2-((2R)-6-(2-((3-((tert-butoxycarbonyl)amino)propyl)amino)-1,4,5,6-tetrahydropyrimidin-5-yl)chroman-2-yl)propanoate Palladium on carbon (40 mg, 0.38 mmol) was added to a stirred mixture of (S)-tert-butyl 2-(((tert-butoxycarbonyl)amino)oxy)-2-((R)-6-(2-((3-((tert-butoxycarbonyl)-amino)propyl)amino)pyrimidin-5-yl)chroman-2-yl)propanoate (200 mg, 0.31 mmol) in MeOH (6 ml) and 1N hydrochloric acid (1.6 ml, 1.6 mmol). The reaction mixture was vacuum/$H_2$ exchanged 3 times, and then stirred under a hydrogen balloon at room temperature for 2.5 hrs. Then the mixture was diluted with DCM and filtered through a sintered funnel. The filtrate was diluted with DCM and washed with 1N aqueous NaOH solution (~5 mL). The aqueous phase was separated and extracted with DCM (×2). The combined organic layers were washed with brine, dried with $MgSO_4$, filtered and concentrated to give the title compound. LC-MS [M+H]$^+$: m/z 648.6.

Step E: (2S)-tert-butyl 2-(aminooxy)-2-((2R)-6-(2-((3-aminopropyl)amino)-1,4,5,6-tetrahydropyrimidin-5-yl)chroman-2-yl)propanoate TFA (1 ml) was added to a solution of (2S)-tert-butyl 2-(((tert-butoxycarbonyl)amino)oxy)-2-((2R)-6-(2-((3-((tert-butoxy-carbonyl)amino)propyl)amino)-1,4,5,6-tetrahydropyrimidin-5-yl)chroman-2-yl)propanoate (170 mg, 0.26 mmol) in $CH_2Cl_2$ (1 ml). The reaction mixture was stirred at room temperature for 1 hr, and then concentrated in vacuo. Ether was added to the resulting residue to give a solid residue, which was dried under vacuum to give the title compound as the TFA salt. LC-MS [M+H]$^+$: m/z 448.5.

Step F: (2S)-tert-butyl 2-((2R)-6-(2-((3-aminopropyl)amino)-1,4,5,6-tetrahydropyrimidin-5-yl)chroman-2-yl)-2-(((Z)-(1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)propanoate To a solution of (2S)-tert-butyl 2-(aminooxy)-2-((2R)-6-(2-((3-aminopropyl)amino)-1,4,5,6-tetrahydropyrimidin-5-yl)chroman-2-yl)propanoate (210 mg, 0.26 mmol) in methanol (3.5 ml) at rt was added (S)-3-(2-(2-(((tert-butoxycarbonyl)amino)thiazol-4-yl)-2-oxoacetamido)-2,2-dimethyl-4-oxoazetidin-1-yl hydrogen sulfate (146 mg, 0.31 mmol). The reaction mixture was stirred at rt for 4 hours, and then concentrated to give the title compound, which was used in the next step without further purification. LC-MS [M+H]$^+$: m/z 894.6.

Step G: (2S)-2-((2R)-6-(2-((3-aminopropyl)amino)-1,4,5,6-tetrahydropyrimidin-5-yl)-chroman-2-yl)-2-(((Z)-(1-(2-aminothiazol-4-yl)-2-(((S)-22-dimethyl-4-oxo-1-(sulfooxy)-azetidin-3-yl)amino)-2-oxoethylidene)amino)oxy)propanoic Acid TFA (2 ml) was added to a solution of (2S)-tert-butyl 2-((2R)-6-(2-((3-aminopropyl)amino)-1,4,5,6-tetrahydropyrimidin-5-yl)chroman-2-yl)-2-(((Z)-(1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)-propanoate (260 mg, 0.29 mmol) in $CH_2Cl_2$ (1 mL). The reaction mixture was stirred at room temperature for 45 min, and then the solvent was removed under reduced pressure. Ether was added to the resulting residue and solvent was removed under reduced pressure. Ether was added to the resulting residue to give a solid residue, which was dried under vacuum, dissolved in DMSO (5 mL) and purified by reverse phase HPLC with standard formic acid conditions (0-25% MeCN with 0.1% formic acid/water with 0.1% formic acid) to give the title compound as the formic acid salt. LC-MS [M+H]$^+$: m/z 788.5. H$^1$NMR (500 MHz, $D_2O$, ppm): δ 6.90 (s, 1H), 6.87 (d, J=10 Hz, 1H), 6.85 (s, 1H), 6.69 (d, J=10 Hz, 1H), 4.56 (s, 1H), 4.42 (d, J=10 Hz, 1H), 3.38 (m, 2H), 3.32 (m, 2H), 3.18 (t, J=5 Hz, 2H), 3.11 (m, 1H), 2.90 (t, J=5 Hz, 2H), 2.62 (m, 2H), 1.94 (m, 1H), 1.79 (m, 2H), 1.66 (m, 1H), 1.45 (s, 3H), 1.35 (s, 3H), 1.14 (s, 3H).

TABLE 4

The compounds of Examples 28-31 were prepared using a similar procedure to Example 27 and the appropriate intermediates.

| Example | Structure | Name | LCMS [M + H]$^+$ |
|---|---|---|---|
| 28 | 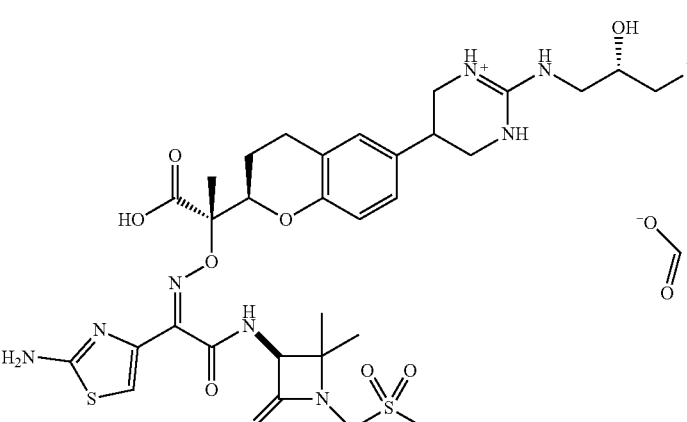 | 2-(((R)-3-amino-2-hydroxypropyl)amino)-5-((R)-2-((S)-1-((((E)-1-(2-aminothiazol-4-yl)-2-(((S)-2,2-dimethyl-4-oxo-1-(sulfooxy)azetidin-3-yl)amino)-2-oxoethylidene)amino)oxy)-1-carboxyethyl)chroman-6-yl)-3,4,5,6-tetrahydropyrimidin-1-ium formate | 754.6 |

TABLE 4-continued

The compounds of Examples 28-31 were prepared using a similar procedure to Example 27 and the appropriate intermediates.

| Example | Structure | Name | LCMS [M + H]+ |
|---|---|---|---|
| 29 | 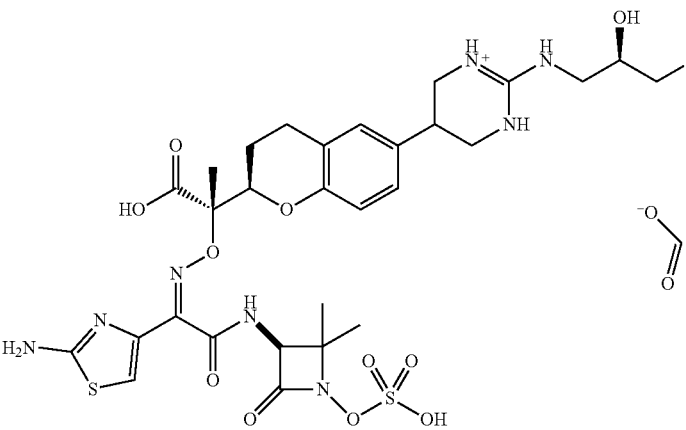 | 2-(((S)-3-amino-2-hydroxypropyl)amino)-5-((R)-2-((S)-1-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-1-carboxyethyl)chroman-6-yl)-3,4,5,6-tetrahydropyrimidin-1-ium formate | 754.6 |
| 30 | 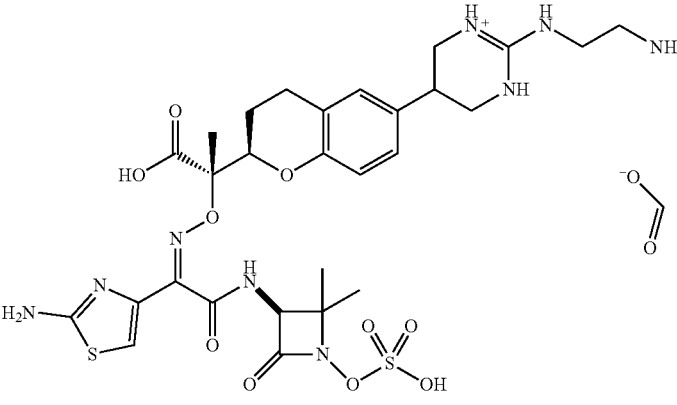 | 2-((2-aminoethyl)amino)-5-((R)-2-((S)-1-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-1-carboxyethyl)chroman-6-yl)-3,4,5,6-tetrahydropyrimidin-1-ium formate | 724.6 |
| 31 | 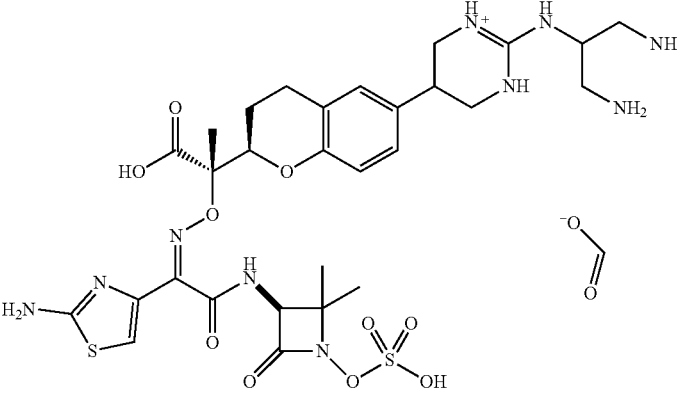 | 5-((R)-2-((S)-1-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-1-carboxyethyl)chroman-6-yl)-2-((1,3-diaminopropan-2-yl)amino)-3,4,5,6-tetrahydropyrimidin-1-ium formate | 753.6 |

Example 32 and Example 33

2-((3-aminopropyl)amino)-5-((R)-2-((S)-1-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-1-carboxyethyl)chroman-6-yl)-3,4-dihydropyrimidin-1-ium Formate

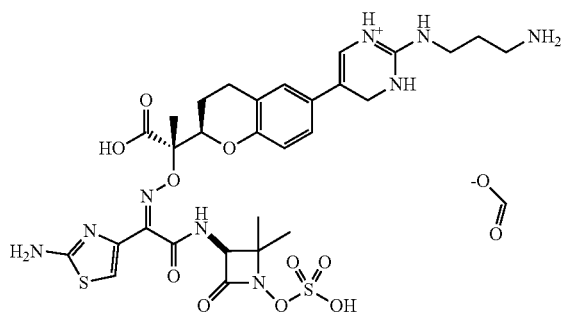

3-((5-((R)-2-((S)-1-((((Z)-1-(2-aminothiazol-4-yl)-2-(((S)-2,2-dimethyl-4-oxo-1-(sulfooxy)azetidin-3-yl)amino)-2-oxoethylidene)amino)oxy)-1-carboxyethyl)chroman-6-yl)pyrimidin-2-yl)amino)propan-1-aminium Formate

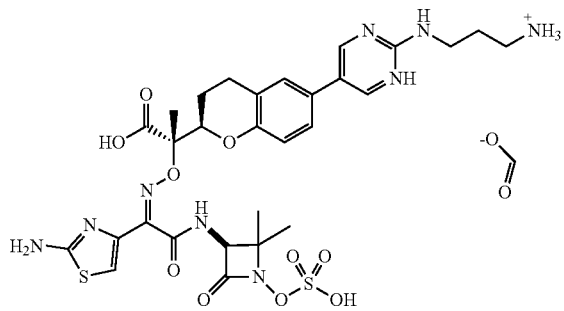

Step A: (S)-tert-butyl 2-(aminooxy)-2-((R)-6-(2-((3-aminopropyl)amino)-1,6-dihydro-pyrimidin-5-yl)chroman-2-yl)propanoate Triethylsilane (0.19 ml, 1.2 mmol) was added to a stirred mixture of (S)-tert-butyl 2-(((tert-butoxycarbonyl)amino)oxy)-2-((R)-6-(2-((3-((tert-butoxycarbonyl)amino)propyl)amino)pyrimidin-5-yl)chroman-2-yl)propanoate (150 mg, 0.23 mmol) in TFA (1 ml). The reaction mixture was stirred at room temperature for 2 hrs, then the solvent was removed under reduced pressure. Ether was added to the resulting residue and the solvent was removed under reduced pressure. Ether was added to the resulting residue to give a solid residue, which was dried under vacuum to give the title compound. LC-MS [M+H]⁺: m/z 446.4.

Step B: (S)-tert-butyl 2-((R)-6-(2-((3-aminopropyl)amino)-1,6-dihydropyrimidin-5-yl)chroman-2-yl)-2-(((Z)-(1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)oxy)propanoate To a solution of (S)-tert-butyl 2-(aminooxy)-2-((R)-6-(2-((3-aminopropyl)amino)-1,6-dihydropyrimidin-5-yl)chroman-2-yl)propanoate (184 mg, 0.23 mmol) in methanol (3 mL) at rt was added (S)-3-(2-(2-((tert-butoxycarbonyl)amino)thiazol-4-yl)-2-oxoacetamido)-2,2-dimethyl-4-oxoazetidin-1-yl hydrogen sulfate (130 mg, 0.28 mmol). The reaction mixture was stirred at rt for 4 hours, then concentrated to give the title compound, which was used directly in the next step.

Step C: (S)-2-((R)-6-(2-((3-aminopropyl)amino)-1,6-dihydropyrimidin-5-yl)chroman-2-yl)-2-(((Z)-(1-(2-aminothiazol-4-yl)-2-(((S)-2,2-dimethyl-4-oxo-1-(sulfooxy)azetidin-3-yl)amino)-2-oxoethylidene)amino)oxy)propanoic acid and (S)-2-((R)-6-(2-((3-aminopropyl)-amino)pyrimidin-5-yl)chroman-2-yl)-2-(((Z)-(1-(2-aminothiazol-4-yl)-2-(((S)-2,2-dimethyl-4-oxo-1-(sulfooxy)azetidin-3-yl)amino)-2-oxoethylidene)amino)oxy)propanoic Acid TFA (2 ml) was added to a solution of (S)-tert-butyl 2-((R)-6-(2-((3-aminopropyl)amino)-1,6-dihydropyrimidin-5-yl)chroman-2-yl)-2-(((Z)-(1-(2-((tert-butoxycarbonyl)amino)thiazol-4-yl)-2-(((S)-2,2-dimethyl-4-oxo-1-(sulfooxy)azetidin-3-yl)amino)-2-oxoethylidene)amino)-oxy)propanoate (200 mg, 0.22 mmol) in CH₂Cl₂ (1 mL). The reaction mixture was stirred at room temperature for 45 min, then the solvent was removed under reduced pressure. Ether was added to the resulting residue and then the solvent was removed under reduced pressure. To the resulting residue was added ether to give a solid residue, which was dried under vacuum, then dissolved in DMSO (5 mL) and purified by reverse-phase HPLC with standard 0-25% MeCN/water (both with 0.1% formic acid) conditions to give (S)-2-((R)-6-(2-((3-aminopropyl)amino)-1,6-dihydropyrimidin-5-yl)chroman-2-yl)-2-(((Z)-(1-(2-aminothiazol-4-yl)-2-(((S)-2,2-dimethyl-4-oxo-1-(sulfooxy)azetidin-3-yl)amino)-2-oxoethylidene)-amino)oxy)propanoic acid as the formic acid salt (LC-MS [M+H]⁺: m/z 736.8), and (S)-2-((R)-6-(2-((3-aminopropyl)amino)pyrimidin-5-yl)chroman-2-yl)-2-(((Z)-(1-(2-aminothiazol-4-yl)-2-(((S)-2,2-dimethyl-4-oxo-1-(sulfooxy)azetidin-3-yl)amino)-2-oxoethylidene)amino)-oxy)propanoic acid as the formic acid salt (LC-MS [M+H]⁺: m/z 734.8).

TABLE 5

The compounds of Examples 34-36 were prepared using the procedure of
Example 1 using Intermediates 1 and 7.

| Example | Structure | Name | LCMS [M + H]+ |
|---|---|---|---|
| 34 | 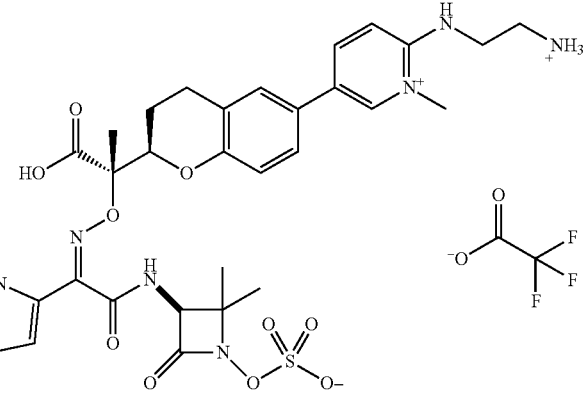 | mono((S)-3-((Z)-2-(2-aminothiazol-3-ium-4-yl)-2-(((S)-1-((R)-6-(6-((2-ammonioethyl)amino)-1-methylpyridin-1-ium-3-yl)chroman-2-yl)-1-carboxy-ethoxy)imino)acetamido)-2,2-dimethyl-4-oxoazetidin-1-yl sulfate) mono(2,2,2-trifluoroacetate) | 733.4 |
| 35 | 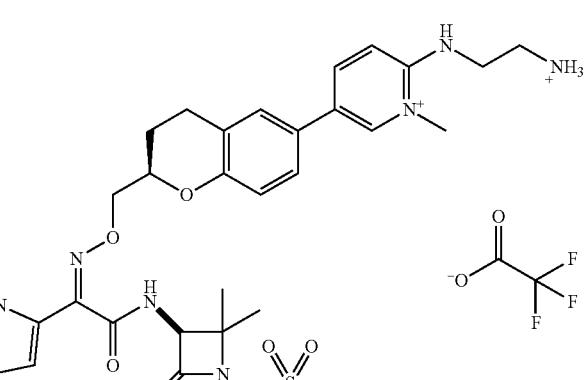 | mono((R)-3-((Z)-2-(2-aminothiazol-3-ium-4-yl)-2-((((R)-6-(6-((2-ammonioethyl)amino)-1-methyl-pyridin-1-ium-3-yl)chroman-2-yl)methoxy)imino)acetamido)-2,2-dimethyl-4-oxoazetidin-1-yl sulfate) mono(2,2,2-trifluoroacetate) | 675.5 |
| 36 | 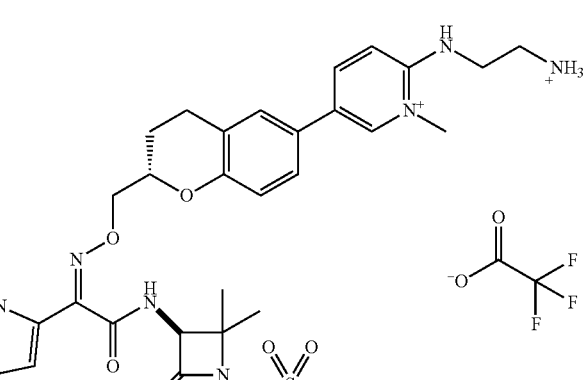 | mono((R)-3-((Z)-2-(2-aminothiazol-3-ium-4-yl)-2-((((S)-6-(6-((2-ammonioethyl)amino)-1-methyl-pyridin-1-ium-3-yl)chroman-2-yl)methoxy)imino)acetamido)-2,2-dimethyl-4-oxoazetidin-1-yl sulfate) mono(2,2,2-trifluoroacetate) | 675.5 |

TABLE 6

The compounds of Examples 37 and 38 were prepared using the procedure of Example 1 using Intermediate 8.

| Example | Structure | Name | LCMS [M + H]+ |
|---|---|---|---|
| 37 | 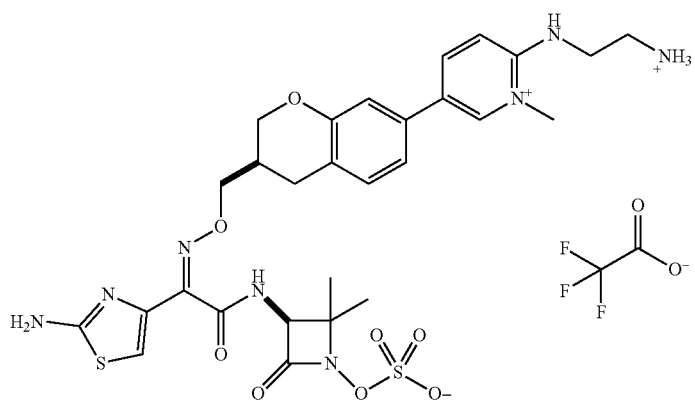 | mono((S)-3-((Z)-2-(2-aminothiazol-3-ium-4-yl)-2-((((R)-7-(6-((2-ammonioethyl)amino)-1-methylpyridin-1-ium-3-yl)chroman-3-yl)methoxy)imino)acetamido)-2,2-dimethyl-4-oxoazetidin-1-yl sulfate) mono(2,2,2-trifluoroacetate) | 675.3 |
| 38 | 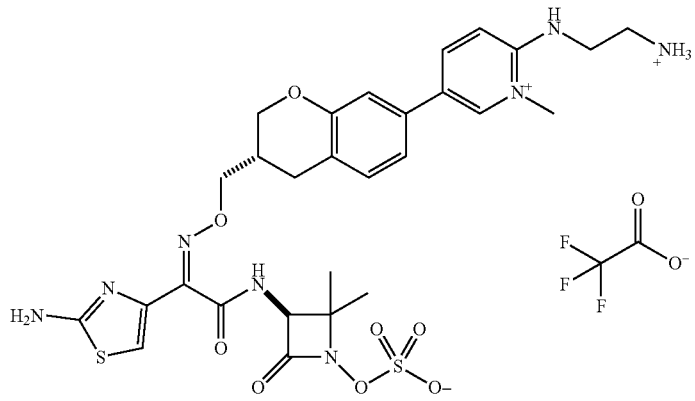 | mono((S)-3-((Z)-2-(2-aminothiazol-3-ium-4-yl)-2-(((((S)-7-(6-((2-ammonioethyl)amino)-1-methylpyridin-1-ium-3-yl)chroman-3-yl)methoxy)imino)acetamido)-2,2-dimethyl-4-oxoazetidin-1-yl sulfate) mono(2,2,2-trifluoroacetate) | 675.3 |

Example 39

Preparation of 3S)-3-((Z)-2-(((1S)-1-((2R)-6-(3-(aminomethyl)-1-(2-ammonioethyl)-1,2,3,4-tetrahydropyrido[1,2-a]pyrimidin-5-ium-7-yl)chroman-2-yl)-1-carboxyethoxy)imino)-2-(2-aminothiazol-4-yl) acetamido)-2,2-dimethyl-4-oxoazetidin-1-yl sulfate Formate

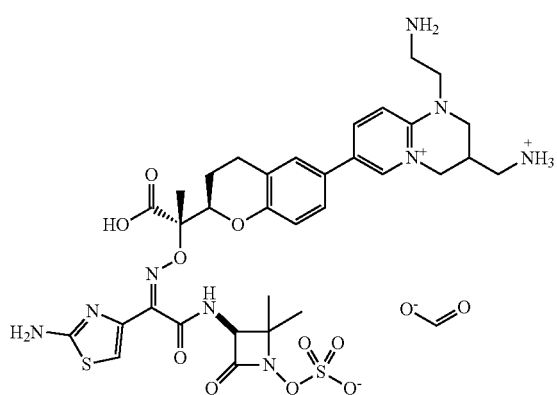

Sodium bicarbonate (290 mg, 3.47 mmol) was added to a stirred mixture of (S)-3-((Z)-2-(((S)-1-((R)-6-(6-((2-aminoethyl)amino)-1-(azetidin-3-ylmethyl)pyridin-1-ium-3-yl)chroman-2-yl)-1-carboxyethoxy)imino)-2-(2-aminothiazol-4-yl)acetamido)-2,2-dimethyl-4-oxoazetidin-1-yl sulfate (460 mg, 0.58 mmol, Example 14) containing <1 eq of TFA in DMSO (4 ml). The reaction mixture was stirred at room temperature for 4 hrs, then filtered through a filtration plug (PTFE 0.45 uM). The filtrate was diluted with water with 0.1% formic acid (50 mL) and purified on a reverse phase silica gel column (330 g, ISCO) eluting with 0-40% MeCN/water (both with 0.1% formic acid) to give the title compound. LC-MS [M+H]⁺: m/z 788.7.

Example 40

Mono((S)-3-((Z)-2-(((S)-1-((R)-6-(1-((S)-3-amino-2-hydroxypropyl)-2-((R)-pyrrolidin-3-ylmethyl)-1H-pyrazol-2-ium-4-yl)chroman-2-yl)-1-carboxy ethoxy)imino)-2-(2-aminothiazol-4-yl)acetamido)-2,2-dimethyl-4-oxoazetidin-1-yl sulfate) mono (2,2,2-trifluoroacetate)

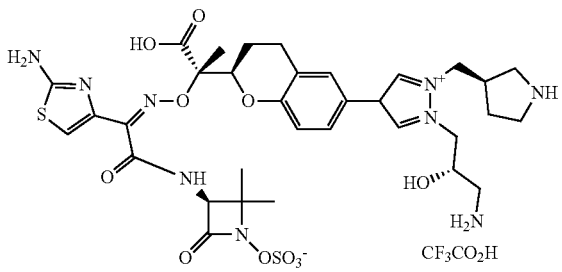

Step A: (S)-tert-butyl (3-(4-bromo-1H-pyrazol-1-yl)-2-hydroxypropyl)carbamate To a mixture of 4-bromo-1H-pyrazole (5.09 g, 34.6 mmol) and (S)-tert-butyl (oxiran-2-ylmethyl)carbamate (5 g, 28.9 mmol) in DMF (80 ml) was added Cs₂CO₃ (14.11 g, 43.3 mmol). The reaction mixture was stirred at 20° C. for 15 hours, then diluted with EtOAc (200 mL) and water (200 mL). The aqueous layer was extracted with EtOAc (3×150 mL). The combined organic layers were washed by brine (3×150 mL), dried over Na₂SO₄, filtered and concentrated in vacuo. The resulting residue was purified by column chromatography (SiO₂, PE:EtOAc=20:1 to 1:1) to give the title compound.

Step B: (S)-tert-butyl (3-(4-bromo-1H-pyrazol-1-yl)-2-((tert-butyldimethylsilyl)oxy)-propyl)carbamate To a mixture of tert-butyl (3-(4-bromo-1H-pyrazol-1-yl)-2-hydroxy-propyl)carbamate (9 g, 28.1 mmol) and imidazole (2.87 g, 42.2 mmol) in DMF (100 ml) was added TBSCl (5.08 g, 33.7 mmol). The reaction mixture was stirred at 15° C. for 16 hours, then diluted with EtOAc (200 mL) and water (200 mL). The aqueous layer was extracted with EtOAc (3×200 mL). The combined organic layers were washed by brine (3×200 mL), dried over anhydrous Na₂SO₄, filtered and concentrated in vacuo. The resulting residue was purified by column chromatography (SiO₂, PE:EtOAc=50:1 to 3:1) to give the title compound.

Step C: (2S)-tert-butyl 2-(6-bromochroman-2-yl)-2-(((tert-butoxycarbonyl)amino)-oxy)propanoate Boc-anhydride (6.79 ml, 29.3 mmol) was added to a stirred mixture of (2S)-tert-butyl 2-(aminooxy)-2-(6-bromochroman-2-yl)propanoate (3300 mg, 8.86 mmol) in DCM (10 ml). The reaction mixture was stirred at 50° C. for 1 h, then cooled. The solvent was removed, and the resulting residue was purified by ISCO (80 g gold) eluting with a 0-30% EtOAc/isohexane gradient to give the title compound. LC-MS [M]⁺: m/z 472.29.

Step D: (S)-tert-butyl 2-((R)-6-(1-((S)-3-((tert-butoxycarbonyl)amino)-2-((tert-butyldimethyl-silyl) oxy)propyl)-1H-pyrazol-4-yl)chroman-2-yl)-2-(((tert-butoxy-carbonyl)amino)oxy)-propanoate A mixture of (2S)-tert-butyl 2-(6-bromochroman-2-yl)-2-(((tert-butoxy-carbonyl)amino)oxy)propanoate (6.3 g, 13.34 mmol), bis(pinacolato)-diboron (3.56 g, 14.00 mmol), potassium acetate (3.93 g, 40.0 mmol), and 1,1'-bis(di-tert-butylphosphino)ferrocene palladium dichloride (1.304 g, 2.001 mmol) in dioxane (65 ml) was flushed with N₂. The reaction mixture was heated at 70° C. overnight, then cooled. To the reaction mixture was added 1,1'-bis(di-tert-butylphosphino) ferrocene palladium dichloride (0.869 g, 0.1 eq), (S)-tert-butyl (3-(4-bromo-1H-pyrazol-1-yl)-2-((tert-butyldimethyl-silyl)-oxy)propyl)carbamate (6.95 g, 16.00 mmol), and potassium phosphate tribasic (1 M aqueous solution, 40 ml, 40 mmol). The mixture was degassed via vacuum/N₂ refill three times, then heated at 70° C. for 5 hours. Then the reaction mixture was diluted with EtOAc, dried over MgSO$_4$ and filtered. The filtrate was concentrated and the residue was purified by ISCO (220 g) using 0-50% EA/hex to give the title compound. LC-MS [M]$^+$: m/z 747.79.

Step E: (R)-tert-butyl 3-((((trifluoromethyl)sulfonyl) oxy)methyl)pyrrolidine-1-carboxylate Trifluoromethanesulfonic anhydride (2.508 ml, 14.91 mmol) was added to a stirred, cooled −78° C. mixture of (R)-tert-butyl 3-(hydroxymethyl)pyrrolidine-1-carboxylate (2.5 g, 12.42 mmol), and DIPEA (4.34 ml, 24.84 mmol) in CH$_2$Cl$_2$ (50 ml). The reaction mixture was stirred at −78° C. for 90 min, then diluted with DCM and saturated NaHCO$_3$. The aqueous phase was separated, and extracted with DCM. The combined organic layers were washed with brine, dried over MgSO$_4$, filtered and concentrated to give the title compound.

Step F: 1-((S)-3-((tert-butoxycarbonyl)amino)-2-((tert-butyldimethylsilyl)oxy)propyl)-2-(((R)-1-(tert-butoxycarbonyl)pyrrolidin-3-yl)methyl)-4-((R)-2-((S)-2,2,7,10,10-pentamethyl-4,8-dioxo-3,6,9-trioxa-5-azaundecan-7-yl)chroman-6-yl)-1H-pyrazol-2-ium A solution of (R)-tert-butyl 3-((((trifluoro-methyl)sulfonyl)oxy)methyl)pyrrolidine-1-carboxylate (4.12 g, 12.37 mmol) in MeCN (5 mL) was added to a solution of (2S)-tert-butyl 2-((2R)-6-(1-(3-((tert-butoxycarbonyl)-amino)-2-((tert-butyldimethylsilyl)oxy)propyl)-1H-pyrazol-4-yl)chroman-2-yl)-2-(((tert-butoxycarbonyl)amino)oxy) propanoate (2.1 g, 2.81 mmol) and sodium bicarbonate (1.889 g, 22.49 mmol) in CH$_3$CN (anhydrous, 18 ml). The resulting mixture was heated at 60° C. overnight, then cooled, filtered and concentrated. The resulting residue was purified by column chromatography on silica gel (ISCO gold, 120 g) eluting with EtOAc/Hexane (0-100%) to give the title compound. LC-MS [M]$^+$: m/z 930.90.

Step G: 1-((S)-3-((tert-butoxycarbonyl)amino)-2-hydroxypropyl)-2-(((R)-1-(tert-butoxycarbonyl)pyrrolidin-3-yl)methyl)-4-((R)-2-((S)-2,2,7,10,10-pentamethyl-4,8-dioxo-3,6,9-trioxa-5-azaundecan-7-yl) chroman-6-yl)-1H-pyrazol-2-ium TBAF (2.336 ml, 2.336 mmol) was added to a stirred mixture of 1-((S)-3-((tert-butoxycarbonyl)amino)-2-((tert-butyldimethylsilyl)oxy)propyl)-2-(((R)-1-(tert-butoxycarbonyl)pyrrolidin-3-yl)methyl)-4-((R)-2-((S)-2,2,7,10,10-pentamethyl-4,8-dioxo-3,6,9-trioxa-5-azaundecan-7-yl) chroman-6-yl)-1H-pyrazol-2-ium (1.74 g, 1.868 mmol) in THF (8 ml). The reaction mixture was stirred at room temperature for 1 h, then concentrated to the title compound, which was used directly for next step without further purification. LC-MS [M]$^+$: m/z 817.36.

Step H: 1-((S)-3-amino-2-hydroxypropyl)-4-((R)-2-((S)-2-(aminooxy)-1-(tert-butoxy)-1-oxopropan-2-yl)chroman-6-yl)-2-((R)-pyrrolidin-3-ylmethyl)-1H-pyrazol-2-ium To the solution of 1-((S)-3-((tert-butoxycarbonyl)amino)-2-hydroxypropyl)-2-(((R)-1-(tert-butoxycarbonyl)-pyrrolidin-3-yl)methyl)-4-((R)-2-((S)-2,2,7,10,10-pentamethyl-4, 8-dioxo-3,6,9-trioxa-5-azaundecan-7-yl)chroman-6-yl)-1H-pyrazol-2-ium (1.52 g, 1.860 mmol) in CH$_2$Cl$_2$ (8 ml) was added dropwise TFA (3.94 ml, 51.2 mmol) at 0° C. The resulting solution was stirred at rt for 45 min, then concentrated. The resulting residue was treated with Et$_2$O (50 mL), followed by removal of the Et$_2$O phase. The resulting solid residue was dried under vacuum to give the title compound, as the TFA salt. LC-MS [M]$^+$: m/z 516.28.

Step I: (S)-3-((Z)-2-((((S)-2-((R)-6-(1-((S)-3-amino-2-hydroxypropyl)-2-((R)-pyrrolidin-3-ylmethyl)-1H-pyrazol-2-ium-4-yl)chroman-2-yl)-1-(tert-butoxy)-1-oxopropan-2-yl)oxy)imino)-2-(2-((tert-butoxycarbonyl)amino)thiazol-4-yl)acetamido)-2,2-dimethyl-4-oxoazetidin-1-yl Sulfate To a solution of 1-((S)-3-amino-2-hydroxypropyl)-4-((R)-2-((S)-2-(aminooxy)-1-(tert-butoxy)-1-oxopropan-2-yl) chroman-6-yl)-2-((R)-pyrrolidin-3-ylmethyl)-1H-pyrazol-2-ium (960 mg, 1.858 mmol) in methanol (9 mL) at rt was added (S)-3-(2-(2-((tert-butoxycarbonyl)amino)-thiazol-4-yl)-2-oxoacetamido)-2,2-dimethyl-4-oxoazetidin-1-yl hydrogen sulfate (1036 mg, 2.230 mmol). The resulting solution was stirred at rt for 3 hours, then concentrated to give the title compound, which was used directly for next step without further purification. LC-MS [M]$^+$: m/z 962.22.

Step J: (S)-3-((Z)-2-(((S)-1-((R)-6-(1-((S)-3-amino-2-hydroxypropyl)-2-((R)-pyrrolidin-3-ylmethyl)-1H-pyrazol-2-ium-4-yl)chroman-2-yl)-1-carboxyethoxy) imino)-2-(2-aminothiazol-4-yl)acetamido)-2,2-dimethyl-4-oxoazetidin-1-yl sulfate compound with 2,2,2-trifluoroacetic Acid (1:1)

A solution of TFA (8 ml) and CH$_2$Cl$_2$ (4 ml) was added to (S)-3-((Z)-2-((((S)-2-((R)-6-(1-((S)-3-amino-2-hydroxypropyl)-2-((R)-pyrrolidin-3-ylmethyl)-1H-pyrazol-2-ium-4-yl) chroman-2-yl)-1-(tert-butoxy)-1-oxopropan-2-yl)oxy) imino)-2-(2-((tert-butoxycarbonyl)amino)thiazol-4-yl) acetamido)-2,2-dimethyl-4-oxoazetidin-1-yl sulfate (1780 mg, 1.850 mmol). The reaction mixture was stirred at room temperature for 45 min, then the solvent was removed under reduced pressure. Ether was added to the residue, followed by removal of the solvent by pipette. The resulting solid residue was dissolved in DMSO (3 mL) and purified with reverse HPLC eluting with a MeCN with 0.1% formic acid/water with 0.1% formic acid (0-20%) gradient to give the title compound as the TFA salt. LC-MS [M]$^+$: m/z 806.24 $^1$H-NMR (400 MHz, D$_2$O, ppm): δ 8.53 (s, 1H), 8.51 (s, 1H), 7.23 (s, 1H), 7.20 (d, J=12 Hz, 1H), 6.85 (s, 1H), 6.70 (d, J=12 Hz, 1H), 4.59 (m, 2H), 4.44 (m, 2H), 4.26 (s, 1H), 4.21 (m, 1H), 3.43 (m, 2H), 3.21 (m, 2H), 2.97 (m, 3H), 2.68 (m, 2H), 2.12 (m, 1H), 2.00 (m, 1H), 1.72 (m, 2H), 1.48 (s, 3H), 1.23 (s, 3H), 1.01 (s, 3H).

TABLE 7

The compound of Example 41 was prepared using a procedure similar to Example 40 starting from the appropriate intermediates.

| Example | Structure | Name | LCMS [M + H]+ |
|---|---|---|---|
| 41 | 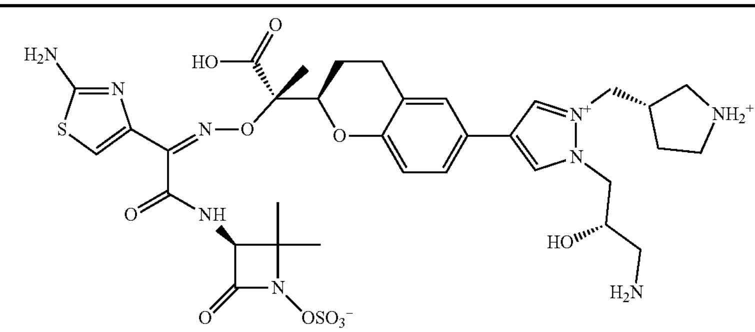 | mono((S)-3-((Z)-2-(((S)-1-((R)-6-(1-((S)-3-amino-2-hydroxypropyl)-2-(((S)-pyrrolidin-1-ium-3-yl)methyl)-1H-pyrazol-2-ium-4-yl)chroman-2-yl)-1-carboxyethoxy)imino)-2-(2-aminothiazol-4-yl)acetamido)-2,2-dimethyl-4-oxoazetidin-1-yl sulfate) mono (2,2,2-trifluoroacetate) | 806.1 |

Biological Assays

Antibiotic Activity: Determination of Growth Inhibitory Concentration

The concentrations of compounds required to inhibit the growth of various strains of bacteria were determined in an assay that assessed bacterial growth by measuring optical density at 600 nm (OD600). The bacterial strains tested included the clinical strains *Escherichia coli* expressing NDM-1 (CLB30016), *Klebsiella pneumoniae* expressing KPC-1 (CL6569), *Acinetobacter baumannii* expressing TEM-1, AmpC, and Oxa-24/40 (CL6188) and *Pseudomonas aeruginosa* expressing AmpC (CL5701). All compounds were tested in the presence of a β lactamase inhibitor (BLi, Relebactam) in 384-well microplates. The clinical strains were stored as frozen single use stocks, thawed and diluted into 1.1× cation-adjusted Mueller-Hinton II broth to achieve approximately $2\times10^5$ CFU/mL. Test compounds were dissolved in DMSO and diluted 1:50 in the assay, resulting in a final concentration range of 100 μM to 0.098 μM. On the day of the assay, 1 μL of test compound was added to the plate followed by 4 μL of 50 μg/mL BLi in MOPS buffer and 45 μL of diluted bacteria. Plates were centrifuged at 1000 rpm for 30 seconds, shaken at approximately 800 rpm for 1 minute, and incubated at 35±2° C. for 22 hours. The concentration of BLi used in the assay was 4 g/mL. At the end of the incubation, absorbance at 600 nm was determined using a spectrophotometer. Inhibition was quantitated by identifying the lowest concentration of test compound that was required to inhibit 95% of the growth of the bacteria. The results for Examples 1-39 are reported in Table I, expressed as the concentration of compound that inhibited 95% of bacterial growth (Minimum Inhibitory Threshold Concentration; MITC95).

Representative compounds of the present invention display a growth inhibitory effect. For example, representative compounds of Examples 1-41 were determined to inhibit growth at concentrations of 100 μM or less.

TABLE I

Antibacterial activity of Examples 1-41

| EXAMPLE # | AB_CL6188 MITC95 (μM) | EC_CLB30016 MITC95 (μM) | KP_CL6569 MITC95 (μM) | PA_CL5701 MITC95 (μM) |
|---|---|---|---|---|
| 1 | 2.734 | 4.688 | 0.3906 | 3.125 |
| 2 | 1.563 | 12.5 | 0.3906 | 3.125 |
| 3 | 6.25 | 3.13 | 0.39 | 6.25 |
| 4 | 6.25 | 12.5 | 1.281 | 25 |
| 5 | 25 | 100 | 6.25 | 50 |
| 6 | 100 | 100 | 12.5 | 100 |
| 7 | 25 | 25 | 1.563 | 12.5 |
| 8 | 100 | 100 | 3.125 | 25 |
| 9 | 12.5 | 12.5 | 0.3906 | 6.25 |
| 10 | 12.5 | 6.25 | 0.3906 | 6.25 |
| 11 | 3.125 | 6.25 | 0.7813 | 3.125 |
| 12 | 6.25 | 100 | 0.3906 | 3.125 |
| 13 | 25 | 12.5 | 0.7813 | 12.5 |
| 14 | 50 | 12.5 | 0.7813 | 12.5 |
| 15 | 3.125 | 6.25 | 0.3906 | 6.25 |
| 16 | 3.125 | 6.25 | 0.3906 | 3.125 |
| 17 | 12.5 | 6.25 | 0.3906 | 6.25 |
| 18 | 3.125 | 6.25 | 0.3906 | 6.25 |
| 19 | 12.5 | 6.25 | 0.7813 | 12.5 |
| 20 | 6.25 | 6.25 | 0.3906 | 6.25 |
| 21 | 3.125 | 6.25 | 0.3906 | 12.5 |
| 22 | 12.5 | 12.5 | 0.7813 | 25 |
| 23A | 6.25 | 12.5 | 0.3906 | 3.125 |
| 23B | 12.5 | 100 | 3.125 | 25 |

TABLE I-continued

Antibacterial activity of Examples 1-41

| EXAMPLE # | AB_CL6188 MITC95 (μM) | EC_CLB30016 MITC95 (μM) | KP_CL6569 MITC95 (μM) | PA_CL5701 MITC95 (μM) |
|---|---|---|---|---|
| 24 | 1.563 | 3.125 | 0.3906 | 3.125 |
| 25 | 50 | 6.25 | 0.3906 | 3.125 |
| 26 | 12.5 | 100 | 1.563 | 50 |
| 27 | 12.5 | 12.5 | 0.7813 | 6.25 |
| 28 | 3.13 | 6.25 | 0.2 | 3.13 |
| 29 | 3.125 | 25 | 1.563 | 6.25 |
| 30 | 25 | 25 | 3.125 | 6.25 |
| 31 | 3.125 | 6.25 | 0.3906 | 3.125 |
| 32 | 3.125 | 3.125 | 0.1953 | 3.125 |
| 33 | 3.125 | 6.25 | 0.3906 | 6.25 |
| 34 | 12.5 | 25 | 0.78 | 25 |
| 35 | 6.25 | 25 | 1.281 | 50 |
| 36 | 3.125 | 12.5 | 0.7813 | 6.25 |
| 37A | 12.5 | 12.5 | 0.78 | 3.13 |
| 37B | 50 | 100 | 6.25 | 25 |
| 38 | 6.25 | 6.25 | 0.3906 | 6.25 |
| 39 | 7.292 | 12.5 | 0.3255 | 3.125 |
| 40 | 1.56 | >50 | 0.1 | 0.78 |
| 41 | 1.56 | >50 | 0.1 | 0.78 |

What is claimed is:

1. A compound of Formula I

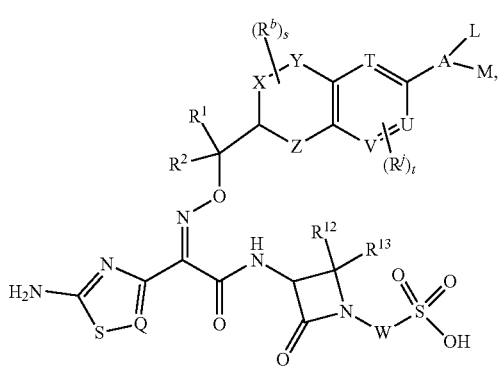

(I)

or a pharmaceutically acceptable salt thereof, wherein:
T, U and V are each CH;
W is O;
Q is $CR^3$;
X is $CH_2$;
Y is O or $CH_2$,
Z is O or $CH_n$,
A is
 1) —C(=NH)—NH,
 2) AryC, or
 3) HetC,
wherein A is unsubstituted or substituted with one to four $R^i$;
AryC is a 5- to 6-membered monocyclic aromatic ring with 0, 1, 2, or 3 ring atoms independently selected from N, N as a quaternary salt, O and S, unsubstituted or substituted with one to four $R^i$, wherein AryC is optionally fused to a 4- to 7-membered heterocycloalkyl ring containing one to two heteroatoms selected from O, S and —$NR^g$;
HetC is a 4- to 7-membered saturated or monounsaturated monocyclic ring with 1, 2, or 3 heteroatom ring atoms independently selected from N, N as a quaternary salt, O and S, unsubstituted or substituted with one to four $R^i$;

L is
 1) absent,
 2) $R^4$,
 3) —$NHR^4$,
 4) —$N(R^4)_2$,
 5) —$OR^4$,
 6) —$(CH_2)_nR^4$,
 7) —$C(O)R^4$,
 8) —$C(NH)R^4$, or
 9) —$S(O)_mR^4$,
wherein L is unsubstituted or substituted with 1-4 substituents selected from $R^e$;
M is
 1) $R^5$,
 2) —$NHR^5$,
 3) —$N(R^5)_2$,
 4) —$OR^5$,
 5) —$(CH_2)_uR^5$,
 6) —$C(O)R^5$,
 7) —$C(NH)R^5$, or
 8) —$S(O)_tR^5$,
wherein M is unsubstituted or substituted with 1-4 substituents selected from $R^6$;
$R^1$ and $R^2$ are independently selected from:
 1) hydrogen,
 2) —$C_1$-$C_8$ alkyl, and
 3) —$C(O)OR^e$,
wherein —$C_1$-$C_8$ alkyl is unsubstituted or substituted with one to three $R^a$,
provided that if $R^1$ is —$C(O)OR^e$, then $R^2$ is not —$C(O)OR^e$,
$R^3$ is hydrogen;
each occurrence of $R^4$ is independently:
 1) hydrogen,
 2) —$C_1$-$C_{10}$ alkyl,
 3) —$C_2$-$C_8$ alkenyl,
 4) —$(CH_2)_nOR^e$,
 5) —$S(O)_mR^e$,
 6) —$S(O)_mNR^cR^d$,
 7) —$(CH_2)_nNR^cR^d$,
 8) —$OC(O)R^e$,
 9) —$C(O)OR^e$,
 10) —CN, 11) —C(O)NR$^c$R$^d$,
12) —NR$^c$(O)R$^e$,
13) —NR$^c$C(O)OR$^e$,
14) —NR$^c$(O)NR$^c$R$^d$,
15) —NR$^c$S(O)$_m$R$^e$,
16) =NR$^{11}$,
17) —C$_3$-C$_7$ cycloalkyl,
18) —O—C$_3$-C$_6$cycloalkyl,
19) —C$_1$-C$_{10}$alkylene-C$_3$-C$_6$cycloalkyl,
20) —O—C$_1$-C$_{10}$alkylene-C$_3$-C$_6$cycloalkyl,
21) HetB,
22) —O-HetB,
23) —C$_1$-C$_{10}$alkylene-HetB,
24) —O—C$_1$-C$_{10}$alkylene-HetB,
25) AryB,
26) —O-AryB,
27) —C$_1$-C$_{10}$alkylene-AryB, or
28) —O—C$_1$-C$_{10}$alkylene-AryB,
wherein R$^4$ is unsubstituted or substituted with one to four R$^6$;
AryB is a 5- to 6-membered monocyclic aromatic ring with 0, 1, 2, or 3 ring atoms independently selected from N, O and S, unsubstituted or substituted with one to four W;
HetB is a 4- to 7-membered saturated or monounsaturated monocyclic ring with 1, 2, or 3 heteroatom ring atoms independently selected from N, N as a quaternary salt, O and S, unsubstituted or substituted with one to three R$^a$;
R$^5$ is
1) hydrogen,
2) C$_1$-C$_{10}$ alkyl,
3) —C$_2$-C$_8$ alkenyl,
4) —(CH$_2$)$_u$OR$^e$,
5) —S(O)$_v$R$^e$,
6) —S(O)$_v$NR$^c$R$^d$,
7) —(CH$_2$)$_u$NR$^c$R$^d$,
8) —OC(O)R$^e$,
9) —C(O)OR$^e$,
10) —CN,
11) —C(O)NR$^c$R$^d$,
12) —NR$^c$C(O)R$^e$,
13) —NR$^c$C(O)OR$^e$,
14) —NR$^c$C(O)NR$^c$R$^d$,
15) —NR$^c$S(O)$_v$R$^e$,
16) =NR$^{11}$,
17) —C$_3$-C$_7$ cycloalkyl,
18) —O—C$_3$-C$_6$cycloalkyl,
19) —C$_1$-C$_{10}$alkylene-C$_3$-C$_6$cycloalkyl,
20) —O—C$_1$-C$_{10}$ alkylene-C$_3$-C$_6$cycloalkyl,
21) HetB,
22) —O-HetB,
23) —C$_1$-C$_{10}$alkylene-HetB,
24) —O—C$_1$-C$_{10}$ alkylene-HetB,
25) AryB,
26) —O-AryB,
27) —C$_1$-C$_{10}$alkylene-AryB, or
28) —O—C$_1$-C$_{10}$alkylene-AryB,
wherein R$^5$ is unsubstituted or substituted with one to four R$^6$;
each occurrence of R$^6$ is independently:
1) halogen,
2) —C$_1$-C$_6$alkyl,
3) —OR$^e$,
4) —S(O)$_v$R$^e$,
5) —S(O)$_v$NR$^c$R$^d$,
6) —C(O)R$^e$,
7) —OC(O)R$^e$,
8) —C(O)OR$^e$,
9) —CN,
10) —C(O)NR$^c$R$^d$,
11) —C(NH)NR$^c$R$^d$,
12) —(CH$_2$)$_u$NR$^c$R$^d$,
13) —(CH$_2$)$_u$NR$^c$R$^d$,
14) —N(R$^c$)(C(O)R$^e$),
15) —N(R$^c$)(C(O)OR$^e$),
16) —N(R$^c$)(C(O)NR$^c$R$^d$),
17) —N(R$^c$)(S(O)$_v$R$^e$), or
18) HetB;
R$^7$ is
1) hydrogen,
2) C$_1$-C$_3$ alkyl, or
3) C$_3$-C$_7$ cycloalkyl,
wherein C$_1$-C$_3$ alkyl and C$_3$-C$_7$ cycloalkyl are unsubstituted or substituted with one to three R$^a$;
R$^8$ is
1) hydrogen,
2) C$_1$-C$_4$ alkyl, or
3) C$_3$-C$_7$ cycloalkyl;
R$^9$ is
1) hydrogen,
2) C$_1$-C$_4$ alkyl, or
3) C$_3$-C$_7$ cycloalkyl;
R$^{10}$ is
1) hydrogen,
2) C$_1$-C$_4$ alkyl, or
3) C$_3$-C$_7$ cycloalkyl;
R$^{11}$ is
1) hydrogen,
2) C$_1$-C$_4$ alkyl, or
3) C$_3$-C$_7$ cycloalkyl;
R$^{12}$ and R$^{13}$ are independently C$_1$-C$_3$ alkyl, wherein C$_1$-C$_3$ alkyl is unsubstituted or substituted with one to seven fluorines,
or alternatively R$^{12}$ and R$^{13}$ together with the carbon to which they are attached form a monocyclic C$_4$-C$_6$ cycloalkyl unsubstituted or substituted with one to three substituents independently selected from —F, —OH and —OC$_1$-C$_3$alkyl;
each occurrence of R$^a$ is independently:
1) hydrogen,
2) halogen,
3) C$_1$-C$_3$alkyl,
4) —NR$^c$R$^d$, or
5) —OR$^e$;
each occurrence of R$^b$ is independently:
1) hydrogen,
2) —C$_1$-C$_6$ alkyl,
3) —OC$_1$-C$_6$ alkyl,
4) OH,
5) N(R$^9$)$_2$, or
6) halogen,
wherein —C$_1$-C$_3$ alkyl is unsubstituted or substituted with one to three R$^a$;
R$^c$ and R$^d$ are independently selected from:
1) hydrogen,
2) —C1-C10 alkyl, and
3) —C2-C10 alkenyl,
wherein each Rc and Rd is unsubstituted or substituted with one to three Rf;
each occurrence of R$^e$ is independently hydrogen, or —C$_1$-C$_{10}$alkyl, wherein each R$^e$ is unsubstituted or substituted with one to three R$^h$;

each occurrence of $R^f$ is independently:
  1) halogen,
  2) —$C_1$-$C_{10}$ alkyl,
  3) —OH,
  4) —$OC_1$-$C_4$ alkyl,
  5) —$S(O)_mC_1$-$C_4$ alkyl,
  6) —CN,
  7) —$CF_3$,
  8) —$OCHF_2$,
  9) —$OCF_3$, or
  10) $NH_2$,
wherein —$C_1$-$C_{10}$ alkyl is unsubstituted or substituted with one to three substituents independently selected from —OH, halogen, cyano, and —$S(O)_2CH_3$;
each occurrence of $R^g$ is independently:
  1) hydrogen,
  2) —$C(O)R^e$, or
  3) —$C_1$-$C_{10}$ alkyl,
wherein —$C_1$-$C_{10}$alkyl is unsubstituted or substituted with one to five fluorines;
each occurrence of $R^h$ is independently:
  1) halogen,
  2) —$C_1$-$C_{10}$alkyl,
  3) —OH,
  4) —$OC_1$-$C_4$ alkyl,
  5) —$S(O)_mC_1$-$C_4$ alkyl,
  6) —CN,
  7) —$CF_3$,
  8) —$OCHF_2$, or
  9) —$OCF_3$,
wherein —$C_1$-$C_{10}$ alkyl is unsubstituted or substituted with one to three substituents independently selected from: —OH, halogen, cyano, or —$S(O)_2CH_3$;
each occurrence of $R^i$ is independently:
  1) —$C_1$-$C_8$ alkyl,
  2) —$C_2$-$C_8$ alkenyl,
  3) —$C_2$-$C_8$ alkynyl,
  4) halogen,
  5) —$OR^e$,
  6) —$S(O)_mR^e$,
  7) —$S(O)_mNR^cR^d$,
  8) —$C(O)R^e$,
  9) —$OC(O)R^e$,
  10) —$C(O)OR^e$,
  11) —CN,
  12) —$C(O)NR^cR^d$,
  13) —$NR^cR^d$,
  14) —$(CH_2)_nNR^cR^d$,
  15) —$NR^cC(O)R^e$,
  16) —$NR^cC(O)OR^e$,
  17) —$NR^cC(O)NR^cR^d$,
  18) —$NR^cS(O)_mR^e$,
  19) =NH,
  20) —$CF_3$,
  21) —$OCF_3$, or
  22) —$OCHF_2$;
each occurrence of $R^j$ is independently:
  1) hydrogen,
  2) $C_1$-$C_3$ alkyl,
  3) $OR^{10}$,
  4) =$NR^{10}$,
  5) $N(R^{10})_2$, or
  6) halogen,
wherein $C_1$-$C_3$ alkyl unsubstituted or substituted with one to three $R^b$;
each n is independently 0, 1, 2, 3, 4, 5 or 6;
each m is independently 0, 1 or 2;
each p is independently 1 or 2;
each q is independently 0, 1, 2, 3, 4, 5 or 6;
each s is independently 0, 1, 2 or 3;
each t is independently 0, 1, 2 or 3;
each u is independently 0, 1, 2, 3, 4, 5 or 6; and
each v is independently 0, 1, or 2.

2. The compound of claim 1 wherein
Y is $CH_2$; and
Z is O;
or a pharmaceutically acceptable salt thereof.

3. The compound of claim 1 wherein
$R^1$ and $R^2$ are independently selected from
  1) —$C_1$-$C_8$ alkyl, and
  2) —$C(O)OR^e$,
provided if $R^1$ is —$C(O)OR^e$, then $R^2$ is —$C_1$-$C_8$ alkyl, and if $R^2$ is —$C(O)OR^e$, then $R^1$ is —$C_1$-$C_8$ alkyl;
or a pharmaceutically acceptable salt thereof.

4. The compound of claim 1 wherein A is
  1) AryC, or
  2) HetC,
wherein A is unsubstituted or substituted with one to four $R^i$;
or a pharmaceutically acceptable salt thereof.

5. The compound of claim 1 wherein
A is —C(=NH)—NH, wherein A is unsubstituted or substituted with one to four $R^i$;
or a pharmaceutically acceptable salt thereof.

6. The compound of claim 1 wherein
A is AryC, wherein A is unsubstituted or substituted with one to four $R^i$;
or a pharmaceutically acceptable salt thereof.

7. The compound of claim 1 wherein
L is
  1) absent, or
  2) $R^4$,
wherein L is unsubstituted or substituted with 1-4 substituents selected from $R^e$; and
each occurrence of $R^4$ is independently:
  1) hydrogen,
  2) —$C_1$-$C_{10}$ alkyl,
  3) —$(CH_2)_nOR^e$,
  4) —$(CH_2)_nNR^cR^d$, or
  5) —$C_1$-$C_{10}$alkylene-HetB,
wherein $R^4$ is unsubstituted or substituted with one to four $R^6$;
or a pharmaceutically acceptable salt thereof.

8. The compound of claim 5 wherein
each occurrence of $R^4$ is independently:
  1) —$C_1$-$C_{10}$ alkyl,
  2) —$(CH_2)_nNR^cR^d$, or
  3) —$C_1$-$C_{10}$alkylene-HetB,
wherein $R^4$ is unsubstituted or substituted with one to four $R^6$;
or a pharmaceutically acceptable salt thereof.

9. The compound of claim 1 wherein
M is
  1) $R^5$, or
  2) —$NHR^5$,
wherein M is unsubstituted or substituted with 1-4 substituents selected from $R^6$; and
$R^5$ is
  1) hydrogen,
  2) $C_1$-$C_6$ alkyl,
  3) —$C_1$-$C_4$alkyl-$(NR^cR^d)_2$,
  4) —$(CH_2)_uNR^cR^d$, or
  5) —$C_1$-$C_{10}$alkylene-HetB,
wherein $R^5$ is unsubstituted or substituted with one to four $R^6$;
or a pharmaceutically acceptable salt thereof.

10. The compound of claim 7 wherein
R$^5$ is
1) —C$_1$-C$_4$alkyl-(NR$^c$R$^d$)$_2$, or
2) —(CH$_2$)$_u$NR$^c$R$^d$,
wherein R$^5$ is unsubstituted or substituted with one to four R$^6$;
or a pharmaceutically acceptable salt thereof.

11. The compound of claim 1 wherein
T, U and V are CH;
W is O;
Q is CR$^3$;
X is CH$_2$;
Y is O or CH$_2$;
Z is O or CH$_2$;
R$^1$ and R$^2$ are independently selected from:
1) hydrogen,
2) —C$_1$-C$_8$ alkyl, and
3) —C(O)OR$^e$,
wherein —C$_1$-C$_8$ alkyl is unsubstituted or substituted with one to three R$^a$, provided that if R$^1$ is —C(O)OR$^e$, then R$^2$ is independently selected from hydrogen and —C$_1$-C$_8$ alkyl;
R$^3$ is hydrogen;
R$^{12}$ and R$^{13}$ are independently C$_1$-C$_3$ alkyl, wherein C$_1$-C$_3$ alkyl is unsubstituted or substituted with one to seven fluorines,
or alternatively R$^{12}$ and R$^{13}$ together with the carbon to which they are attached form a monocyclic C$_4$-C$_6$ cycloalkyl unsubstituted or substituted with one to three substituents independently selected from —F, —OH and —OC$_1$-C$_3$alkyl;
A is
1) —C(=NH)—NH,
2) AryC, or
3) HetC,
wherein A is unsubstituted or substituted with one to four R$^i$;
L is
1) absent, or
2) R$^4$,
wherein L is unsubstituted or substituted with 1-4 substituents selected from R$^e$;
each occurrence of R$^4$ is independently:
1) hydrogen,
2) —C$_1$-C$_{10}$ alkyl,
3) —(CH$_2$)$_n$OR$^e$,
4) —(CH$_2$)$_n$NR$^c$R$^d$, or
5) —C$_1$-C$_{10}$alkylene-HetB,
wherein R$^4$ is unsubstituted or substituted with one to four R$^6$;
M is
1) R$^5$, or
2) —NHR$^5$,
wherein M is unsubstituted or substituted with 1-4 substituents selected from R$^6$; and
R$^5$ is
1) hydrogen,
2) —C$_1$-C$_6$ alkyl,
3) —C$_1$-C$_4$alkyl-(NR$^c$R$^d$)$_2$,
4) —(CH$_2$)$_u$NR$^c$R$^d$, or
5) —C$_1$-C$_{10}$alkylene-HetB,
wherein R$^5$ is unsubstituted or substituted with one to four R$^6$;
or a pharmaceutically acceptable salt thereof.

12. The compound of claim 1 wherein
T, U and V are CH;
W is O;
Q is CR$^3$;
R$^3$ is hydrogen;
X is CH$_2$;
Y is CH$_2$;
Z is O;
R$^1$ and R$^2$ are independently selected from
1) —C$_1$-C$_6$ alkyl, and
2) —C(O)OR$^e$,
wherein —C$_1$-C$_6$ alkyl is unsubstituted or substituted with one to three R$^a$, provided that if R$^1$ is —C(O)OR$^e$, then R$^2$ is —C$_1$-C$_6$ alkyl;
R$^{12}$ and R$^{13}$ are independently C$_1$-C$_3$ alkyl, wherein C$_1$-C$_3$ alkyl is unsubstituted or substituted with one to seven fluorines;
A is
1) AryC, or
2) HetC,
wherein A is unsubstituted or substituted with one to four R$^i$;
L is
1) absent, or
2) R$^4$,
wherein L is unsubstituted or substituted with 1-4 substituents selected from R$^e$;
each occurrence of R$^4$ is independently:
1) —C$_1$-C$_{10}$ alkyl,
2) —(CH$_2$)$_n$NR$^c$R$^d$, or
3) —C$_1$-C$_{10}$alkylene-HetB,
wherein R$^4$ is unsubstituted or substituted with one to four R$^6$;
M is
1) R$^5$, or
2) —NHR$^5$,
wherein M is unsubstituted or substituted with 1-4 substituents selected from R$^6$;
R$^5$ is
1) —C$_1$-C$_4$alkyl-(NR$^c$R$^d$)$_2$, or
2) —(CH$_2$)$_u$NR$^c$R$^d$,
wherein R$^5$ is unsubstituted or substituted with one to four R$^6$;
or a pharmaceutically acceptable salt thereof.

13. A compound selected from:

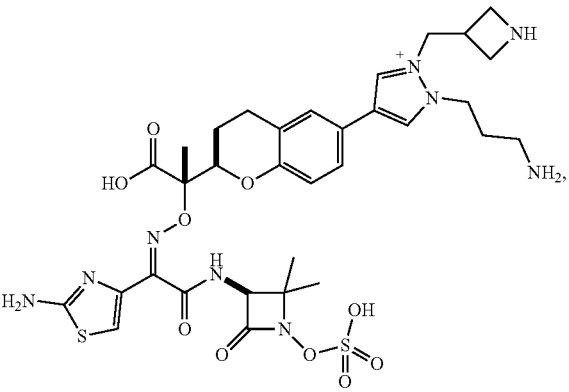

141
-continued
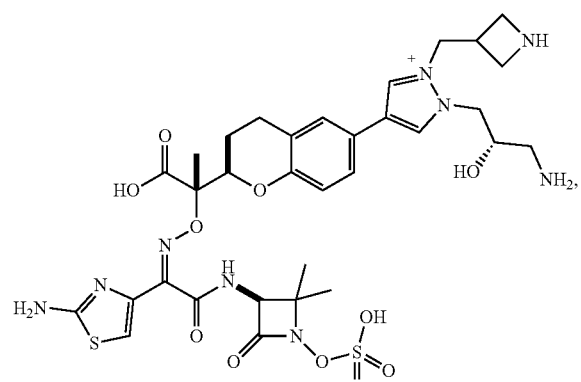
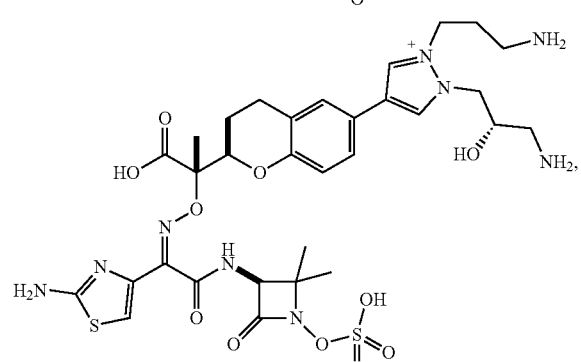
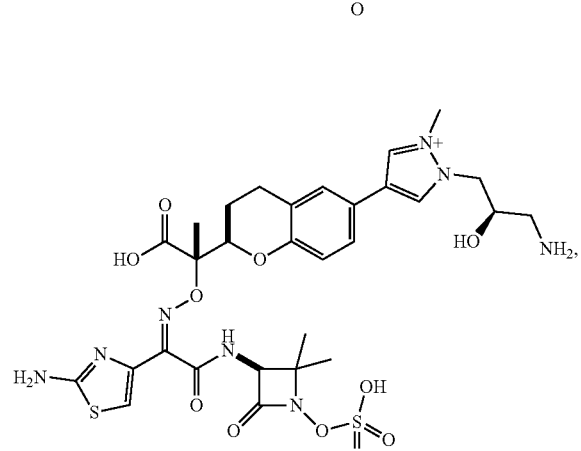
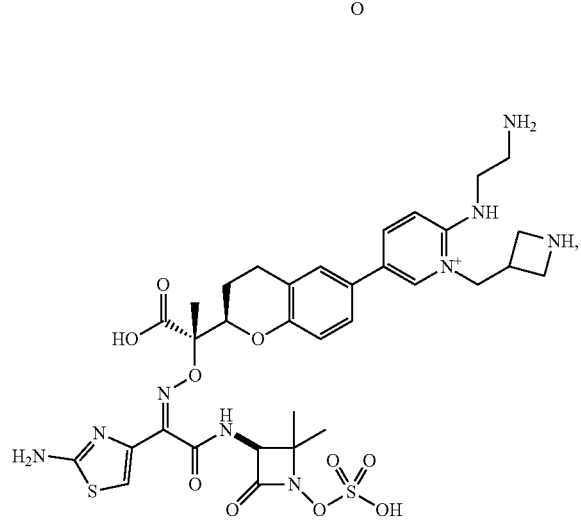
142
-continued
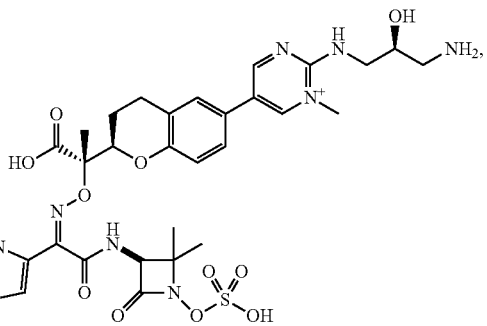
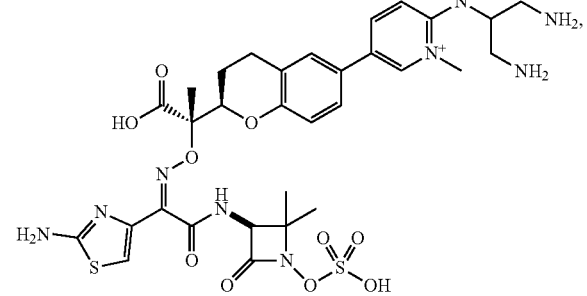
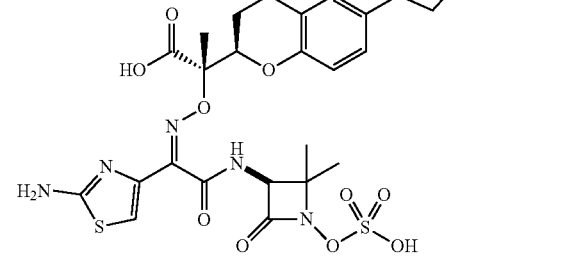
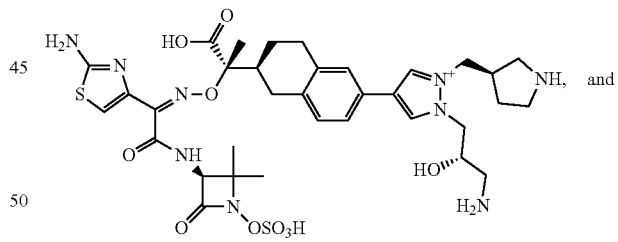
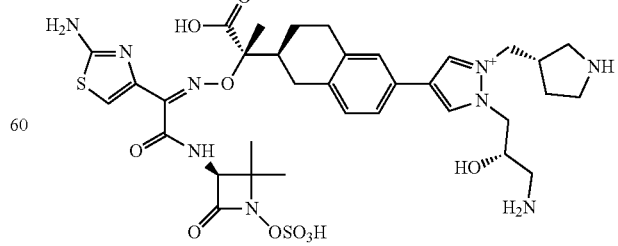
or a pharmaceutically acceptable salt thereof.

14. A compound which is:

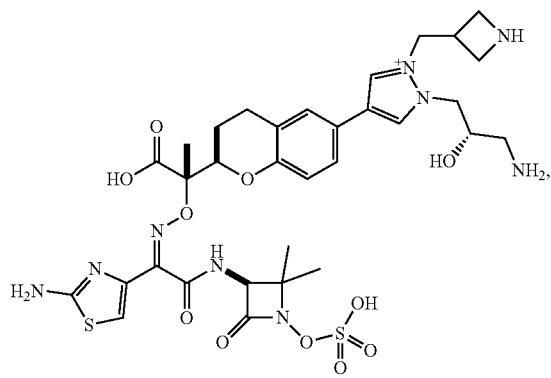 [SMILES: CC1(C)[C@H](NC(=O)/C(=N\O[C@](C)(C(=O)O)[C@H]2CCc3cc(-c4cn(C[C@@H](O)CN)[n+](CC5CNC5)c4)ccc3O2)c2csc(N)n2)C(=O)N1OS(=O)(=O)O]

or a pharmaceutically acceptable salt thereof.

15. A compound which is:

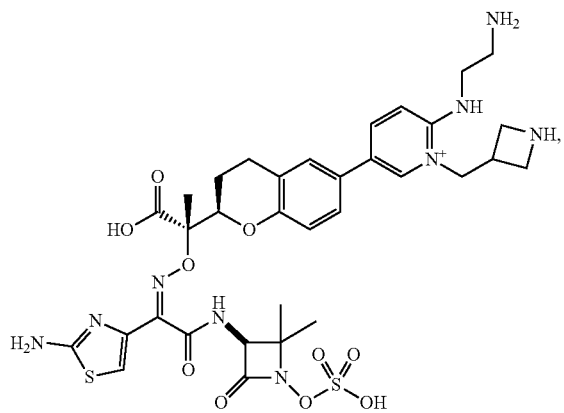 [SMILES: CC1(C)[C@H](NC(=O)/C(=N\O[C@](C)(C(=O)O)[C@H]2CCc3cc(-c4ccc(NCCN)[n+](CC5CNC5)c4)ccc3O2)c2csc(N)n2)C(=O)N1OS(=O)(=O)O]

or a pharmaceutically acceptable salt thereof.

16. A compound which is:

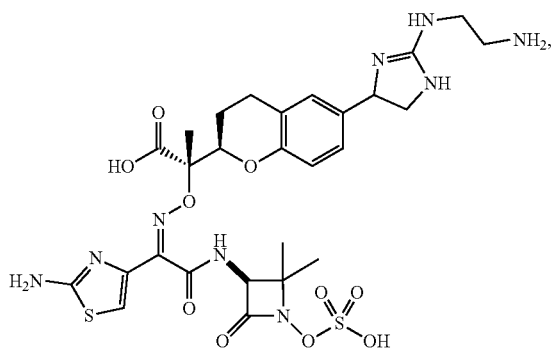 [SMILES: CC1(C)[C@H](NC(=O)/C(=N\O[C@](C)(C(=O)O)[C@H]2CCc3cc(C4CNC(NCCN)=N4)ccc3O2)c2csc(N)n2)C(=O)N1OS(=O)(=O)O]

or a pharmaceutically acceptable salt thereof.

17. A compound which is:

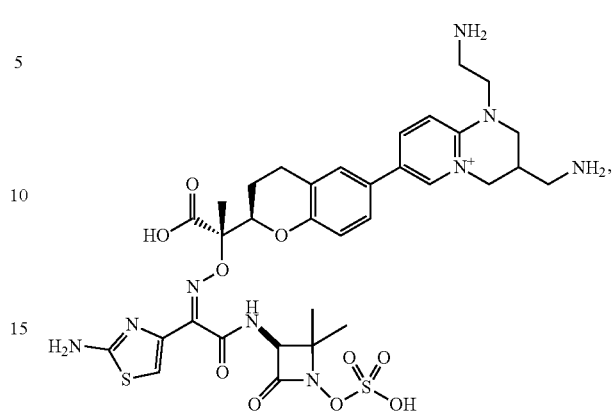

or a pharmaceutically acceptable salt thereof.

18. A compound which is:

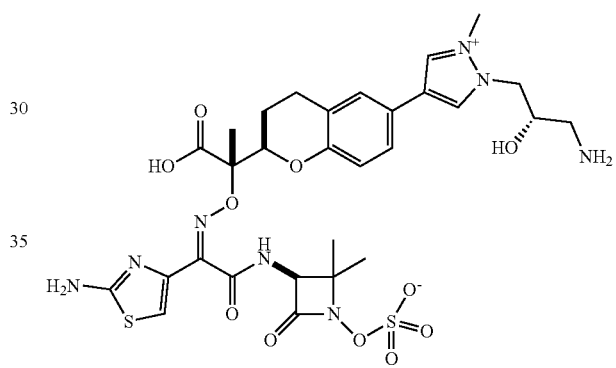

or a pharmaceutically acceptable salt thereof.

19. A pharmaceutical composition comprising a therapeutically effective amount of a compound of claim 1, or a pharmaceutically acceptable salt thereof, and a pharmaceutically acceptable carrier.

20. A pharmaceutical composition according to claim 19, which further comprises a therapeutically effective amount of a beta-lactamase inhibitor compound.

21. A pharmaceutical composition according to claim 20, wherein the beta-lactamase inhibitor compound is selected from the group consisting of relebactam, tazobactam, clavulanic acid, sulbactam, and avibactam.

* * * * *